(12) United States Patent
Tamura et al.

(10) Patent No.: US 10,478,425 B2
(45) Date of Patent: Nov. 19, 2019

(54) 5-PHENYLAZAINDOLE DERIVATIVE HAVING AMPK-ACTIVATING ACTIVITY

(71) Applicant: Shionogi & Co., Ltd., Osaka (JP)

(72) Inventors: Yuusuke Tamura, Osaka (JP); Hiroki Ozasa, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 16/078,875

(22) PCT Filed: Feb. 24, 2017

(86) PCT No.: PCT/JP2017/006984
§ 371 (c)(1),
(2) Date: Aug. 22, 2018

(87) PCT Pub. No.: WO2017/146186
PCT Pub. Date: Aug. 31, 2017

(65) Prior Publication Data
US 2019/0060293 A1    Feb. 28, 2019

(30) Foreign Application Priority Data
Feb. 26, 2016  (JP) ................................ 2016-035014

(51) Int. Cl.
| | | |
|---|---|---|
| *C07D 401/10* | (2006.01) | |
| *C07D 401/14* | (2006.01) | |
| *A61K 31/437* | (2006.01) | |
| *A61K 31/4355* | (2006.01) | |
| *A61K 31/444* | (2006.01) | |
| *A61K 31/496* | (2006.01) | |
| *A61K 31/5377* | (2006.01) | |
| *C07D 471/04* | (2006.01) | |
| *C07D 519/00* | (2006.01) | |
| *A61P 3/10* | (2006.01) | |
| *C07F 9/6561* | (2006.01) | |

(52) U.S. Cl.
CPC ........ *A61K 31/4355* (2013.01); *A61K 31/444* (2013.01); *A61K 31/496* (2013.01); *A61K 31/5377* (2013.01); *A61P 3/10* (2018.01); *C07D 471/04* (2013.01); *C07D 519/00* (2013.01); *C07F 9/6561* (2013.01); *Y02P 20/55* (2015.11)

(58) Field of Classification Search
CPC ... C07D 401/10; C07D 401/14; A61K 31/437
USPC .......................................... 546/119; 514/303
See application file for complete search history.

(56) References Cited

U.S. PATENT DOCUMENTS

| | | |
|---|---|---|
| 2013/0184240 A1 | 7/2013 | Tonogaki et al. |
| 2014/0194420 A1 | 7/2014 | Kojima et al. |
| 2015/0203450 A1 | 7/2015 | Tamura et al. |
| 2017/0273955 A1 | 9/2017 | Tamura et al. |
| 2017/0333398 A1 | 11/2017 | Kojima et al. |

FOREIGN PATENT DOCUMENTS

| | | |
|---|---|---|
| WO | 2009/100130 | 8/2009 |
| WO | 2010/036613 | 4/2010 |
| WO | 2010/047982 | 4/2010 |
| WO | 2010/051176 | 5/2010 |
| WO | 2010/051206 | 5/2010 |
| WO | 2011/106273 | 9/2011 |
| WO | 2012/116145 | 8/2012 |
| WO | 2013/153479 | 10/2013 |
| WO | 2014/031441 | 2/2014 |
| WO | 2014/031445 | 2/2014 |
| WO | 2014/031465 | 2/2014 |
| WO | 2014/031468 | 2/2014 |
| WO | 2014/031515 | 2/2014 |
| WO | 2014/031517 | 2/2014 |
| WO | 2014/069426 | 5/2014 |
| WO | 2014/128549 | 8/2014 |
| WO | 2014/139388 | 9/2014 |
| WO | 2014/140704 | 9/2014 |
| WO | 2014133008 | * 9/2014 |
| WO | 2014139388 | * 9/2014 |
| WO | 2014/175330 | 10/2014 |
| WO | 2014/202528 | 12/2014 |
| WO | 2014/202580 | 12/2014 |
| WO | 2015/007669 | 1/2015 |

(Continued)

OTHER PUBLICATIONS

International Preliminary Report on Patentability dated Sep. 7, 2018 in International Application No. PCT/JP2017/006984.
International Search Report dated Apr. 18, 2017 in International Application No. PCT/JP2017/006984.
Bei B. Zhang et al., "AMPK: An Emerging Drug Target for Diabetes and the Metabolic Syndrome", Cell Metabolism vol. 9, Issue 5, p. 407-416, 2009.

*Primary Examiner* — Niloofar Rahmani
(74) *Attorney, Agent, or Firm* — Wenderoth, Lind & Ponack, L.L.P.

(57) ABSTRACT

Provided is a compound which is useful as an AMPK activator. The compound is represented by formula:

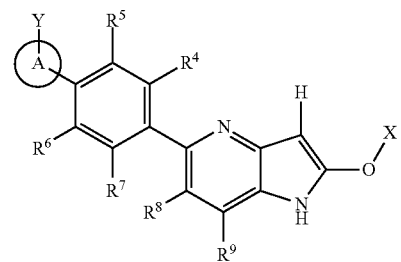

wherein the symbols are defined in the specification.

26 Claims, No Drawings

(56) References Cited

FOREIGN PATENT DOCUMENTS

| WO | 2015/063011 | | 5/2015 |
|----|-------------|---|--------|
| WO | 2016/001224 | | 1/2016 |
| WO | 2016/023789 | | 2/2016 |
| WO | 2016031842 | * | 3/2016 |
| WO | 2016/113299 | | 7/2016 |
| WO | 2016/113300 | | 7/2016 |
| WO | 2017/188288 | | 11/2017 |
| WO | 2017/200068 | | 11/2017 |

* cited by examiner

5-PHENYLAZAINDOLE DERIVATIVE HAVING AMPK-ACTIVATING ACTIVITY

FIELD OF THE INVENTION

The present invention relates to a compound which has an activating effect on adenosine monophosphate-activated protein kinase (hereinafter referred to as AMPK) and is useful as a medicine.

BACKGROUND ART

AMPK is a serine-threonine kinase, which is activated by AMP, and has three subunits, α, β and γ. In each subunit, there exist multiple isoforms (α1, α2, β1, β2, γ1, γ2 and γ3).

AMPK is involved in various physiological functions, such as suppression of gluconeogenesis and inhibition of fatty acid synthesis in hepatic and incorporation of sugars and an increase in fatty acid oxidation in skeletal muscles, as an energy sensor in living organisms, and has attracted attention as a target molecule of a therapeutic agent for diabetes. Therefore, an AMPK activator is expected to be effective in the treatment of diabetes as an insulin resistance improving drug, which has an insulin independent hypoglycemic effect and a lipid improving effect (Non-Patent Document 1).

Patent Documents 1 to 16, 19 to 20 and 22 to 26 disclose a variety of compounds having an AMPK activating effect. However, an azaindole derivative like the compound of the present invention is not disclosed in any of the documents.

Patent Document 17 describes the compound shown below as a compound having an AMPK activating effect.

[Chemical formula 1]

[Chemical formula 2]

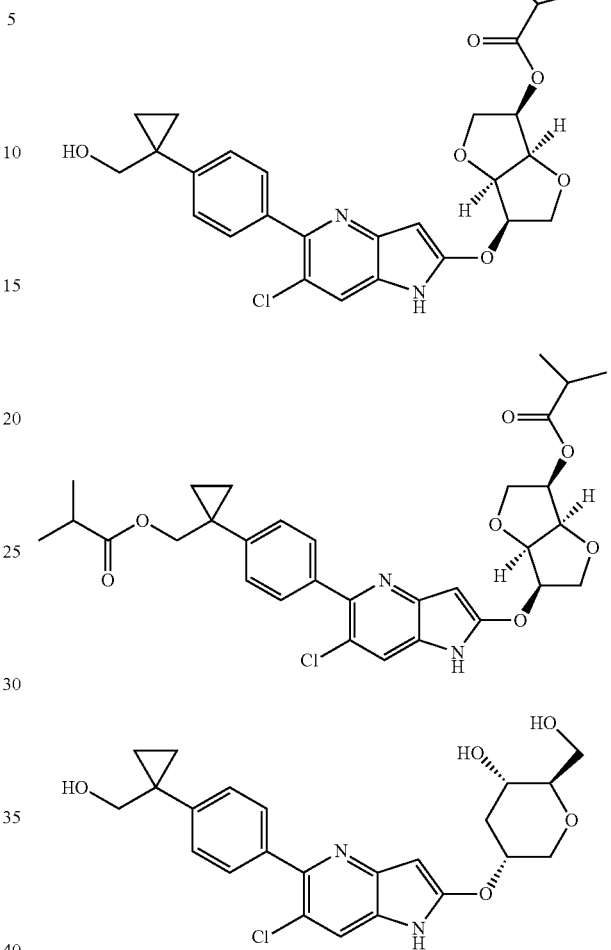

Patent Document 18 describes the compounds shown below as a compound having an AMPK activating effect.

Patent Document 21 describes the compounds shown below as a compound having an AMPK activating effect.

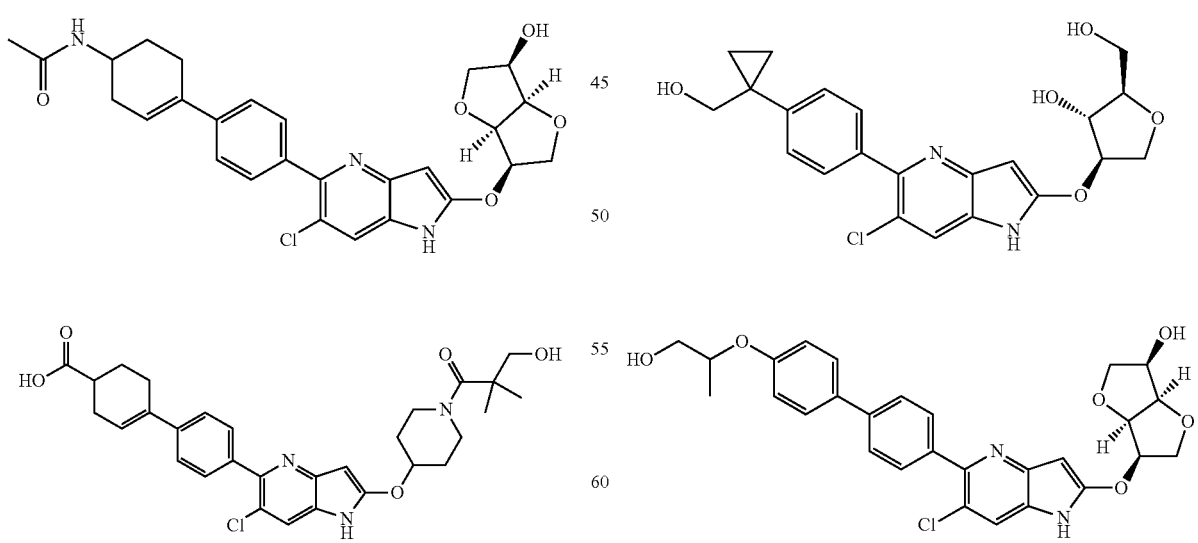

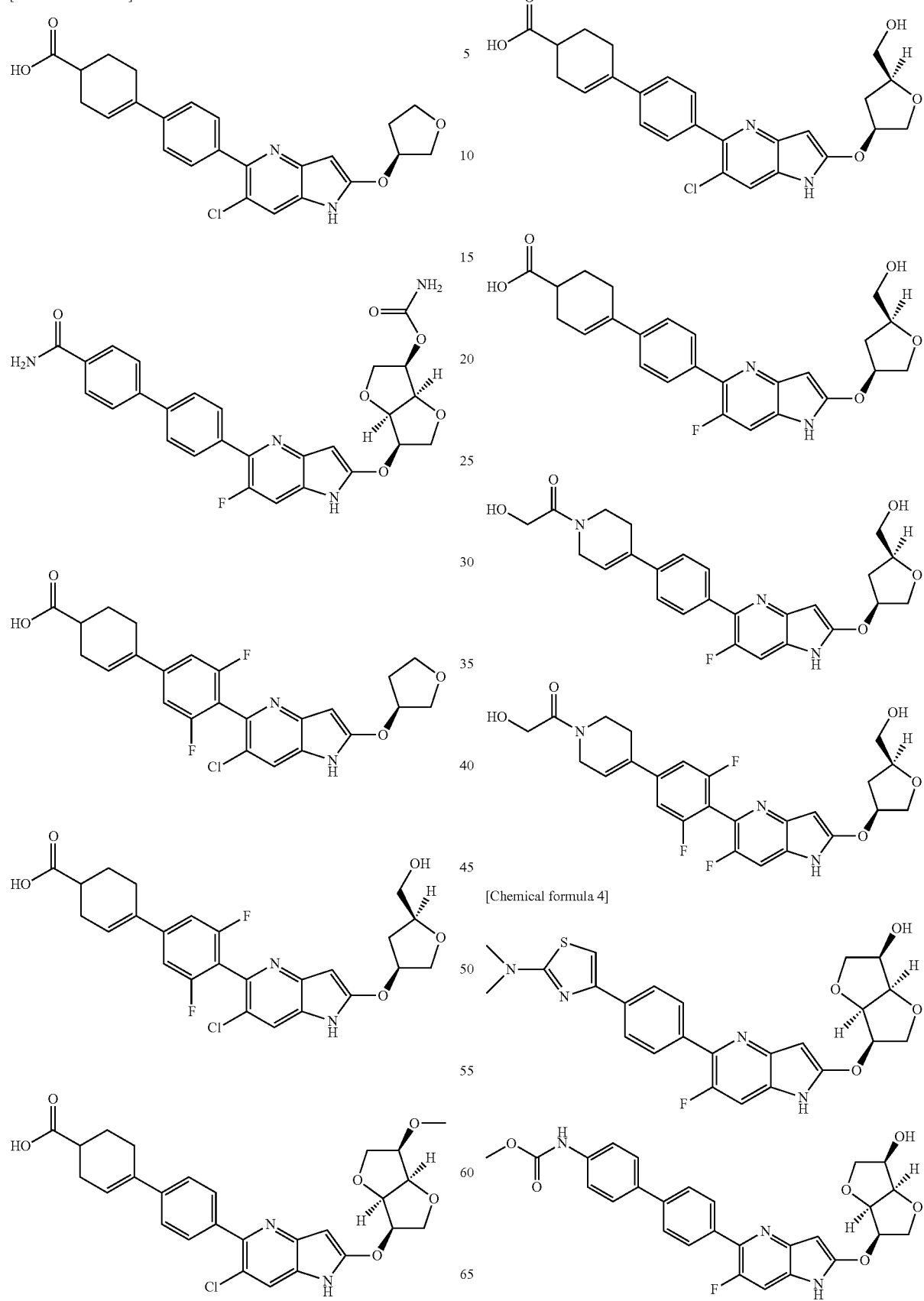

-continued

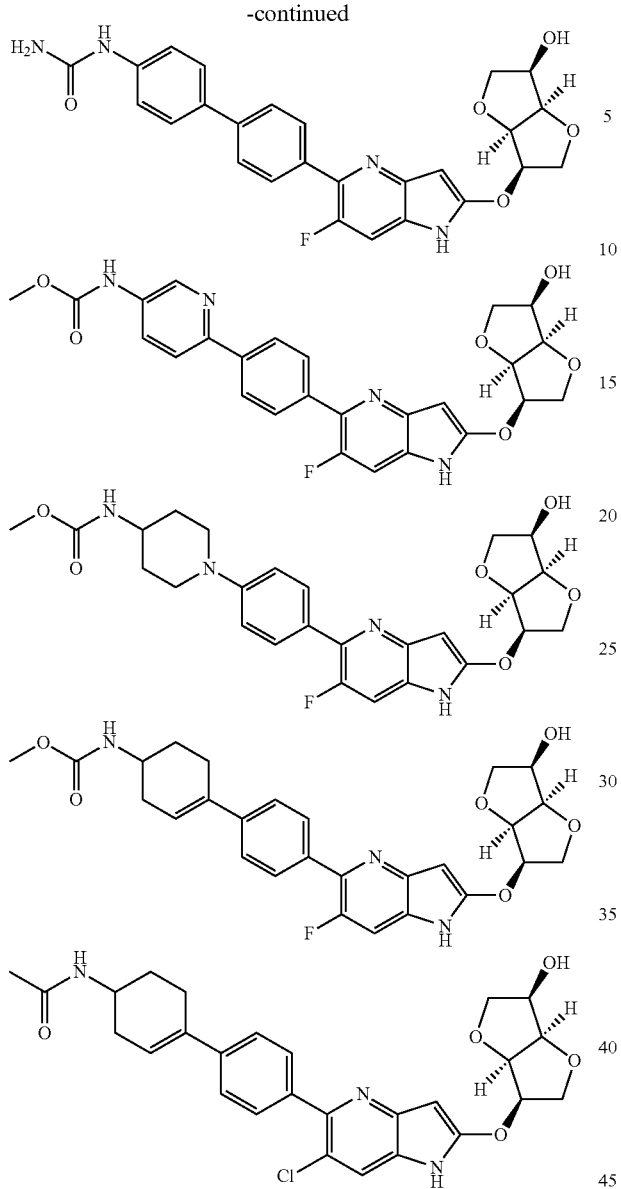

PRIOR ART DOCUMENT

Patent Document

Patent Document 1: WO 2010/036613
Patent Document 2: WO 2010/047982
Patent Document 3: WO 2010/051176
Patent Document 4: WO 2010/051206
Patent Document 5: WO 2011/106273
Patent Document 6: WO 2012/116145
Patent Document 7: WO 2012/033149
Patent Document 8: WO 2013/011932
Patent Document 9: WO 2014/069426
Patent Document 10: WO 2014/031441
Patent Document 11: WO 2014/031445
Patent Document 12: WO 2014/031468
Patent Document 13: WO 2014/031517
Patent Document 14: WO 2014/031465
Patent Document 15: WO 2014/031515
Patent Document 16: WO 2009/100130
Patent Document 17: WO 2014/133008
Patent Document 18: WO 2014/139388
Patent Document 19: WO 2015/007669
Patent Document 20: WO 2015/063011
Patent Document 21: WO 2016/031842
Patent Document 22: WO 2016/023789
Patent Document 23: WO 2016/001224
Patent Document 24: WO 2013/153479
Patent Document 25: WO 2014/140704
Patent Document 26: WO 2014/128549

Non-Patent Document

Non-Patent Document 1: Cell Metabolism Vol. 9, Issue 5, 407-416, 2009

DISCLOSURE OF INVENTION

Problems to be Solved by the Invention

An object of the present invention is to provide an excellent AMPK activator.

Means for Solving the Problem

As a result of intensive research, the present inventors succeeded in synthesizing an excellent compound having an AMPK activating effect.

The present invention relates to the following.

(1)
A compound represented by formula (I):

[Chemical formula 5]

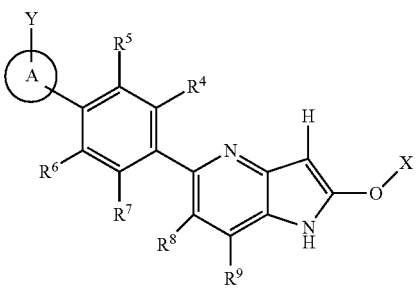

or its pharmaceutically acceptable salt,
wherein
X is substituted or unsubstituted monocyclic heterocyclyl, or

[Chemical formula 6]

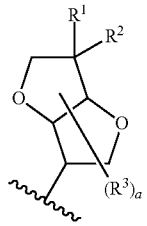

wherein $R^1$ and $R^2$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

$R^3$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

a is an integer from 0 to 7;

with the proviso that the compounds wherein one of $R^1$ and $R^2$ is hydrogen, the other is hydroxy, and a is 0 are excluded;

ring A is substituted aryl, substituted heteroaryl, substituted cycloalkyl, substituted cycloalkenyl, or substituted heterocyclyl, the ring A may further have (a) substituent(s) other than Y;

Y is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted alkyloxycarbonyl, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted alkylsulfinyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted alkylaminosulfonyl, substituted or unsubstituted acyl, substituted or unsubstituted carbamoyl, substituted or unsubstituted carbamoyloxy, substituted or unsubstituted sulfamoyl, substituted or unsubstituted amino, $R^S R^{S'} (O=)S=N-$, $R^S R^{S'}(O=)S=N-R^{2f}-$, $R^S R^{S'}(O=)S=N-C(=O)-$, $(R^N)N=S(=O)(R^S)-$, $(R^N)N=S(=O)(R^S)-R^{2f}-$, $R^S R^{S'}(R^{N'}-N=)S=N-$, $((R^N)N=)_2 S(R^S)-$, $(R^N R^{N'})N-C(=O)-O-$, $R^O O-C(=O)-N(R^N)-$, $R^O O-C(=O)-O-$, $R^S(R^N R^{N'} N)(O=)S=N-$, $R^S (R^N R^{N'} N)(O=)S=N-R^{2f}-$, $(R^{N''})N=S(=O)(NR^N R^{N'})-$, $(R^{N''})N=S(=O)(NR^N R^{N'})-R^{2f}-$, $R^{P1} R^{P2} (O=)P-$

[Chemical formula 7]

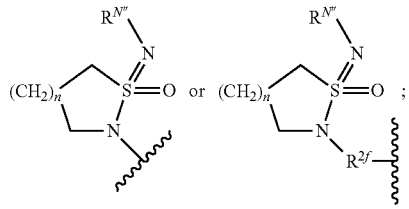

wherein n is an integer 1 or 2;

$R^S$ and $R^{S'}$ are each independently substituted or unsubstituted alkyl, substituted or unsubstituted cycloalkyl, substituted or unsubstituted heterocyclyl, substituted or unsubstituted aryl, substituted or unsubstituted heteroaryl, or substituted or unsubstituted amino;

$R^S$ and $R^{S'}$ bound to the same sulfur atom may form a substituted or unsubstituted ring together with the sulfur atom;

$R^{2f}$ is substituted or unsubstituted alkylene;

$R^N$ is each independently hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl, or substituted or unsubstituted carbamoyl;

$R^N$ together with the adjacent nitrogen atom may form a substituted or unsubstituted ring when Y is $((R^N)N=)_2 S(R^S)-$;

$R^{N'}$ is hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl or substituted or unsubstituted carbamoyl;

$R^N$ and $R^{N'}$ bound to the same nitrogen atom may form a substituted or unsubstituted ring together with the nitrogen atom;

$R^{N''}$ is hydrogen, cyano, substituted or unsubstituted alkyl, substituted or unsubstituted alkenyl, substituted or unsubstituted alkynyl, substituted or unsubstituted alkylcarbonyl, substituted or unsubstituted alkyloxycarbonyl, substituted or unsubstituted alkylcarbamoyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heterocyclyl, substituted or unsubstituted acyl, substituted or unsubstituted aryloxycarbonyl, substituted or unsubstituted arylsulfonyl, substituted or unsubstituted alkylsulfonyl, or substituted or unsubstituted carbamoyl;

$R^O$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^{P1}$ and $R^{P2}$ is each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^4$, $R^5$, $R^6$ and $R^7$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

$R^8$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

$R^9$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substitute d or unsubstituted amino;

with the proviso that compounds shown below are excluded:

[Chemical formula 8]

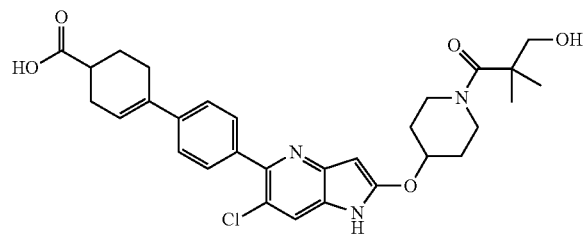

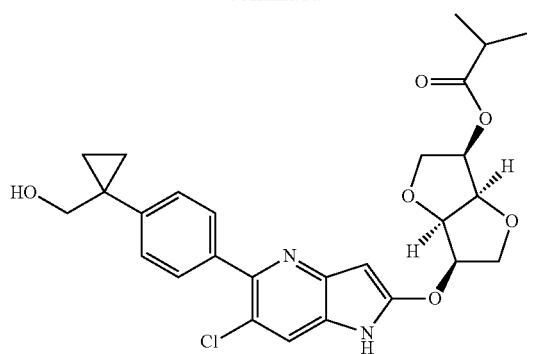

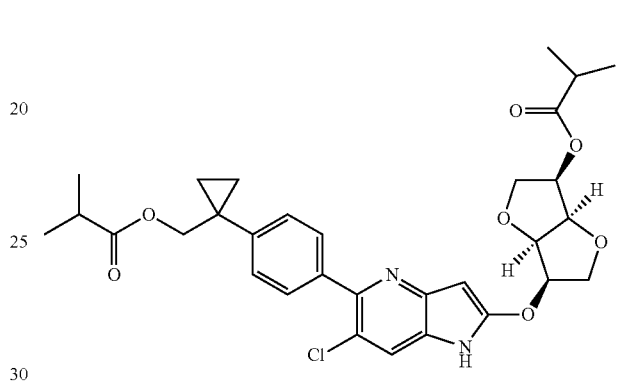

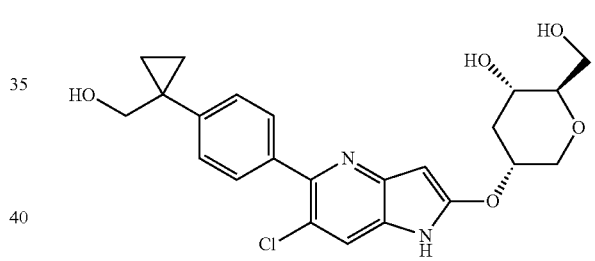

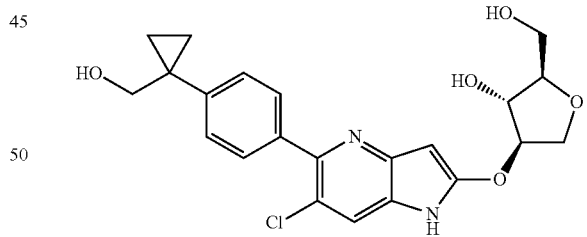

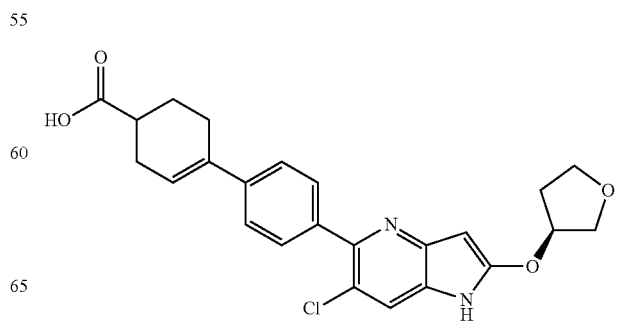

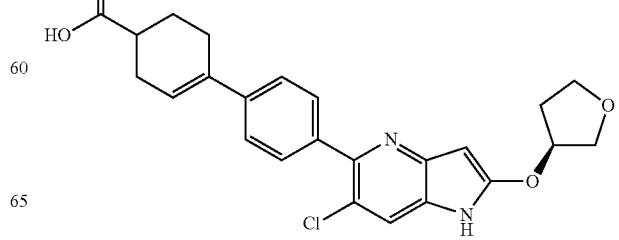

-continued

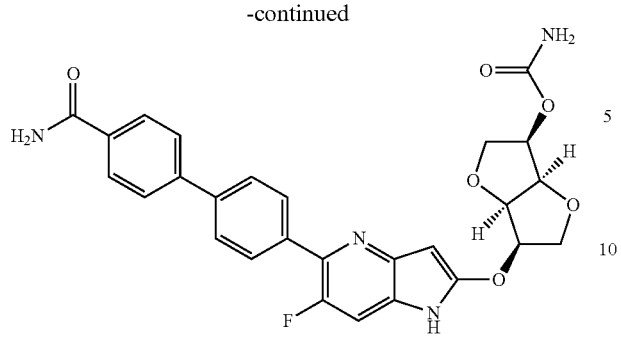

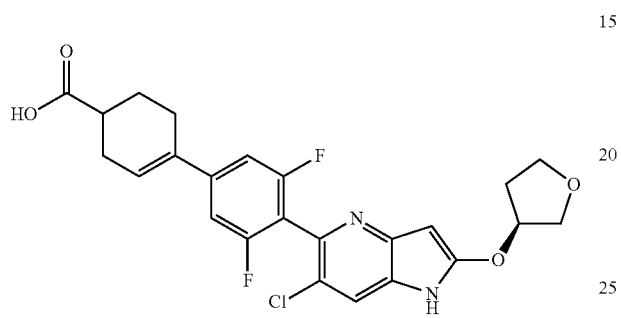

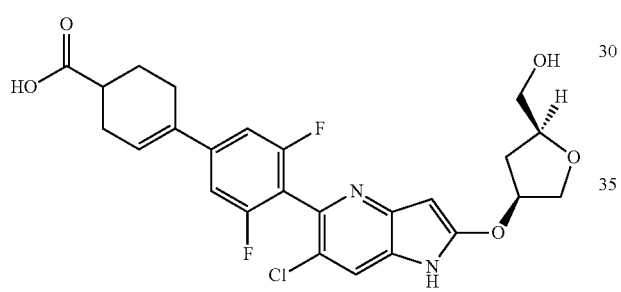

[Chemical formula 9]

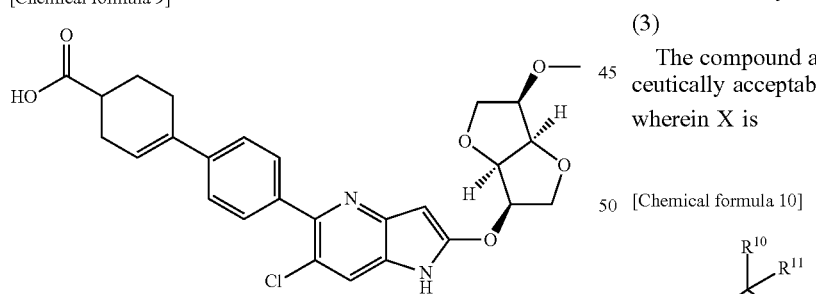

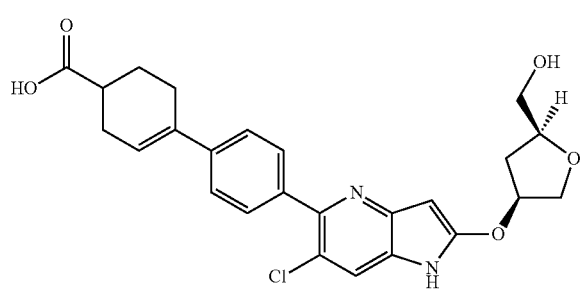

-continued

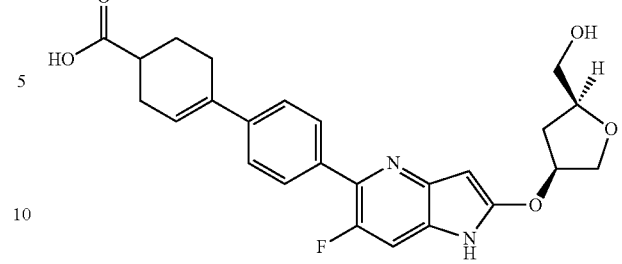

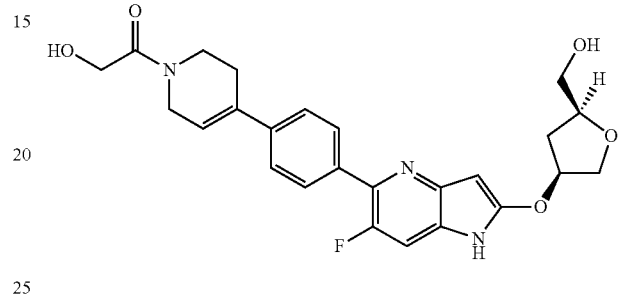

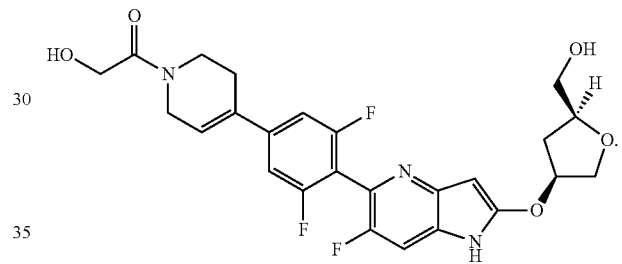

(2) The compound according to the above (1) or its pharmaceutically acceptable salt, wherein X is substituted or unsubstituted monocyclic heterocyclyl.

(3) The compound according to the above (2) or its pharmaceutically acceptable salt,
wherein X is

[Chemical formula 10]

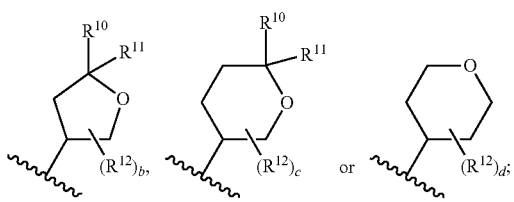

wherein $R^{10}$ and $R^{11}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

$R^{12}$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

b is an integer from 0 to 5;

c is an integer from 0 to 7;

d is an integer from 0 to 9.

(4)

The compound according to the above (3) or its pharmaceutically acceptable salt, wherein $R^{10}$ and $R^{11}$ are each independently hydrogen, halogen, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, or substituted or unsubstituted carbamoyl.

(5)

The compound according to the above (3) or its pharmaceutically acceptable salt, wherein one of $R^{10}$ and $R^{11}$ is hydrogen, halogen, or carboxy; the other of $R^{10}$ and $R^{11}$ is substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, or substituted or unsubstituted carbamoyl.

(6)

The compound according to any one of the above (3) to (5) or its pharmaceutically acceptable salt, wherein $R^{12}$ is each independently halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

b is an integer from 0 to 3;

c is an integer from 0 to 3;

d is an integer from 0 to 4.

(7)

The compound according to any one of the above (3) to (6) or its pharmaceutically acceptable salt, wherein one of $R^{10}$ and $R^{11}$ is hydrogen; the other of $R^{10}$ and $R^{11}$ is halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

b is an integer from 0 to 3;

c is an integer from 0 to 3;

d is an integer from 0 to 4.

(8)

A compound represented by formula (I):

[Chemical formula 11]

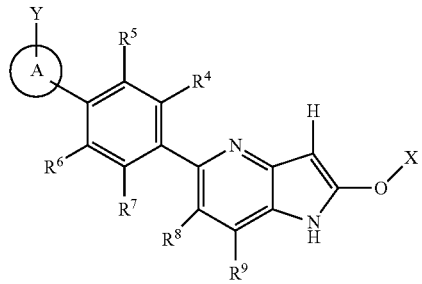

or its pharmaceutically acceptable salt, wherein

X is

[Chemical formula 12]

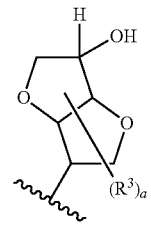

wherein $R^3$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

a is an integer from 0 to 7;

ring A is substituted aryl, substituted heteroaryl, substituted cycloalkyl, substituted cycloalkenyl, or substituted heterocyclyl, the ring A may further have (a) substituent(s) other than Y;

Y is $R^{Y1}$—O— or $(R^{Y2}R^{Y3})N$—;

$R^{Y1}$ is substituted or unsubstituted alkyl, substituted or unsubstituted alkenyl, substituted or unsubstituted alkynyl, substituted or unsubstituted acyl, substituted or unsubstituted aryl, substituted or unsubstituted heteroaryl, substituted or unsubstituted cycloalkyl, substituted or unsubstituted cycloalkenyl, substituted or unsubstituted heterocyclyl, $(R^N R^{N'})$N—C(=O)—, or $R^O$ O—C(=O)—;

$R^{Y2}$ and $R^{Y3}$ are each independently hydrogen, substituted or unsubstituted alkyl, substituted or unsubstituted alkenyl, substituted or unsubstituted alkynyl, substituted or unsubstituted acyl, substituted or unsubstituted aryl, substituted or unsubstituted heteroaryl, substituted or unsubstituted cycloalkyl, substituted or unsubstituted cycloalkenyl, substituted or unsubstituted heterocyclyl, $(R^N R^{N'})$N—C(=O)—, or $R^O$O—C(=O)—;

$R^N$ is each independently hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl, or substituted or unsubstituted carbamoyl;

$R^{N'}$ is hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl or substituted or unsubstituted carbamoyl; $R^N$ and $R^{N'}$ attached to the same N-atom may form a substituted or unsubstituted ring together with the N-atom;

$R^O$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^4$, $R^5$, $R^6$ and $R^7$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

$R^8$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

$R^9$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

with the proviso that compounds shown below are excluded:

[Chemical formula 13]

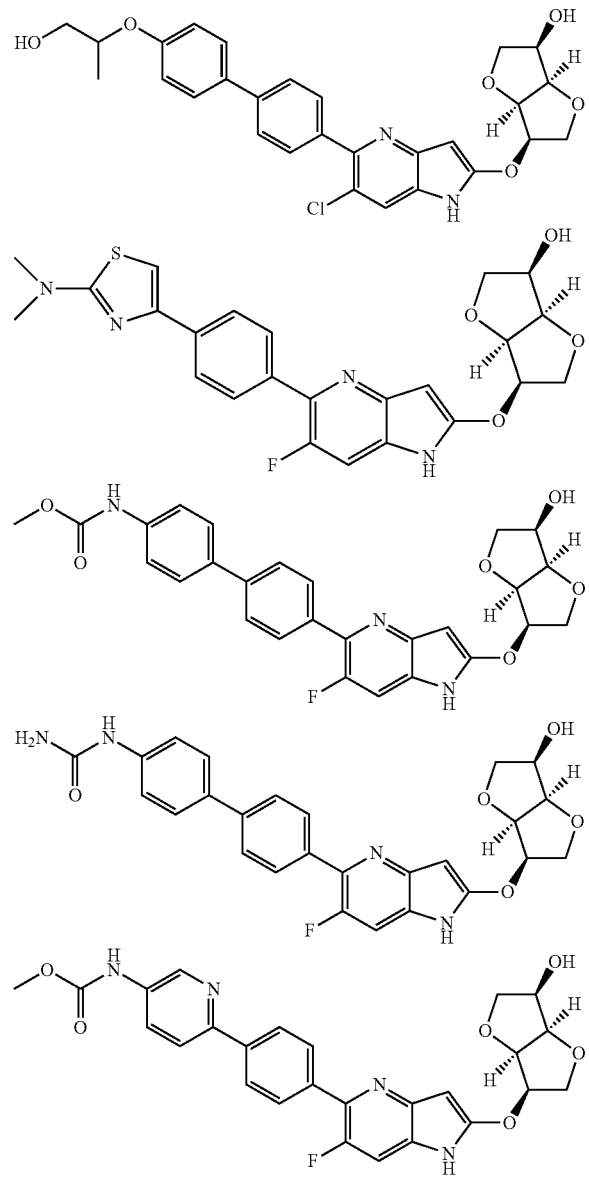

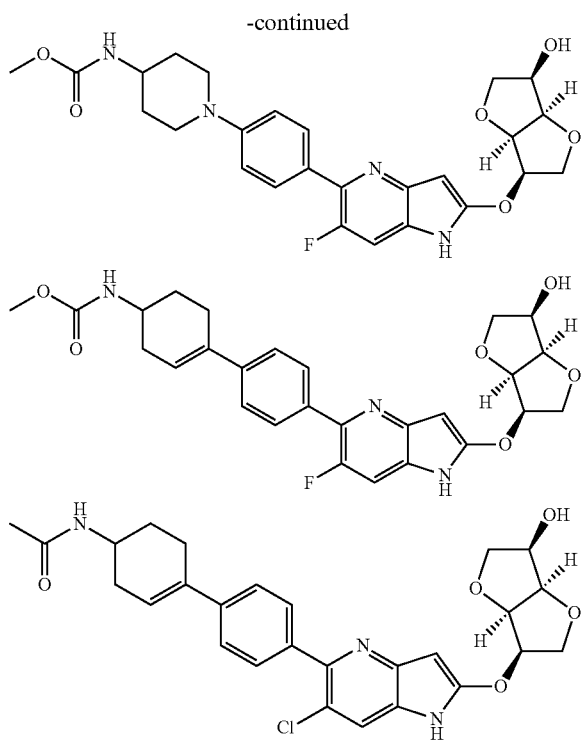

(9)

The compound according to any one of the above (1) to (8) or its pharmaceutically acceptable salt, wherein ring A is substituted aryl, substituted heteroaryl, substituted cycloalkenyl, or substituted heterocyclyl.

(10)

The compound according to any one of the above (1) to (9) or its pharmaceutically acceptable salt, wherein ring A is substituted aryl.

(11)

The compound according to any one of the above (1) to (10) or its pharmaceutically acceptable salt, wherein Y is substituted or unsubstituted alkyloxy, substituted or unsubstituted alkyloxycarbonyl, substituted or unsubstituted alkylsulfinyl, substituted or unsubstituted acyl, substituted or unsubstituted carbamoyloxy, substituted or unsubstituted amino, $R^S R^{S'}(O=)S=N-$, $(R^N)N=S(=O)(R^S)-$, $R^O O-C(=O)-N(R^N)-$, $R^{Y1}-O-$ or $(R^{Y2} R^{Y3})N-$.

(12)

The compound according to any one of the above (1) to (11) or its pharmaceutically acceptable salt, wherein $R^4$, $R^5$, $R^6$ and $R^7$ are each independently hydrogen, halogen, hydroxy, cyano, substituted or unsubstituted alkyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

(13)

The compound according to any one of the above (1) to (12) or its pharmaceutically acceptable salt, wherein $R^8$ is hydrogen, halogen, cyano, carboxy, substituted or unsubstituted alkyl, substituted or unsubstituted alkylsulfonyl, or substituted or unsubstituted carbamoyl.

(14)

The compound according to the above (13) or its pharmaceutically acceptable salt, wherein $R^S$ is hydrogen, fluoro, chloro, cyano, or substituted or unsubstituted alkyl, wherein the substituent of the substituted alkyl is halogen.

(15)

The compound according to any one of the above (1) to (14) or its pharmaceutically acceptable salt, wherein $R^9$ is hydrogen.

(16)

The compound according to the above (1) or its pharmaceutically acceptable salt, wherein the compound is selected from compound (I-1-01), (I-1-02), (I-1-03), (I-1-04), (I-1-06), (I-1-07), (I-1-46), or (I-1-47).

(17)

The compound according to the above (8) or its pharmaceutically acceptable salt, wherein the compound is selected from compound (I-1-08), (I-1-10), (I-1-11), (I-1-12), (I-1-14), (I-1-22), (I-1-23), (I-1-26), (I-1-27), (I-1-28), (I-1-31), (I-1-34), (I-1-35), (I-1-36), (I-1-39), (I-1-40), (I-1-41), (I-1-49), (I-1-50), (I-1-60), (I-1-61), (I-1-62), (I-1-63), (I-1-66), (I-1-68), (I-1-69), (I-1-71), or (I-1-72).

(18)

The compound according to the above (1) or its pharmaceutically acceptable salt, wherein the compound is selected from compound (I-2-01), (I-2-02), (I-2-06), (I-2-08), (I-2-19), (I-2-21), (I-2-23), (I-2-25), (I-2-26), (I-2-38), (I-2-42), (I-2-43), (I-2-46), (I-2-49), (I-2-55), (I-2-65), (I-2-73), (I-2-74), (I-2-75), (I-2-78), (I-2-79), (I-2-80), (I-2-81), (I-2-82), (I-2-83), (I-2-86), (I-2-88), (I-2-89), (I-2-90), (I-2-92), (I-2-94), or (I-2-97).

(19)

The compound according to the above (8) or its pharmaceutically acceptable salt, wherein the compound is selected from compound (I-2-05), (I-2-10), (I-2-12), (I-2-13), (I-2-24), (I-2-27), (I-2-28), (I-2-31), (I-2-32), (I-2-33), (I-2-34), (I-2-36), (I-2-37), (I-2-40), (I-2-45), (I-2-47), (I-2-48), (I-2-51), (I-2-52), (I-2-54), (I-2-57), (I-2-59), (I-2-60), (I-2-61), (I-2-62), (I-2-63), (I-2-69), (I-2-76), (I-2-84), or (I-2-85).

(20)

A compound or its pharmaceutically acceptable salt, wherein the compound is selected from compound (I-1-09), (I-1-15), (I-1-16), (I-1-17), (I-1-18), (I-1-19), (I-1-20), (I-1-30), (I-1-32), (I-1-33), (I-1-37), (I-1-38), (I-1-42), (I-1-43), (I-1-45), (I-1-48), (I-1-51), (I-1-52), (I-1-53), (I-1-54), (I-1-55), (I-1-57), (I-1-58), (I-1-59), or (I-1-64).

(21)

A compound or its pharmaceutically acceptable salt, wherein the compound is selected from compound (I-2-04), (I-2-08), (I-2-09), (I-2-11), (I-2-14), (I-2-15), (I-2-16), (I-2-17), (I-2-18), (I-2-20), (I-2-22), (I-2-29), (I-2-30), (I-2-41), (I-2-44), (I-2-53), (I-2-56), (I-2-58), (I-2-64), (I-2-66), (I-2-67), (I-2-72), (I-2-93), (I-2-95), or (I-2-96).

(22)

A pharmaceutical composition comprising the compound according to any one of the above (1) to (21) or its pharmaceutically acceptable salt.

(23)

The pharmaceutical composition according to the above (22), which has an activating effect on adenosine monophosphate-activated protein kinase.

(24)

The pharmaceutical composition according to the above (23) for the treatment and/or prevention of diabetes.

(25)

A method for preventing or treating diabetes, comprising administering the compound according to any one of the above (1) to (21), or its pharmaceutically acceptable salt.

(26)

The compound according to any one of the above (1) to (21), or its pharmaceutically acceptable salt, for the treatment and/or prevention of diabetes.

(27)

A pharmaceutical composition for oral administration, comprising any one of a compound represented by formula (I), compounds to the above (16) to (21), or pharmaceutically acceptable salt thereof.

(28)

The pharmaceutical composition according to the above (27), which is a tablet, powder, granule, capsule, pill, film, suspension, emulsion, elixir, syrup, lemonade, spirit, aromatic water, extract, decoction or tincture.

(29)

The pharmaceutical composition according to the above (28), which is a sugar-coated tablet, film-coated tablet, enteric-coated tablet, sustained-release tablet, troche tablet, sublingual tablet, buccal tablet, chewable tablet, orally disintegrating tablet, dry syrup, soft capsule, micro capsule or sustained-release capsule.

(30)

A pharmaceutical composition for parenteral administration, comprising any of a compound represented by formula (I), compounds to the above (16) to (21), or pharmaceutically acceptable salt thereof.

(31)

The pharmaceutical composition according to the above (30), for dermal, subcutaneous, intravenous, intraarterial, intramuscular, intraperitoneal, transmucosal, inhalation, transnasal, ophthalmic, inner ear or vaginal administration.

(32)

The pharmaceutical composition according to the above (30) or (31), which is injection, infusion, ophthalmic drop, nose drop, ear drop, aerosol, inhalation, lotion, impregnation, liniment, mouthwash, enema, ointment, plaster, jelly, cream, patch, cataplasm, external powder or suppository.

(33)

A pharmaceutical composition for a pediatric or geriatric patient, comprising any of a compound represented by formula (I), compounds to the above (16) to (21), or pharmaceutically acceptable salt thereof.

(34)

A pharmaceutical composition consisting of a combination of a compound represented by formula (I), compounds to the above (16) to (21), or pharmaceutically acceptable salt thereof, and an insulin secretagogue, a fast-acting insulin secretagogue, a glucose uptake inhibitor, an insulin resistance improving drug, a thiazolidine derivative, an insulin formulation, a peptidyl peptidase IV inhibitor, a GLP-1 receptor agonist, a sodium-dependent glucose transporter 1 inhibitor, or a sodium-dependent glucose transporter 2 inhibitor.

(35)

A pharmaceutical composition comprising a compound represented by formula (I), compounds to the above (16) to (21), or pharmaceutically acceptable salt thereof, for a combination therapy with an insulin secretagogue, a fast-acting insulin secretagogue, a glucose uptake inhibitor, an insulin resistance improving drug, a thiazolidine derivative, an insulin formulation, a peptidyl peptidase IV inhibitor, a GLP-1 receptor agonist, a sodium-dependent glucose transporter 1 inhibitor, or a sodium-dependent glucose transporter 2 inhibitor.

(1A)

A compound represented by formula (I):

[Chemical formula 14]

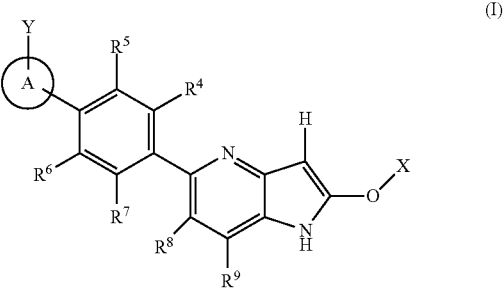

or its pharmaceutically acceptable salt,
wherein
X is substituted or unsubstituted monocyclic heterocyclyl, or

[Chemical formula 15]

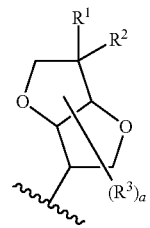

wherein $R^1$ and $R^2$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

$R^3$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

a is an integer from 0 to 7;

with the proviso that the compounds wherein one of $R^1$ and $R^2$ is hydrogen, the other is hydroxy, and a is 0 are excluded;

ring A is substituted aryl, substituted heteroaryl, substituted cycloalkyl, substituted cycloalkenyl, or substituted heterocyclyl, the ring A may further have (a) substituent(s) other than Y;

Y is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted alkyloxycarbonyl, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted alkylsulfinyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted alkylaminosulfonyl, substituted or unsubstituted acyl, substituted or unsubstituted carbamoyl, substituted or unsubstituted carbamoyloxy, substituted or unsubstituted sulfamoyl, substituted or unsubstituted amino, $R^S R^{S'}(O=)S=N-$, $R^S R^{S'}(O=)S=N-R^{2f}-$, $R^S R^{S'}(O=)S=N-C(=O)-$, $(R^N)N=S(=O)(R^S)-$, $(R^N)N=S(=O)(R^S)-R^{2f}-$, $R^S R^{S'}(R^{N'}-N=)S=N-$, $((R^N)N=)_2 S(R^S)-$, $(R^N R^{N'})N-C(=O)-O-$, $R^O O-C(=O)-N(R^N)-$, $R^O O-C(=O)-O-$, $R^S (R^N R^{N'} N)(O=)S=N-$, $R^S(R^N R^{N'} N)(O=)S=N-R^{2f}-$, $(R^{N''})N=S(=O)(NR^N R^{N'})-$, $(R^{N'})N=S(=O)(NR^N R^{N'})-R^{2f}-$,

[Chemical formula 16]

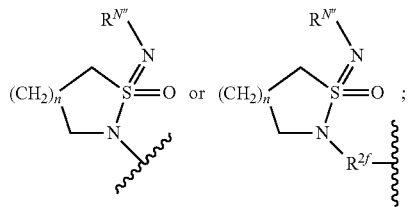

wherein n is an integer 1 or 2;

$R^S$ and $R^{S'}$ are each independently substituted or unsubstituted alkyl, substituted or unsubstituted cycloalkyl, substituted or unsubstituted heterocyclyl, substituted or unsubstituted aryl, or substituted or unsubstituted heteroaryl;

$R^S$ and $R^{S'}$ bound to the same sulfur atom may form a substituted or unsubstituted ring together with the sulfur atom;

$R^{2f}$ is substituted or unsubstituted alkylene;

$R^N$ is each independently hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl, or substituted or unsubstituted carbamoyl;

$R^N$ together with the adjacent nitrogen atom may form a substituted or unsubstituted ring when Y is $((R^N)N=)_2 S(R^S)-$;

$R^{N'}$ is hydrogen, cyano, substituted or unsubstituted alkyl, substituted or unsubstituted alkylcarbonyl, substituted or unsubstituted alkyloxycarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl or substituted or unsubstituted carbamoyl;

$R^N$ and $R^{N'}$ bound to the same nitrogen atom may form a substituted or unsubstituted ring together with the nitrogen atom $R^{N''}$ is hydrogen, cyano, substituted or unsubstituted alkyl, substituted or unsubstituted alkenyl, substituted or unsubstituted alkynyl, substituted or unsubstituted alkylcarbonyl, substituted or unsubstituted alkyloxycarbonyl, substituted or unsubstituted alkylcarbamoyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heterocyclyl, substituted or unsubstituted acyl, substituted or unsubstituted aryloxycarbonyl, substituted or unsubstituted arylsulfonyl, substituted or unsubstituted alkylsulfonyl, or substituted or unsubstituted carbamoyl;

$R^O$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^4$, $R^5$, $R^6$ and $R^7$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

$R^8$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

$R^9$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

with the proviso that compounds shown below are excluded:

[Chemical formula 17]

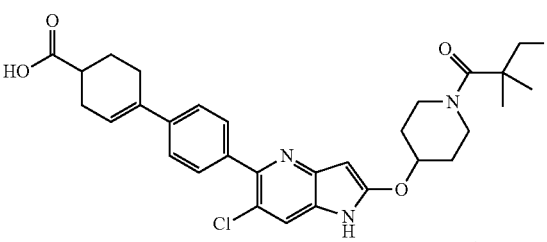

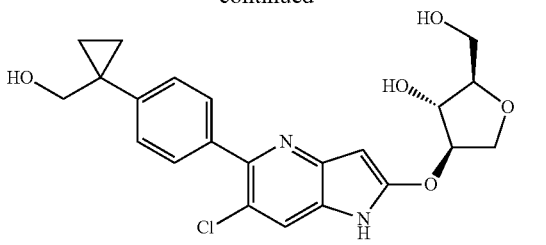

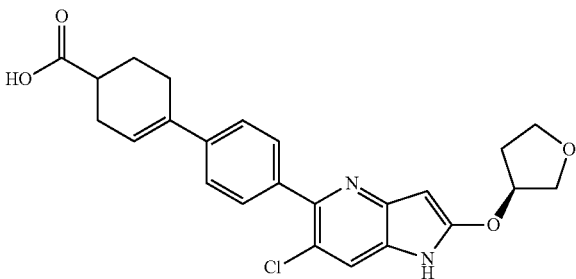

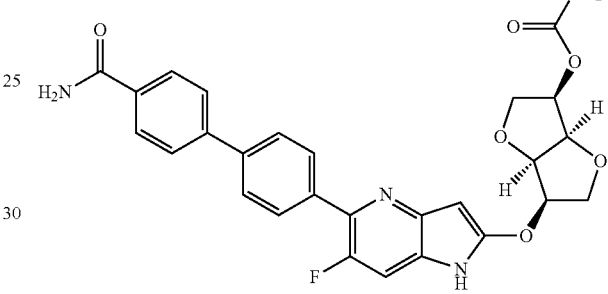

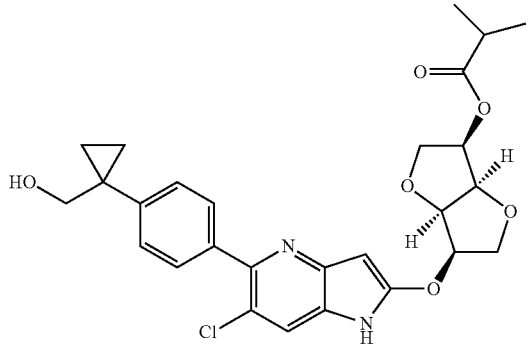

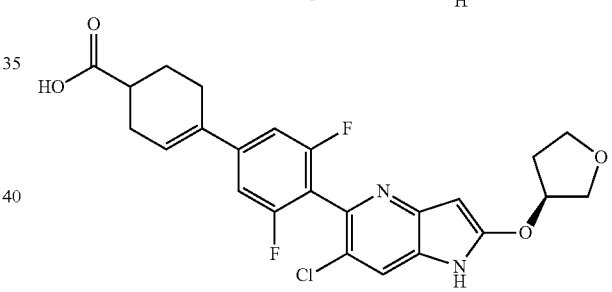

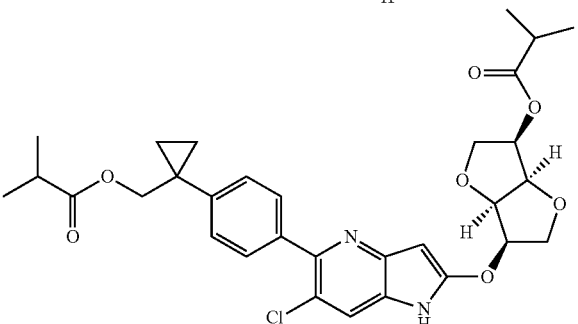

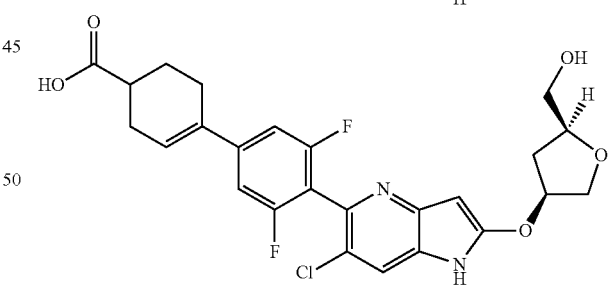

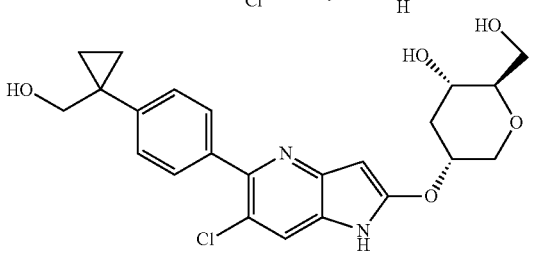

[Chemical formula 18]

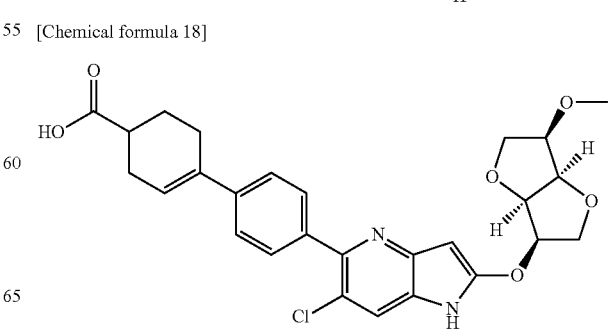

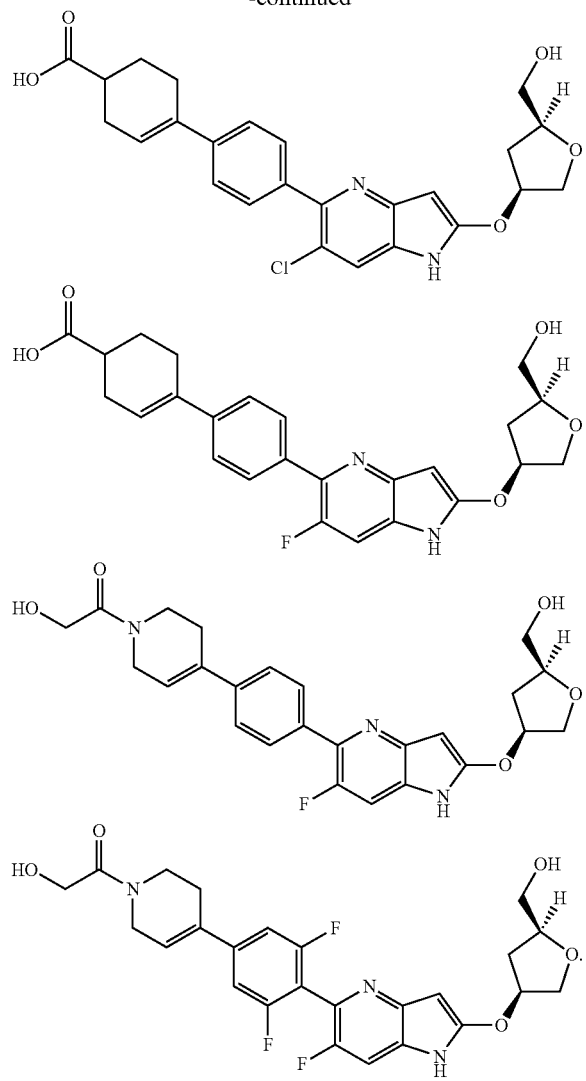

(2A)

The compound according to the above (1A), or its pharmaceutically acceptable salt, wherein X is substituted or unsubstituted monocyclic heterocyclyl.

(3A)

The compound according to the above (2A), or its pharmaceutically acceptable salt,
wherein X is

[Chemical formula 19]

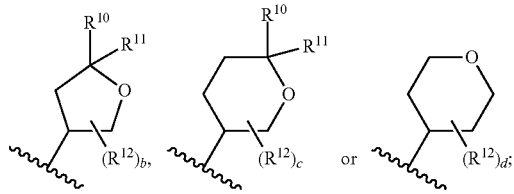

wherein $R^{10}$ and $R^{11}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

$R^{12}$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

b is an integer from 0 to 5;
c is an integer from 0 to 7;
d is an integer from 0 to 9.

(4A)

The compound according to the above (3A), or its pharmaceutically acceptable salt, wherein $R^{10}$ and $R^{11}$ are each independently hydrogen, halogen, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, or substituted or unsubstituted carbamoyl.

(5A)

The compound according to the above (3A), or its pharmaceutically acceptable salt, wherein one of $R^{10}$ and $R^{11}$ is hydrogen, halogen, or carboxy; the other of $R^{10}$ and $R^{11}$ is substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, or substituted or unsubstituted carbamoyl.

(6A)

The compound according to any one of the above (3A) to (5A), or its pharmaceutically acceptable salt, wherein $R^{12}$ is each independently halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

b is an integer from 0 to 3;
c is an integer from 0 to 3;
d is an integer from 0 to 4.

(7A)

The compound according to any one of the above (3A) to (6A), or its pharmaceutically acceptable salt, wherein one of $R^{10}$ and $R^{11}$ is hydrogen; the other of $R^{10}$ and $R^{11}$ is halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

b is an integer from 0 to 3;
c is an integer from 0 to 3;
d is an integer from 0 to 4.

(8A)

The compound according to any one of the above (1A) to (7A), or its pharmaceutically acceptable salt, wherein ring A is substituted aryl, substituted heteroaryl, substituted cycloalkenyl, or substituted heterocyclyl.

(9A)

The compound according to any one of the above (1A) to (8A), or its pharmaceutically acceptable salt, wherein ring A is substituted aryl.

(10A)

The compound according to any one of the above (1A) to (9A), or its pharmaceutically acceptable salt, wherein Y is substituted or unsubstituted alkyloxy, substituted or unsubstituted alkyloxycarbonyl, substituted or unsubstituted alkylsulfinyl, substituted or unsubstituted acyl, substituted or unsubstituted carbamoyloxy, substituted or unsubstituted amino, $R^S R^{S'}(O=)S=N-$, $(R^N)N=S(=O)(R^S)-$, or $R^O O-C(=O)-N(R^N)-$.

(11A)

The compound according to any one of the above (1A) to (10A), or its pharmaceutically acceptable salt, wherein $R^4$, $R^5$, $R^6$ and $R^7$ are each independently hydrogen, halogen, hydroxy, cyano, substituted or unsubstituted alkyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

(12A)

The compound according to any one of the above (1A) to (11A), or its pharmaceutically acceptable salt, wherein $R^8$ is hydrogen, halogen, cyano, carboxy, substituted or unsubstituted alkyl, substituted or unsubstituted alkylsulfonyl, or substituted or unsubstituted carbamoyl.

(13A)

The compound according to the above (12A), or its pharmaceutically acceptable salt, wherein $R^8$ is hydrogen, fluoro, chloro, cyano, or substituted or unsubstituted alkyl, wherein the substituent of the substituted alkyl is halogen.

(14A)

The compound according to any one of the above (1A) to (13A), or its pharmaceutically acceptable salt, wherein $R^9$ is hydrogen.

(15A)

The compound according to the above (1A), or its pharmaceutically acceptable salt, wherein the compound is selected from compound (I-1-02), (I-1-03), (I-1-04), (I-1-06), (I-1-07), (I-1-46), or (I-1-47).

(15A-1) A compound selected from compound (I-1-08), (I-1-09), (I-1-10), (I-1-12), (I-1-14), (I-1-15), (I-1-17), (I-1-18), (I-1-20), (I-1-22), (I-1-23), (I-1-32), (I-1-36), (I-1-38), (I-1-39), (I-1-40), (I-1-42), (I-1-43), (I-1-45), (I-1-48), (I-1-54), (I-1-58), (I-1-60), (I-1-64), (I-1-66), or (I-1-69), or its pharmaceutically acceptable salt.

(16A)

A pharmaceutical composition comprising the compound according to any one of the above (1A) to (15A), or (15A-1), or its pharmaceutically acceptable salt.

(17A)

The pharmaceutical composition according to the above (16A), which has an activating effect on adenosine monophosphate-activated protein kinase.

(18A)

The pharmaceutical composition according to the above (16A) or (17A), for the treatment and/or prevention of diabetes.

(19A)

A method for preventing or treating diabetes, comprising administering the compound according to any one of the above (1A) to (15A), or (15A-1), or its pharmaceutically acceptable salt.

(20A)

The compound according to any one of the above (1A) to (15A), or (15A-1), or its pharmaceutically acceptable salt, for the treatment and/or prevention of diabetes.

(21A)

A pharmaceutical composition for oral administration, comprising any one of a compound represented by formula (I), compounds (I-1-02), (I-1-03), (I-1-04), (I-1-06), (I-1-07), (I-1-08), (I-1-09), (I-1-10), (I-1-12), (I-1-14), (I-1-15), (I-1-17), (I-1-18), (I-1-20), (I-1-22), (I-1-23), (I-1-32), (I-1-36), (I-1-38), (I-1-39), (I-1-40), (I-1-42), (I-1-43), (I-1-45), (I-1-46), (I-1-47), (I-1-48), (I-1-54), (I-1-58), (I-1-60), (I-1-64), (I-1-66) or (I-1-69), or pharmaceutically acceptable salt thereof.

(22A)

The pharmaceutical composition according to the above (21A), which is a tablet, powder, granule, capsule, pill, film, suspension, emulsion, elixir, syrup, lemonade, spirit, aromatic water, extract, decoction or tincture.

(23A)

The pharmaceutical composition according to the above (22A), which is a sugar-coated tablet, film-coated tablet, enteric-coated tablet, sustained-release tablet, troche tablet, sublingual tablet, buccal tablet, chewable tablet, orally disintegrating tablet, dry syrup, soft capsule, micro capsule or sustained-release capsule.

(24A)

A pharmaceutical composition for parenteral administration, comprising any of a compound represented by formula (I), compounds (I-1-02), (I-1-03), (I-1-04), (I-1-06), (I-1-07), (I-1-08), (I-1-09), (I-1-10), (I-1-12), (I-1-14), (I-1-15), (I-1-17), (I-1-18), (I-1-20), (I-1-22), (I-1-23), (I-1-32), (I-1-36), (I-1-38), (I-1-39), (I-1-40), (I-1-42), (I-1-43), (I-1-45), (I-1-46), (I-1-47), (I-1-48), (I-1-54), (I-1-58), (I-1-60), (I-1-64), (I-1-66) or (I-1-69), or pharmaceutically acceptable salt thereof.

(25A)

The pharmaceutical composition according to the above (24A), for dermal, subcutaneous, intravenous, intraarterial, intramuscular, intraperitoneal, transmucosal, inhalation, transnasal, ophthalmic, inner ear or vaginal administration.

(26A)

The pharmaceutical composition according to the above (24A) or (25A), which is injection, infusion, ophthalmic drop, nose drop, ear drop, aerosol, inhalation, lotion, impregnation, liniment, mouthwash, enema, ointment, plaster, jelly, cream, patch, cataplasm, external powder or suppository.

(27A)

A pharmaceutical composition for a pediatric or geriatric patient, comprising any of a compound represented by formula (I), compounds (I-1-02), (I-1-03), (I-1-04), (I-1-06), (I-1-07), (I-1-08), (I-1-09), (I-1-10), (I-1-12), (I-1-14), (I-1-15), (I-1-17), (I-1-18), (I-1-20), (I-1-22), (I-1-23), (I-1-32), (I-1-36), (I-1-38), (I-1-39), (I-1-40), (I-1-42), (I-1-43), (I-1-45), (I-1-46), (I-1-47), (I-1-48), (I-1-54), (I-1-58), (I-1-60), (I-1-64), (I-1-66) or (I-1-69), or pharmaceutically acceptable salt thereof.

(28A)

A pharmaceutical composition consisting of a combination of a compound represented by formula (I), compounds (I-1-02), (I-1-03), (I-1-04), (I-1-06), (I-1-07), (I-1-08), (I-1-09), (I-1-10), (I-1-12), (I-1-14), (I-1-15), (I-1-17), (I-1-18), (I-1-20), (I-1-22), (I-1-23), (I-1-32), (I-1-36), (I-1-38), (I-1-39), (I-1-40), (I-1-42), (I-1-43), (I-1-45), (I-1-46), (I-1-47), (I-1-48), (I-1-54), (I-1-58), (I-1-60), (I-1-64), (I-1-66) or (I-1-69), or pharmaceutically acceptable salt thereof, and an insulin secretagogue, a fast-acting insulin secretagogue, a glucose uptake inhibitor, an insulin resistance improving drug, a thiazolidine derivative, an insulin formulation, a peptidyl peptidase IV inhibitor, a GLP-1 receptor agonist, a sodium-dependent glucose transporter 1 inhibitor, or a sodium-dependent glucose transporter 2 inhibitor.

(29A)

A pharmaceutical composition comprising a compound represented by formula (I), compounds (I-1-02), (I-1-03), (I-1-04), (I-1-06), (I-1-07), (I-1-08), (I-1-09), (I-1-10), (I-1-12), (I-1-14), (I-1-15), (I-1-17), (I-1-18), (I-1-20), (I-1-22), (I-1-23), (I-1-32), (I-1-36), (I-1-38), (I-1-39), (I-1-40), (I-1-42), (I-1-43), (I-1-45), (I-1-46), (I-1-47), (I-1-48), (I-1-54), (I-1-58), (I-1-60), (I-1-64), (I-1-66) or (I-1-69), or pharmaceutically acceptable salt thereof, for a combination therapy with an insulin secretagogue, a fast-acting insulin secretagogue, a glucose uptake inhibitor, an insulin resistance improving drug, a thiazolidine derivative, an insulin formulation, a peptidyl peptidase IV inhibitor, a GLP-1 receptor agonist, a sodium-dependent glucose transporter 1 inhibitor, or a sodium-dependent glucose transporter 2 inhibitor.

EFFECT OF THE INVENTION

The compound of the present invention has an AMPK activating effect, and thus a pharmaceutical composition comprising a compound of the present invention is very useful as a medicinal product, particularly, a medicine for treating and/or preventing type II diabetes, hyperglycemia, metabolic syndrome, obesity, hypercholesterolemia and/or hypertension. Further, the compound of the present invention is a compound which has usefulness as a medicine. The usefulness as a medicine herein comprises good metabolic stability, slight induction of a drug-metabolizing enzyme, slight inhibition of drug-metabolizing enzymes which metabolize other drugs, high oral absorption, low clearance, a sufficiently long half-life period to express the efficacy of a medicine, a high enzyme activity, a high maximal activation rate, a low protein binding rate, high penetration into target tissue, high solubility, high safety, an insulin resistance improving effect based on an energy consumption increase, the effect of decreasing hemoglobin $A_{1C}$(HbA1c), the effect of improving fatty hepatic or the like.

MODE FOR CARRYING OUT THE INVENTION

Each term used in this description will be described below. In this description, even when each term is used individually or used with other terms, the term has the same meaning.

"Halogen" includes fluorine, chlorine, bromine and iodine.

"Alkyl" means a C1 to C10 straight or branched alkyl group, and examples thereof include methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, n-decyl and the like. Preferable is C1 to C6 or C1 to C4 alkyl, and examples thereof include methyl, ethyl, n-propyl, isopropyl, n-butyl, isobutyl, sec-butyl, tert-butyl, n-pentyl, isopentyl, neopentyl, n-hexyl and isohexyl.

"Alkenyl" means C2 to C8 straight or branched alkenyl having one or more double bond(s) in the above "alkyl", and examples thereof include vinyl, 1-propenyl, 2-propenyl, 1-butenyl, 2-butenyl, 3-butenyl, 1,3-butadienyl, 3-methyl-2-butenyl and the like.

"Alkynyl" means C2 to C8 straight or branched alkynyl having one or more triple bond(s) in the above "alkyl", and examples thereof include ethynyl, propynyl, butynyl and the like. Furthermore, an "alkynyl" may have a double bond.

"Cycloalkyl" means a C3 to C15 cyclic saturated hydrocarbon group, and examples thereof include cyclopropyl, cyclobutyl, cyclopentyl, cyclohexyl, cycloheptyl, cyclooctyl, bridged cyclic hydrocarbon group, spiro hydrocarbon group and the like. Preferable examples include cyclopropyl, cyclobutyl, cyclopentyl, cyclohexyl or bridged cyclic hydrocarbon group.

A "bridged cyclic hydrocarbon group" includes a group which is derived by removing one hydrogen from a C5 to C8 aliphatic cycle which consists of two or more rings that share two or more atoms. Specific examples thereof include bicyclo[2.1.0]pentyl, bicyclo[2.2.1]heptyl, bicyclo[2.2.2]octyl, bicyclo[3.2.1]octyl, tricyclo[2.2.1.0]heptyl and the like.

A "spiro hydrocarbon group" includes a group which is derived by removing one hydrogen from a cycle which consists of two hydrocarbon rings that share one carbon atom. Specific examples thereof include spiro[3.4]octyl and the like.

"Cycloalkenyl" means C3 to C10 cyclic unsaturated aliphatic hydrocarbon group, and examples thereof include cyclopropenyl (e.g., 1-cyclopropenyl), cyclobutenyl (e.g., 1-cyclobutenyl), cyclopentenyl (e.g., 1-cyclopenten-1-yl, 2-cyclopenten-1-yl and 3-cyclopenten-1-yl), cyclohexenyl (e.g., 1-cyclohexen-1-yl, 2-cyclohexen-1-yl and 3-cyclohexen-1-yl), cycloheptenyl (e.g., 1-cycloheptenyl), cyclooctenyl (e.g., 1-cyclooctenyl) and the like. Preferable is cyclopropenyl, cyclobutenyl, cyclopentenyl or cyclohexenyl. Cycloalkenyls also include bridged cyclic hydrocarbon group and spiro hydrocarbon group which both have an unsaturated bond in the ring.

"Aryl" means a monocyclic aromatic hydrocarbon group (e.g., phenyl) and a polycyclic aromatic hydrocarbon group (e.g., 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, etc.). Preferable examples include phenyl or naphthyl (1-naphthyl or 2-naphthyl).

"Heteroaryl" means a monocyclic aromatic heterocyclic group and a fused aromatic heterocyclic group.

A "monocyclic aromatic heterocyclic group" means a group which is derived from a 5 to 8-membered aromatic ring which has one or more same or different heteroatoms optionally selected from oxygen, sulfur and nitrogen atoms in the ring, which group may have a bond to a substituent at any substitutable position.

A "fused aromatic heterocyclic group" means a group in which a 5 to 8-membered aromatic ring which has one or more same or different heteroatoms optionally selected from oxygen, sulfur and nitrogen atoms in the ring is fused with one to four 5 to 8-membered aromatic carbocyclic rings or another 5 to 8-membered aromatic hetero ring, which group may have a bond to a substituent at any substitutable position.

Examples of a "heteroaryl" include furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl and 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,4-triazol-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazol-2-yl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl (e.g., 1-benzimidazolyl, 2-benzimidazolyl, 4-benzimidazolyl, 5-benzimidazolyl), dibenzofuryl, benzoxazolyl, benzothiazolyl, quinoxalinyl (e.g., 2-quinoxalinyl, 5-quinoxalinyl, 6-quinoxalinyl), cinnolinyl (e.g., 3-cinnolinyl, 4-cinnolinyl, 5-cinnolinyl, 6-cinnolinyl, 7-cinnolinyl, 8-cinnolinyl), quinazolinyl (e.g., 2-quinazolinyl, 4-quinazolinyl, 5-quinazolinyl, 6-quinazolinyl, 7-quinazolinyl, 8-quinazolinyl), quinolyl (e.g., 2-quinolyl, 3-quinolyl, 4-quinolyl, 5-quinolyl, 6-quinolyl, 7-quinolyl, 8-quinolyl), phthalazinyl (e.g., 1-phthalazinyl, 5-phthalazinyl, 6-phthalazinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), puryl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenazinyl (e.g., 1-phenazinyl, 2-phenazinyl), phenothiazinyl (e.g., 1-phenothiazinyl, 2-phenothiazinyl, 3-phenothiazinyl, 4-phenothiazinyl) and the like.

"Heterocyclyl" means a non-aromatic heterocyclic group, which may have a bond to a substituent at any substitutable position of a ring which has at least one or more nitrogen, oxygen or sulfur atoms in the ring, or a ring in which such ring is fused with a cycloalkane (preferably 5 to 6-membered), a benzene ring and/or a ring which has at least one or more nitrogen, oxygen or sulfur atoms in the ring. A "non-aromatic heterocyclic group" can be saturated or unsaturated as long as it is non-aromatic. Preferable is a 5- to 8-membered ring. Examples thereof include 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidinyl, 3-piperidinyl, 4-piperidinyl, 1-piperazinyl, 2-piperazinyl, 2-morpholinyl, 3-morpholinyl, morpholino, tetrahydropyranyl, tetrahydrofuranyl, 1,2,3,4-tetrahydroisoquinolinyl, 1,2,3,4-tetrahydroquinolinyl, 1,3-dihydro-2H-isoindol-5-yl, the following group and the like.

[Chemical formula 20]

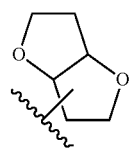

Further, examples of a "heterocyclyl" group also include a bridged group or a spiro ring forming group shown below.

[Chemical formula 21]

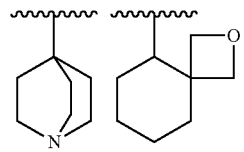

"Acyl" means formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heteroarylcarbonyl or substituted or unsubstituted heterocyclylcarbonyl. The "alkyl" part of "alkylcarbonyl", the "alkenyl" part of "alkenylcarbonyl", the "cycloalkyl" part of "cycloalkylcarbonyl", the "cycloalkenyl" part of "cycloalkenylcarbonyl", the "aryl" part of "arylcarbonyl", the "heteroaryl" part of "heteroarylcarbonyl" and the "heterocyclyl" part of "heterocyclylcarbonyl" mean the above "alkyl", the above "alkenyl", the above "cycloalkyl", the above "cycloalkenyl", the above "aryl", the above "heteroaryl" and the above "heterocyclyl", respectively.

The alkyl parts of "alkylthio", "alkylsulfinyl", "alkylsulfonyl", "alkyloxycarbonyl" and "alkyloxy" mean the above "alkyl".

The aryl parts of "aryloxy", "arylthio" and "arylsulfonyl" mean the above "aryl". The heteroaryl parts of "heteroaryloxy", "heteroarylthio" and "heteroarylsulfonyl" mean the above "heteroaryl".

The cycloalkyl parts of "cycloalkyloxy", "cycloalkylthio" and "cycloalkylsulfonyl" mean the above "cycloalkyl".

The cycloalkenyl parts of "cycloalkenyloxy", "cycloalkenylthio" and "cycloalkenylsulfonyl" mean the above "cycloalkenyl".

The heterocyclyl parts of "heterocyclyloxy", "heterocyclylthio" and "heterocyclylsulfonyl" mean the above "heterocyclyl".

Substituted aryl, substituted heteroaryl, substituted cycloalkyl, substituted cycloalkenyl or substituted heterocyclyl of ring A means aryl substituted with Y, substituted heteroaryl substituted with Y, substituted cycloalkyl substituted with Y, substituted cycloalkenyl substituted with Y, or substituted heterocyclyl substituted with Y, respectively. Ring A may have a substituent described below, other than Y.

Examples of substituents of a "substituted alkyl", "substituted alkenyl", "substituted alkynyl", "substituted aryl", "substituted heteroaryl", "substituted cycloalkyl", "substituted cycloalkenyl", "substituted heterocyclyl", "substituted acyl", "substituted carbamoyl", "substituted alkylthio", "substituted alkylsulfinyl", "substituted alkylsulfonyl", "substituted alkyloxycarbonyl", "substituted alkyloxy", "substituted aryloxy", "substituted heteroaryloxy", "substituted cycloalkyloxy", "substituted cycloalkenyloxy", "substituted heterocyclyloxy", "substituted arylthio", "substituted heteroarylthio", "substituted cycloalkylthio", "substituted cycloalkenylthio", "substituted heterocyclylthio", "substituted arylsulfonyl", "substituted heteroarylsulfonyl", "substituted cycloalkylsulfonyl", "substituted cycloalkenylsulfonyl", "substituted heterocyclylsulfonyl", "substituted sulfamoyl", "substituted amino", "a ring formed by $R^S$ and $R^{S'}$ which are bound to the same sulfur atom, together with the sulfur atom", or "a ring formed by $R^N$ together with the adjacent nitrogen atom when Y is $S=N—$, $R^S(R^NR^{N'}N)(O=)S=N—R^{2f}$, $(R^{N''})N=S(=O)(NR^NR^{N'})—$, $(R^{N''})N=S(=O)(NR^NR^{N'})—R^{2f}—$, $R^{P1}R^{P2}(O=)P—$

[Chemical formula 23]

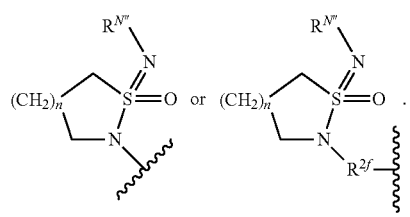

e.g., cyclopropyl, cyclobutyl.);

substituted or unsubstituted cycloalkenyl (when substituted, substituents include halogen, hydroxy, carboxy, nitro, cyano, alkyl, alkenyl, alkynyl, aryl, cycloalkyl, cycloalkenyl, heteroaryl, heterocyclyl, substituted or unsubstituted carbamoyl (when substituted, substituents include $R^SR^{S'}(O=)S=$), sulfamoyl, amino, acylamino, alkylsulfonylamino, alkyloxycarbonylamino, substituted or unsubstituted amino, $R^SR^{S'}(O=)S=N—$, $R^SR^{S'}(O=)S=N—R^{2f}—$, $R^SR^{S'}(O=)S=N—C(=O)—$, $(R^N)N=S(=O)(R^S)—$, $(R^N)N=S(=O)(R^S)—R^{2f}—$, $R^SR^{S'}(R^{N'}—N=)S=N—$, $((R^N)N=)_2S(R^S)—$, $(R^NR^{N'})N—C(=O)—O—$, $R^OO—C(=O)—N(R^N)—$, $R^OO—C(=O)—O—$, $R^S(R^NR^{N'}N)(O=)S=N—$, $R^S(R^NR^{N'}N)(O=)S=N—R^{2f}—$, $(R^{N''})N=S(=O)(NR^NR^{N'})—$, $(R^{N''})N=S(=O)(NR^NR^{N'})—R^{2f}—$, $R^{P1}R^{P2}(O=)P—$

[Chemical formula 24]

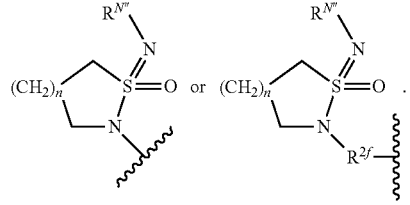

e.g., cyclopropenyl);

substituted or unsubstituted heteroaryl (when substituted, substituents include halogen, hydroxy, carboxy, nitro, cyano, substituted or unsubstituted alkyl (when substituted, substituents include hydroxy.), alkenyl, alkynyl, aryl, cycloalkyl, cycloalkenyl, heteroaryl, heterocyclyl, carbamoyl, sulfamoyl, substituted or unsubstituted amino (when substituted, substituents include alkyl, acyl, alkylsulfonyl, alkylaminosulfonyl, and alkyloxycarbonyl.), alkylsulfonyl, substituted or unsubstituted amino, $R^SR^{S'}(O=)S=N—$, $R^SR^{S'}(O=)S=N—R^{2f}—$, $R^SR^{S'}(O=)S=N—C(=O)—$, $(R^N)N=S(=O)(R^S)—$, $(R^N)N=S(=O)(R^S)—R^{2f}—$, $R^SR^{S'}(R^{N'}—N=)S=N—$, $((R^N)N=)_2S(R^S)—$, $(R^NR^{N'})N—C(=O)—O—$, $R^OO—C(=O)—N(R^N)—$, $R^OO—C(=O)—O—$, $R^S(R^NR^{N'}N)(O=)S=N—$, $R^S(R^NR^{N'}N)(O=)S=N—R^{2f}—$, $(R^{N''})N=S(=O)(NR^NR^{N'})—$, $(R^{N''})N=S(=O)(NR^NR^{N'})—R^{2f}—$, $R^{P1}R^{P2}(O=)P—$ ((R^N)N=)_2S(R^S)—" include groups selected from the group consisting of halogen; hydroxy; carboxy; nitro; cyano; substituted or unsubstituted alkyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino. e.g., methyl, ethyl, isopropyl, tert-butyl, $CF_3$);

substituted or unsubstituted alkenyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino, and substituted or unsubstituted acylamino (when substituted, substituents include hydroxy.). e.g., vinyl);

substituted or unsubstituted alkynyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino. e.g., ethynyl); substituted or unsubstituted aryl (when substituted, substituents include halogen, hydroxy, carboxy, nitro, cyano, alkyl, alkenyl, alkynyl, aryl, cycloalkyl, cycloalkenyl, substituted or unsubstituted heteroaryl (when substituted, substituents include hydroxyalkyl), heterocyclyl, substituted or unsubstituted carbamoyl (when substituted, substituents include $R^SR^{S'}(O=)S=$), sulfamoyl, substituted or unsubstituted amino (when substituted, substituents include alkyloxycarbonyl and carbamoyl.), substituted or unsubstituted alkyloxy (when substituted, substituents include dialkylamino.), alkylsulfonyl, alkylaminosulfonyl, substituted or unsubstituted amino, $R^SR^{S'}(O=)S=N—$, $R^SR^{S'}(O=)S=N—R^{2f}—$, $R^SR^{S'}(O=)S=N—C(=O)—$, $(R^N)N=S(=O)(R^S)—$, $(R^N)N=S(=O)(R^S)—R^{2f}—$, $R^SR^{S'}(R^{N'}—N=)S=N—$, $((R^N)N=)_2S(R^S)—$, $(R^NR^{N'})N—C(=O)—O—$, $R^OO—C(=O)—N(R^N)—$, $R^OO—C(=O)—O—$, $R^S(R^NR^{N'}N)(O=)S=N—$, $R^S(R^NR^{N'}N)(O=)S=N—R^{2f}—$, $(R^{N''})N=S(=O)(NR^NR^{N'})—$, $(R^{N''})N=S(=O)(NR^NR^{N'})—R^{2f}—$, $R^{P1}R^{P2}(O=)P—$

[Chemical formula 22]

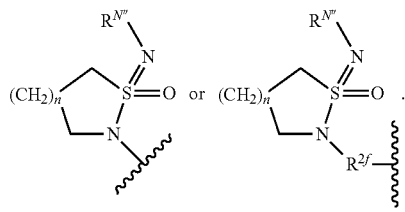

e.g., phenyl, naphthyl);

substituted or unsubstituted cycloalkyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino, acyl, substituted or unsubstituted amino, $R^SR^{S'}(O=)S=N—$, $R^SR^{S'}(O=)S=N—R^{2f}—$, $R^SR^{S'}(O=)S=N—C(=O)—$, $(R^N)N=S(=O)(R^S)—$, $(R^N)N=S(=O)(R^S)—R^{2f}—$, $R^SR^{S'}(R^{N'}—N=)S=N—$, $((R^N)N=)_2S(R^S)—$, $(R^NR^{N'})N—C(=O)—O—$, $R^OO—C(=O)—O—$, $R^S(R^NR^{N'}N)(O=)$

[Chemical formula 25]

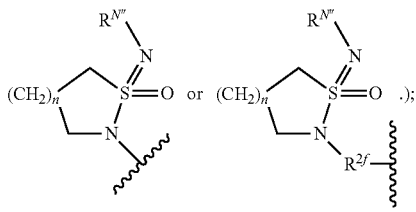

substituted or unsubstituted heterocyclyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino, substituted or unsubstituted acyl (when substituted, substituents include hydroxy.), aryloxy, alkylsulfonyl, alkyloxycarbonylamino, oxo, substituted or unsubstituted amino, $R^SR^{S'}(O=)S=N-$, $R^SR^{S'}(O=)S=N-R^{2f}-$, $R^SR^{S'}(O=)S=N-C(=O)-$, $(R^N)N=S(=O)(R^S)-$, $(R^N)N=S(=O)(R^S)-R^{2f}-$, $R^SR^{S'}(R^{N'}-N=)S=N-$, $((R^N)N=)_2S(R^S)-$, $(R^NR^{N'})N-C(=O)-O-$, $R^OO-C(=O)-N(R^N)-$, $R^OO-C(=O)-O-$, $R^S(R^NR^{N'}N)(O=)S=N-$, $R^S(R^N R^{N'}N)(O=)S=N-R^{2f}-$, $(R^{N''}\,N=S(=O)(NR^NR^{N'})-$, $(R^{N''})N=S(=O)(NR^NR^{N'})-R^{2f}-$, $R^{P1}R^{P2}\,(O=)P-$

[Chemical formula 26]

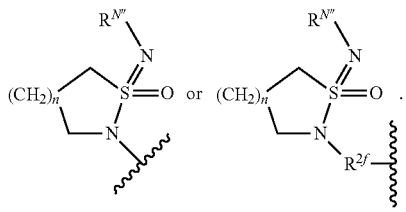

e.g., morpholinyl, piperidyl, pyrrolidinyl);

substituted or unsubstituted alkyloxy (when substituted, substituents include halogen, hydroxy, carboxy, nitro, cyano, alkyl, alkenyl, alkynyl, aryl, cycloalkyl, cycloalkenyl, substituted or unsubstituted heteroaryl (example of a substituent include alkyl.), substituted or unsubstituted heterocyclyl (when substituted, substituents include alkyl.), carbamoyl, sulfamoyl, substituted or unsubstituted amino (when substituted, substituents include substituted or unsubstituted acyl (when substituted, substituents include hydroxy.), alkyloxy, alkylsulfonyl, substituted or unsubstituted amino, $R^SR^{S'}(O=)S=N-$, $R^SR^{S'}(O=)S=N-R^{2f}-$, $R^SR^{S'}(O=)S=N-C(=O)-$, $(R^N)N=S(=O)(R^S)-$, $(R^N)N=S(=O)(R^S)-R^{2f}-$, $R^SR^{S'}(R^{N'}-N=)S=N-$, $((R^N)N=)_2S(R^S)-$, $(R^NR^{N'})N-C(=O)-O-$, $R^OO-C(=O)-N(R^N)-$, $R^OO-C(=O)-O-$, $R^S(R^NR^{N'}N)(O=)S=N-$, $R^S(R^NR^{N'}N)(O=)S=N-R^{2f}-$, $(R^{N''})N=S(=O)(NR^NR^{N'})-$, $(R^{N''})N=S(=O)(NR^NR^{N'})-R^{2f}-$, $R^{P1}R^{P2}\,(O=)P-$

[Chemical formula 27]

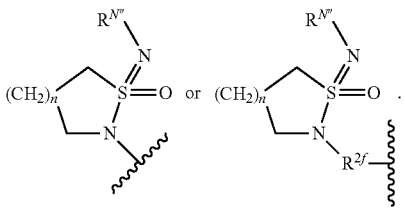

e.g., methoxy, ethoxy);

substituted or unsubstituted alkenyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino. e.g., vinyloxy, aryloxy);

substituted or unsubstituted aryloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino. e.g., phenyloxy);

substituted or unsubstituted cycloalkyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted cycloalkenyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted heteroaryloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.); substituted or unsubstituted heterocyclyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted arylalkyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino. e.g., benzyl);

substituted or unsubstituted amino (e.g., alkylamino (e.g., methylamino, ethylamino, dimethylamino), arylamino, cycloalkylamino, cycloalkenylamino, heteroarylamino, heterocyclylamino, acylamino (e.g., acetylamino, benzoylamino), arylalkylamino (e.g., benzylamino, tritylamino), hydroxyamino, substituted or unsubstituted alkyloxycarbonylamino (when substituted, substituents include halogen.), carbamoylamino, alkylsulfonylamino, arylsulfonylamino, cycloalkylsulfonylamino, cycloalkenylsulfonylamino, heteroarylsulfonylamino, heterocyclylsulfonylamino, alkylcarbamoylamino, substituted or unsubstituted alkylcarbonylamino (when substituted, substituents include halogen.);

substituted or unsubstituted carbamoyl (when substituted, substituents include halogen, hydroxy, carboxy, nitro, cyano, alkyl, alkenyl, alkynyl, aryl, cycloalkyl, cycloalkenyl, heteroaryl, heterocyclyl. e.g., alkylcarbamoyl (e.g., methylcarbamoyl, ethylcarbamoyl, dimethylcarbamoyl, phenylethylcarbamoyl, dimethylaminoethylcarbamoyl, isopropylcarbamoyl, hydroxyethylcarbamoyl), alkylsulfonylcarbamoyl, heteroarylalkylcarbamoyl, alkyloxycarbamoyl.);

substituted or unsubstituted carbamoyloxy (when substituted, substituents include halogen, hydroxy, carboxy, nitro, cyano, alkyl, alkenyl, alkynyl, aryl, cycloalkyl, cycloalkenyl, heteroaryl, heterocyclyl.);

substituted or unsubstituted acyl (when substituted, substituents include halogen, hydroxy, carboxy, nitro, cyano, alkyl, alkyloxy, alkenyl, alkynyl, aryl, cycloalkyl, cycloalkenyl, heteroaryl, heterocyclyl, carbamoyl, sulfamoyl, amino. e.g., alkylcarbonyl, arylcarbonyl, cycloalkylcarbonyl, cycloalkenylcarbonyl, heteroarylcarbonyl, heterocyclylcarbonyl, formyl, acetyl.);

substituted or unsubstituted alkylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino. e.g., methanesulfonyl, ethanesulfonyl);

substituted or unsubstituted arylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted cycloalkylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.); substituted or unsubstituted cycloalkenylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted heteroarylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted heterocyclylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted alkylthio (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted arylthio (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted cycloalkylthio (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted cycloalkenylthio (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted heteroarylthio (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted heterocyclylthio (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted sulfamoyl (when substituted, substituents include halogen, hydroxy, carboxy, nitro, cyano, alkyl, alkenyl, alkynyl, aryl, cycloalkyl, cycloalkenyl, heteroaryl, heterocyclyl, alkylamino.);

substituted or unsubstituted alkyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino. e.g., methoxycarbonyl, ethoxycarbonyl, tert-butoxycarbonyl);

substituted or unsubstituted aryloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted cycloalkyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted cycloalkenyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted heteroaryloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted heterocyclyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted alkylsulfinyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted arylsulfinyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted cycloalkylsulfinyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted cycloalkenylsulfinyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted heteroarylsulfinyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted heterocyclylsulfinyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.); nitroso;

azido;

isocyano; isocyanato; thiocyanato; isothiocyanato; mercapto;

formyloxy; haloformyl; oxalo; thioformyl; thiocarboxy; dithiocarboxy; thiocarbamoyl; sulfino; sulfo; sulfoamino; hydrazino; ureido; amidino; guanidino; phthalimido; oxo, $R^SR^{S'}(O=)S=N—$, $R^SR^{S'}(O=)S=N—R^{2f}—$, $R^SR^{S'}(O=)S=N—C(=O)—$, $(R^N)N=S(=O)(R^S)—$, $(R^N)N=S(=O)(R^S)—R^{2f}$-, $R^SR^{S'}(R^{N'}—N=)S=N—$, $((R^N)N=)_2S(R^S)—$, $(R^NR^{N'})N—C(=O)—O—$, $R^OO—C(=O)—N(R^N)—$, $R^OO—C(=O)—O—$, $R^S(R^{N'}R^{N'}N)(O=)S=N—$, $R^S(R^{N'}R^{N'}N)(O=)S=N—R^{2f}—$, $(R^{N''})N=S(=O)(NRNR^{N'})—$, $(R^{N''})N=S(=O)(NR^NR^{N'})—R^{2f}—$, $R^{P1}R^{P2}(O=)P—$

[Chemical formula 28]

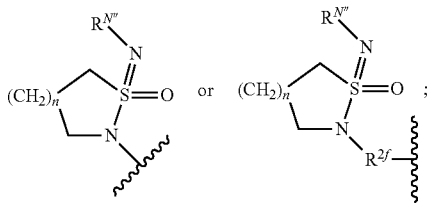

and the like. The above-described substituted groups may have one to four of these substituents.

Preferred examples of substituents of a "substituted carbamoyl", "substituted sulfamoyl" or "substituted amino" include substituted or unsubstituted alkyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino, alkyloxy. e.g., methyl, ethyl, isopropyl, tert-butyl, $CF_3$);

substituted or unsubstituted alkenyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino. e.g., vinyl);

substituted or unsubstituted aryl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino. e.g., phenyl, naphthyl);

substituted or unsubstituted cycloalkyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino. e.g., cyclopropyl, cyclobutyl);

substituted or unsubstituted cycloalkenyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino. e.g., cyclopropenyl);

substituted or unsubstituted heteroaryl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted heterocyclyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted arylalkyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted alkyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino. e.g., methoxy, ethoxy);

substituted or unsubstituted aryloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino. e.g., phenyloxy);

substituted or unsubstituted cycloalkyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted cycloalkenyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted heteroaryloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted heterocyclyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted acyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted alkyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino. e.g., methoxycarbonyl, ethoxycarbonyl, tert-butoxycarbonyl);

substituted or unsubstituted aryloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted cycloalkyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted cycloalkenyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);

substituted or unsubstituted heteroaryloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);
substituted or unsubstituted heterocyclyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);
substituted or unsubstituted sulfamoyl (when substituted, substituents include halogen, hydroxy, carboxy, nitro, cyano, alkyl, alkenyl, alkynyl, aryl, cycloalkyl, cycloalkenyl, heteroaryl, heterocyclyl.);
substituted or unsubstituted alkylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino. e.g., methanesulfonyl, ethanesulfonyl);
substituted or unsubstituted arylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);
substituted or unsubstituted heteroarylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);
substituted or unsubstituted cycloalkylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);
substituted or unsubstituted cycloalkenylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);
substituted or unsubstituted heterocyclylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino.);
substituted or unsubstituted carbamoyl (when substituted, substituents include halogen, hydroxy, carboxy, nitro, cyano, alkyl, alkenyl, alkynyl, aryl, cycloalkyl, cycloalkenyl, heteroaryl, heterocyclyl.);
halogen, hydroxy, carboxy, nitro, cyano, alkylsulfinyl, cycloalkylsulfinyl, cycloalkenylsulfinyl, arylsulfinyl, heteroarylsulfinyl, heterocyclylsulfinyl, amino, substituted or unsubstituted amino, $R^SR^{S'}(O=)S=N-$, $R^SR^{S'}(O=)S=N-R^{2f}$, $R^SR^{S'}(O=)S=N-C(=O)-$, $(R^N)N=S(=O)(R^S)-$, $(R^N)N=S(=O)(R^S)-R^{2f}-$, $R^SR^{S'}$ $(R^{N'}=N=)S=N-$, $((R^N)N=)_2S(R^S)-$, $(R^NR^{N'})N-C(=O)-O-$, $R^OO-C(=O)-N(R^N)-$, $R^OO-C(=O)-O-$, $R^S(R^NR^{N'}N)(O=)S=N-$, $R^S(R^NR^{N'}N)(O=)S=N-R^{2f}-$, $(R^{N'})N=S(=O)(NR^NR^{N'})-$, $R^{P1}R^{P2}$ $(O=)P-$ $(R^{N'})N=S(=O)(NR^NR^{N'})-R^{2f}-$,

[Chemical formula 29]

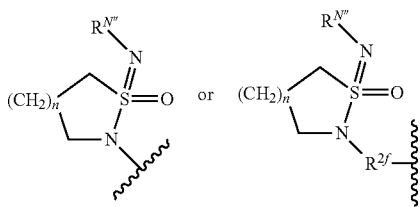

and the like.

The alkyl parts of "alkylamino", "arylalkylamino", "alkyloxycarbonylamino", "alkylsulfonylamino", "alkylcarbamoyl", "alkylsulfonylcarbamoyl", "heteroarylalkylcarbamoyl", "alkyloxycarbamoyl", "arylalkyl", "dialkylamino" and "hydroxyalkyl" mean the above-described "alkyl".

The alkenyl part of "alkenyloxy" means the above-described "alkenyl".

The aryl parts of "arylalkyl", "arylamino", "arylalkylamino", "arylsulfonylamino", "aryloxycarbonyl" and "arylsulfinyl" mean the above-described "aryl".

The heteroaryl parts of "heteroarylamino", "heteroarylsulfonylamino", "heteroarylalkylcarbamoyl", "heteroaryloxycarbonyl" and "heteroarylsulfinyl" mean the above-described "heteroaryl".

The cycloalkyl parts of "cycloalkylamino", "cycloalkylsulfonylamino", "cycloalkyloxycarbonyl" and "cycloalkylsulfinyl" mean the above-described "cycloalkyl".

The cycloalkenyl parts of "cycloalkenylamino", "cycloalkenylsulfonylamino", "cycloalkenyloxycarbonyl" and "cycloalkenylsulfinyl" mean the above-described "cycloalkenyl".

The heterocyclyl parts of "heterocyclylamino", "heterocyclylsulfonylamino", "heterocyclyloxycarbonyl" and "heterocyclylsulfinyl" mean the above-described "heterocyclyl".

Among the compounds of the present invention, the compounds in the following embodiments are preferred.

X is substituted or unsubstituted monocyclic heterocyclyl,

[Chemical formula 30]

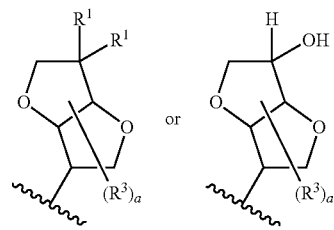

wherein $R^1$ and $R^2$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino; $R^3$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino; and a is an integer from 0 to 7.

Examples include the following groups.

[Chemical formula 31]

$R^{10}$ and $R^{11}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

Preferably, $R^{10}$ and $R^{11}$ are each independently hydrogen, halogen, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, or substituted or unsubstituted carbamoyl.

More preferably, either one of $R^{10}$ and $R^{11}$ is hydrogen, halogen or carboxy; the other of $R^{10}$ and $R^{11}$ is substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, or substituted or unsubstituted carbamoyl.

$R^{12}$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino, b is an integer of 0 to 5, c is an integer of 0 to 7, and d is an integer of 0 to 9.

Preferably, $R^{12}$ is each independently halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino, b is an integer of 0 to 3, c is an integer of 0 to 3, and d is an integer of 0 to 4.

$R^1$ and $R^2$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

Preferably, $R^1$ and $R^2$ are each independently hydrogen, halogen, hydroxy, cyano, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

$R^3$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino, and a is an integer of 0 to 7.

Preferably, $R^3$ is each independently halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino, and a is an integer of 0 to 3.

$R^4$ is hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

Preferably, $R^4$ is hydrogen, halogen, hydroxy, cyano, substituted or unsubstituted alkyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

Further preferably, $R^4$ is hydrogen, halogen, hydroxy, cyano or substituted alkyl, and the substituent of the substituted alkyl is halogen.

More preferably, $R^4$ is hydrogen or halogen.

$R^5$ is hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

Preferably, $R^5$ is hydrogen, halogen, hydroxy, cyano, substituted or unsubstituted alkyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

Further preferably, $R^5$ is hydrogen, halogen, hydroxy, cyano or substituted alkyl, and the substituent of the substituted alkyl is halogen.

More preferably, $R^5$ is hydrogen or halogen.

$R^6$ is hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

Preferably, $R^6$ is hydrogen, halogen, hydroxy, cyano, substituted or unsubstituted alkyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

Further preferably, $R^6$ is hydrogen, halogen, hydroxy, cyano or substituted alkyl, and the substituent of the substituted alkyl is halogen.

More preferably, $R^6$ is hydrogen or halogen.

$R^7$ is hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

Preferably, $R^7$ is hydrogen, halogen, hydroxy, cyano, substituted or unsubstituted alkyl, substituted or unsubstituted alkyloxy, substituted or unsubstituted alkylthio, substituted or unsubstituted alkylsulfonyl, sub stituted or unsubstituted acyl, substituted or unsubstituted carbamoyl, substituted or unsubstituted sulfamoyl, or substituted or unsubstituted amino.

Further preferably, $R^7$ is hydrogen, halogen, hydroxy, cyano or substituted alkyl, and the substituent of the substituted alkyl is halogen.

More preferably, $R^7$ is hydrogen or halogen.

$R^8$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

Preferably, $R^8$ is halogen, cyano, carboxy, substituted or unsubstituted alkyl, substituted or unsubstituted alkylsulfonyl, or substituted or unsubstituted carbamoyl.

Further preferably, $R^8$ is halogen, cyano or substituted alkyl, and the substituent of the substituted alkyl is halogen.

$R^9$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

Preferably, $R^9$ is hydrogen, halogen, hydroxy, cyano, or substituted or unsubstituted alkyl.

Further preferably, $R^9$ is hydrogen or halogen.

Ring A is substituted aryl, substituted heteroaryl, substituted cycloalkyl, substituted cycloalkenyl, or substituted heterocyclyl.

Preferably, ring A is substituted aryl, substituted heteroaryl, substituted cycloalkenyl, or substituted heterocyclyl.

Further preferably, ring A is substituted aryl, substituted cycloalkenyl, or substituted heterocyclyl.

More preferably, ring A is substituted aryl.

Y is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted alkyloxycarbonyl, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted alkylsulfinyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted carbamoyloxy, substituted or unsubstituted sulfamoyl, substituted or unsubstituted amino, $R^{Y1}$—O—, $(R^{Y2}R^{Y3})N$—, $R^S R^{S'}$ (O=)S=N—, $R^S R^{S'}(O=)S=N$—$R^{2f}$—$R^S R^{S'}(O=)S=N$—C(=O)—, $(R^N)N=S(=O)(R^S)$—, $(R^{N'})N=S(=O)(R^S)$—$R^{2f}$—, $R^S R^{S'}$ $(R^{N'}$—N=) S=N—, $((R^N)N=)_2 S(R^S)$—, $(R^N R^{N'})N$—C(=O)—O—, $R^O O$—C(=O)—N$(R^N)$—, $R^O O$—C(=O)—O—, $R^S (R^{N'} R^{N'}N)(O=)S=N$—, $R^S (R^N R^{N'}N)(O=)S=N$—$R^{2f}$—, $(R^{N'})N=S(=O)(NR^N R^{N'})$—, $(R^{N''})N=S(=O)(NR^N R^{N'})$—$R^{2f}$—, $R^{P1} R^{P2}$ (O=)P—

[Chemical formula 32]

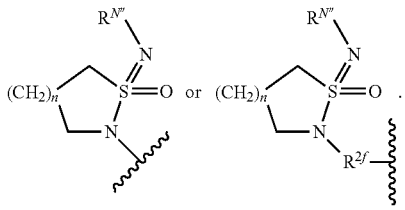

Preferably, Y is halogen, hydroxy, cyano, substituted or unsubstituted alkyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted alkyloxycarbonyl, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted alkylsulfinyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted carbamoyloxy, substituted or unsubstituted sulfamoyl, substituted or unsubstituted amino, $R^{Y1}$—O—, $(R^{Y2}R^{Y3})N$—, $R^S R^{S'}(O=)S=N$—, $R^S R^{S'}(O=)S=N-R^{2f}-R^S R^{S'}(O=)S=N-C(=O)$—, $(R^N)N=S(=O)(R^S)$—, $(R^N)N=S(=O)(R^S)-R^{2f}$—, $R^S R^{S'}(R^{N'}-N=)S=N$—, $((R^N)N=)_2 S(R^S)$—, $(R^N R^{N'})N-C(=O)-O$—, $R^O O-C(=O)-N(R^N)$—, $R^O O-C(=O)-O$—, $R^S(R^N R^{N'}N)(O=)S=N$—, $R^S(R^{N'}R^{N'}N)(O=)S=N-R^{2f}$—, $(R^{N''})N=S(=O)(NR^N R^{N'})$—, or $(R^{N''})N=S(=O)(NR^N R^{N'})-R^{2f}$, or $R^{P1} R^{P2}(O=)P$—.

Further preferably, Y is substituted or unsubstituted alkyloxy, substituted or unsubstituted alkyloxycarbonyl, substituted or unsubstituted alkylsulfinyl, substituted or unsubstituted acyl, substituted or unsubstituted carbamoyloxy, substituted or unsubstituted amino, $R^{Y1}$—O—, $(R^{Y2}R^{Y3})N$—, $R^S R^{S'}(O=)S=N$—, $(R^N)N=S(=O)(R^S)$—, or $R^O O-C(=O)-N(R^N)$—.

$R^{Y1}$ is substituted or unsubstituted alkyl, substituted or unsubstituted alkenyl, substituted or unsubstituted alkynyl, substituted or unsubstituted acyl, substituted or unsubstituted aryl, substituted or unsubstituted heteroaryl, substituted or unsubstituted cycloalkyl, substituted or unsubstituted cycloalkenyl, substituted or unsubstituted heterocyclyl, $(R^N R^{N'})N-C(=O)$—, or $R^O O-C(=O)$—.

Preferably, $R^{Y1}$ is substituted or unsubstituted alkyl, substituted or unsubstituted acyl, substituted or unsubstituted heteroaryl, substituted or unsubstituted heterocyclyl, or $(R^N R^{N'})N-C(=O)$—.

$R^{Y2}$ and $R^{Y3}$ are each independently hydrogen, substituted or unsubstituted alkyl, substituted or unsubstituted alkenyl, substituted or unsubstituted alkynyl, substituted or unsubstituted acyl, substituted or unsubstituted aryl, substituted or unsubstituted heteroaryl, substituted or unsubstituted cycloalkyl, substituted or unsubstituted cycloalkenyl, substituted or unsubstituted heterocyclyl, $(R^N R^{N'})N-C(=O)$—, or $R^O O-C(=O)$—.

Preferably, $R^{Y2}$ and $R^{Y3}$ are each independently substituted or unsubstituted alkyl, substituted or unsubstituted acyl, substituted or unsubstituted heterocyclyl, or $R^O O-C(=O)$—.

$R^S$ and $R^{S'}$ are each independently substituted or unsubstituted alkyl, substituted or unsubstituted cycloalkyl, substituted or unsubstituted heterocyclyl, substituted or unsubstituted aryl, substituted or unsubstituted heteroaryl, or substituted or unsubstituted amino. $R^S$ and $R^{S'}$ bound to the same sulfur atom may form a substituted or unsubstituted ring together with the sulfur atom.

Preferably, $R^S$ and $R^{S'}$ are each independently substituted or unsubstituted alkyl or substituted or unsubstituted amino.

The ring, which is formed by $R^S$ and $R^{S'}$ which are bound to the same sulfur atom, together with the sulfur atom, means a 3 to 15-membered saturated or unsaturated hetero ring that may contain one to four oxygen, nitrogen and/or sulfur atom(s) in the ring, other than the sulfur atom. Preferred is a non-aromatic ring, and such non-aromatic ring may be further cross-linked by a C1 to C4 alkyl chain, and may be fused with cycloalkane (preferably 5 to 6-membered) and a benzene ring. Examples thereof include as follows.

[Chemical formula 33]

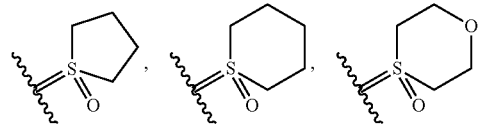

$R^{2f}$ is substituted or unsubstituted alkylene.

$R^N$ is each independently hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl, or substituted or unsubstituted carbamoyl.

$R^N$ together with the adjacent nitrogen atom may form a substituted or unsubstituted ring when Y is $((R^N)N=)_2 S(R^S)$—.

Preferably, $R^N$ is hydrogen, substituted or unsubstituted alkyl, or substituted or unsubstituted carbamoyl.

Examples of the ring formed by $R^N$ together with the adjacent nitrogen atom when Y is $((R^N)N=)_2 S(R^S)$— include as follows.

[Chemical formula 34]

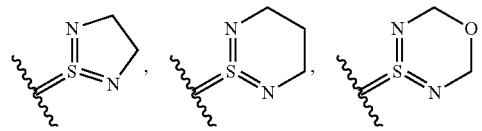

$R^{N'}$ is hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl, or substituted or unsubstituted carbamoyl.

Preferably, $R^{N'}$ is hydrogen, cyano, substituted or unsubstituted alkyl, substituted or unsubstituted cycloalkyl, substituted or unsubstituted aryl, or substituted or unsubstituted heteroaryl.

$R^N$ and $R^{N'}$ bound to the same nitrogen atom may form a substituted or unsubstituted ring together with the nitrogen atom.

$R^{N''}$ is hydrogen, cyano, substituted or unsubstituted alkyl, substituted or unsubstituted alkenyl, substituted or unsubstituted alkynyl, substituted or unsubstituted alkylcarbonyl, substituted or unsubstituted alkyloxycarbonyl, substituted or unsubstituted alkylcarbamoyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heterocyclyl, substituted or unsubstituted acyl, substituted or unsubstituted aryloxycarbonyl, substituted or unsubstituted arylsulfonyl, substituted or unsubstituted alkylsulfonyl, or substituted or unsubstituted carbamoyl.

$R^O$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

$R^{P1}$ and $R^{P2}$ is each independently hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

Preferably, $R^{P1}$ and $R^{P2}$ is each independently substituted or unsubstituted alkyl.

Preferred embodiments of a compound represented by formula (I) include the following 1) to 4):

1) a compound wherein X is substituted or unsubstituted monocyclic heterocyclyl, ring A is substituted aryl, $R^8$ is halogen, and $R^9$ is hydrogen;

2) a compound wherein X is substituted or unsubstituted monocyclic heterocyclyl, ring A is substituted aryl, Y is substituted or unsubstituted alkyloxy, substituted or unsubstituted alkyloxycarbonyl, substituted or unsubstituted alkylsulfinyl, substituted or unsubstituted acyl, substituted or unsubstituted carbamoyloxy, substituted or unsubstituted amino, $R^SR^{S'}(O=)S=N-$, $R^SR^{S'}(O=)S=N-R^{2f}-$, $R^SR^{S'}(O=)S=N-C(=O)-$, $(R^N)N=S(=O)(R^S)-$, $(R^N)N=S(=O)(R^S)-R^{2f}-$, $R^SR^{S'}(R^{N'}-N=)S=N-$, $((R^N)N=)_2S(R^S)-$, $(R^NR^{N'})N-C(=O)-O-$, $R^OO-C(=O)-N(R^N)-$, $R^OO-C(=O)-O-$, $R^S(R^NR^{N'}N)(O=)S=N-$, $R^S(R^{N'}R^{N'}N)(O=)S=N-R^{2f}-$, $(R^{N''})N=S(=O)(NR^NR^{N'})-$, $(R^{N''})N=S(=O)(NR^NR^{N'})-R^{2f}-$, or $R^{P1}R^{P2}(O=)P-$, $R^8$ is halogen, and $R^9$ is hydrogen;

3) a compound wherein X is

[Chemical formula 35]

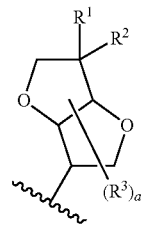

$R^1$ is hydrogen, $R^2$ is substituted or unsubstituted alkyloxy, a is 0, ring A is substituted aryl, $R^8$ is halogen, and $R^9$ is hydrogen; and 4) a compound wherein X is

[Chemical formula 36]

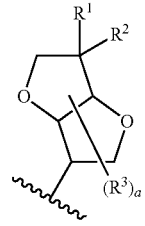

$R^1$ is hydrogen, $R^2$ is substituted or unsubstituted alkyloxy, a is 0, ring A is substituted aryl, Y is substituted or unsubstituted alkyloxy, substituted or unsubstituted alkyloxycarbonyl, substituted or unsubstituted alkylsulfinyl, substituted or unsubstituted acyl, substituted or unsubstituted carbamoyloxy, substituted or unsubstituted amino, $R^SR^{S'}(O=)S=N-$, $R^SR^{S'}(O=)S=N-R^{2f}-$, $R^SR^{S'}(O=)S=N-C(=O)-$, $(R^N)N=S(=O)(R^S)-$, $(R^N)N=S(=O)(R^S)-R^{2f}-$, $R^SR^{S'}(R^{N'}-N=)S=N-$, $((R^N)N=)_2S(R^S)-$, $(R^NR^{N'})N-C(=O)-O-$, $R^OO-C(=O)-N(R^N)-$, $R^OO-C(=O)-O-$, $R^S(R^NR^{N'}N)(O=)S=N-$, $R^S(R^NR^{N'}N)(O=)S=N-R^{2f}-$, $(R^{N''})N=S(=O)(NR^NR^{N'})-$, $(R^{N''})N=S(=O)(NR^NR^{N'})-R^{2f}-$ or $R^{P1}R^{P2}(O=)P-$, $R^8$ is halogen, and $R^9$ is hydrogen.

5) a compound wherein X is

[Chemical formula 37]

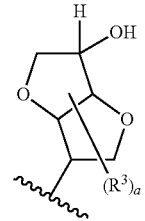

a is 0, ring A is substituted aryl, Y is $R^{Y1}-O-$ or $(R^{Y2}R^{Y3})N-$, $R^8$ is halogen, and $R^9$ is hydrogen.

One or more hydrogen, carbon or other atoms of the compounds of formula (I) of the present invention can be replaced by an isotope of the hydrogen, carbon or other atoms.

For example, the compounds of formula (I) include all radiolabeled forms of compounds of formula (I). Such "radioactive labeling," "radiolabeled form" and the like of the compound of formula (I) are encompassed by the present invention and useful as a research and/or diagnostic tool in metabolism pharmacokinetic studies and in binding assays. Examples of isotopes that can be incorporated into a compound of formula (I) of the present invention include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Radiolabeled compounds of the present invention can be prepared by methods well-known in the art. For example, tritium-labeled compounds of formula (I) can be prepared by introducing tritium into a particular compound of formula (I), for example, by catalytic dehalogenation with tritium. This method may include reacting a suitably halogen-substituted precursor of a compound of formula (I) with tritium gas in the presence of a suitable catalyst such as Pd/C, in the presence or absence of a base. Other suitable methods for preparing tritiated compounds can be found in Isotopes in the Physical and Biomedical Sciences, Vol. 1, Labeled Compounds (Part A), Chapter 6 (1987). $^{14}C$-labeled compounds can be prepared by employing starting materials having a $^{14}C$ carbon.

As a pharmaceutically acceptable salt of the compound of the present invention, the following salts can be included.

As a basic salt, examples include alkali metal salts such as sodium salts and potassium salts; alkaline earth metal salts such as calcium salts and strontium salts; beryllium salts, magnesium salts; transition metal salts such as zinc salts; ammonium salts; aliphatic amine salts such as trimethylamine salts, triethylamine salts, dicyclohexylamine salts, ethanolamine salts, diethanolamine salts, triethanolamine salts, procaine salts, meglumine salts, diethanolamine salts and ethylenediamine salts; aralkylamine salts such as N,N-dibenzylethylenediamine and benethamine salts; heterocyclic aromatic amine salts such as pyridine salts, picoline salts, quinoline salts, and isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts, and tetrabutylammonium salts; basic amino acid salts such as arginine salts and lysine salts; and the like.

As an acidic salt, examples include inorganic acid salts such as hydrochlorides, sulfates, nitrates, phosphates, carbonates, hydrogencarbonates, and perchlorates; organic acid salts such as acetates, propionates, lactates, maleates, fumarates, tartrates, malates, citrates and ascorbates; sulfonate salts such as methanesulfonates, isethionates, benzenesulfonates and p-toluenesulfonates; acidic amino acid salts such as aspartates and glutamates; and the like.

A compound represented by formula (I) of the present invention or its pharmaceutically acceptable salt may form a solvate (e.g., hydrate, etc.), cocrystal and/or a crystal polymorph, and the present invention also contains such various types of solvates, cocrystal and crystal polymorphs. In a "solvate", any number of solvent molecules (e.g., water molecule, etc.) may be coordinated with a compound represented by formula (I). When left in the atmosphere, a compound represented by formula (I) or its pharmaceutically acceptable salt may absorb water, and a case where adsorbed water is attached thereto or a case where hydrate is formed may arise. In addition, by recrystallization of a compound represented by formula (I) or its pharmaceutically acceptable salt, a crystal polymorph thereof can be formed. The "cocrystal" means that a compound represented by formula (I) or its salt and a counter molecule are present in the same crystal lattice, and may be formed with any number of counter molecule.

A compound represented by formula (I) of the present invention or its pharmaceutically acceptable salt may form a prodrug, and the present invention also contains such various types of prodrugs. The prodrugs are a derivative of the compound of the present invention, which has a chemically or metabolically decomposable group, and a compound which is changed into the compound of the present invention, which is pharmaceutically active, by solvolysis or in vivo under physiological conditions. The prodrugs contain a compound which is converted into a compound represented by formula (I) by enzymatic oxidation, reduction, hydrolysis and the like in living organisms under physiological conditions; a compound which is converted into a compound represented by formula (I) by hydrolysis by e.g., gastric acid; and the like. A method for selecting and a method for producing a proper prodrug derivative are described in e.g., Design of Prodrugs, Elsevier, Amsterdam 1985. Prodrugs can have activity in themselves.

When a compound represented by formula (I) or its pharmaceutically acceptable salt has a hydroxyl group, prodrugs such as acyloxy derivatives and sulfonyloxy derivatives are exemplified, which derivatives are produced, for example, by a reaction of a compound having a hydroxyl group and a proper acyl halide, a proper acid anhydride, a proper sulfonyl chloride, a proper sulfonyl anhydride and a mixed anhydride, or a reaction using a condensing agent. Examples thereof include $CH_3COO-$, $C_2H_5COO-$, tert-BuCOO—, $C_{15}H_{31}COO-$, PhCOO—, (m-NaOOCPh) COO—, $NaOOCCH_2CH_2COO-$, $CH_3CH(NH_2)COO-$, $CH_2N(CH_3)_2COO-$, $CH_3SO-$, $CH_3CH_2SO_3$, $CF_3SO_3-$, $CH_2FSO_3-$, $CF_3CH_2SO_3-$, p-$CH_3O$-$PhSO_3-$, $PhSO_3-$ and p-$CH_3PhSO_3-$.

The term "activating" means that the compound of the present invention activates the function of AMPK.

The term "pharmaceutically acceptable" means preventively or therapeutically harmless.

A general method for producing the compound of the present invention will be illustrated below. For extraction, purification and the like, treatments which are carried out in common experiments in organic chemistry may be carried out.

A compound represented by formula (I) can be synthesized as follows.

[Chemical formula 38]

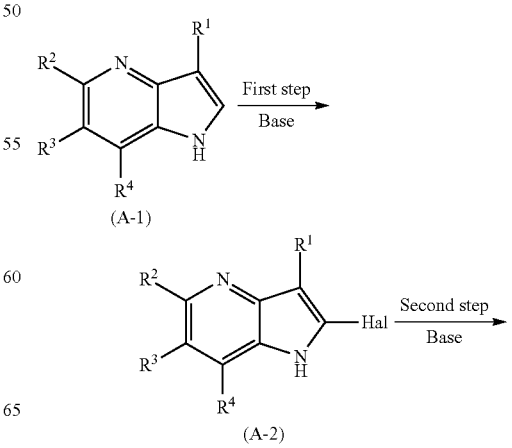

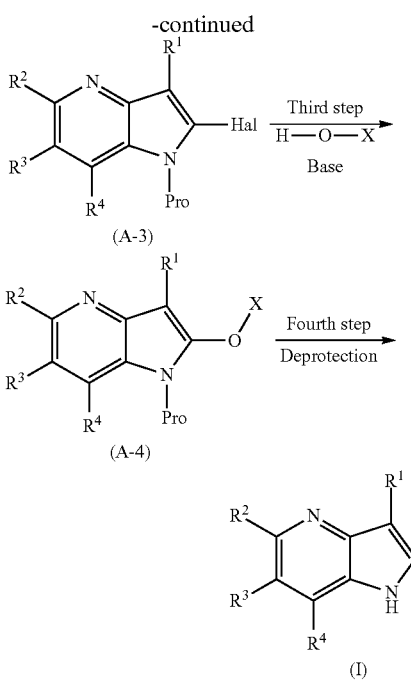

(A-3)

(A-4)

(I)

wherein each symbol has the same meaning as above, and as a compound represented by formula (A-1), a known compound can be used, or a compound which is derived from a known compound by a conventional method may be used. "Hal" means a halogen, and Pro means a protecting group. Pro includes a benzyl group, a benzoyl group and SEM (trimethylsilylethoxymethyl) and the like.

First Step

The first step is a step in which a compound represented by formula (A-2) is produced by halogenation of a compound represented by formula (A-1).

As a reaction solvent, examples include N,N-dimethylformamide, dimethyl sulfoxide, aromatic hydrocarbons (e.g., toluene, benzene, xylene, etc.), saturated hydrocarbons (e.g., cyclohexane, hexane, etc.), halogenated hydrocarbons (e.g., dichloromethane, chloroform, 1,2-dichloroethane, etc.), ethers (e.g., tetrahydrofuran, diethyl ether, dioxane, 1,2-dimethoxyethane, etc.), esters (e.g., methyl acetate, ethyl acetate, etc.), ketones (e.g., acetone, methyl ethyl ketone, etc.), nitriles (e.g., acetonitrile, etc.), alcohols (e.g., methanol, ethanol, t-butanol, etc.), water, a mixed solvent thereof and the like.

Preferred examples include N,N-dimethylformamide, halogenated hydrocarbons (e.g., dichloromethane, chloroform, 1,2-dichloroethane, etc.), ethers (e.g., tetrahydrofuran, diethyl ether, dioxane, 1,2-dimethoxyethane, etc.) or nitriles (e.g., acetonitrile, etc.) and the like. Further preferably, alcohols (e.g., methanol, ethanol, t-butanol, etc.) can be used.

As a base, examples include metal hydrides (e.g., sodium hydride, etc.), metal hydroxides (e.g., sodium hydroxide, potassium hydroxide, lithium hydroxide, barium hydroxide, etc.), metal carbonates (e.g., sodium carbonate, calcium carbonate, cesium carbonate, etc.), metal alkoxides (e.g., sodium methoxide, sodium ethoxide, potassium t-butoxide, etc.), sodium hydrogen carbonate, metal sodium, metal amides, organic amines (e.g., triethylamine, diisopropylethylamine, DBU, 2,6-lutidine, etc.), pyridine, alkyllithiums (n-BuLi, sec-BuLi, tert-BuLi) and the like.

A base may be used, or may not be used. Preferred examples of the base include metal hydrides (e.g., sodium hydride, etc.), metal amides (e.g., lithium hexamethyldisilazide, etc.), alkyllithiums (n-BuLi, sec-BuLi, tert-BuLi) and the like.

The reaction can be carried out at −78 to 100° C. for 0.5 to 24 hours.

As a halogenating agent, $I_2$, $Br_2$, NIS (N-iodosuccinimide), NBS (N-bromosuccinimide) or NCS (N-chlorosuccinimide) can be used.

Second Step

The second step is a step in which a compound represented by formula (A-3) is produced from a compound represented by formula (A-2).

As a reaction solvent, solvents described for the first step can be used.

Preferred examples include N,N-dimethylformamide, ethers (e.g., tetrahydrofuran, diethyl ether, dioxane, 1,2-dimethoxyethane, etc.), halogenated hydrocarbons (e.g., dichloromethane, chloroform, 1,2-dichloroethane, etc.), nitriles (e.g., acetonitrile, etc.) and the like.

As a base, bases described for the first step can be used. Preferably, metal hydrides (e.g., sodium hydride, etc.), metal sodium, organic amines (e.g., triethylamine, diisopropylethylamine, DBU, 2,6-lutidine, etc.), pyridine or the like can be used.

The reaction can be carried out at 0 to 100° C. for 0.5 to 12 hours.

Third Step

The third step is a step in which a compound represented by formula (A-4) is produced by reacting a compound represented by formula (A-3) and a compound represented by formula: H—O—X.

As a compound represented by formula: H—O—X, examples include phenol, methanol, ethanol and the like.

As a reaction solvent, solvents described for the first step can be used. Preferred examples include N,N-dimethylformamide, dimethyl sulfoxide, ethers (e.g., tetrahydrofuran, diethyl ether, dioxane, 1,2-dimethoxyethane, etc.), nitriles (e.g., acetonitrile, etc.) or the like.

As a base, bases described for the first step can be used. Preferred examples include metal hydrides (e.g., sodium hydride, etc.), metal carbonates (e.g., sodium carbonate, calcium carbonate, cesium carbonate, etc.), metal amides, organic amines (e.g., triethylamine, diisopropylethylamine, DBU, 2,6-lutidine, etc.), pyridine, alkyllithiums (n-BuLi, sec-BuLi, tert-BuLi) and the like.

Further preferably, metal hydrides (e.g., sodium hydride, etc.) or metal carbonates (e.g., sodium carbonate, calcium carbonate, cesium carbonate, etc.) can be used.

The reaction can be carried out at 0 to 100° C. for 0.5 to 12 hours.

(When Hal is Bromine or Iodine)

The reaction can be carried out using conditions for a reaction which is known as the Ullmann reaction.

As a reaction solvent, solvents described for the first step can be used. Preferred examples include N,N-dimethylformamide, dimethyl sulfoxide, ethers (e.g., tetrahydrofuran, diethyl ether, dioxane, 1,2-dimethoxyethane, etc.), nitriles (e.g., acetonitrile, etc.) and the like.

As a base, bases described for the first step can be used. Preferred examples include metal hydrides (e.g., sodium hydride, etc.), metal carbonates (e.g., sodium carbonate, calcium carbonate, cesium carbonate, etc.), metal amides, organic amines (e.g., triethylamine, diisopropylethylamine, DBU, 2,6-lutidine, etc.), pyridine, alkyllithiums (n-BuLi, sec-BuLi, tert-BuLi) and the like.

Further preferably, metal carbonates (e.g., sodium carbonate, calcium carbonate, cesium carbonate, etc.) can be used.

As a catalyst, copper iodide can be used.

The reaction can be carried out at room temperature to 100° C. for 0.5 to 12 hours.

Fourth Step

The fourth step is a step in which a compound represented by formula (I) is produced by deprotection of a compound represented by formula (A-4).

As a reaction solvent, solvents described for the first step can be used. Preferred examples include N,N-dimethylformamide, halogenated hydrocarbons (e.g., dichloromethane, chloroform, 1,2-dichloroethane, etc.), ethers (e.g., tetrahydrofuran, diethyl ether, dioxane, 1,2-dimethoxyethane, etc.), esters (e.g., methyl acetate, ethyl acetate, etc.), nitriles (e.g., acetonitrile, etc.), alcohols (e.g., methanol, ethanol, t-butanol, etc.) and the like.

The reaction can be carried out in the presence of hydrochloric acid, TFA (trifluoroacetic acid), TBAF (tetrabutylammoniumfluoride) or the like at 0 to 100° C. for 0.5 to 168 hours.

The substituents $R^4$, $R^5$, $R^6$, $R^7$, $R^8$ and $R^9$ can be introduced in any step of the above-described first to fourth steps.

For example, a substituent

[Chemical formula 39]

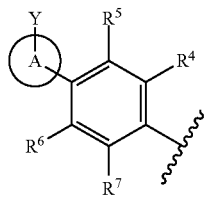

can be introduced as follows.

[Chemical formula 40]

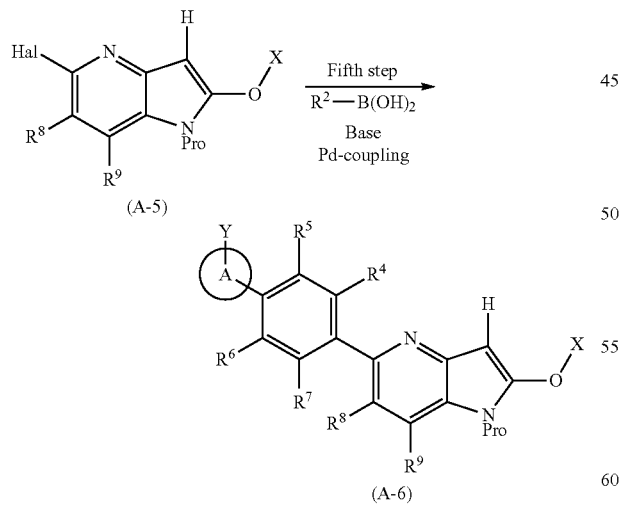

wherein each symbol has the same meaning as above, and as a compound represented by formula (A-5), a known compound can be used, or a compound which is derived from a known compound by a conventional method can be used. "Hal" means a halogen, and Pro means a protecting group. Pro includes a benzyl group, a benzoyl group and SEM (trimethylsilylethoxymethyl) and the like.

Fifth Step

The fifth step is a step in which a compound represented by formula (A-6) is produced by reacting a compound represented by formula (A-5) and a compound represented by formula: $R^2$—$B(OH)_2$ in the presence of a palladium catalyst. As a compound represented by formula: $R^2$—$B(OH)_2$, boronic acid ester can be used.

As a solvent, solvents described for the first step can be used. Preferably, N,N-dimethylformamide, aromatic hydrocarbons (e.g., toluene, benzene, xylene, etc.) or ethers (e.g., tetrahydrofuran, diethyl ether, dioxane, 1,2-dimethoxyethane, etc.) can be used.

As a base, bases described for the first step can be used. Preferably, metal carbonates (e.g., sodium carbonate, calcium carbonate, cesium carbonate, etc.) or organic amines (e.g., triethylamine, diisopropylethylamine, DBU, 2,6-lutidine, etc.) can be used.

The reaction may be carried out in the presence of a palladium catalyst (e.g., Pd(PPh$_3$)$_4$, PdCl$_2$, Pd(OAc)$_2$, Pd(dba)$_2$, etc.) and a phosphine ligand (e.g., PPh$_3$, BINAP, etc.) at a temperature, at which a solvent to be used is refluxed, for 0.5 to 12 hours.

When using microwave, the reaction can be carried out at 80 to 200° C. for 5 minutes to one hour.

Example of a compound represented by formula: $R^2$—$B(OH)_2$ includes phenylboronic acid or the like.

Among compounds represented by formula (A-6), a compound wherein $R^2$ is substituted or unsubstituted alkyloxy, substituted or unsubstituted cycloalkyloxy, substituted or unsubstituted cycloalkenyloxy or substituted or unsubstituted heterocyclyloxy, can be synthesized, by converting the halogen group of the compound represented by formula (A-5) into the hydroxyl group via boronic acid ester, and an alkylation reaction using Mitsunobu reaction or various halide.

As a boronic acid ester, examples include pinacol boronic acid ester and the like.

A compound represented by formula (A-2) can also be synthesized by the following method.

[Chemical formula 41]

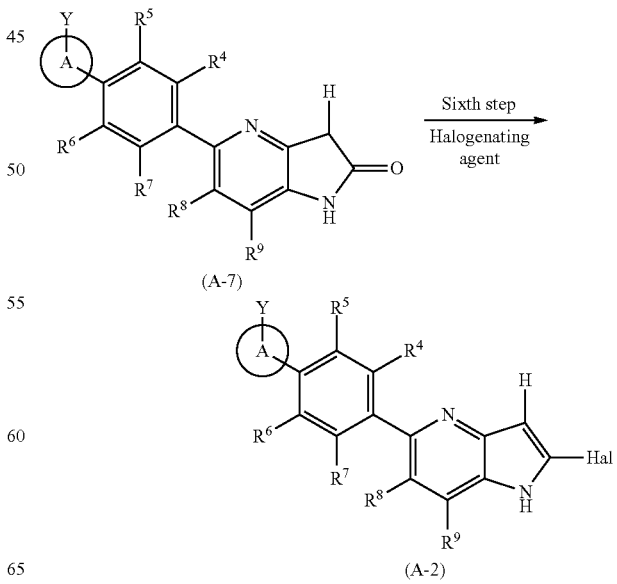

wherein each symbol has the same meaning as above, and as a compound represented by formula (A-7), a known compound can be used, or a compound which is derived from a known compound by a conventional method can be used. "Hal" means a halogen.

Sixth Step

The sixth step is a step in which a compound represented by formula (A-2) is produced by reacting a compound represented by formula (A-7) and a halogenating agent.

Although solvents described for the first step can be used as a reaction solvent, there is no need to use them.

As a halogenating agent, examples include phosphorus oxychloride, phosphorus pentachloride, oxalyl chloride, thionyl chloride, sulfuryl chloride, dichlorotriphenylphosphorane and the like. Particularly preferably, a halogenating agent is phosphorus oxychloride, phosphorus pentachloride, oxalyl chloride or thionyl chloride.

The reaction can be carried out at 0 to 120° C. for 0.5 to 24 hours.

Various types of substituents on compounds of the present invention can be introduced by reference to (1) Alan R. Katriszly et al., Comprehensive Heterocyclic Chemistry, (2) Alan R. Katriszly et al., Comprehensive Heterocyclic Chemistry II, (3) RODD'S CHEMISTRY OF CARBON COMPOUNDS VOLUME IV HETEROCYCLIC COMPOUNDS and the like.

A compound of the present invention has an excellent AMPK activating effect. Therefore, the compound can be used for the treatment or prevention of diseases associated with AMPK, particularly disease such as type II diabetes, hyperglycemia, metabolic syndrome, obesity, hypercholesterolemia and/or hypertension. Particularly, the compound is useful in the treatment or prevention of type II diabetes, hyperglycemia, metabolic syndrome or obesity.

A pharmaceutical composition of the present invention can be administered orally or parenterally. Methods for parenteral administration include dermal, subcutaneous, intravenous, intraarterial, intramuscular, intraperitoneal, transmucosal, inhalation, transnasal, ophthalmic, inner ear or vaginal administration and the like.

In the case of oral administration, any forms, which are usually used, such as oral solid formulations (e.g., tablets, powders, granules, capsules, pills, films or the like), oral liquid formulations (e.g., suspension, emulsion, elixir, syrup, lemonade, spirit, aromatic water, extract, decoction, tincture or the like) and the like may be prepared according to the usual method and administered. The tablets can be sugar-coated tablets, film-coated tablets, enteric-coating tablets, sustained-release tablets, troche tablets, sublingual tablets, buccal tablets, chewable tablets or orally disintegrating tablets. Powders and granules can be dry syrups. Capsules can be soft capsules, micro capsules or sustained-release capsules.

In the case of parenteral administration, any forms, which are usually used, such as injections, drips, external preparations (e.g., ophthalmic drops, nasal drops, ear drops, aerosols, inhalations, lotion, infusion, liniment, mouthwash, enema, ointment, plaster, jelly, cream, patch, cataplasm, external powder, suppository or the like) and the like can be preferably administered. Injections can be emulsions whose type is O/W, W/O, O/W/O, W/O/W or the like.

The pharmaceutical composition may be manufactured by mixing an effective amount of the compound of the present invention with various pharmaceutical additives suitable for the formulation, such as excipients, binders, disintegrants, lubricants and the like. Furthermore, the pharmaceutical composition can be for pediatric patients, geriatric patients, serious cases or operations by appropriately changing the effective amount of the compound of the present invention, formulation and/or various pharmaceutical additives. The pediatric pharmaceutical compositions are preferably administered to patients under 12 or 15 years old. In addition, the pediatric pharmaceutical compositions can be administered to patients who are under 27 days old after the birth, 28 days to 23 months old after the birth, 2 to 11 years old, 12 to 16 years old, or 18 years old. The geriatric pharmaceutical compositions are preferably administered to patients who are 65 years old or over.

Although the dosage of a pharmaceutical composition of the present invention should be determined in consideration of the patient's age and body weight, the type and degree of diseases, the administration route and the like, a usual oral dosage is 0.05 to 100 and preferably 0.1 to 10 mg/kg/day. For parenteral administration, although the dosage highly varies with administration routes, a usual dosage is 0.005 to 10 and preferably 0.01 to 1 mg/kg/day. The dosage may be administered in one to several divisions per day.

A compound of the present invention can be used in combination with an insulin secretagogue (e.g., a sulfonylurea (SU) drug), a fast-acting insulin secretagogue (e.g., a phenylalanine derivative), a glucose uptake inhibitor (e.g., an α-glucosidase inhibitor (α-GI drug)), an insulin resistance improving drug (e.g., a biguanide drug (BG drug), a thiazolidine derivative (TZD drug)), an insulin formulation, a peptidyl peptidase IV (DPP-IV) inhibitor, a GLP-1 receptor agonist, a sodium-dependent glucose transporter 1 (SGLT1) inhibitor, a sodium-dependent glucose transporter 2 (SGLT2) inhibitor and the like (hereinafter, abbreviated as concomitant drugs) for the purpose of an increase in the effect of the compound, a decrease in a dose of the compound or the like. In this case, the time when a compound of the present invention and a concomitant drug are administered is not restricted, and they can be administered to a subject of administration simultaneously or at intervals. Further, a compound of the present invention and a concomitant drug can be administered as two kinds of formulations comprising each active ingredient and as a single formulation comprising both active ingredients.

The dose of a concomitant drug can be suitably selected on the basis of a dosage which is clinically used. In addition, the mixing ratio of a compound of the present invention and a concomitant drug can be suitably selected depending on a subject of administration, an administration route, a target disease, symptoms, combination and the like. When a subject of administration is a human, for example, 0.01 to 100 parts by weight of a concomitant drug can be used per part by weight of a compound of the present invention.

The present invention is described in more detail below with reference to Examples, which are not intended to limit the scope of the present invention.

NMR spectrum data of the compounds of the present invention and intermediates thereof are shown. NMR analysis obtained in each example was performed at 400 MHz using $CDCl_3$, deuterated methanol (MeOD) or dimethyl sulfoxide (d6-DMSO).

LC/MS was measured under the following conditions.

(Method A)

Column: ACQUITY UPLC BEH C18 (1.7 μm i.d.2.1×50 mm) (Waters)

Flow rate: 0.8 mL/min

UV detection wavelength: 254 nm

Mobile phase: [A] 0.1% formic acid-containing aqueous solution, [B] 0.1% formic acid-containing acetonitrile solution Gradient: a linear gradient of the solvent [B] from 5 to 100% was carried out for 3.5 minutes, and the solvent [B] at 100% was maintained for 0.5 minutes.

(Method B)

Column: Shim-pack XR-ODS (2.2 μm, i.d. 3.0×50 mm) (Shimadzu)

Flow rate: 1.6 mL/min

UV detection wavelength: 254 nm

Mobile phase: [A] 0.1% formic acid-containing aqueous solution, [B] 0.1% formic acid-containing acetonitrile solution Gradient: a linear gradient of the solvent [B] from 10 to 100% was carried out for 3 minutes, and the solvent [B] at 100% was maintained for 0.5 minutes.
(Method C)

Column: ACQUITY UPLC(Registered trademark)BEH C18 (1.7 μm i.d. 2.1×50 mm)
(Waters)

Flow rate: 0.55 mL/min

UV detection wavelength: 254 nm

Mobile phase: [A] 0.1% formic acid-containing aqueous solution, [B] 0.1% formic acid-containing acetonitrile solution Gradient: a linear gradient of the solvent [B] from 5 to 100% was carried out for 3 minutes, and the solvent [B] at 100% was maintained for 0.5 minutes.

The meaning of each term in Examples is as follows.
CDI: 1,1'-Carbonyldiimidazole
DMF: N,N-Dimethylformamide
THF: Tetrahydrofuran
Pd(PPh$_3$)$_4$: Tetrakis(triphenylphosphine)palladium(0)
POCl$_3$: Phosphorus oxychloride
PdCl$_2$(dtbpf): [1,1'-Bis(di-tert-butylphosphino)ferrocene]dichloropalladium(II)
NCS: N-Chlorosuccinimide
NBS: N-Bromosuccinimide
NIS: N-Iodosuccinimide
TFA: Trifluoroacetic acid
TBAF: Tetrabutylammonium fluoride
DIAD: Diisopropyl azodicarboxylate
UHP: Urea-hydrogen peroxide
mCPBA: m-Chloroperoxybenzoic acid
HMPA: Hexamethylphosphoric triamide
DMAP: N,N-Dimethyl-4-aminopyridine
MTBE: Methyl tert-butyl ether
TEMPO: 2,2,6,6-Tetramethylpiperidine 1-oxyl free radical
MS4A: Molecular sieve 4A
TMEDA: N,N,N',N'-Tetramethylethylenediamine
NFSI: N-Fluorobenzenesulfonimide
RuPhos: 2-Dicyclohexylphosphino-2',6'-diisopropoxybiphenyl
PdCl$_2$(dppf)CH$_2$Cl$_2$: [1,1'-Bis(diphenylphosphino)ferrocene]palladium(II) dichloride dichloromethane adduct
NMO: 4-Methylmorpholine N-oxide
DMSO: Dimethyl sulfoxide
Pd$_2$(dba)$_3$: Tris(dibenzylideneacetone)dipalladium
DME: 1,2-Dimethoxyethane
HOBt: 1-Hydroxybenzotriazole
EDC.HCl: 1-(3-Dimethylaminopropyl)-3-ethylcarbodiimide hydrochloride
HATU: O-(7-Azabenzotriazol-1-yl)-N,N,N',N'-tetramethyluronium hexafluorophosphate
DMT-MM: 4-(4,6-Dimethoxy-1,3,5-triazin-2-yl)-4-methylmorpholinium chloride
Xantphos: 4,5-Bis(diphenylphosphino)-9,9-dimethylxanthene
DMEAD: Bis(2-methoxyethyl) azodicarboxylate
X-phos: 2-Dicyclohexylphosphino-2',4',6'-triisopropylbiphenyl
Pd(PPh$_3$)$_4$: Tetrakis(triphenylphosphine)palladium(0)

EXAMPLE 1

[Chemical formula 42]

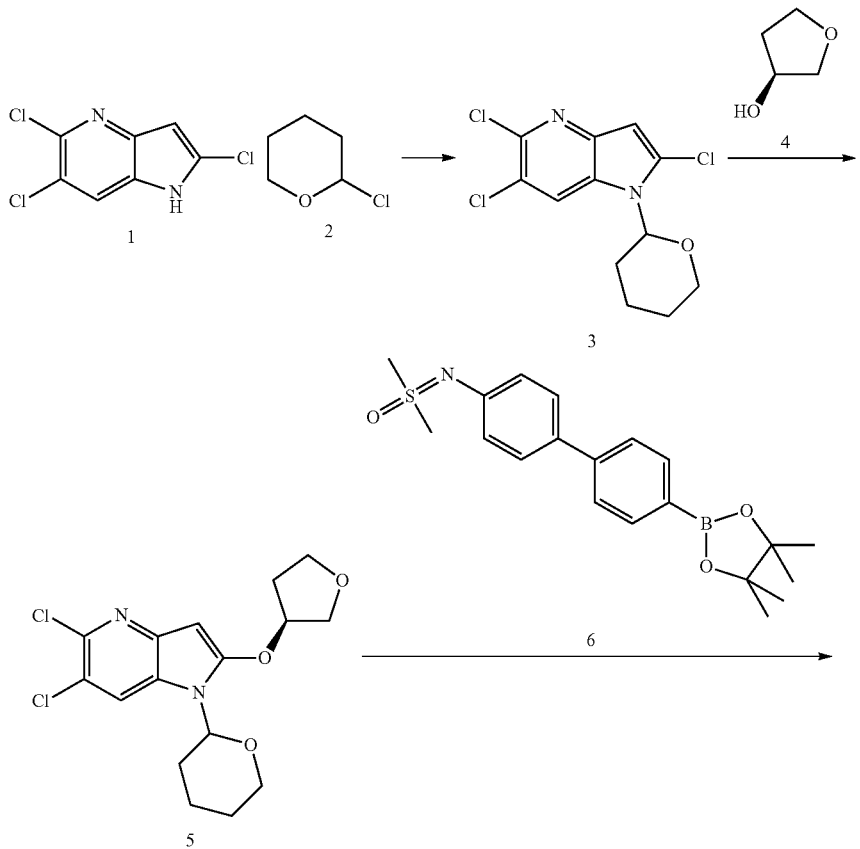

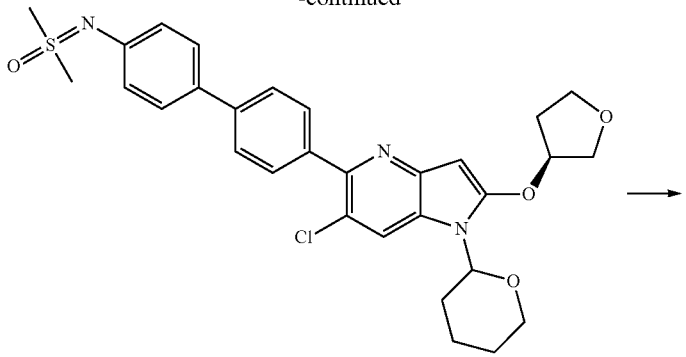

7

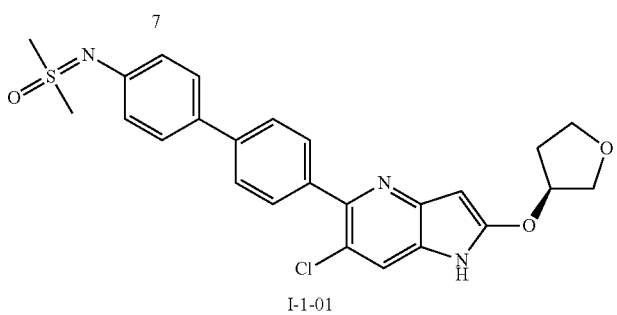

I-1-01

60 wt % sodium hydride (1.062 g, 26.6 mmol) was diluted with DMF (20 ml), and a solution obtained by dissolving Compound 1 (3.92 g, 17.7 mmol) in DMF (20 ml) was added thereto under ice-cooling. Thereafter, Compound 2 (3.20 g, 26.6 mmol) was added thereto, and the mixture was stirred. After completion of the reaction, ice and water were added thereto, and the mixture was extracted with ethyl acetate. The obtained organic layer was dried over magnesium sulfate and filtered, then concentrated under reduced pressure. The obtained residue was purified by silica gel column chromatography to obtain Compound 3 (4.50 g, 83.2%).

Compound 3; Method B
  LC/MS retention time=2.79 min.
  MS (ESI) m/z=305.00 (M+H)+.

Compound 3 (1.00 g, 3.27 mmol) and Compound 4 (0.951 g, 10.8 mmol) were dissolved in DMF (5 ml), then 60 wt % sodium hydride (0.196 g, 4.91 mmol) was added thereto, and the mixture was stirred at room temperature. After completion of the reaction, ethyl acetate was added thereto, and the mixture was washed with an aqueous solution of hydrochloric acid and water. The obtained organic layer was dried over magnesium sulfate and filtered, then concentrated under reduced pressure. The obtained residue was purified by silica gel column chromatography to obtain Compound 5 (1.10 g, 94.3%).

Compound 5; Method B
  LC/MS retention time=2.24 min.
  MS (ESI) m/z=357.15 (M+H)+.

Compound 5 (300 mg, 0.794 mmol) and Compound 6 (383 mg, 1.032 mmol) were dissolved in DMF (2 ml), and the solution was heated to 85° C. under nitrogen atmosphere, then $PdCl_2$(dtbpf) (103 mg, 0.159 mmol) and a 2 mol/L aqueous solution of potassium carbonate (0.595 ml, 1.19 mmol) were added thereto, and the mixture was stirred at 85° C. After completion of the reaction, ethyl acetate was added thereto, and the mixture was washed with water. The obtained organic layer was concentrated under reduced pressure, and purified by silica gel column chromatography to obtain Compound 7 (145 mg, 32.3%).

Compound 7; Method B
  LC/MS retention time=1.85 min.
  MS (ESI) m/z=566.30 (M+H)+.

TFA (2 ml) was added to Compound 7 (135 mg, 0.245 mmol), and the mixture was stirred at room temperature. After completion of the reaction, TFA was removed by concentration under reduced pressure. The obtained residue was diluted with MeOH, and was neutralized by adding to an aqueous solution of sodium hydrogen carbonate. The resulting mixture was extracted with chloroform, and the obtained organic layer was dried over magnesium sulfate, then the solvent was removed by concentration under reduced pressure. The obtained residue was purified by silica gel column chromatography to obtain Compound (I-1-01) (58.6 mg, 49.7%).

Compound (I-1-01); Method B
  LC/MS retention time=1.24 min.
  MS (ESI) m/z=482.50 (M+H)+.

EXAMPLE 2

[Reaction formula 43]

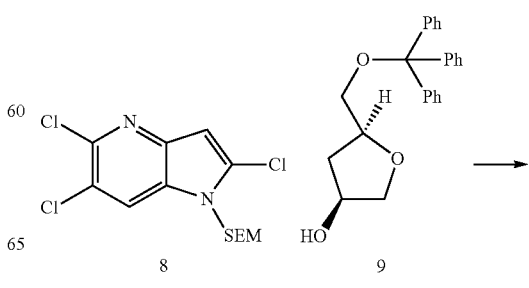

-continued

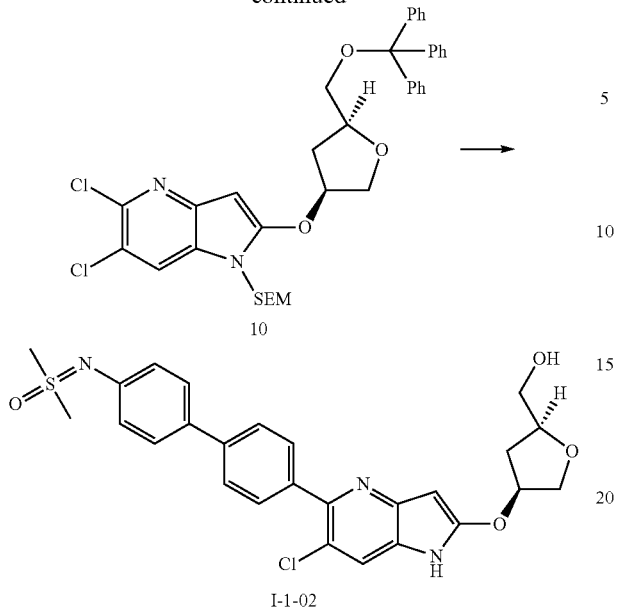

Compound 8 (1.10 g, 3.13 mmol) was dissolved in DMF (5.5 ml), then Compound 9 (1.409 g, 3.91 mmol) and 60 wt % sodium hydride (0.188 g, 4.69 mmol) were added thereto, and the mixture was stirred at room temperature. After completion of the reaction, a saturated aqueous solution of ammonium chloride was added thereto, and the mixture was extracted with ethyl acetate. The obtained organic layer was concentrated under reduced pressure, and purified by silica gel column chromatography to obtain Compound 10 (1.9543 g, 86.4%).

Compound 10; Method B

LC/MS retention time=3.35 min.

MS (ESI) m/z=676.10 (M+H)+.

Compound (I-1-02) was synthesized from Compound 10, in a similar way that Compound (I-1-01) was synthesized from Compound 5.

Compound (I-1-02); Method B

LC/MS retention time=1.17 min.

MS (ESI) m/z=512.3 (M+H)+.

EXAMPLE 3

[Reaction formula 44]

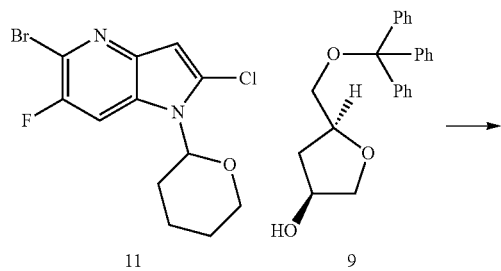

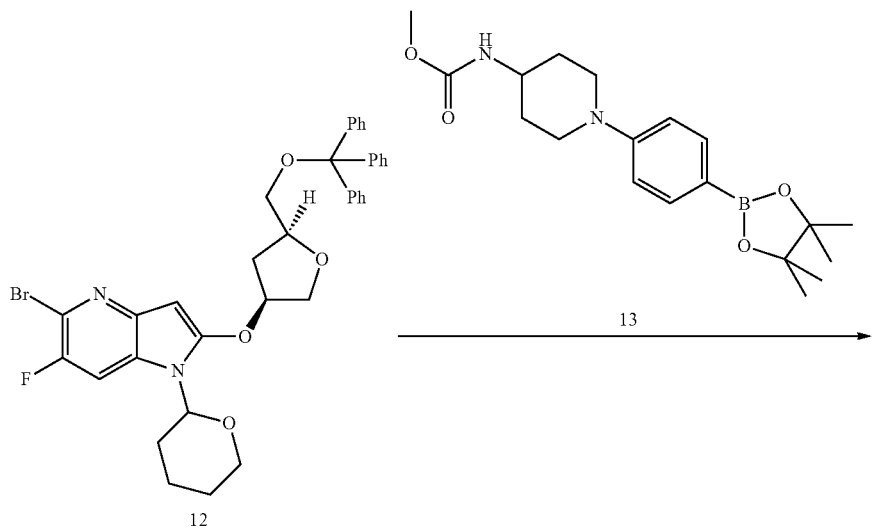

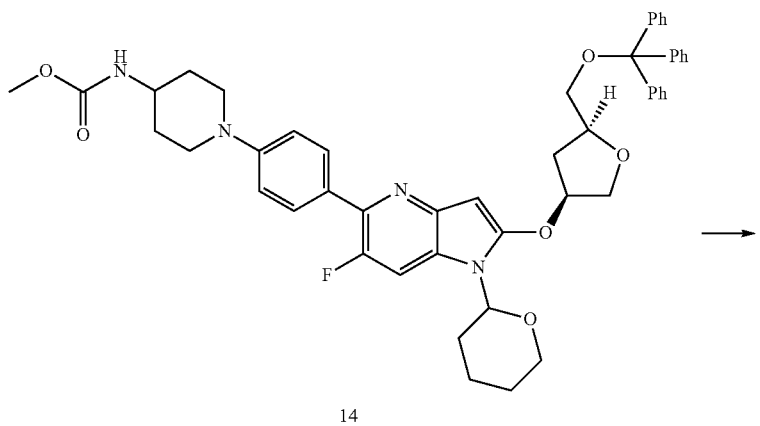

14

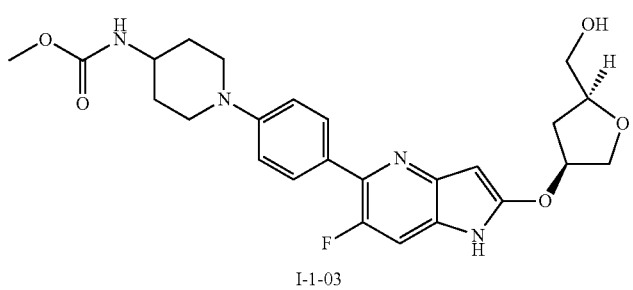

I-1-03

DMF (0.5 ml) was added to Compound 11 (100 mg, 0.300 mmol), Compound 9 (130 mg, 0.360 mmol), 18-crown 6-ether (475 mg, 1.799 mmol) and potassium fluoride (52.2 mg, 0.899 mmol), then 60 wt % sodium hydride (16.8 mg, 0.420 mmol) was added thereto under nitrogen atmosphere, and the mixture was stirred at room temperature. After completion of the reaction, ethyl acetate was added thereto, and the mixture was washed with an aqueous solution of hydrochloric acid and water. The obtained organic layer was concentrated under reduced pressure, and purified by silica gel column chromatography to obtain Compound 12 (188.2 mg, 95.4%).

Compound 12; Method B

LC/MS retention time=3.11 min.

MS (ESI) m/z=657.30 (M+H)+.

Compound 14 was synthesized from Compound 12, in a similar way that Compound 7 was synthesized from Compound 5.

Compound 14; Method B

LC/MS retention time=2.62 min.

MS (ESI) m/z=811.60 (M+H)+.

Compound (I-1-03) was synthesized from Compound 14, in a similar way that Compound (I-1-01) was synthesized from Compound 7.

Compound (I-1-03); Method B

LC/MS retention time=1.08 min.

MS (ESI) m/z=485.35 (M+H)+.

EXAMPLE 4

[Chemical formula 45]

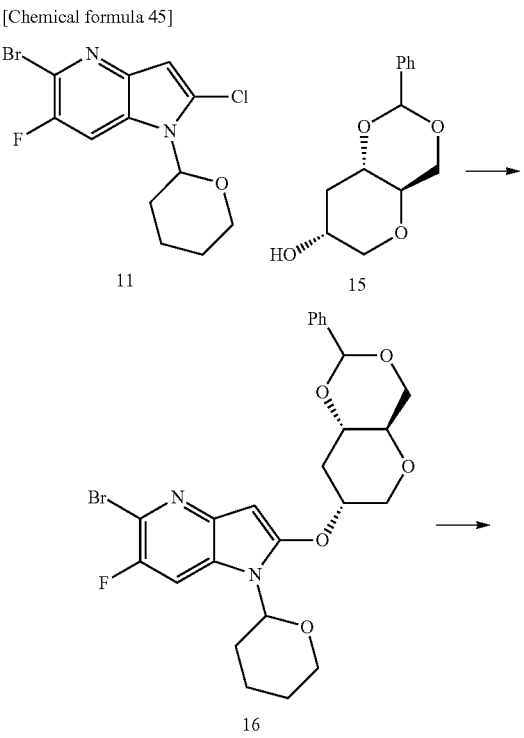

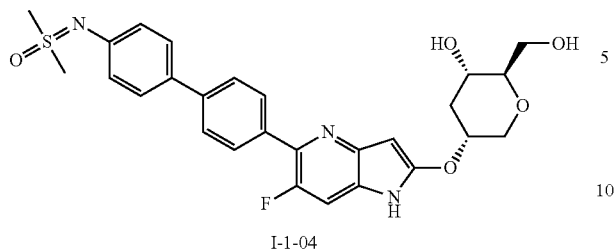

I-1-04

Compound 16 was synthesized from Compound 15, in a similar way that Compound 10 was synthesized from Compound 9.

Compound 16; Method B

LC/MS retention time=2.72 min.

MS (ESI) m/z=535.10 (M+H)+.

Compound (I-1-04) was synthesized from Compound 16, in a similar way that Compound (I-1-01) was synthesized from Compound 5.

Compound (I-1-04); Method B

LC/MS retention time=1.09 min.

MS (ESI) m/z=526.35 (M+H)+.

EXAMPLE 5

[Reaction formula 46]

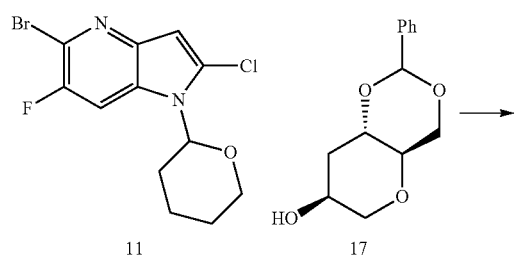

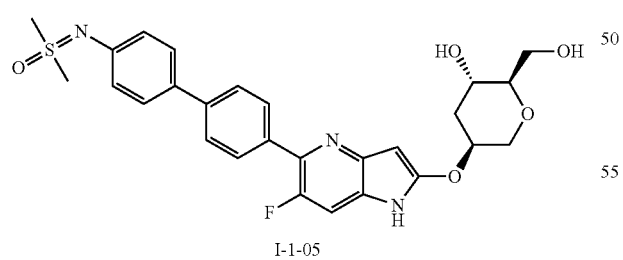

I-1-05

Compound (I-1-05) was synthesized from Compound 17, in a similar way that Compound (I-1-04) was synthesized from Compound 15.

Compound (I-1-05); Method B

LC/MS retention time=0.96 min.

MS (ESI) m/z=526.5 (M+H)+.

EXAMPLE 6

[Chemical formula 47]

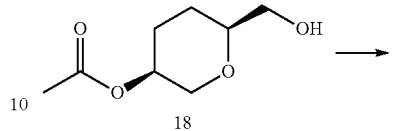

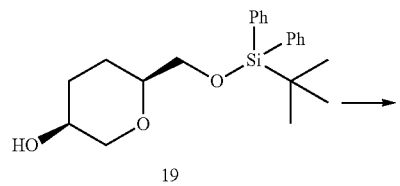

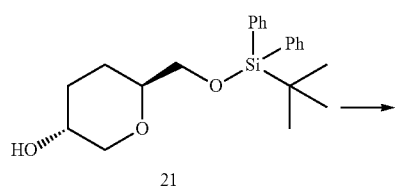

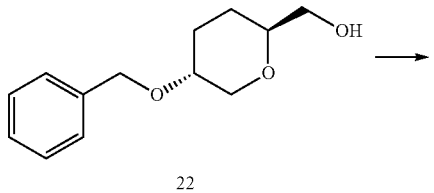

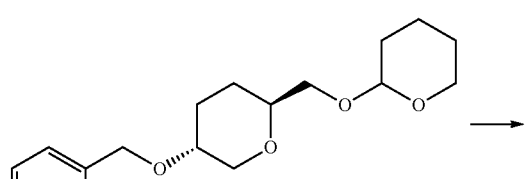

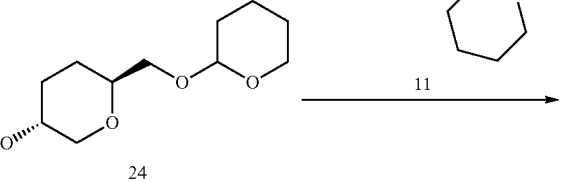

-continued

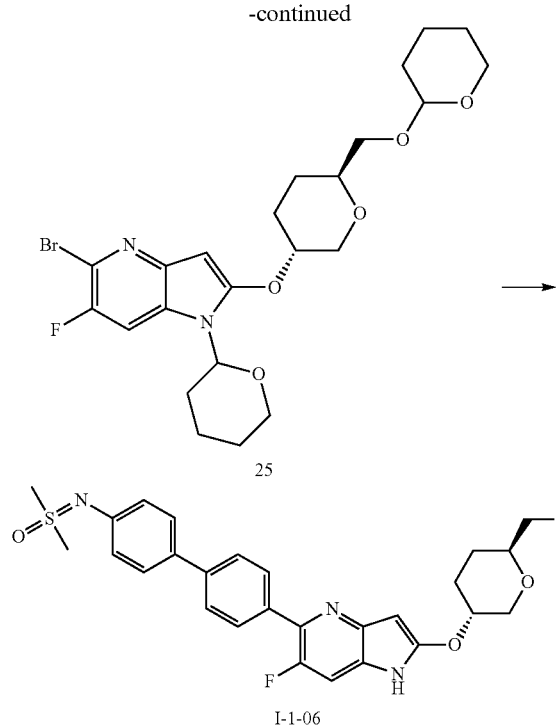

Compound 18 (11.6 g, 66.4 mmol; J. Org. Chem. 1998, 63, 8133 to 8144) was dissolved in methylene chloride (116 mL), and tert-butyldiphenylsilyl chloride (20.5 ml, 80 mmol) and imidazole (6.8 g, 100 mmol) were added thereto, then the mixture was stirred at room temperature for 3 hours. To the reaction mixture was added water, and the mixture was extracted with ethyl acetate. The organic layer was washed with 1 mol/L hydrochloric acid and saturated aqueous NaCl, and dried over anhydrous sodium sulfate. The solvent was removed under reduced pressure to obtain a crude product. The obtained crude product was dissolved in tetrahydrofuran (116 mL) and methanol (58 mL), and 2 mol/L sodium hydroxide (100 mL) was added thereto. The reaction mixture was stirred at room temperature for 2 hours. To the reaction mixture was added water, and the mixture was extracted with ethyl acetate. The organic layer was washed with saturated aqueous NaCl, and dried over anhydrous sodium sulfate. The obtained residue was purified by silica gel column chromatography (hexane-ethyl acetate) to obtain Compound 19 (17.3 g, yield 70%).

Compound 19; $^1$H-NMR (CDCl$_3$) δ: 1.06 (s, 9H), 1.56 (m, 1H), 1.64-1.73 (m, 2H), 1.94 (m, 1H), 2.14 (d, J=8.4 Hz, 1H), 3.45 (m, 1H), 3.57 (d, J=12.0 Hz, 1H), 3.59 (dd, J=5.6, 10.4 Hz, 1H), 3.72 (dd, J=5.6, 10.8 Hz, 1H), 3.75 (m, 1H), 3.85 (ddd, J=2.4, 2.4, 12.0 Hz, 1H), 7.44-7.35 (m, 6H), 7.69-7.65 (m, 4H).

Oxalyl chloride (2.5 g, 16 mmol) was dissolved in methylene chloride (100 mL), and dimethyl sulfoxide (5.4 ml, 76 mmol) was added thereto at −78° C., then the mixture was stirred for 1 hour. A methylene chloride solution (20 mL) of Compound 19 (7.0 g, 18.9 mmol) was added thereto, and then the mixture was stirred for 2 hours. To the reaction mixture was added triethylamine (21 ml, 151 mmol), and then the mixture was stirred at room temperature for 1 hour. To the reaction mixture was added saturated aqueous sodium bicarbonate, and the mixture was extracted with ethyl acetate. The organic layer was washed with water and saturated aqueous NaCl, and dried over anhydrous sodium sulfate. The obtained residue was purified by silica gel column chromatography (hexane-ethyl acetate) to obtain Compound 20 (13.1 g, yield 94%).

Compound 20; $^1$H-NMR (CDCl$_3$) δ: 1.07 (s, 9H), 1.95 (m, 1H), 2.10 (m, 1H), 2.47 (ddd, J=6.8, 10.8, 16.8 Hz, 1H), 2.60 (ddd, J=4.8, 4.8, 16.8 Hz, 1H), 3.69 (m, 1H), 3.79 (m, 1H), 3.81 (m, 1H), 3.94 (d, J=16.8 Hz, 1H), 4.14 (d, J=16.8 Hz, 1H), 7.46-7.36 (m, 6H), 7.69-7.66 (m, 4H).

Compound 20 (8.0 g, 21.7 mmol) was diluted with diethyl ether (240 mL), and lithium aluminum hydride (0.99 g, 26 mmol) was added thereto, then the mixture was stirred at 0° C. for 0.5 hours. To the reaction mixture was added water (2.97 mL) and 2 mol/L sodium hydroxide (0.99 mL), and the mixture was stirred at room temperature for 1 hour. To the reaction mixture was added anhydrous sodium sulfate (30 g), and the mixture was filtered. The obtained filtrate was concentrated under reduced pressure and purified by silica gel column chromatography (hexane-ethyl acetate) to obtain Compound 21 (8.0 g, yield 99.5%).

Compound 21; $^1$H-NMR (CDCl$_3$) δ: 1.05 (s, 9H), 1.36-1.42 (m, 2H), 1.83 (m, 1H), 2.13 (m, 1H), 3.09 (dd, J=10.4, 10.4 Hz, 1H), 3.36 (m, 1H), 3.57 (dd, J=5.6, 10.4 Hz, 1H), 3.68 (m, 1H), 3.72 (dd, J=5.6, 10.4 Hz, 1H), 4.00 (ddd, J=2.0, 4.8, 10.4 Hz, 1H), 7.44-7.35 (m, 6H), 7.69-7.64 (m, 4H).

Compound 21 (12.5 g, 33.7 mmol) was dissolved in DMF (125 mL), and benzyl bromide (4.81 ml, 40.5 mmol) and sodium hydride (2.0 g, 50.6 mmol) were added thereto at 0° C., then the mixture was stirred at room temperature for 2 hours. To the reaction mixture was added water, and the mixture was extracted with ethyl acetate. The organic layer was washed with hydrochloric acid and saturated aqueous NaCl, and dried over anhydrous sodium sulfate. The solvent was removed under reduced pressure to obtain a crude product. The obtained crude product was dissolved in THF (125 mL), and 1 mol/L tetrabutylammonium fluoride (50.6 mL, 50.6 mmol) was added thereto, then the mixture was stirred for 1 hour. The reaction mixture was concentrated under reduced pressure, and the residue was purified by silica gel column chromatography (hexane-ethyl acetate) to obtain Compound 22 (6.84 g, yield 88%).

Compound 22; $^1$H-NMR (CDCl$_3$) δ: 1.32-1.53 (m, 2H), 1.64 (m, 1H), 2.23 (m, 1H), 3.22 (dd, J=10.4, 10.4 Hz, 1H), 3.36-3.52 (m, 3H), 3.60 (d, J=11.2 Hz, 1H), 4.11 (ddd, J=2.0, 4.4, 10.8 Hz, 1H), 4.54 (d, J=11.6 Hz, 1H), 4.60 (d, J=11.6 Hz, 1H), 7.37-7.27 (m, 5H).

To Compound 22 (310 mg, 1.395 mmol) and 3,4-dihydro-2H-pyran (235 mg, 2.79 mmol) was added dichloromethane (3 ml), and the mixture was stirred under ice-cooling. To the reaction mixture was added pyridinium p-toluenesulfonate (17.5 mg, 0.070 mmol), and the mixture was stirred at room temperature. After completion of the reaction, saturated aqueous sodium bicarbonate was added thereto, and the mixture was extracted with ethyl acetate. The obtained organic layer was concentrated under reduced pressure, and purified by silica gel column chromatography to obtain crude product 23 (420 mg, 85%). Crude product 23 (364 mg, 1.188 mmol) was dissolved in methanol (1.5 ml) and tetrahydrofuran (1.5 ml), and 50% wet palladium hydroxide (100 mg, 0.712 mmol) was added thereto. The reaction mixture was stirred at room temperature for 2 hours, under hydrogen atmosphere. The reaction mixture was filtered, concentrated under reduced pressure, and purified by silica gel column chromatography to obtain crude product 24 (57 mg, 22%).

Compound 25 was synthesized from Compound 24, in a similar way that Compound 12 was synthesized from Compound 9.

Compound 25; Method A
LC/MS retention time=2.66 min.
MS (ESI) m/z=513.1 (M+H)+.

Compound (I-1-06) was synthesized from Compound 25, in a similar way that Compound (I-1-01) was synthesized from Compound 5.

Compound (I-1-06); Method A
LC/MS retention time=1.26 min.
MS (ESI) m/z=510.2 (M+H)+.

EXAMPLE 7

[Chemical formula 48]

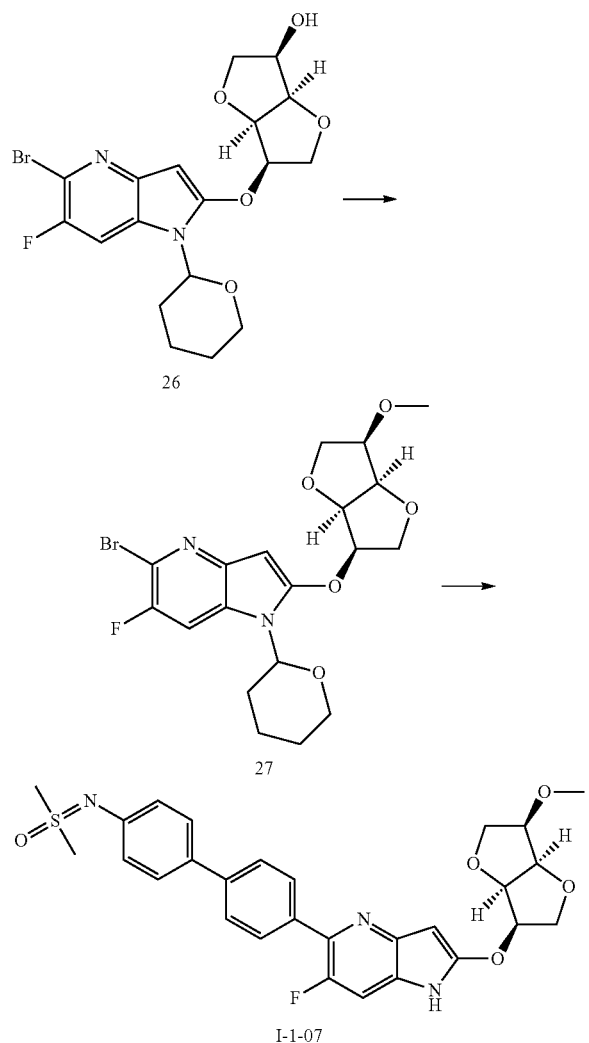

I-1-07

Compound 26 (150 mg, 0.338 mmol) was dissolved in DMF (0.5 ml), then 60 wt % sodium hydride (16.2 mg, 0.406 mmol) and methyl iodide (57.6 mg, 0.406 mmol) were added thereto under ice-cooling, and the mixture was stirred at room temperature. After completion of the reaction, the resulting mixture was purified by silica gel column chromatography to obtain Compound 27 (124 mg, 80.1%).

Compound 27; Method B
LC/MS retention time=1.99 min.
MS (ESI) m/z=457.15 (M+H)+.

Compound (I-1-07) was synthesized from Compound 27, in a similar way that Compound (I-1-01) was synthesized from Compound 5.

Compound (I-1-07); Method B
LC/MS retention time=1.17 min.
MS (ESI) m/z=538.35 (M+H)+.

EXAMPLE 8

[Chemical formula 49]

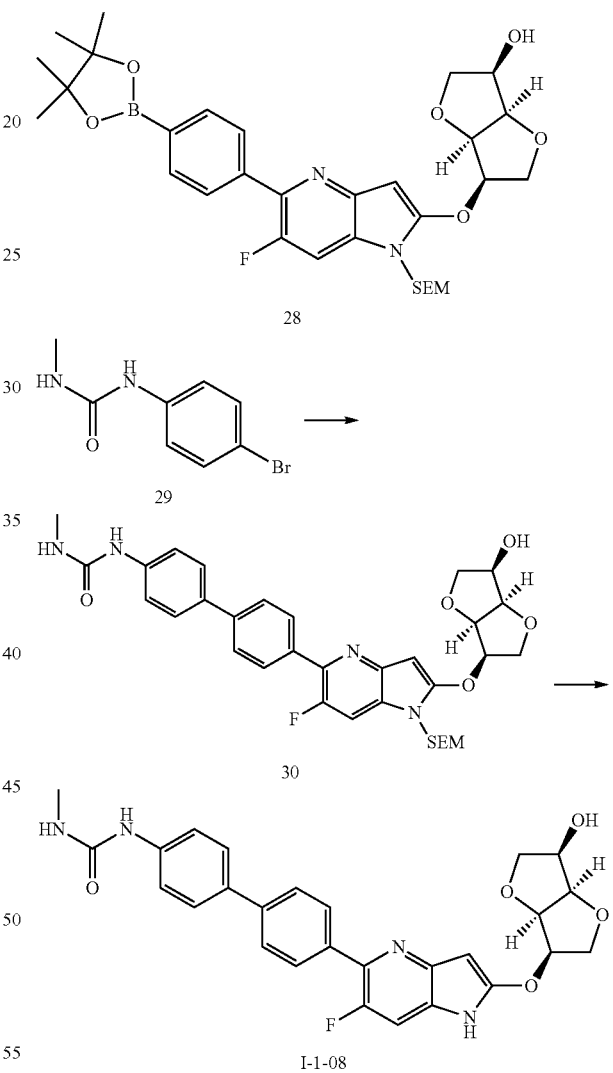

I-1-08

Compound 28 (80 mg, 0.131 mmol) was dissolved in 1,4-dioxane (1 ml), Compound 29 (35.9 mg, 0.157 mmol) was added thereto, and the solution was heated to 80° C. under nitrogen atmosphere, then PdCl$_2$(dtbpf) (17.02 mg, 0.026 mmol) and a 2 mol/L aqueous solution of potassium carbonate (0.131 ml, 0.261 mmol) were added thereto, and the mixture was stirred at 80° C. After completion of the reaction, the resulting mixture was purified by silica gel column chromatography to obtain Compound 30 (82.3 mg, 99.3%).

Compound 30; Method B

LC/MS retention time=2.05 min.

MS (ESI) m/z=635.45 (M+H)+.

Compound (I-1-08) was synthesized from Compound 30, in a similar way that Compound (I-1-01) was synthesized from Compound 7.

Compound (I-1-08); Method B

LC/MS retention time=1.13 min.

MS (ESI) m/z=505.30 (M+H)+.

EXAMPLE 9

[Chemical formula 50]

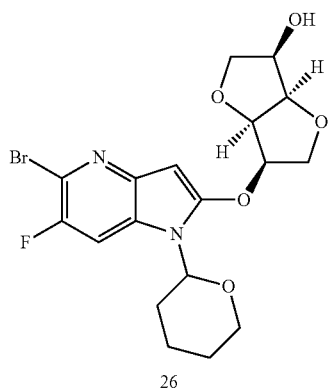

26

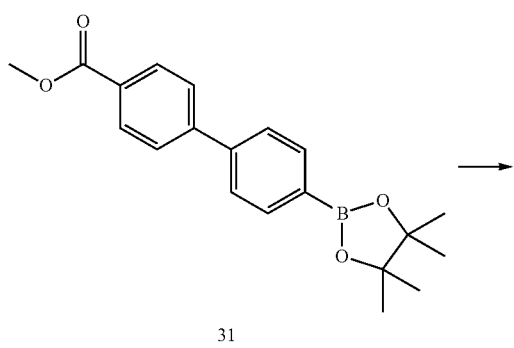

31

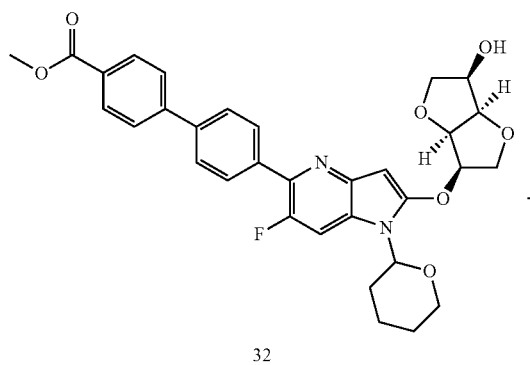

32

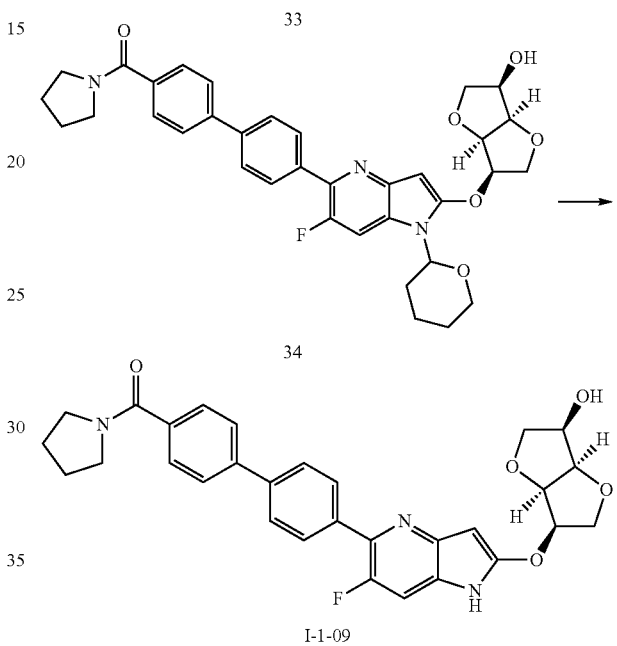

33

34

I-1-09

Compound 26 (7.00 g, 15.79 mmol) and Compound 31 (4.85 g, 18.95 mmol) were dissolved in DMF (60 ml), and the solution was heated to 100° C. under nitrogen atmosphere, then PdCl$_2$(dtbpf) (1.029 g, 1.579 mmol) and a 2 mol/L aqueous solution of potassium carbonate (13.42 ml, 26.8 mmol) were added thereto, and the mixture was stirred at 100° C. After completion of the reaction, the resulting mixture was concentrated under reduced pressure, ethyl acetate was added thereto, and the mixture was washed with water. The obtained organic layer was dried over magnesium sulfate and filtered, then concentrated under reduced pressure. The obtained residue was purified by silica gel column chromatography to obtain Compound 32 (6.85 g, 75.5%).

Compound 32; Method A

LC/MS retention time=2.47 min.

MS (ESI) m/z=575.2 (M+H)+.

Compound 32 (6.849 g, 11.92 mmol) was dissolved in methanol (40 ml), then a 2 mol/L aqueous sodium hydroxide solution (13.11 ml, 26.2 mmol) was added thereto, and the mixture was stirred at room temperature. After completion of the reaction, a 2 mol/L aqueous solution of hydrochloric acid (13.11 ml, 26.2 mmol) was added, and the precipitated solid was separated by filtration, dissolved in a mixed solution of chloroform and methanol, and washed with saturated aqueous NaCl. The obtained organic layer was dried over magnesium sulfate, filtered, and concentrated under reduced pressure to obtain Compound 33 (5.90 g, 88.3%).

Compound 33; Method A

LC/MS retention time=1.77 min.

MS (ESI) m/z=561.5 (M+H)+.

Compound 33 (55 mg, 0.098 mmol) was dissolved in DMF (1 ml), and pyrrolidine (12.29 μl, 0.147 mmol) and triethylamine (20.4 μl, 0.147 mmol) were added thereto. HATU (44.8 mg, 0.118 mmol) was added thereto under ice-cooling, and the mixture was stirred at room temperature. After completion of the reaction, ethyl acetate was added thereto, and the mixture was washed with an aqueous solution of hydrochloric acid and water. The obtained organic layer was dried over magnesium sulfate and filtered, then concentrated under reduced pressure. The obtained residue was purified by silica gel column chromatography to obtain Compound 34.

Compound 34; Method B
  LC/MS retention time=1.90 min.
  MS (ESI) m/z=614.40 (M+H)+.
  Compound (I-1-09) was synthesized from Compound 34, in a similar way that Compound (I-1-01) was synthesized from Compound 7.
Compound (I-1-09); Method B
  LC/MS retention time=1.35 min.
  MS (ESI) m/z=530.35 (M+H)+.

EXAMPLE 10

[Chemical formula 51]

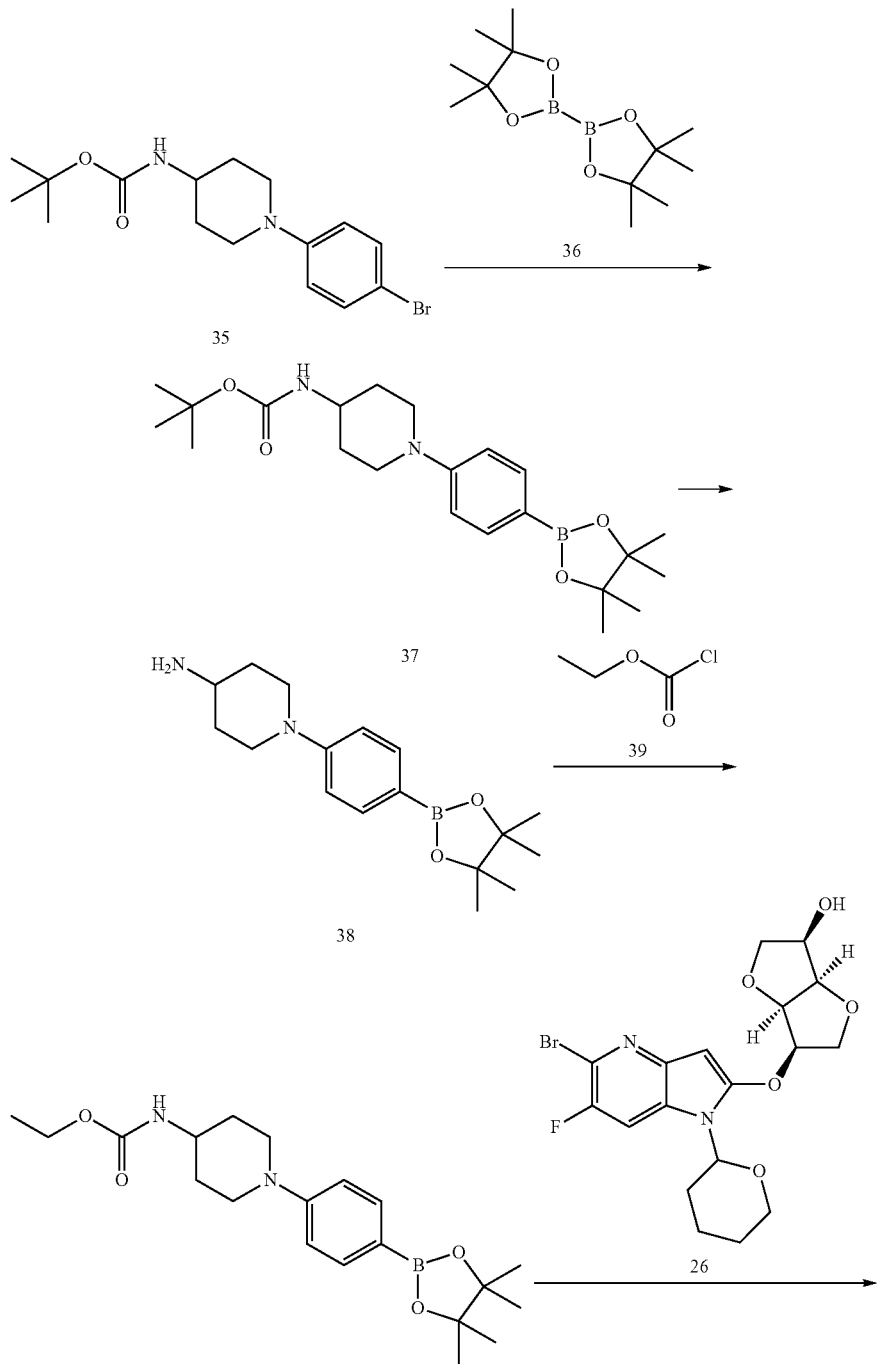

-continued

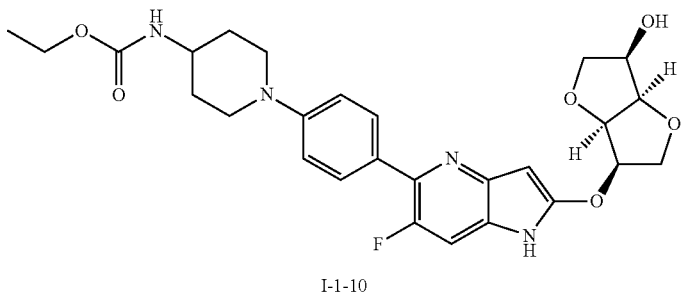

I-1-10

Compound 35 (3.46 g, 9.82 mmol) was dissolved in 1,4-dioxane (70 ml), and PdCl$_2$(dppf)CH$_2$Cl$_2$ (0.802 g, 0.982 mmol), Compound 36 (2.99 g, 11.79 mmol) and potassium acetate (2.89 g, 29.5 mmol) were added thereto, then the mixture was stirred at 80° C. PdCl$_2$(dppf)CH$_2$Cl$_2$ (0.802 g, 0.982 mmol) was added thereto in the middle of the reaction, and the mixture was further stirred at 80° C. The reaction mixture was filtered with celite, and the filtrate was concentrated under reduced pressure. The obtained residue was purified by silica gel column chromatography to obtain Compound 37 (3.43 g, 86.8%).

Compound 37 (130 mg, 0.323 mmol) was dissolved in chloroform (3 ml), and TFA (0.5 ml) was added thereto, then the mixture was stirred at room temperature. After completion of the reaction, the resulting mixture was concentrated under reduced pressure, and the residue was diluted with chloroform. The diluted mixture was neutralized with a saturated aqueous solution of sodium hydrogen carbonate, and the resulting mixture was extracted with chloroform. The obtained organic layer was dried over magnesium sulfate, filtered, and concentrated under reduced pressure to obtain Compound 38 (83.2 mg, 85.2%).
Compound 38; Method B
  LC/MS retention time=1.27 min.
  MS (ESI) m/z=303.25 (M+H)+.

Compound 38 (83 mg, 0.275 mmol) was dissolved in THF (1 ml), and pyridine (33.3 µl, 0.412 mmol) and Compound 39 (31.4 µl, 0.330 mmol) were added thereto, then the mixture was stirred at room temperature. Furthermore, pyridine (99.9 µl, 1.236 mmol), Compound 39 (94.2 µl, 0.990 mmol) and THF (0.5 ml) were added thereto, and the mixture was stirred at room temperature. To the reaction mixture was added ethyl acetate, and the mixture was washed with an aqueous solution of hydrochloric acid, water and a saturated aqueous solution of sodium chloride. The obtained organic layer was dried over magnesium sulfate, filtered, and concentrated under reduced pressure to obtain Compound 40 (58.0 mg, 56.4%).
Compound 40; Method B
  LC/MS retention time=2.27 min.
  MS (ESI) m/z=375.10 (M+H)+.

Compound (I-1-10) was synthesized from Compound 40, in a similar way that Compound (I-1-01) was synthesized from Compound 6.
Compound (I-1-10); Method B
  LC/MS retention time=1.21 min.
  MS (ESI) m/z=527.4 (M+H)+.

EXAMPLE 11

[Chemical formula 52]

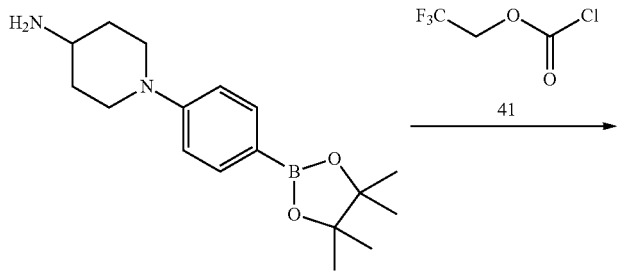

-continued

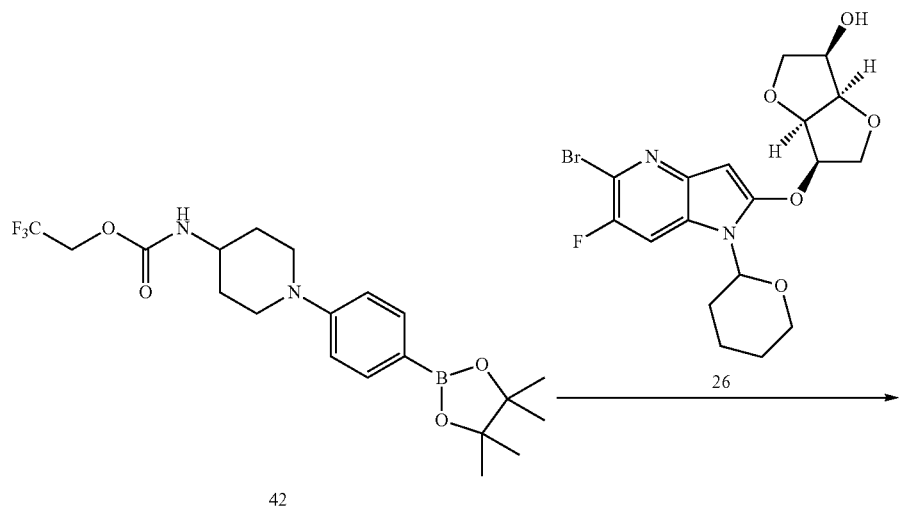

42

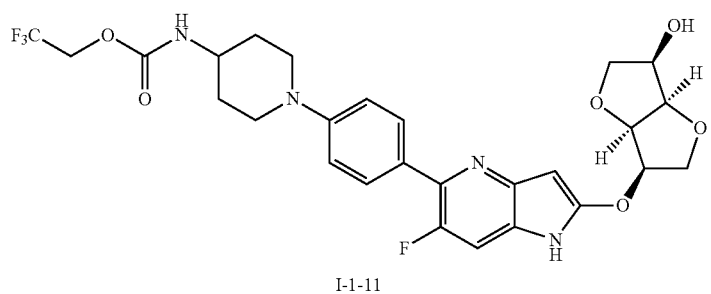

I-1-11

Compound 38 (0.040 g, 0.132 mmol) was dissolved in THF (0.5 ml), and pyridine (21.37 μl, 0.265 mmol) and Compound 41 (32.3 mg, 0.199 mmol) were added thereto, then the mixture was stirred at room temperature. To the reaction mixture was added ethyl acetate, and the mixture was washed with an aqueous solution of hydrochloric acid, water and a saturated aqueous solution of sodium chloride. The obtained organic layer was dried over magnesium sulfate, filtered, and concentrated under reduced pressure to obtain Compound 42 (46.5 mg, 82.0%).

Compound 42; Method B
LC/MS retention time=2.48 min.
MS (ESI) m/z=429.40 (M+H)+.

Compound (I-1-11) was synthesized from Compound 42, in a similar way that Compound (I-1-01) was synthesized from Compound 6.

Compound (I-1-11); Method B
LC/MS retention time=1.40 min.
MS (ESI) m/z=581.35 (M+H)+.

EXAMPLE 12

[Chemical formula 53]

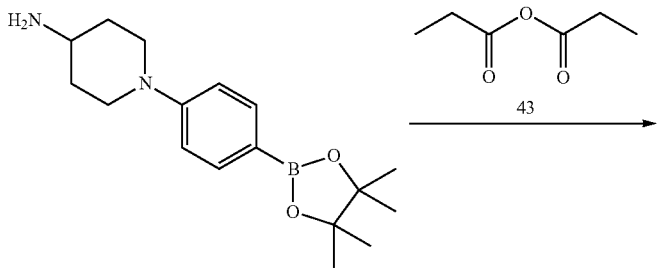

38

-continued

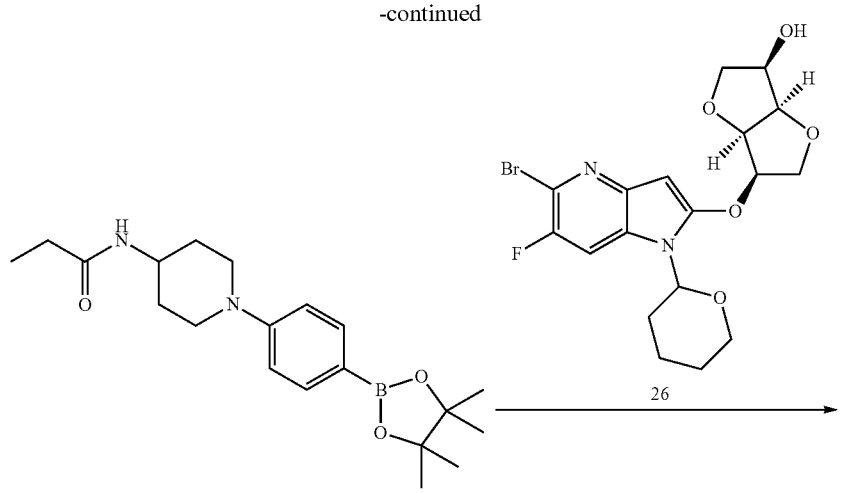

Compound 44 was synthesized from Compound 38, in a similar way that Compound 42 was synthesized from Compound 38.
Compound 44; Method B
  LC/MS retention time=1.88 min.
  MS (ESI) m/z=359.40 (M+H)+.
Compound (I-1-12) was synthesized from Compound 44, in a similar way that Compound (I-1-01) was synthesized from Compound 6.
Compound (I-1-12); Method B
  LC/MS retention time=0.97 min.
  MS (ESI) m/z=511.4 (M+H)+.

EXAMPLE 13

[Chemical formula 54]

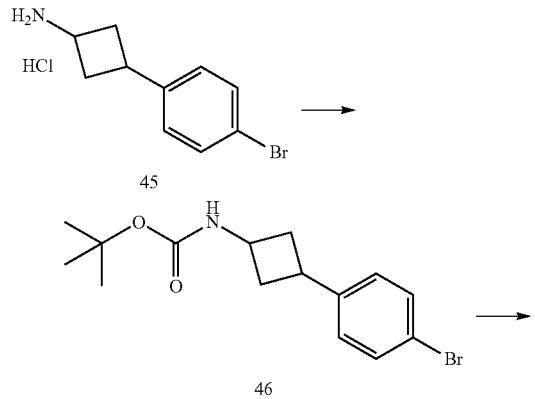

-continued

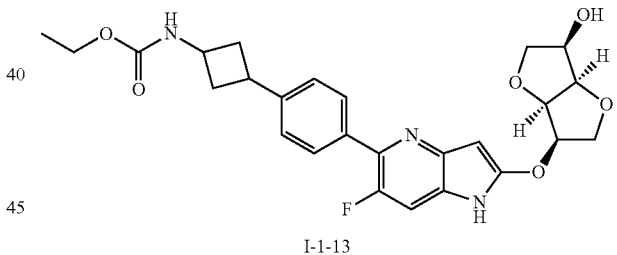

THF (1 ml) and triethylamine (106 μl, 0.762 mmol) were added to Compound 45 (100 mg, 0.381 mmol), and di-tert-butyl dicarbonate (125 mg, 0.571 mmol) was added thereto, then the mixture was stirred at room temperature. After completion of the reaction, the resulting mixture was purified by silica gel column chromatography to obtain Compound 46 (96.3 mg, 77.5%).

Compound (I-1-13) was synthesized from Compound 46, in a similar way that Compound (I-1-10) was synthesized from Compound 35.
Compound (I-1-13); Method B
  LC/MS retention time=1.23 min.
  MS (ESI) m/z=497.2 (M+H)+.

EXAMPLE 14

[Chemical formula 55]

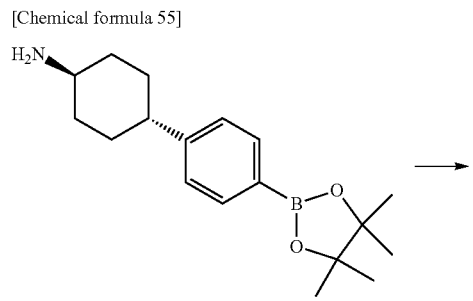

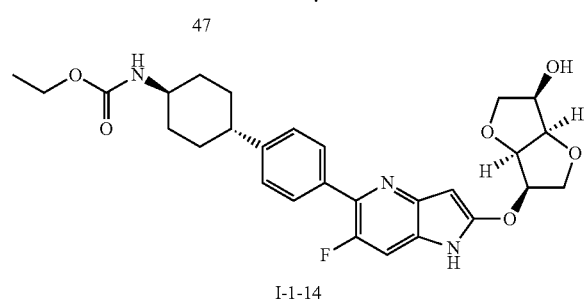

Compound (I-1-14) was synthesized from Compound 47, in a similar way that Compound (I-1-10) was synthesized from Compound 38.

Compound (I-1-14); Method B

LC/MS retention time=1.35 min.

MS (ESI) m/z=526.35 (M+H)+.

EXAMPLE 15

[Chemical formula 56]

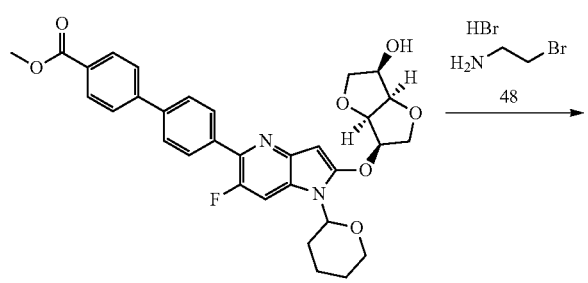

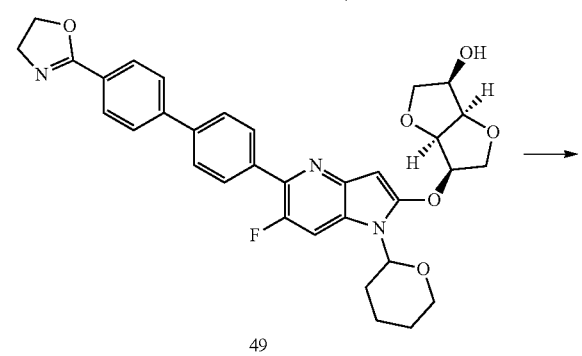

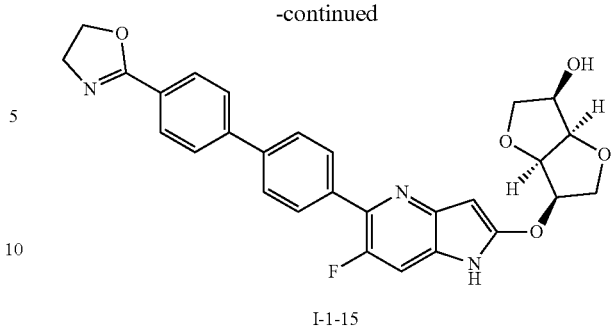

Compound 32 (92 mg, 0.147 mmol) was dissolved in a mixed solvent of THF (0.7 ml) and methanol (0.7 ml), then a 2 mol/L aqueous sodium hydroxide solution (147 μl, 0.295 mmol) was added thereto, and the mixture was stirred at room temperature. Thereafter, a 2 mol/L aqueous solution of hydrochloric acid, Compound 48 (45.3 mg, 0.221 mmol), DMT-MM (84 wt %, 72.8 mg, 0.221 mmol) and triethylamine (122 μl, 0.884 mmol) were added thereto, and the mixture was stirred at room temperature. After completion of the reaction, the resulting mixture was purified by silica gel column chromatography to obtain Compound 49 (32 mg, 39.4%). Compound (I-1-15) was synthesized from Compound 49, in a similar way that Compound (I-1-01) was synthesized from Compound 7.

Compound (I-1-15); Method B

LC/MS retention time=1.10 min.

MS (ESI) m/z=502.3 (M+H)+.

EXAMPLE 16

[Chemical formula 57]

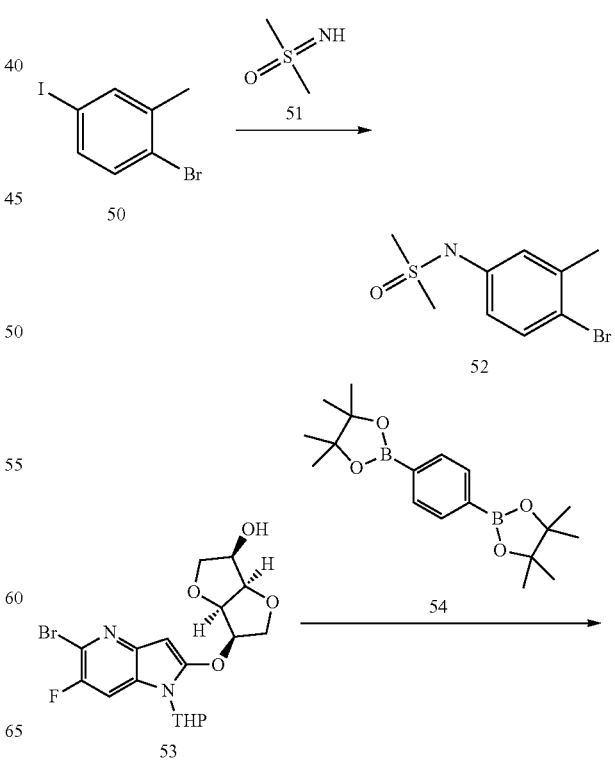

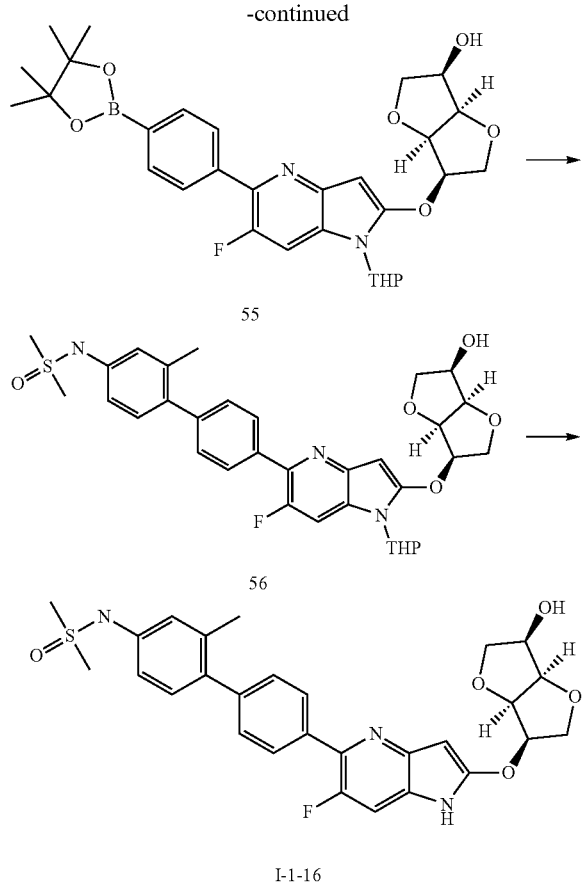

55

56

I-1-16

To Compound 50 (300 mg, 1.01 mmol), cesium carbonate (461 mg, 1.41 mmol), Compound 51 (113 mg, 1.21 mmol) and Xantphos (43.8 mg, 0.076 mmol) was added 1,4-dioxane (3 ml). Pd$_2$(dba)$_3$ (23.1 mg, 0.025 mmol) was added thereto, and the mixture was stirred at 105° C. The reaction mixture was filtered with celite, and the filtrate was concentrated under reduced pressure. The obtained residue was purified by silica gel column chromatography to obtain Compound 52 (259 mg, 98%).

Compound 52; Method A
LC/MS retention time=1.60 min.
MS (ESI) m/z=261.8 (M+H)+.

To Compound 53 (1.0 g, 2.26 mmol) and Compound 54 (2.23 g, 6.77 mmol) were added DMF (25 ml) under nitrogen atmosphere, and the mixture was heated to 100° C. Thereafter, PdCl$_2$(dtbpf) (250 mg, 0.384 mmol) and a 2 mol/L aqueous solution of potassium carbonate (2.26 ml, 4.51 mmol) were added thereto, and the mixture was stirred at 100° C. After completion of the reaction, water was added thereto, and the mixture was extracted with ethyl acetate. The organic layer was dried over magnesium sulfate, and concentrated under reduced pressure. The obtained residue was purified by silica gel column chromatography to obtain Compound 55 (510 mg, 40%).

Compound 55; Method A
LC/MS retention time=2.30 min.
MS (ESI) m/z=567.5 (M+H)+.

Compound 55 (250 mg, 0.441 mmol) was dissolved in 1,4-dioxane (2.5 ml), and Compound 52 (139 mg, 0.530 mmol), a 2 mol/L aqueous solution of potassium carbonate (0.441 ml, 0.883 mmol) and PdCl$_2$(dtbpf) (57.5 mg, 0.088 mmol) were added thereto, and the mixture was stirred at 80° C. under nitrogen atmosphere. After completion of the reaction, the resulting mixture was purified by silica gel column chromatography to obtain Compound 56 (170 mg, 62%).

Compound 56; Method A
LC/MS retention time=1.73 min.
MS (ESI) m/z=622.2 (M+H)+.

Compound (I-1-16) was synthesized from Compound 56, in a similar way that Compound (I-1-01) was synthesized from Compound 7.

Compound (I-1-16); Method A
LC/MS retention time=1.22 min.
MS (ESI) m/z=538.2 (M+H)+.

EXAMPLE 17

[Chemical formula 58]

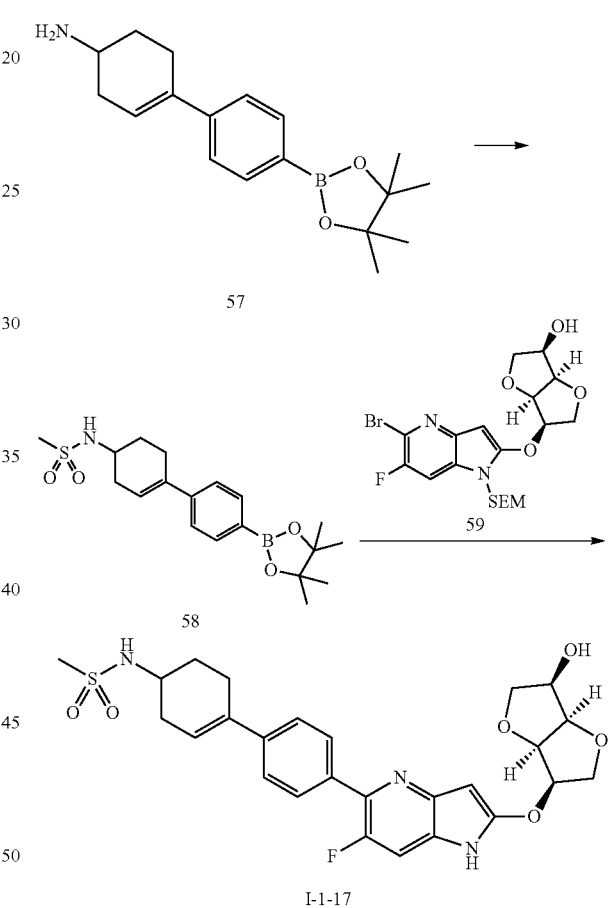

57

58

59

I-1-17

Compound 57 (250 mg, 0.836 mmol) was dissolved in THF (2.5 ml), and the mixture was stirred at 0° C. Methanesulfonyl chloride (97 μl, 1.253 mmol), pyridine (101 μl, 1.253 mmol) and trimethylamine hydrochloride (4 mg, 0.042 mmol) were added thereto, and the mixture was stirred at room temperature. After completion of the reaction, a saturated aqueous solution of ammonium chloride was added thereto, and the mixture was extracted with ethyl acetate. The organic layer was dried over magnesium sulfate, and concentrated under reduced pressure. The obtained residue was purified by silica gel column chromatography to obtain Compound 58 (139 mg, 44%).

Compound 58; Method A
LC/MS retention time=2.32 min.
MS (ESI) m/z=378.3 (M+H)+.

Compound (I-1-17) was synthesized from Compound 58, in a similar way that Compound (I-1-01) was synthesized from Compound 6.
Compound (I-1-17); Method A
  LC/MS retention time=1.26 min.
  MS (ESI) m/z=530.3 (M+H)+.

EXAMPLE 18

Compound 62; Method A

LC/MS retention time=2.02 min.
  MS (ESI) m/z=310.1 (M+H)+.

Compound (I-1-18) was synthesized from Compound 62, in a similar way that Compound (I-1-08) was synthesized from Compound 29.

[Chemical formula 59]

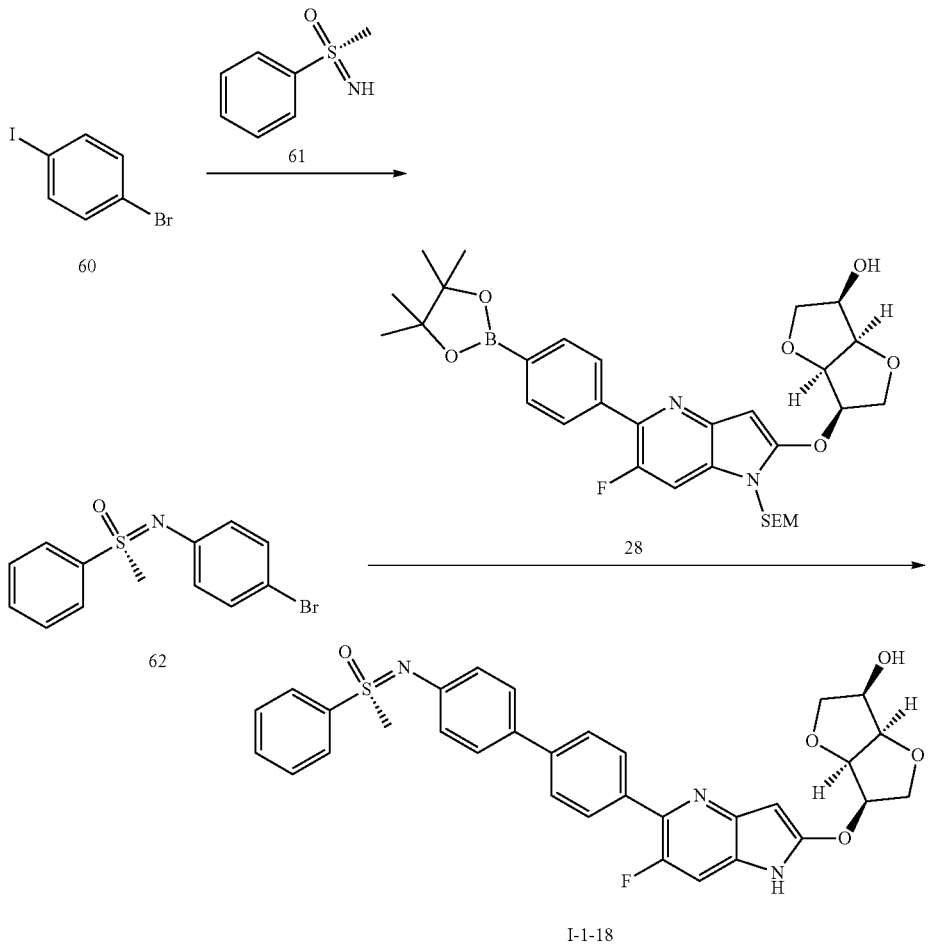

Compound 62 was synthesized from Compound 60, in a similar way that Compound 52 was synthesized from Compound 50.

Compound (I-1-18); Method A
  LC/MS retention time=1.57 min.
  MS (ESI) m/z=586.3 (M+H)+.

EXAMPLE 19

[Chemical formula 60]

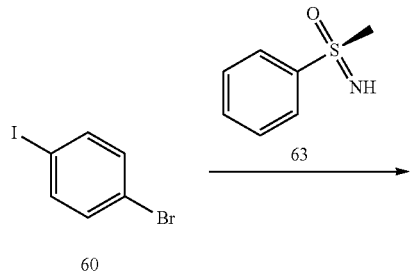

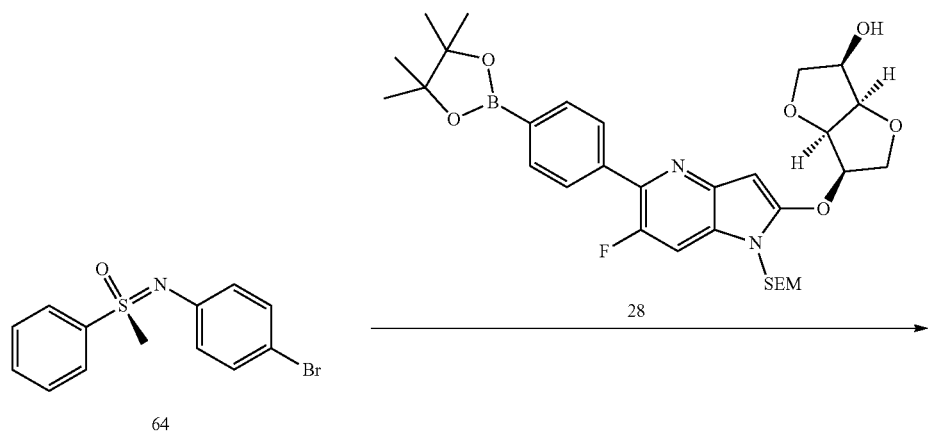
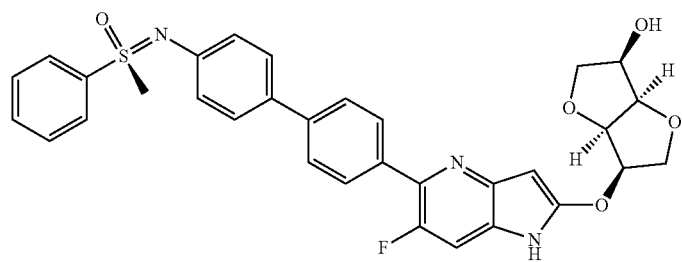
I-1-19
Compound 64 was synthesized from Compound 60, in a similar way that Compound 52 was synthesized from Compound 50.
Compound 64; Method A
LC/MS retention time=2.02 min.
MS (ESI) m/z=310.1 (M+H)+.
Compound (I-1-19) was synthesized from Compound 64, in a similar way that Compound (I-1-08) was synthesized from Compound 29.
Compound (I-1-19); Method A
LC/MS retention time=1.58 min.
MS (ESI) m/z=586.3 (M+H)+.
EXAMPLE 20
[Chemical formula 61]
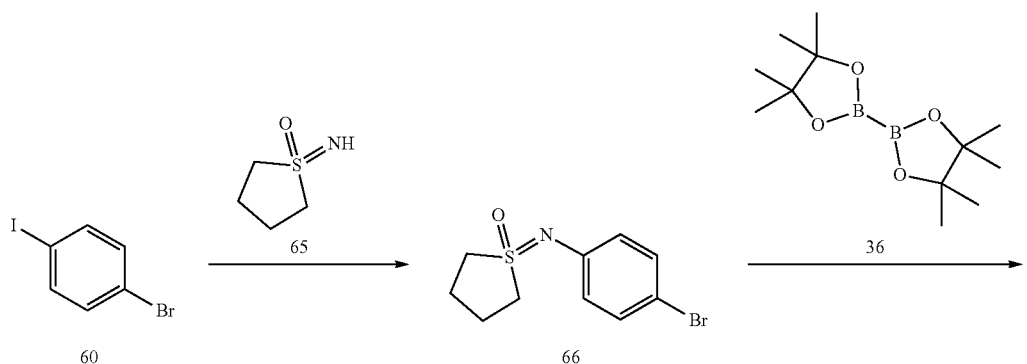

-continued

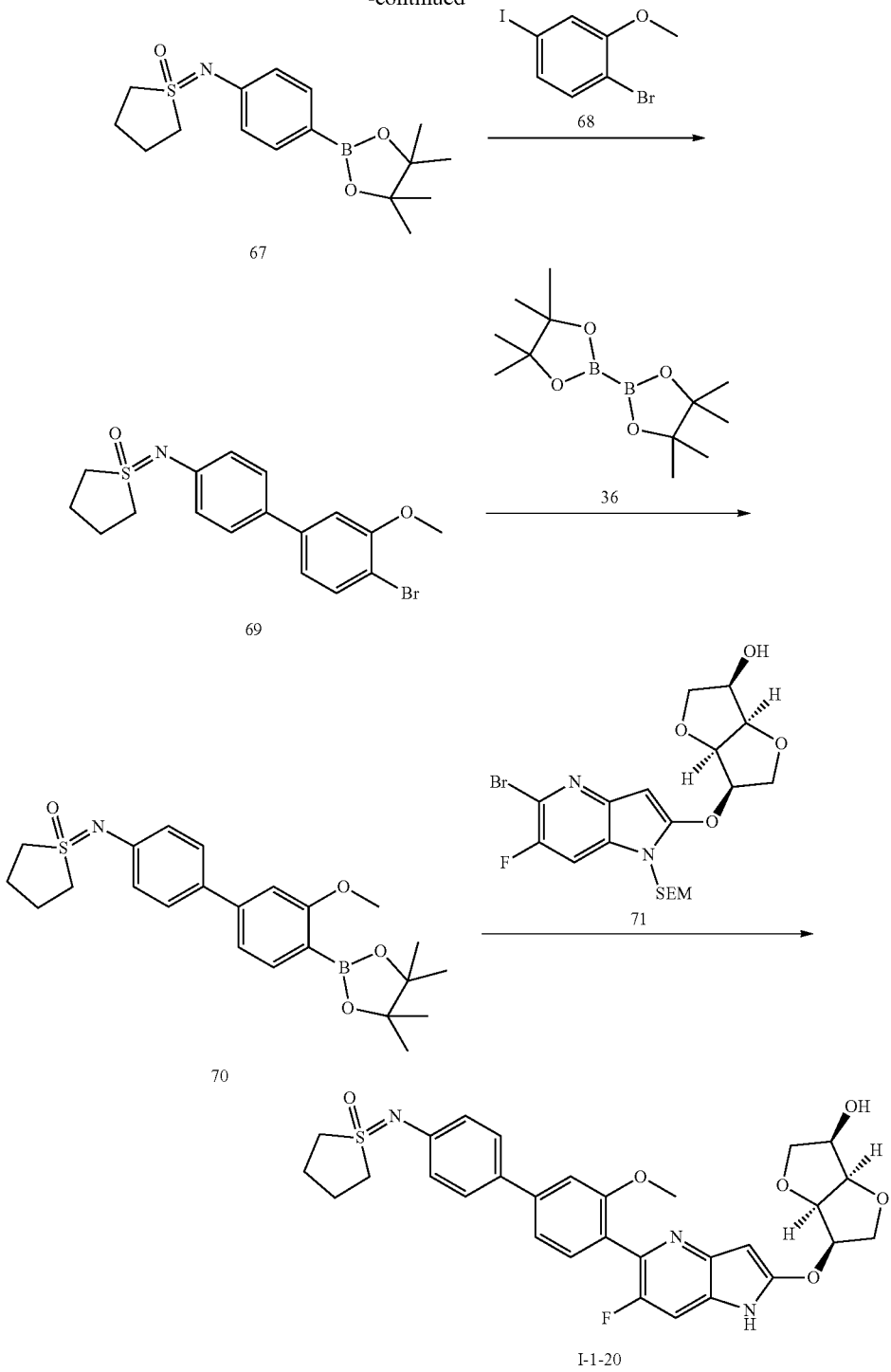

Compound 66 was synthesized from Compound 60, in a similar way that Compound 52 was synthesized from Compound 50.
Compound 66; Method A
LC/MS retention time=1.64 min.
MS (ESI) m/z=273.8 (M+H)+.

Compound 67 was synthesized from Compound 66, in a similar way that Compound 37 was synthesized from Compound 35.

Compound 67; Method A
LC/MS retention time=1.86 min.
MS (ESI) m/z=321.3 (M+H)+.

Compound 67 (120 mg, 0.374 mmol) was dissolved in 1,4-dioxane (1 ml), and Compound 68 (164 mg, 0.523 mmol), a 2 mol/L aqueous solution of potassium carbonate (0.374 ml, 0.747 mmol) and PdCl$_2$(dtbpf) (48.7 mg, 0.075 mmol) were added thereto, and the mixture was stirred 80° C. under nitrogen atmosphere. After completion of the reaction, the resulting mixture was purified by silica gel column chromatography to obtain Compound 69 (56 mg, 39%).

Compound 69; Method A
  LC/MS retention time=2.17 min.
  MS (ESI) m/z=380.1 (M+H)+.

Compound 70 was synthesized from Compound 69, in a similar way that Compound 35 was synthesized from Compound 37.

Compound 70; Method A
  LC/MS retention time=2.19 min.
  MS (ESI) m/z=428.1 (M+H)+.

Compound (I-1-20) was synthesized from Compound 70, in a similar way that Compound (I-1-01) was synthesized from Compound 6.

Compound (I-1-20); Method A
  LC/MS retention time=1.25 min.
  MS (ESI) m/z=580.3 (M+H)+.

EXAMPLE 21

[Chemical formula 62]

Compound 73 was synthesized from Compound 60, in a similar way that Compound 52 was synthesized from Compound 50.

Compound 73; Method A
  LC/MS retention time=1.58 min.
  MS (ESI) m/z=290.0 (M+H)+.

EXAMPLE 22

[Chemical formula 63]

Compound 74 (600 mg, 1.704 mmol) was dissolved in THF (1 ml), and the mixture was stirred at 0° C. Pyridine (550 μl, 6.82 mmol), methyl chloroformate (262 μl, 3.41 mmol) and trimethylamine hydrochloride (4 mg, 0.043 mmol) were added thereto, and the mixture was stirred at room temperature. After completion of the reaction, a saturated aqueous solution of ammonium chloride was added thereto, and the mixture was extracted with chloroform. The organic layer was dried over magnesium sulfate, and concentrated under reduced pressure. The obtained residue was purified by silica gel column chromatography to obtain Compound 75 (361 mg, 64%).

Compound 75; Method A
  LC/MS retention time=2.32 min.
  MS (ESI) m/z=296.0 (M+H)+.

Compound 76 was synthesized from Compound 75, in a similar way that Compound 37 was synthesized from Compound 35.

Compound 76; Method A
  LC/MS retention time=2.52 min.
  MS (ESI) m/z=344.2 (M+H)+.

EXAMPLE 23

[Chemical formula 64]

95
-continued
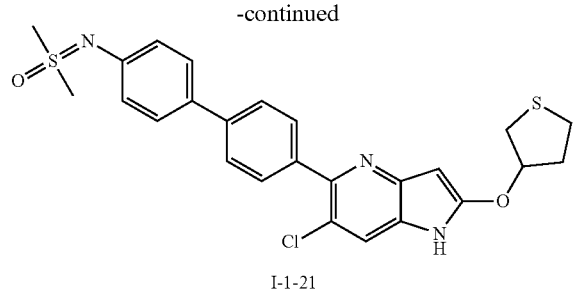
I-1-21
96
Compound 78 was synthesized from Compound 77, in a similar way that Compound 10 was synthesized from Compound 9.
Compound 78; Method B
LC/MS retention time=2.94 min.
MS (ESI) m/z=419.20 (M+H)+.
EXAMPLE 24
[Chemical formula 65]
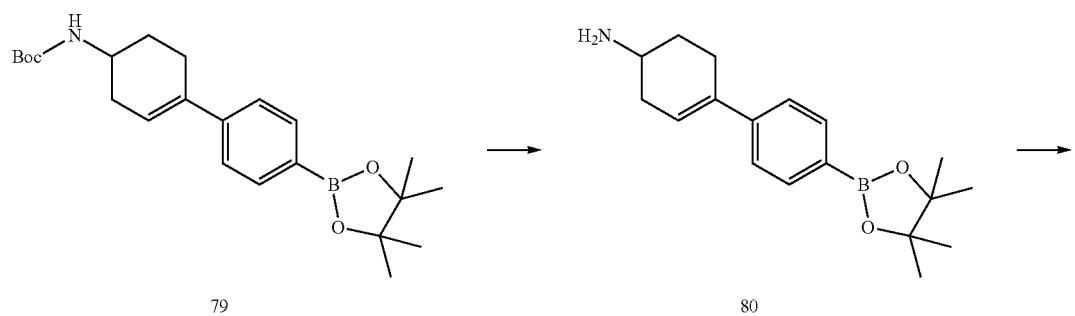
79                                                              80
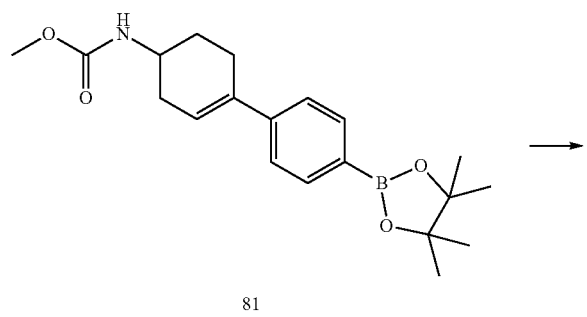
81
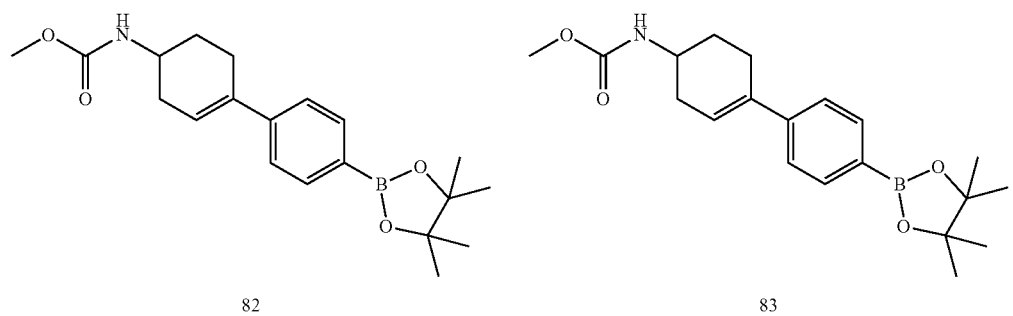
82                                                              83

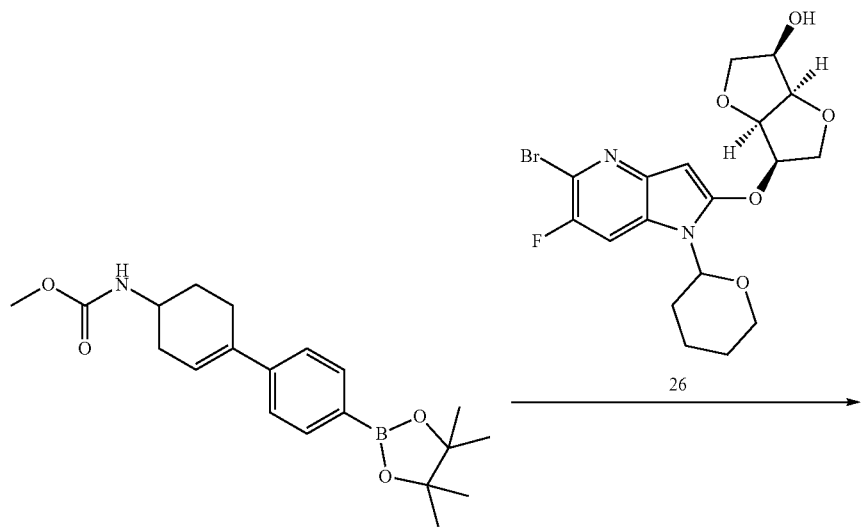

26

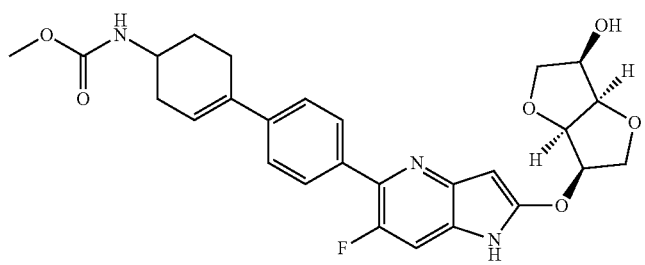

I-1-22

To Compound 79 (3.0 g, 7.51 mmol) were added dichloromethane (12 ml) and TFA (11.58 ml, 150 mmol), and the mixture was stirred at room temperature. After completion of the reaction, TFA was removed by concentration under reduced pressure. The obtained residue was dissolved in chloroform, and the solution was neutralized with saturated aqueous sodium bicarbonate. The obtained organic layer was dried over magnesium sulfate, and then the solvent was removed by concentration under reduced pressure to obtain Compound 80.

Compound 80; Method A
  LC/MS retention time=1.51 min.
  MS (ESI) m/z=300.5 (M+H)+.

Compound 80 (1.0 g, 3.34 mmol) was dissolved in THF (15 ml), methyl chloroformate (0.513 ml, 6.68 mmol) and pyridine (0.540 ml, 6.68 mmol) were added thereto under ice-cooling, and the mixture was stirred at room temperature. To the reaction mixture was added water, and the mixture was extracted with chloroform. The obtained organic layer was washed with saturated aqueous NaCl, dried over magnesium sulfate and filtered. The obtained filtrate was concentrated under reduced pressure, and purified by silica gel column chromatography to obtain Compound 81.

Compound 81; Method A
  LC/MS retention time=2.49 min.
  MS (ESI) m/z=358.3 (M+H)+.

Compound 81 was separated by SFC under the following conditions.
  Instrument: SemiPrep SFC (semipreparative supercritical fluid chromatograph)
  Column: Two CHIRALPAK IF/SFC (5 μm, i.d. 20×250 mm) (DAICEL) are used in series
  Flow rate: 40 mL/min
  UV detection wavelength: 220 nm
  Back pressure: 8 MPa
  Analysis conditions: A liquid was sent for 32 minutes, while maintaining a composition rate of MeOH/CO2=25/75.
  Elution time: The first peak at 15.2 minutes (Compound 82), and the second peak at 19.3 minutes (Compound 83)

Compound (I-1-22) was synthesized from Compound 82, in a similar way that Compound (I-1-01) was synthesized from Compound 6.

Compound (I-1-22); Method A
  LC/MS retention time=1.38 min.
  MS (ESI) m/z=510.3 (M+H)+.

EXAMPLE 25
[Chemical formula 66]
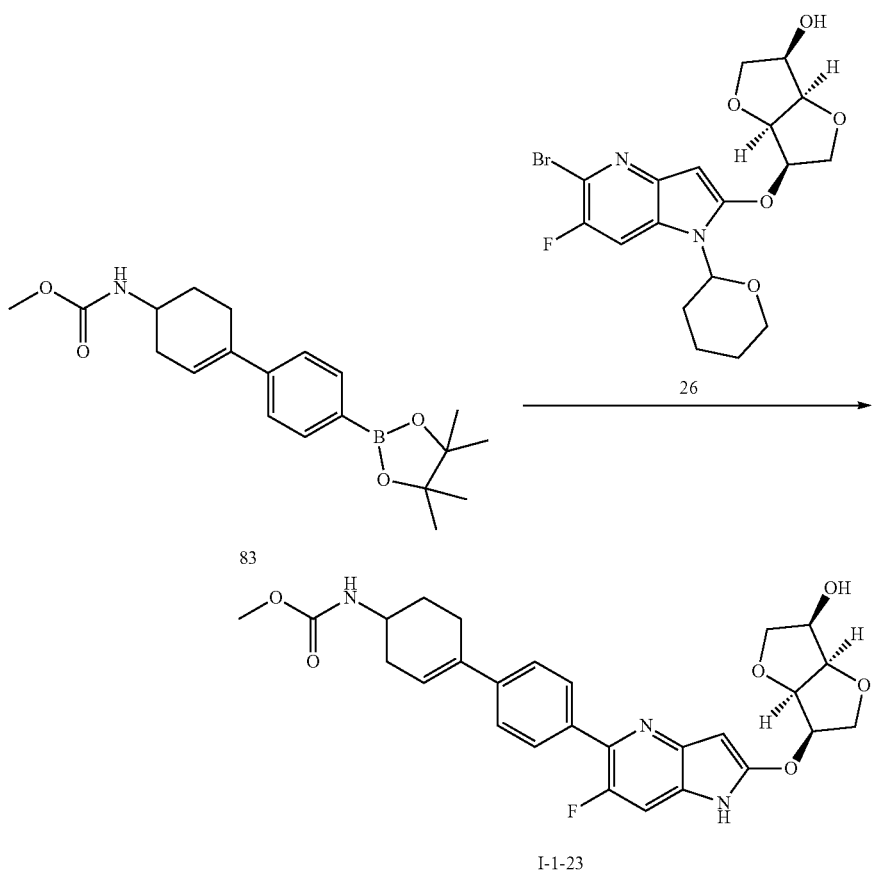
Compound (I-1-23) was synthesized from Compound 83, in a similar way that Compound (I-1-01) was synthesized from Compound 6.
Compound (I-1-23); Method A
LC/MS retention time=1.36 min.
MS (ESI) m/z=510.3 (M+H)+.
EXAMPLE 26
[Chemical formula 67]
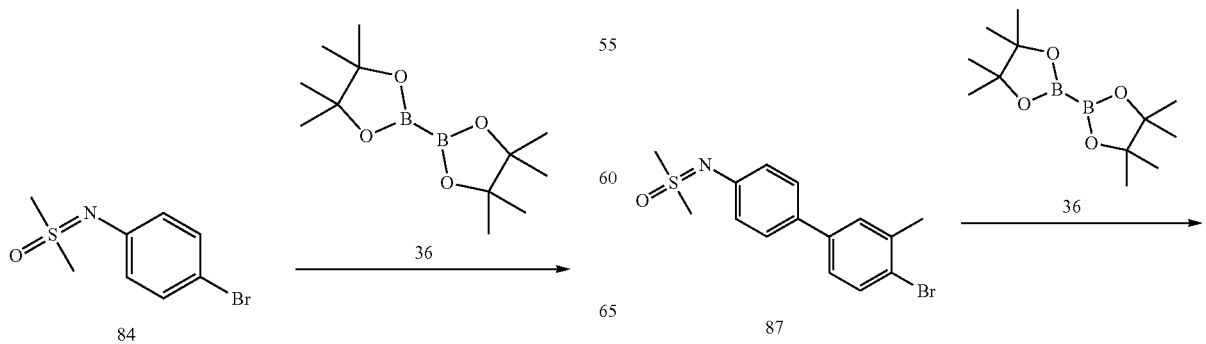
-continued
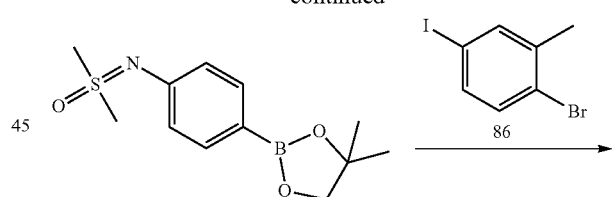

-continued

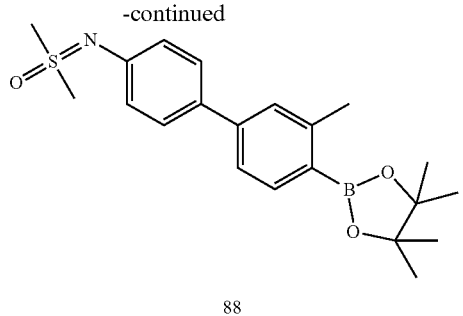

88

Compound 85 was synthesized from Compound 84, in a similar way that Compound 67 was synthesized from Compound 66.

Compound 85; Method A
LC/MS retention time=1.66 min.
MS (ESI) m/z=296.5 (M+H)+.

Compound 87 was synthesized from Compound 85, in a similar way that Compound 69 was synthesized from Compound 67.

Compound 87; Method A
LC/MS retention time=2.21 min.
MS (ESI) m/z=338.1 (M+H)+.

Compound 88 was synthesized from Compound 87, in a similar way that Compound 70 was synthesized from Compound 69.

Compound 88; Method A
LC/MS retention time=2.43 min.
MS (ESI) m/z=386.3 (M+H)+.

EXAMPLE 27

[Chemical formula 68]

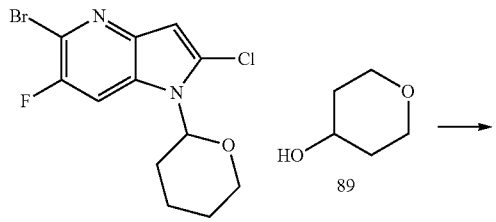

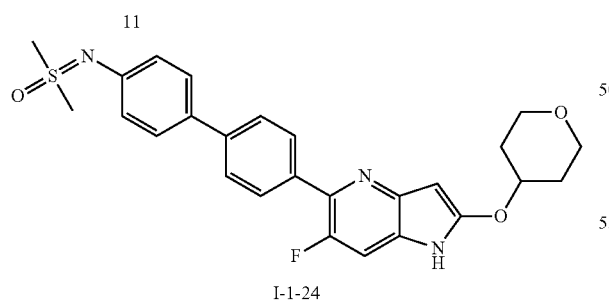

I-1-24

Compound (I-1-24) was synthesized from Compound 11, in a similar way that Compound (I-1-04) was synthesized from Compound 11 and Compound 15.

Compound (I-1-24); Method A
LC/MS retention time=1.36 min.
MS (ESI) m/z=480.2 (M+H)+.

EXAMPLE 28

[Chemical formula 69]

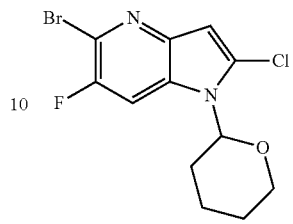

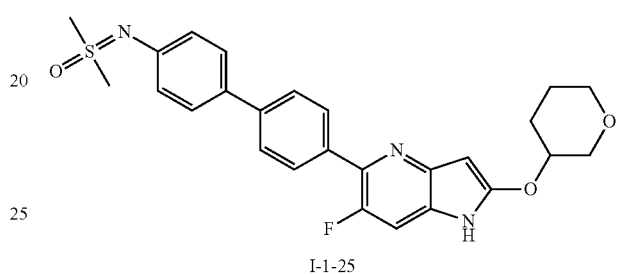

I-1-25

Compound (I-1-25) was synthesized from Compound 11, in a similar way that Compound (I-1-04) was synthesized from Compound 11 and Compound 15.

Compound (I-1-25); Method A
LC/MS retention time=1.37 min.
MS (ESI) m/z=480.2 (M+H)+.

EXAMPLE 29

[Chemical formula 70]

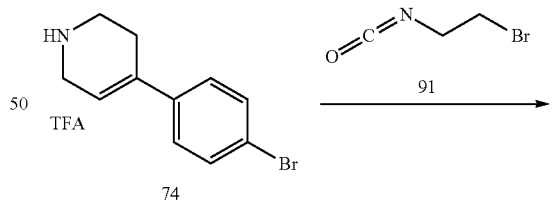

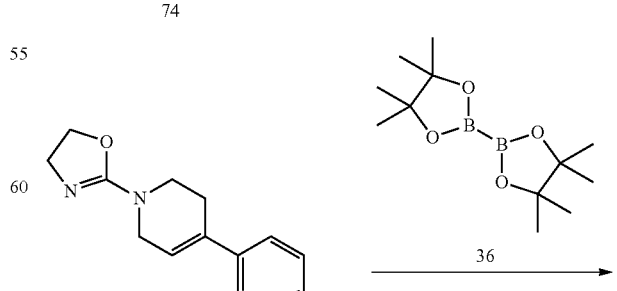

103

-continued

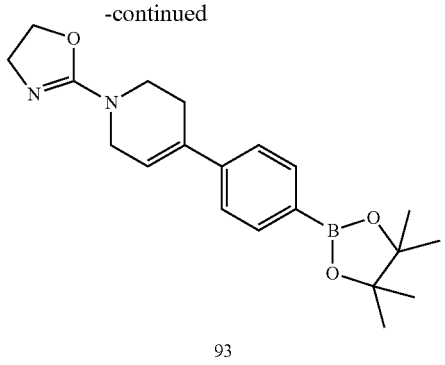

93

To Compound 74 (500 mg, 1.42 mmol) were added DCM (4 ml) and triethylamine (1.18 ml, 8.52 mmol), and the mixture was stirred at 0° C. Compound 91 (0.154 ml, 1.704 mmol) and THF (2 ml) were added thereto, and the mixture was stirred at room temperature. After completion of the reaction, water was added thereto, and the mixture was extracted with ethyl acetate. The obtained organic layer was dried over magnesium sulfate and then concentrated under reduced pressure. The residue was washed with diisopropyl ether to obtain Compound 92 (367 mg, 84%).

Compound 92; Method A

LC/MS retention time=1.46 min.

MS (ESI) m/z=307.4 (M+H)+.

Compound 93 was synthesized from Compound 92, in a similar way that Compound 37 was synthesized from Compound 35.

Compound 93; Method A

LC/MS retention time=1.76 min.

MS (ESI) m/z=355.2 (M+H)+.

EXAMPLE 30

[Chemical formula 71]

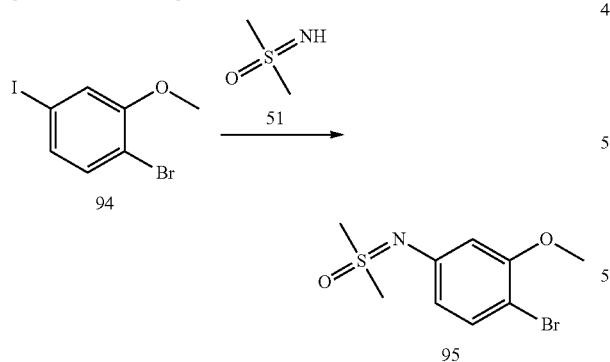

Compound 95 was synthesized from Compound 94, in a similar way that Compound 52 was synthesized from Compound 50.

Compound 95; Method A

LC/MS retention time=1.39 min.

MS (ESI) m/z=278.2 (M+H)+.

104

EXAMPLE 31

[Chemical formula 72]

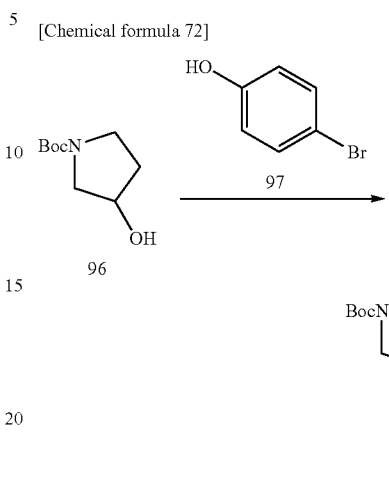

Compound 96 (600 mg, 3.20 mmol) was dissolved in THF (6 ml), then Compound 97 (665 mg, 3.85 mmol), triphenylphosphine (1.0 g, 3.85 mmol) and DMEAD (901 mg, 3.85 mmol) were added thereto, and the mixture was stirred at room temperature. To the reaction mixture was added water, and the mixture was extracted with ethyl acetate. The obtained organic layer was washed with saturated aqueous NaCl, dried over magnesium sulfate and filtered. The obtained filtrate was concentrated under reduced pressure, and purified by silica gel column chromatography to obtain Compound 98 (1.1 g, 100%).

Compound 98; Method A

LC/MS retention time=2.57 min.

MS (ESI) m/z=342.0 (M+H)+.

EXAMPLE 32

[Chemical formula 73]

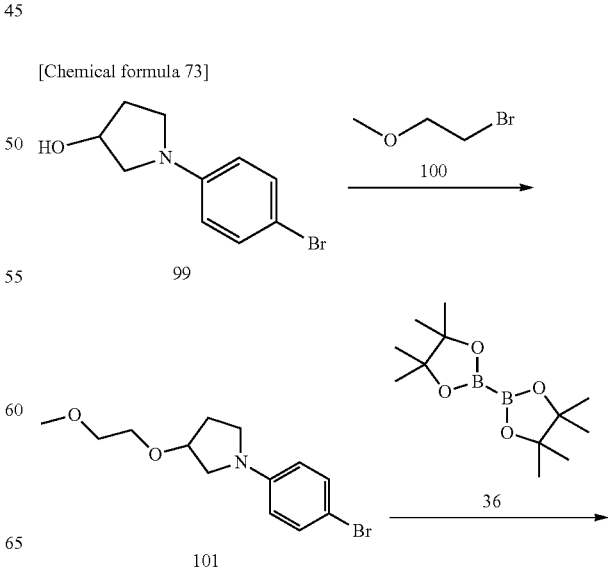

-continued

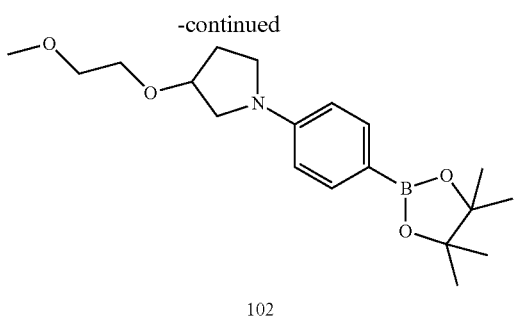

102

Compound 99 (200 mg, 0.826 mmol) was dissolved in DMF (2 ml) under nitrogen atmosphere, 60 wt % sodium hydride (56.2 mg, 1.40 mmol) was added thereto, and the mixture was stirred at room temperature. Compound 100 (0.132 ml, 1.40 mmol) and sodium iodide (12.38 mg, 0.083 mmol) were added thereto, and the mixture was stirred at room temperature. To the reaction mixture was added water, and the mixture was extracted with ethyl acetate. The obtained organic layer was washed with saturated aqueous NaCl, dried over magnesium sulfate and filtered. The obtained filtrate was concentrated under reduced pressure, and purified by silica gel column chromatography to obtain Compound 101 (109 mg, 44%).

Compound 101; Method A
  LC/MS retention time=2.24 min.
  MS (ESI) m/z=300.0 (M+H)+.

Compound 101 (103 mg, 0.343 mmol) was dissolved in 1,4-dioxane (70 ml), and Pd$_2$(dba)$_3$ (31.4 mg, 0.034 mmol), X-phos (32.7 mg, 0.069 mmol), Compound 36 (131 mg, 0.515 mmol) and potassium acetate (135 mg, 1.37 mmol) were added thereto, and the mixture was stirred at 100° C. The reaction mixture was filtered with celite, and the filtrate was concentrated under reduced pressure. The obtained residue was purified by silica gel column chromatography to obtain Compound 102 (120 mg, 100%).

Compound 102; Method A
  LC/MS retention time=2.32 min.
  MS (ESI) m/z=348.5 (M+H)+.

EXAMPLE 33

[Chemical formula 74]

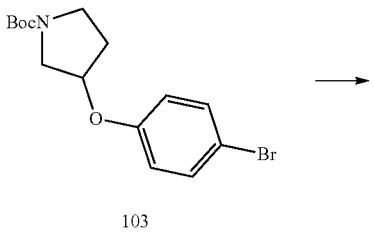

103

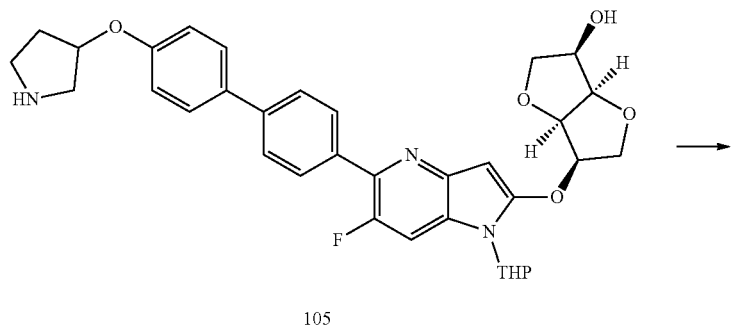

104

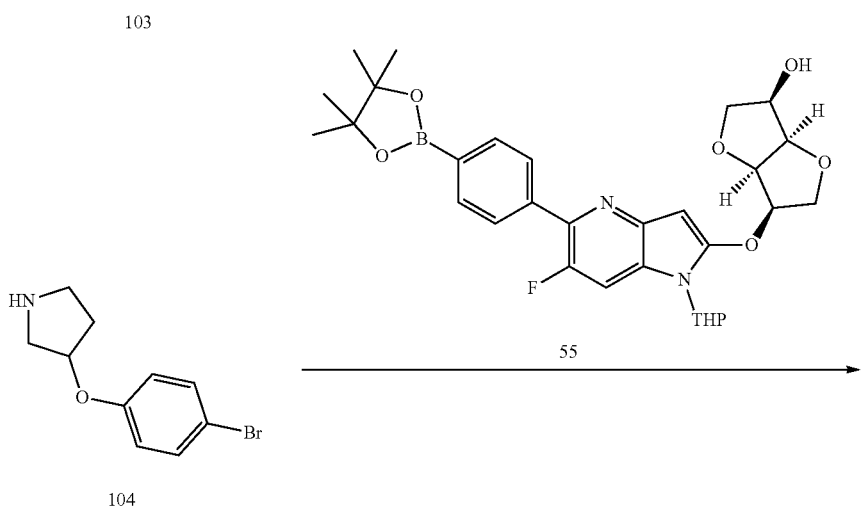

105

-continued

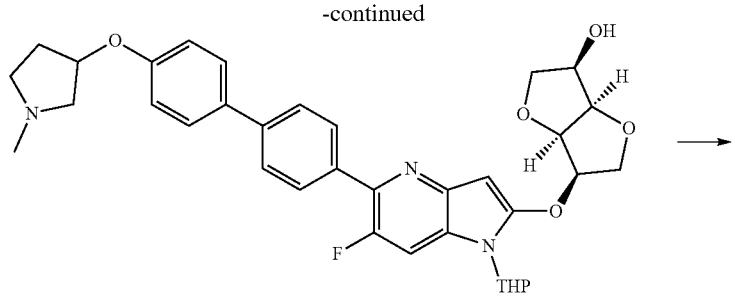

106

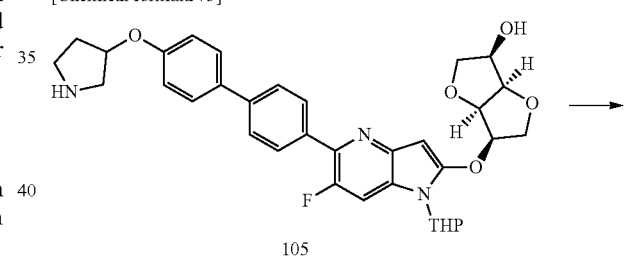

I-1-26

To Compound 103 (527 mg, 1.54 mmol) was added trifluoroacetic acid (5 ml), and the mixture was stirred at room temperature. The mixture was concentrated under reduced pressure and dissolved in chloroform, and the solution was neutralized by adding saturated aqueous sodium bicarbonate. The organic layer was washed with saturated aqueous NaCl, dried over magnesium sulfate and filtered. The obtained filtrate was concentrated under reduced pressure to obtain Compound 104.

Compound 104; Method A
LC/MS retention time=1.16 min.
MS (ESI) m/z=241.9 (M+H)+.

Compound 105 was synthesized from Compound 104, in a similar way that Compound 56 was synthesized from Compound 52.

Compound 105; Method A
LC/MS retention time=1.65 min.
MS (ESI) m/z=602.2 (M+H)+.

Compound 105 (36 mg, 0.060 mmol) was dissolved in methanol (450 μl), and a 36% formaldehyde solution (45.8 μl, 0.598 mmol), acetic acid (45 μl) and 2-picoline borane (9.6 mg, 0.090 mmol) were added thereto, and the mixture was stirred at room temperature. To the reaction mixture was added saturated aqueous sodium bicarbonate, and the mixture was extracted with chloroform. The obtained organic layer was washed with saturated aqueous NaCl, dried over magnesium sulfate and filtered. The obtained filtrate was concentrated under reduced pressure, and purified by silica gel column chromatography to obtain Compound 106 (12 mg, 33%).

Compound 106; Method A
LC/MS retention time=1.73 min.
MS (ESI) m/z=616.1 (M+H)+.

Compound (I-1-26) was synthesized from Compound 106, in a similar way that Compound (I-1-01) was synthesized from Compound 7.

Compound (I-1-26); Method A
LC/MS retention time=1.21 min.
MS (ESI) m/z=532.2 (M+H)+.

EXAMPLE 34

[Chemical formula 75]

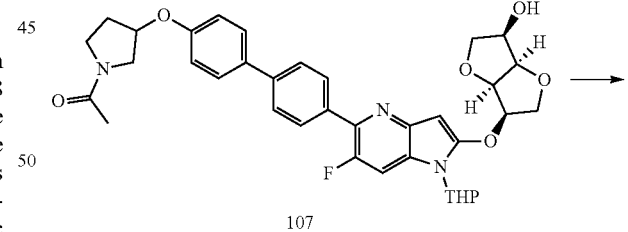

105

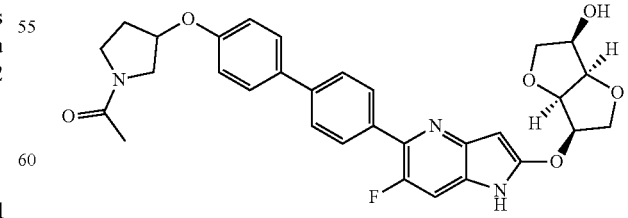

I-1-27

Compound 105 (44 mg, 0.073 mmol) was dissolved in pyridine (500 μl), and acetic anhydride (7.26 μl, 0.077 mmol) was added thereto, and the mixture was stirred at room temperature. To the reaction mixture was added a 2 mol/L aqueous solution of hydrochloric acid, and the mixture was extracted with ethyl acetate. The obtained organic layer was washed with saturated aqueous NaCl, dried over magnesium sulfate and filtered. The obtained filtrate was concentrated under reduced pressure, and purified by silica gel column chromatography to obtain Compound 107 (40 mg, 85%).

Compound 107; Method A

LC/MS retention time=1.33 min.

MS (ESI) m/z=644.2 (M+H)+.

Compound (I-1-27) was synthesized from Compound 107, in a similar way that Compound (I-1-01) was synthesized from Compound 7.

Compound (I-1-27); Method A

LC/MS retention time=1.37 min.

MS (ESI) m/z=560.6 (M+H)+.

EXAMPLE 35

[Chemical formula 76]

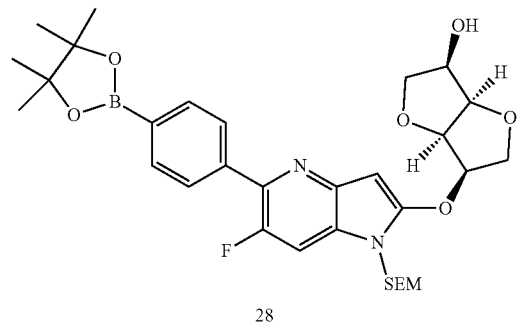

28

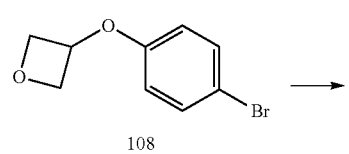

108

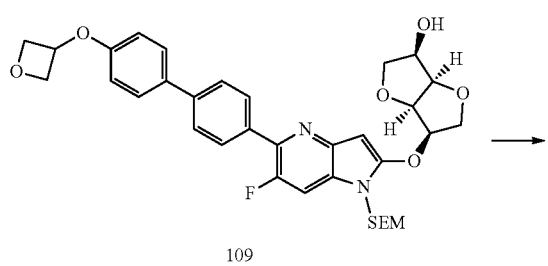

109

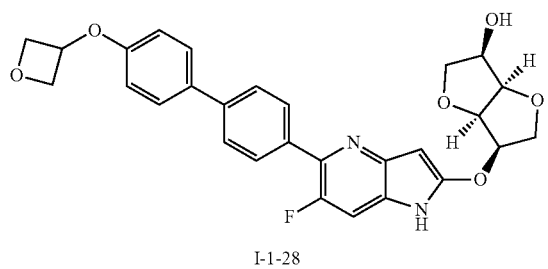

I-1-28

Compound 109 was synthesized from Compound 108, in a similar way that Compound 30 was synthesized from Compound 29.

Compound 109; Method A

LC/MS retention time=2.50 min.

MS (ESI) m/z=635.2 (M+H)+.

To Compound 109 (30 mg, 0.047 mmol) were added a 1 mol/L TBAF solution in tetrahydrofuran (189 μl, 0.189 mmol) and ethylenediamine (6.38 μl, 0.095 mmol), and the mixture was stirred at 70° C. To the reaction mixture was added water, and the mixture was extracted with ethyl acetate. The obtained organic layer was washed with saturated aqueous NaCl, dried over magnesium sulfate and filtered. The obtained filtrate was concentrated under reduced pressure, and purified by silica gel column chromatography to obtain Compound (I-1-28) (9.4 mg, 39%).

Compound (I-1-28); Method A

LC/MS retention time=1.49 min.

MS (ESI) m/z=505.1 (M+H)+.

EXAMPLE 36

[Chemical formula 77]

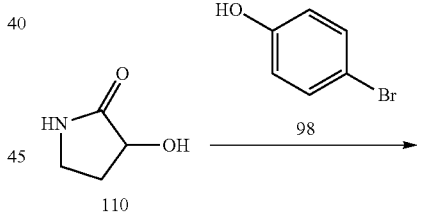

110

111

Compound 110 (160 mg, 1.58 mmol) was dissolved in THF (5 ml), then Compound 98 (329 mg, 1.90 mmol), triphenylphosphine (623 mg, 2.37 mmol) and DIAD (0.462 ml, 2.37 mmol) were added thereto, and the mixture was stirred at room temperature. The reaction mixture was purified by silica gel column chromatography, then washed with diethyl ether to obtain Compound 111 (60 mg, 15%).

Compound 111; Method A

LC/MS retention time=1.47 min.

MS (ESI) m/z=255.9 (M+H)+.

EXAMPLE 37

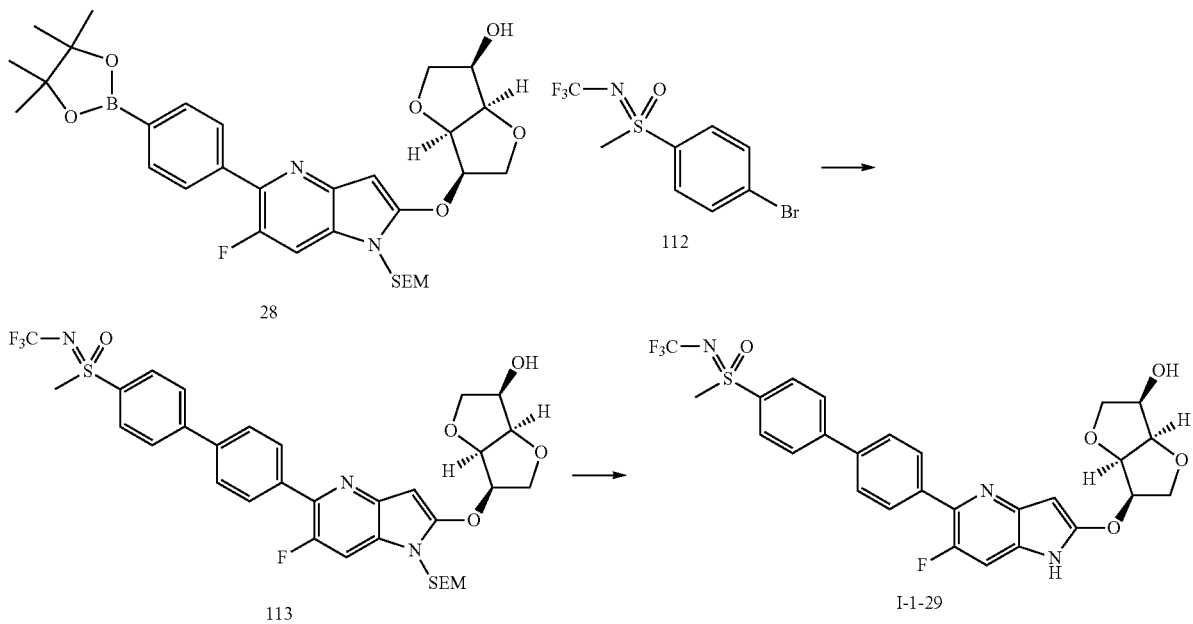

Compound 113 was synthesized from Compound 112, in a similar way that Compound 30 was synthesized from Compound 29.

Compound 113; Method A

LC/MS retention time=2.67 min.

MS (ESI) m/z=708.4 (M+H)+.

Compound (I-1-29) was synthesized from Compound 113, in a similar way that Compound (I-1-28) was synthesized from Compound 109.

Compound (I-1-29); Method A

LC/MS retention time=1.67 min.

MS (ESI) m/z=578.1 (M+H)+.

EXAMPLE 38

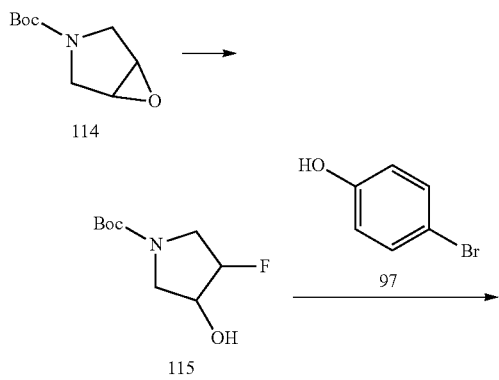

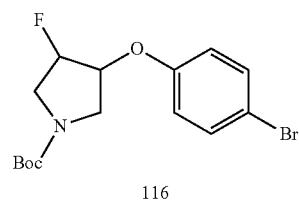

To Compound 114 (100 mg, 0.540 mmol) was added triethylamine trihydrofluoride (0.6 ml, 3.68 mmol), and the mixture was stirred at 100° C. Saturated aqueous sodium bicarbonate was added to the reaction mixture, and the mixture was extracted with ethyl acetate. The obtained organic layer was washed with water and saturated aqueous NaCl, dried over magnesium sulfate and filtered. The obtained filtrate was concentrated under reduced pressure, and purified by silica gel column chromatography to obtain Compound 115 (49 mg, 44%).

Compound 115; $^1$H-NMR (CDCl$_3$) δ: 1.47 (s, 9H), 1.80 (m, 1H), 3.43-3.73 (m, 4H), 4.40-4.42 (m, 1H), 4.86-4.98 (m, 1H).

Compound 116 was synthesized from Compound 115, in a similar way that Compound 98 was synthesized from Compound 96.

Compound 116; $^1$H-NMR (CDCl$_3$) δ: 1.47 (s, 9H), 3.48-3.97 (m, 4H), 4.67-4.70 (m, 1H), 5.13-5.26 (m, 1H), 6.86 (d, J=7.6 Hz, 2H), 7.40 (m, 2H).

EXAMPLE 39

[Chemical formula 80]

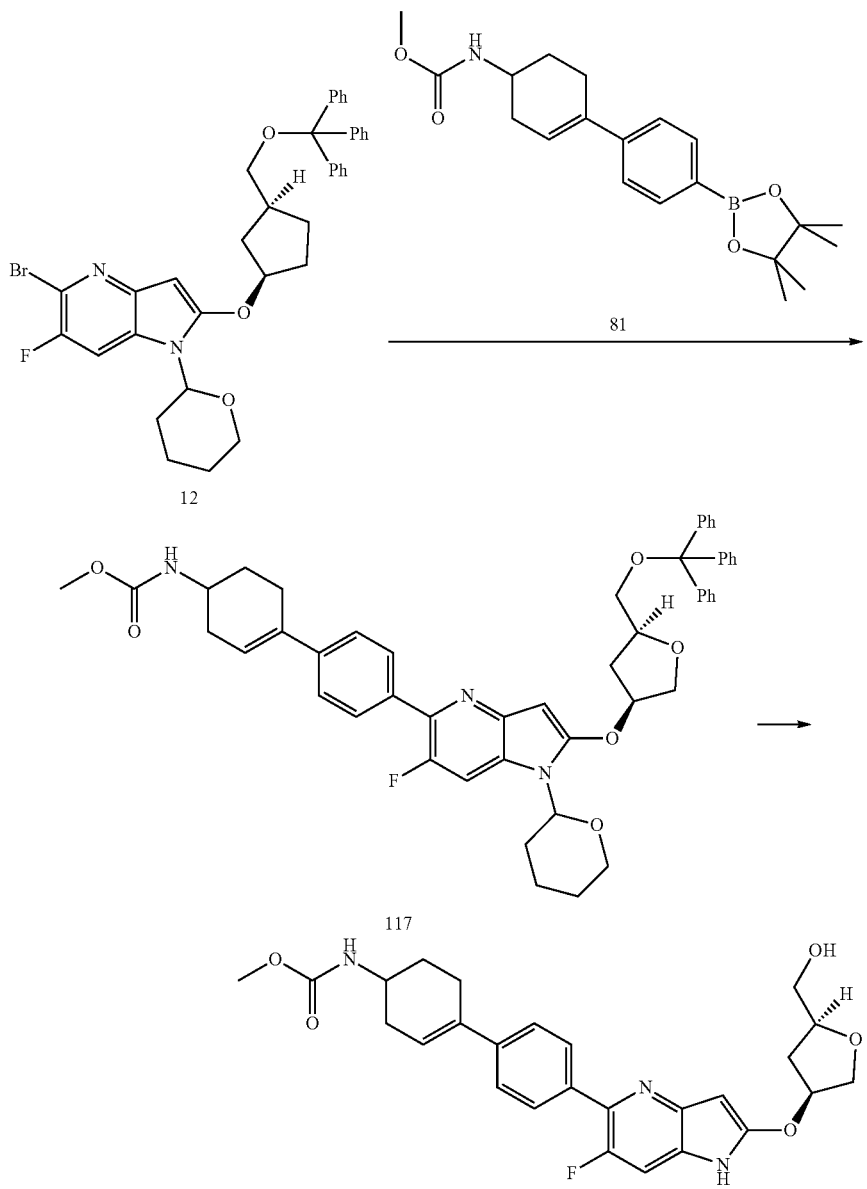

I-2-01

Compound 12 (150 mg, 0.228 mmol) and Compound 81 (98 mg, 0.274 mmol) were dissolved in DMF (1 ml), then PdCl$_2$(dtbpf) (29.7 mg, 0.046 mmol) and a 2 mol/L aqueous solution of potassium carbonate (0.171 ml, 0.342 mmol) were added thereto under nitrogen atmosphere, and the mixture was stirred at 100° C. After completion of the reaction, mixed solvent of ethyl acetate and hexane was added thereto, and the mixture was washed with water. The obtained organic layer was concentrated under reduced pressure, and purified by silica gel column chromatography to obtain Compound 117 (56.4 mg, 30.6%).

Compound 117; Method B
LC/MS retention time=3.07 min.
MS (ESI) m/z=808.55 (M+H)+.

Compound 117 (55 mg, 0.068 mmol) was dissolved in TFA (1 ml), and the solution was stirred at 50° C. After completion of the reaction, the solution was concentrated under reduced pressure, then, the residue was dissolved in methanol and THF, then the solution was added to an aqueous solution of sodium hydrogen carbonate. After the mixture was stirred at room temperature, the resulting mixture was extracted with the mixed solvent of chloroform and methanol. The obtained organic layer was dried over magnesium sulfate and filtered, then concentrated under reduced pressure. The obtained residue was purified by silica gel column chromatography to obtain Compound (2-1-01) (20.1 mg, 61.3%).
Compound (2-1-01); Method B
LC/MS retention time=1.22 min.
MS (ESI) m/z=482.85 (M+H)+.
EXAMPLE 40
[Chemical formula 81]
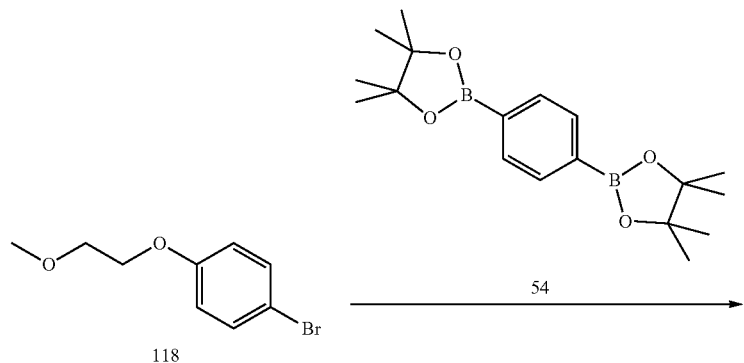
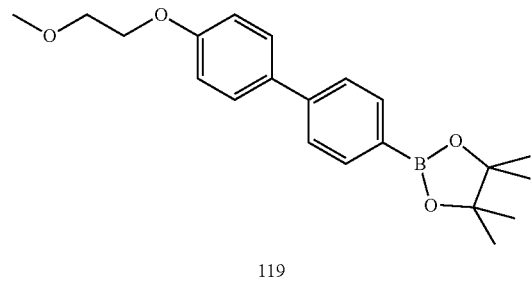
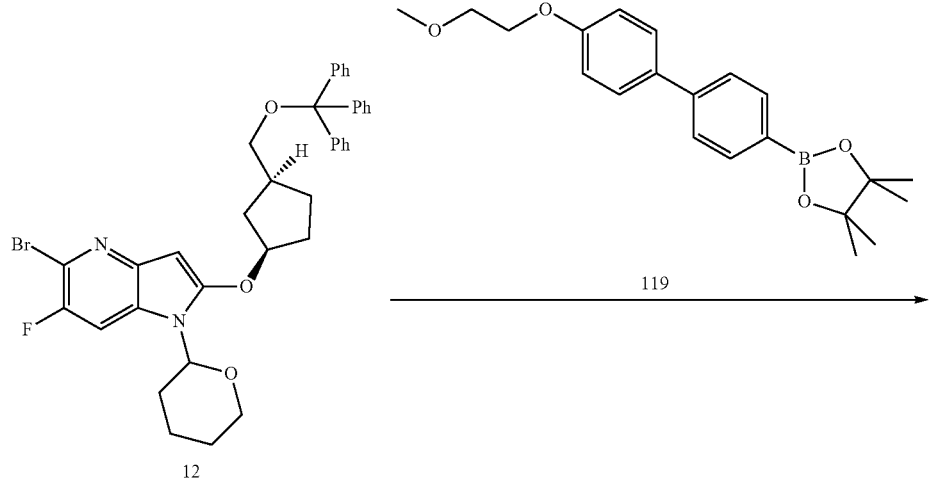

-continued

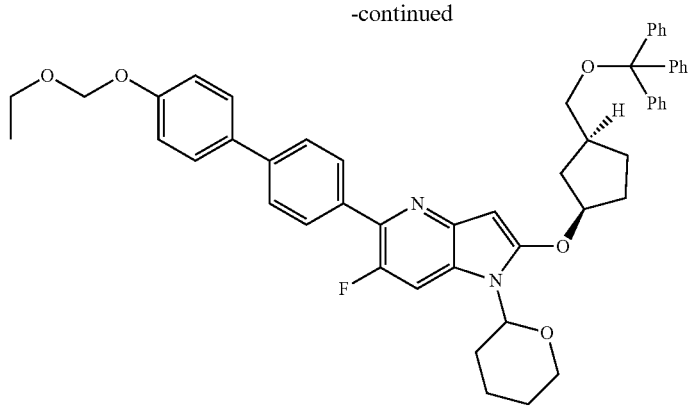

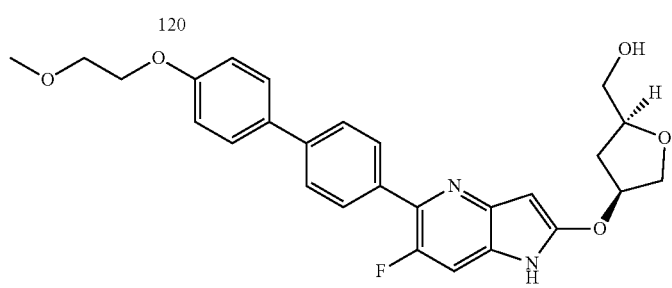

I-2-02

Compound 118 (*European Journal of Medicinal Chemistry*, 2012, 337-344, 567 mg, 2.454 mmol) was dissolved in 1,4-dioxane (11 ml), then compound 54 (2429 mg, 7.36 mmol) was added thereto, and the mixture was dissolved at 100° C. $PdCl_2(dtbpf)$ (320 mg, 0.491 mmol) and a 2 mol/L aqueous solution of potassium carbonate (2.45 mL, 4.91 mmol) were added thereto, and the mixture was stirred at 100° C. A saturated aqueous solution of ammonium chloride was added thereto, and the mixture was extracted with chloroform. The obtained organic layer was washed with water and a saturated aqueous solution of sodium chloride, then was dried over magnesium sulfate, filtered, and concentrated under reduced pressure. The obtained residue was purified by silica gel column chromatography to obtain Compound 119 (535 mg, 61.6%).

Compound (I-2-02) was synthesized from Compound 119, in a similar way that Compound (I-2-01) was synthesized from Compound 81.

Compound (I-2-02); Method B
  LC/MS retention time=1.39 min.
  MS (ESI) m/z=479.85 (M+H)+.

EXAMPLE 41

[Chemical formula 82]

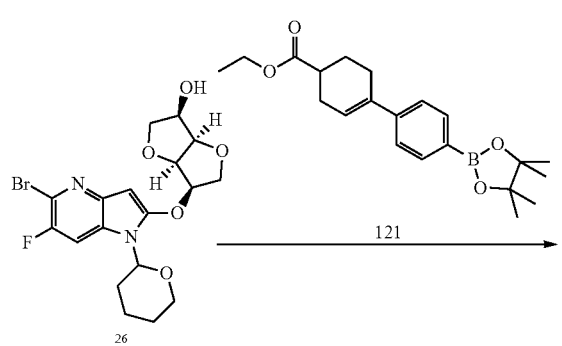

-continued

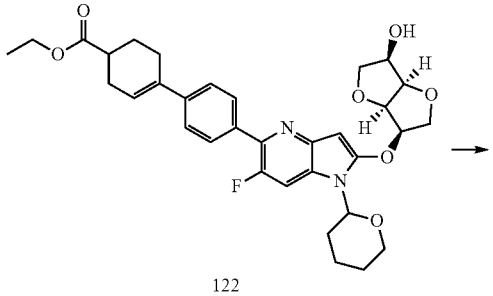

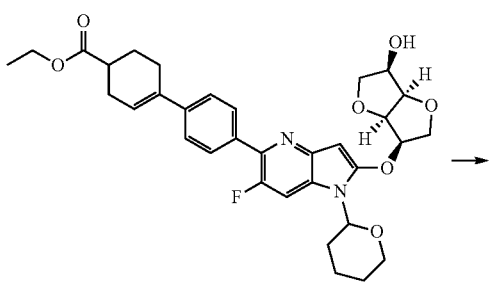

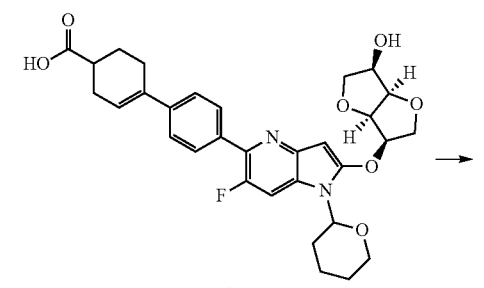

119
-continued
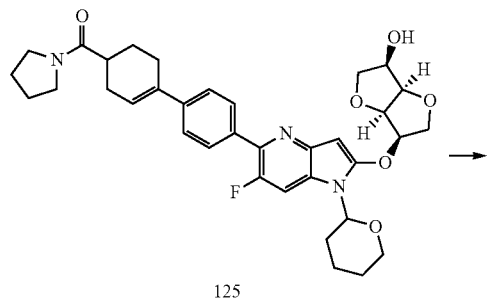
125
120
-continued
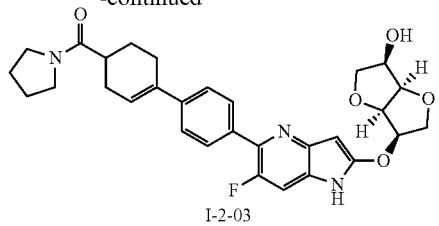
I-2-03
Compound (I-2-03) was synthesized from Compound 26, in a similar way that Compound (I-1-09) was synthesized from Compound 26.
Compound (I-2-03); Method B
LC/MS retention time=1.24 min.
MS (ESI) m/z=534.4 (M+H)+.
EXAMPLE 42
[Chemical formula 83]
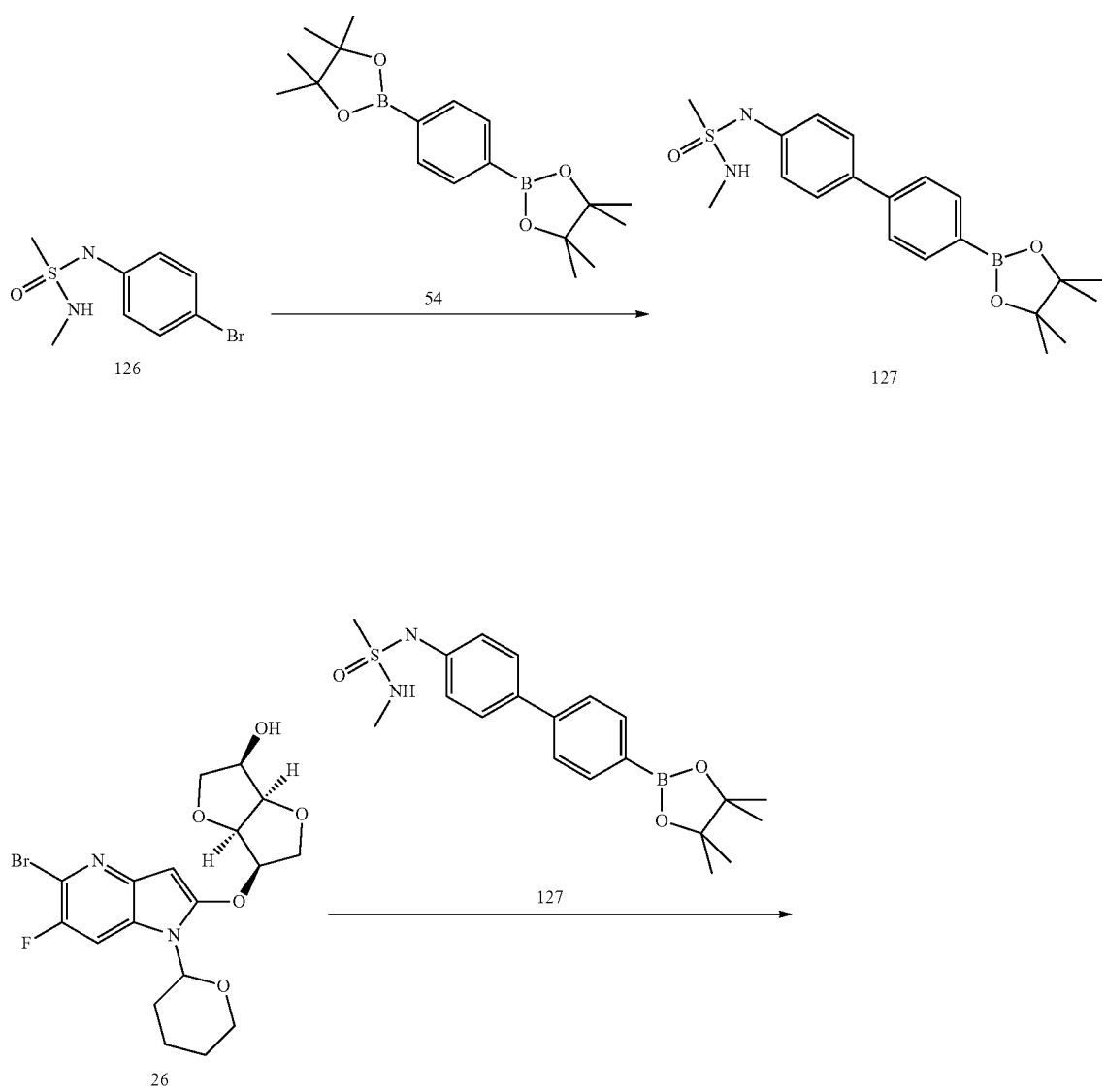

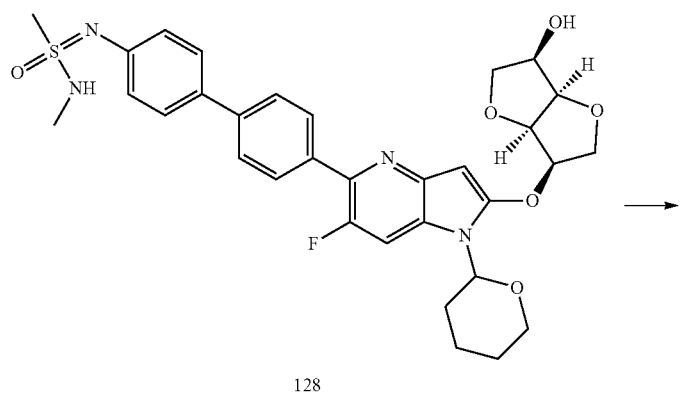
128
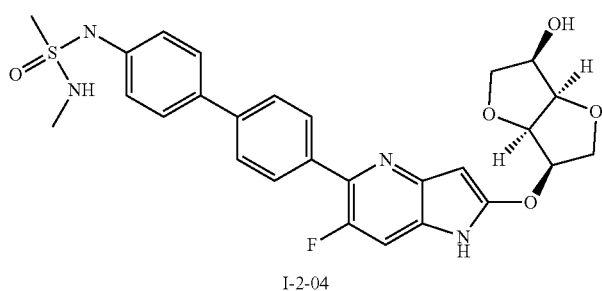
I-2-04
Compound (I-2-04) was synthesized from Compound 126, in a similar way that Compound (I-2-02) was synthesized from Compound 118.
Compound (I-2-04); Method B
LC/MS retention time=0.99 min.
MS (ESI) m/z=539.3 (M+H)+.
EXAMPLE 43
[Chemical formula 84]
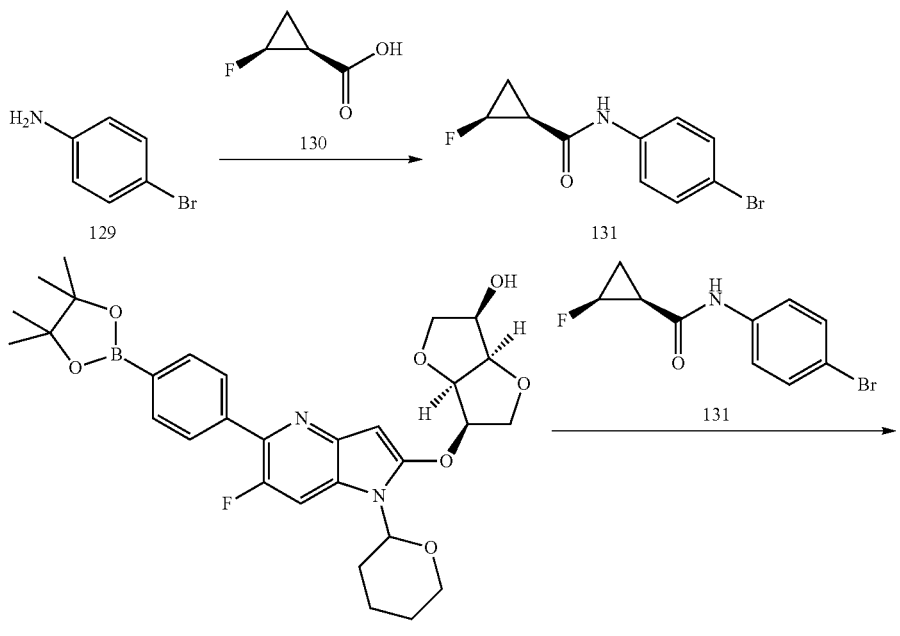

-continued

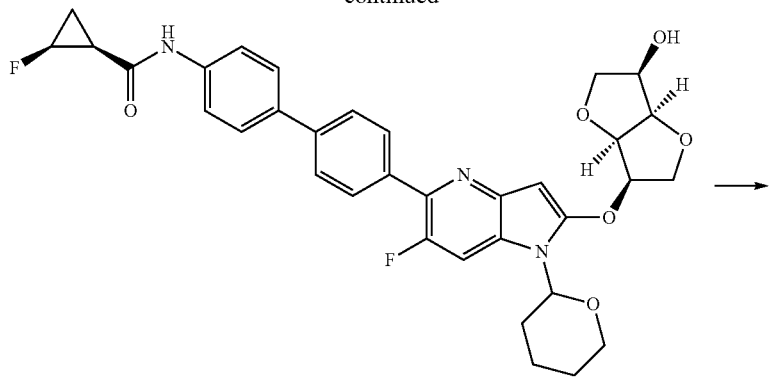

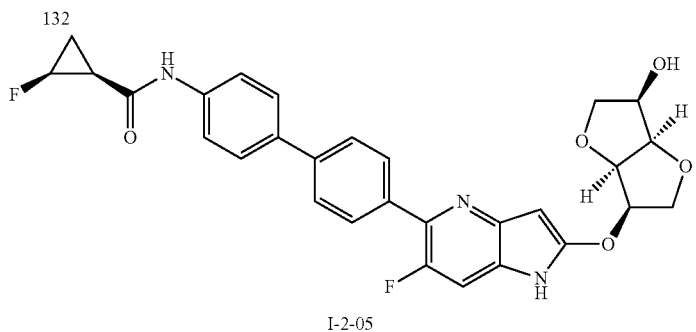

I-2-05

To compound 130 (145 mg, 1.395 mmol) was added dichloromethane (2 ml). Oxalyl chloride (0.122 mL, 1.395 mmol 1) was added thereto under nitrogen atmosphere. To the reaction mixture was added DMF (0.025 ml), and the mixture was stirred at room temperature for 5 minutes. The mixture was cooled to 0° C. To the reaction mixture was added compound 129 (200 mg, 1.163 mmol) dissolved in dichloromethane and the mixture was stirred at 0° C. To the reaction mixture was added pyridine (0.469 mL, 5.81 mmol), and the mixture was stirred at 0° C. Ethyl acetate was added thereto, and the mixture was washed with water. The obtained organic layer was concentrated under reduced pressure. The obtained residue was purified by reversed phase silica gel column chromatography to obtain Compound 131 (219 mg, 73.0%). Compound (I-2-05) was synthesized from Compound 55, in a similar way that Compound (I-1-16) was synthesized from Compound 55.
Compound (I-2-05); Method B
LC/MS retention time=1.21 min.
MS (ESI) m/z=534.3 (M+H)+.

EXAMPLE 44

[Chemical formula 85]

-continued

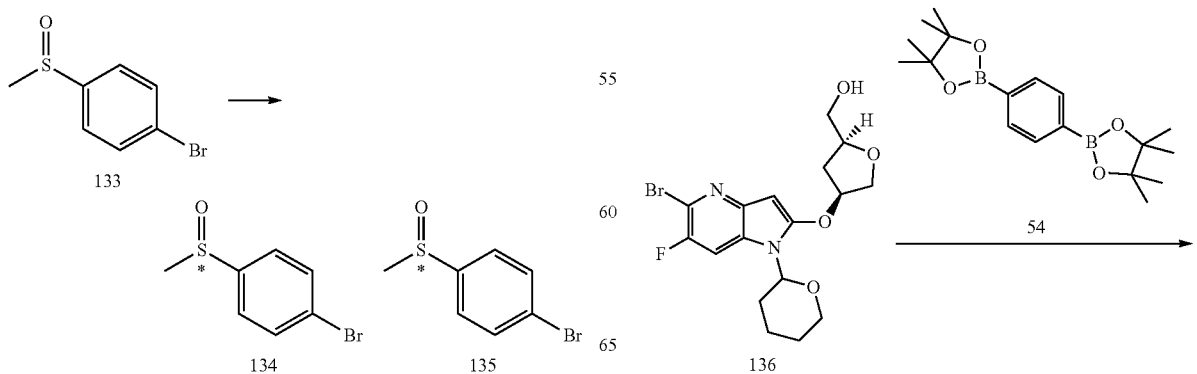

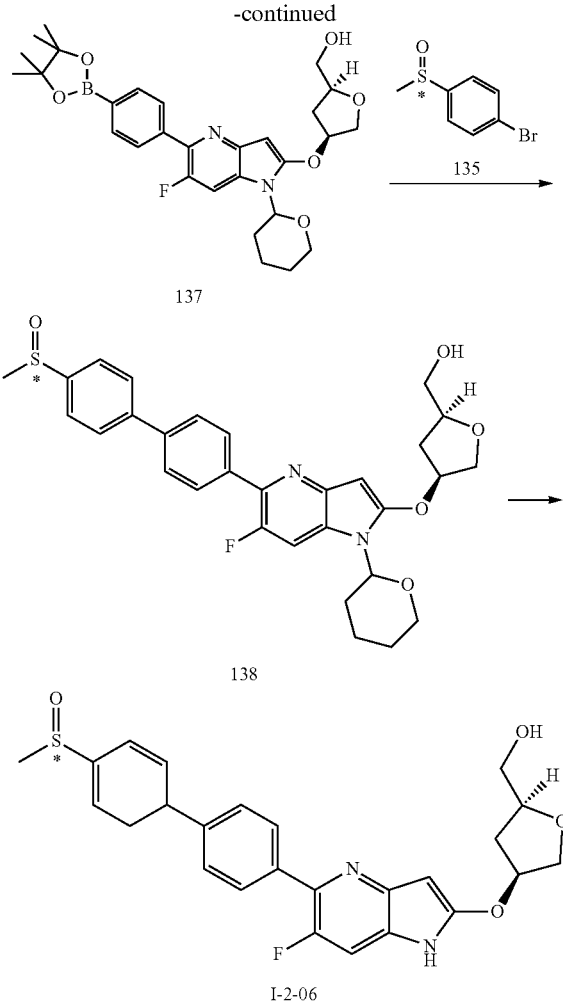

Optical resolution of Compound 133 was carried out in the following conditions, and Compound 134 and Compound 135 were obtained as 1$^{st}$ peak and 2$^{nd}$ peak, respectively (* shows that it is optically resolved (the same applies hereafter).).

Instrument: 321 PUMP(GILSON), 215 LIQUID HANDLER(GILSON), UV/VIS-155(GILSON)

Column: CHIRALPAK IC/SFC manufactured by DAICEL Corporation (5 μm, i.d. 20×250 mm)

Mobile phase: ethyl acetate:hexane=50:50

Flow rate: 11.4 mL/min

Compound 12 (12.5 g, 19.0 mmol) was dissolved in THF (50 ml), methanol (50 ml) was added thereto. The reaction mixture was cooled to 0° C. and acetyl chloride (4.07 mL, 57.0 mmol) was added dropwise thereto. The reaction mixture was raised to room temperature and stirred. Subsequently, the reaction mixture was cooled to 10° C., then the mixture was neutralized with 2 mol/l aqueous solution of potassium carbonate. Water was added thereto to dissolve extracted salt, and the mixture was extracted with a mixed solvent of chloroform and methanol. The obtained organic layer was dried over magnesium sulfate, filtered, and concentrated under reduced pressure. The obtained residue was purified by silica gel column chromatography to obtain Compound 136 (5.923 g, 75.0%).

Compound 136; Method B

LC/MS retention time=1.81 min.

MS (ESI) m/z=441.95 (M+H)+.

Compound 137 was synthesized from Compound 136, in a similar way that Compound 55 was synthesized from Compound 53. Compound (I-2-06) was synthesized from Compound 137 and Compound 135, in a similar way that Compound (I-1-16) was synthesized from Compound 55 and Compound 52.

Compound (I-2-06); Method B

LC/MS retention time=1.08 min.

MS (ESI) m/z=467.05 (M+H)+.

EXAMPLE 451

[Chemical formula 86]

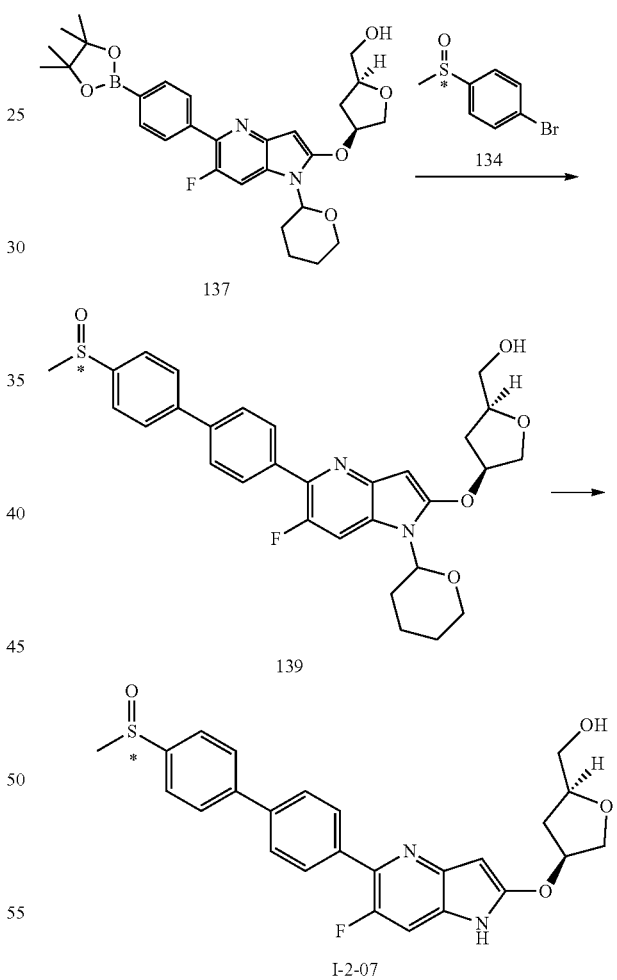

Compound (I-2-07) was synthesized from Compound 137 and Compound 134, in a similar way that Compound (I-2-06) was synthesized from Compound 137 and Compound 135.

Compound (I-2-07); Method B

LC/MS retention time=1.08 min.

MS (ESI) m/z=467.00 (M+H)+.

EXAMPLE 46

[Chemical formula 87]

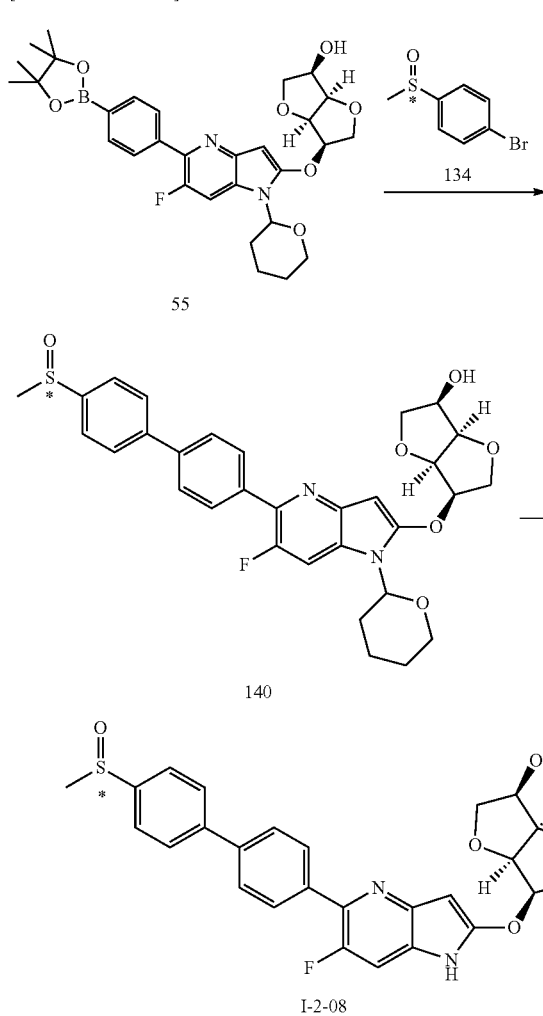

Compound (I-2-08) was synthesized from Compound 55 and Compound 134, in a similar way that Compound (I-2-06) was synthesized from Compound 137 and Compound 135.

Compound (I-2-08); Method B

LC/MS retention time=1.05 min.

MS (ESI) m/z=495.05 (M+H)+.

EXAMPLE 47

[Chemical formula 88]

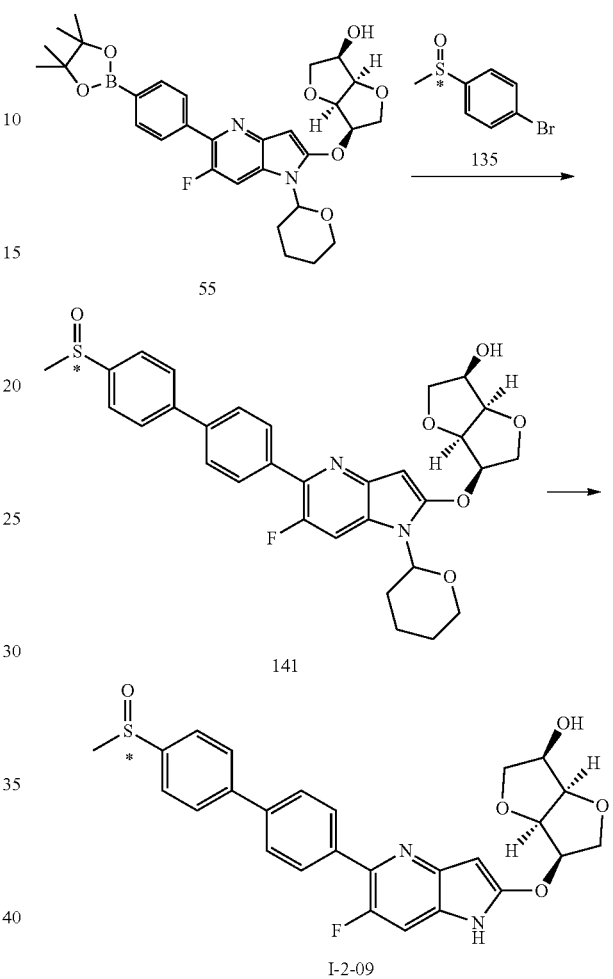

Compound (I-2-09) was synthesized from Compound 55 and Compound 135, in a similar way that Compound (I-2-06) was synthesized from Compound 137 and Compound 135.

Compound (I-2-09); Method B

LC/MS retention time=1.05 min.

MS (ESI) m/z=495.10 (M+H)+.

EXAMPLE 48

[Chemical formula 89]

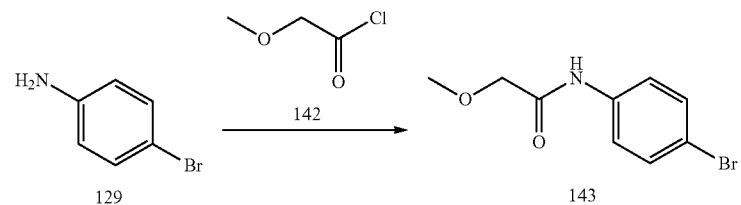

-continued

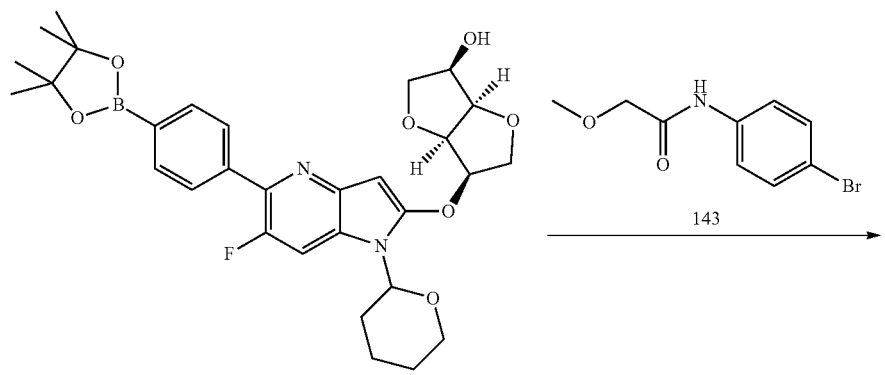

143

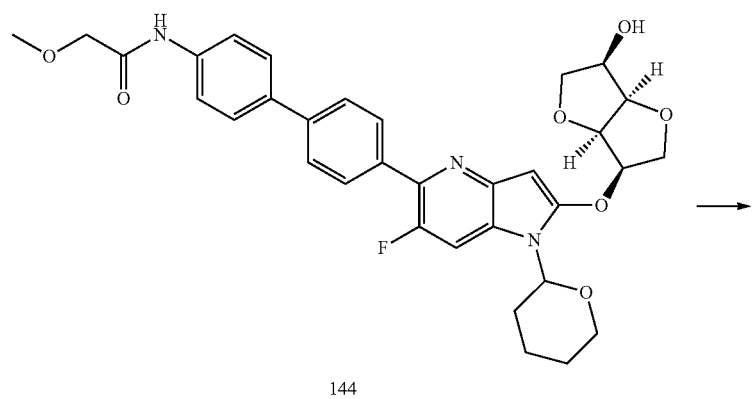

144

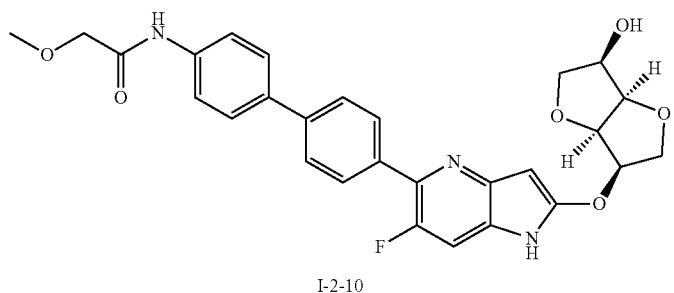

I-2-10

Compound 129 (1000 mg, 5.81 mmol) was dissolved in THF (10 ml), then pyridine (0.938 mL, 11.63 mmol) was added thereto. The reaction mixture was cooled to 0° C. under nitrogen atmosphere. Compound 142 (0.584 mL, 6.39 mmol) was added thereto and the mixture was stirred at 0° C. Water and a 2 mol/L aqueous solution of hydrochloric acid were added thereto, and the mixture was extracted with ethyl acetate. The organic layer was washed with water and an aqueous solution of hydrochloric acid. The obtained organic layer dried over magnesium sulfate, filtered, and concentrated under reduced pressure. Hexane was added to the obtained residue and Compound 143 was obtained by filtration. Compound (I-2-10) was synthesized from Compound 55 and Compound 143, in a similar way that Compound (I-2-05) was synthesized from Compound 55 and Compound 131.

Compound (I-2-10); Method B
  LC/MS retention time=1.19 min.
  MS (ESI) m/z=520.15 (M+H)+.

EXAMPLE 49

[Chemical formula 90]

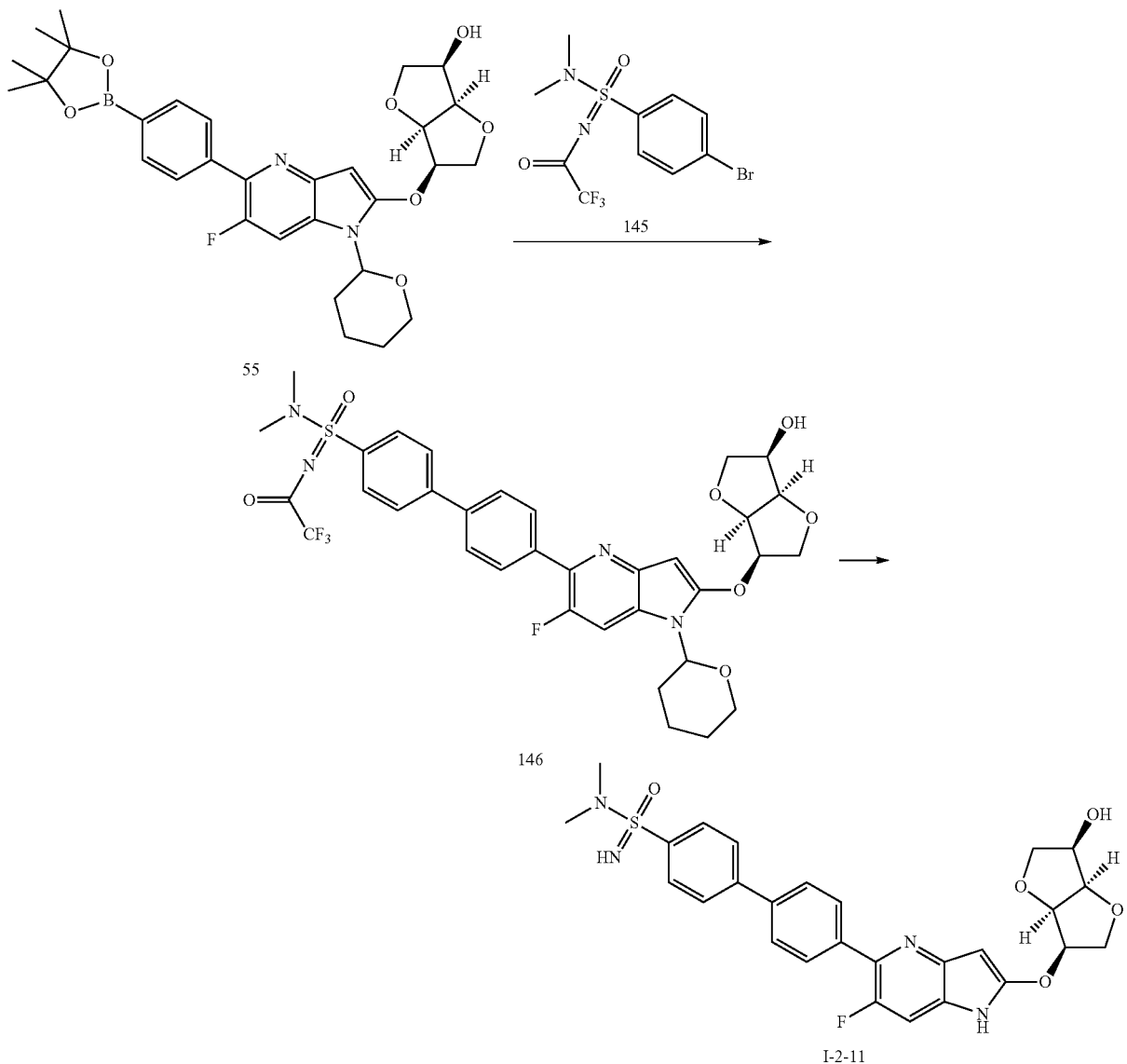

Compound 146 was synthesized from Compound 55 and Compound 145, in a similar way that Compound 132 was synthesized from Compound 55 and Compound 131.
Compound 146; Method B
LC/MS retention time=2.27 min.
MS (ESI) m/z=719.05 (M+H)+.

TFA (1 ml) was added to compound 146 (55 mg, 0.077 mmol), and the mixture was stirred at 60° C. After 4 hours, TFA was removed by concentration under reduced pressure. The obtained residue was diluted with methanol, and the mixture was neutralized with an aqueous solution of sodium hydrogen carbonate. The mixture was extracted with chloroform and the solvent was removed under reduced pressure. The obtained residue was dissolved in methanol (1 ml), and a 2 mol/l aqueous solution of $Na_2CO_3$ (0.469 mL, 5.81 mmol) was added thereto, and the mixture was stirred at room temperature. The obtained residue was purified by silica gel column chromatography to obtain Compound (I-2-11) (28 mg, 68%).

Compound 136; Method B
LC/MS retention time=1.15 min.
MS (ESI) m/z=539.25 (M+H)+.

EXAMPLE 50

[Chemical formula 91]

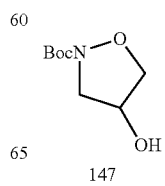

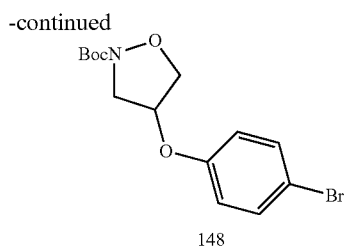

148

Compound 148 was synthesized from Compound 147 and Compound 97, in a similar way that Compound 98 was synthesized from Compound 96 and Compound 97.
Compound 148; Method A
 LC/MS retention time=2.43 min.
 MS (ESI) m/z=344.0 (M+H)+.

EXAMPLE 51

[Chemical formula 92]

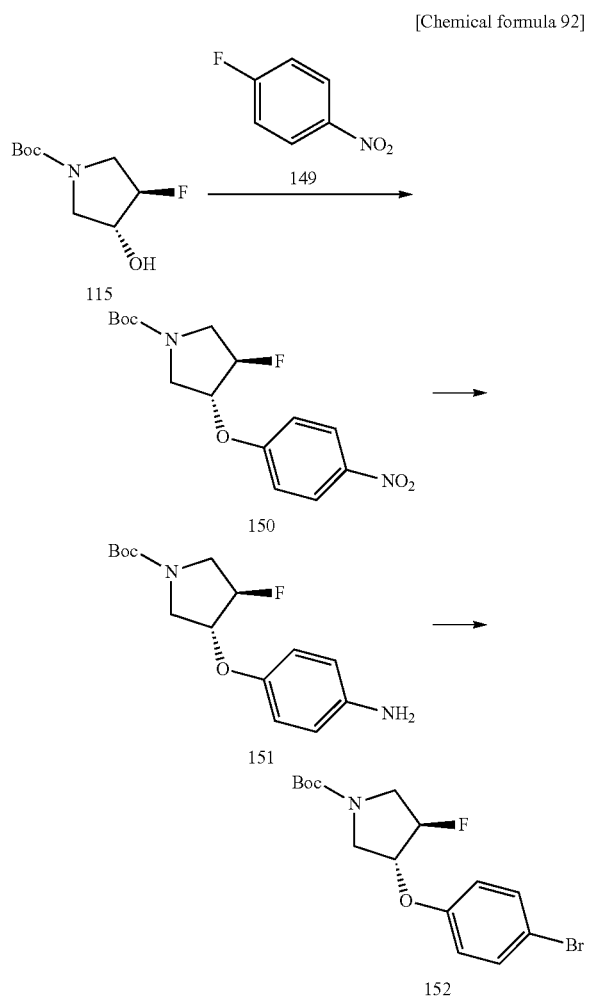

Compound 115 (350 mg, 1.71 mmol) was dissolved in THF (7 ml), and the reaction mixture was cooled to 0° C. under nitrogen atmosphere. 60 wt % sodium hydride (82 mg, 2.05 mmol) was added thereto and the mixture was stirred at 0° C. for 30 minutes. Compound 149 (0313 mg 2.22 mmol) was added thereto and the mixture was stirred at room temperature. After completion of the reaction, a saturated aqueous solution of ammonium chloride was added thereto, and the mixture was extracted with ethyl acetate. The obtained organic layer was washed with water and a saturated aqueous solution of sodium chloride, then was dried over magnesium sulfate, filtered, and concentrated under reduced pressure. The obtained residue was purified by silica gel column chromatography to obtain Compound 150 (497 mg, 89%).
Compound 150; Method A
 LC/MS retention time=2.33 min.
 MS (ESI) m/z=327.3 (M+H)+.
Compound 150 (485 mg, 1.49 mmol) was dissolved in methanol (12 ml) and water (4 ml) and then, ferrous (415 mg, 7.43 mmol) and ammonium chloride (795 mg, 14.86 mmol) was added thereto. The reaction mixture was stirred at 80° C. for 2 hours under nitrogen atmosphere. The reaction mixture was filtered with celite and the resulting mixture was extracted with chloroform. The obtained organic layer was washed with water and a saturated aqueous solution of sodium chloride and was dried over magnesium sulfate. The solvent was removed by filtration under reduced pressure to obtain Compound 151 as a crude product.
Compound 151; Method A
 LC/MS retention time=1.31 min.
 MS (ESI) m/z=297.0 (M+H)+.
To copper (II) bromide (90 mg, 0.405 mmol) and tert-butyl nitrite (52 mg, 0.506 mmol) were added acetonitrile (1 ml) and the mixture was stirred at 0° C. To the reaction mixture was added compound 151 (100 mg, 0.0337 mmol) dissolved in acetonitrile and the mixture was stirred at 0° C. To the reaction mixture was added water and the mixture was extracted with ethyl acetate. The obtained organic layer was washed with water and a saturated aqueous solution of sodium chloride and was dried over magnesium sulfate, filtered, and concentrated under reduced pressure. The obtained residue was purified by silica gel column chromatography to obtain Compound 152 (55 mg, 45%).
Compound 152; Method A
 LC/MS retention time=2.57 min.
 MS (ESI) m/z=360.1 (M+H)+.

EXAMPLE 52

[Chemical formula 93]

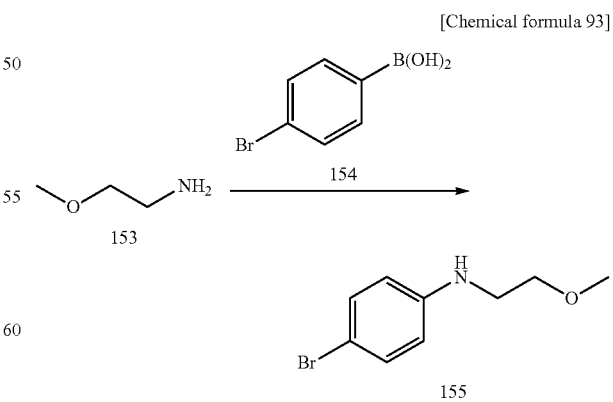

To Compound 154 (1.5 g, 7.47 mmol), copper (II) acetate (74.6 mg, 0.373 mmol) and MS4A (2 g) was added dichloromethane (30 ml) and the mixture was stirred at room temperature. To the reaction mixture was added compound 153 (281 mg, 3.73 mmol) and the mixture was stirred at 40° C. all night. The reaction mixture was filtered with celite and the resulting mixture was concentrated under reduced pressure. The obtained residue was purified by silica gel column chromatography to obtain Compound 155 (375 mg, 44%).

Compound 155; Method A

LC/MS retention time=1.81 min.

MS (ESI) m/z=230.2 (M+H)+.

EXAMPLE 53

[Chemical formula 94]

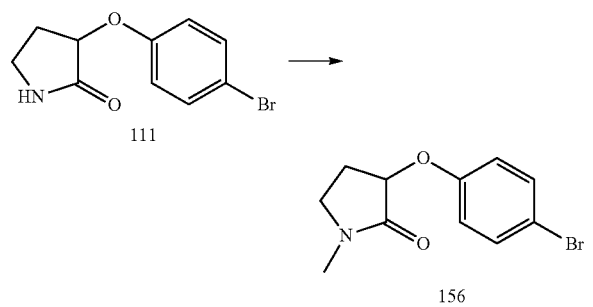

Compound 111 (30 mg, 0.117 mmol) was dissolved in THF (1 ml) under nitrogen atmosphere, and 60 wt % sodium hydride (82 mg, 2.05 mmol) was added thereto and the mixture was stirred at room temperature. Methyl iodide (0.037 ml, 0.586 mmol) was added thereto and the mixture was stirred at room temperature. Water was added thereto, and the mixture was extracted with ethyl acetate. The obtained organic layer was washed with a saturated aqueous solution of sodium chloride, then was dried over magnesium sulfate, filtered, and concentrated under reduced pressure. The obtained residue was concentrated under reduced pressure to obtain Compound 156 (39 mg) as a crude product.

Compound 156; Method A

LC/MS retention time=1.58 min.

MS (ESI) m/z=270.2 (M+H)+.

EXAMPLE 54

[Chemical formula 95]

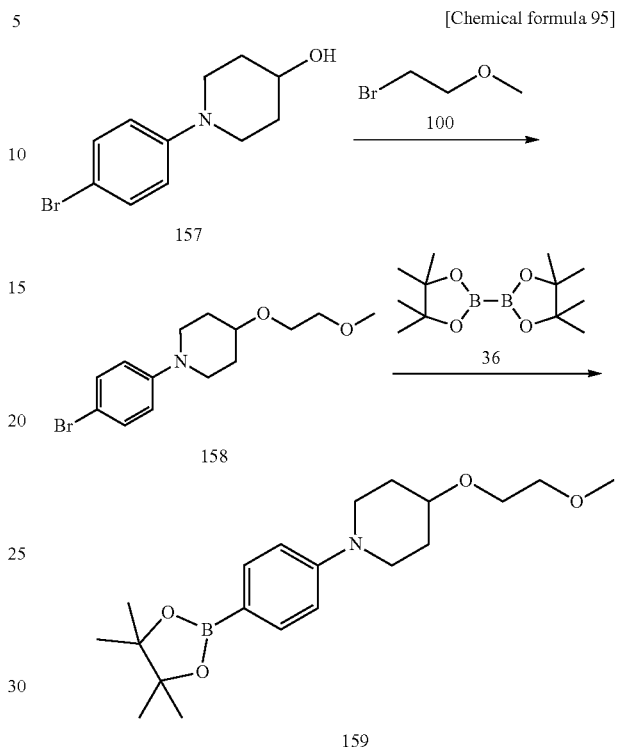

Compound 158 was synthesized from Compound 157 and Compound 100, in a similar way that Compound 101 was synthesized from Compound 99 and Compound 100.

Compound 158; Method A

LC/MS retention time=1.65 min.

MS (ESI) m/z=314.0 (M+H)+.

Compound 159 was synthesized from Compound 158 and Compound 36, in a similar way that Compound 102 was synthesized from Compound 101 and Compound 36.

Compound 159; Method A

LC/MS retention time=2.19 min.

MS (ESI) m/z=362.0 (M+H)+.

EXAMPLE 55

[Chemical formula 96]

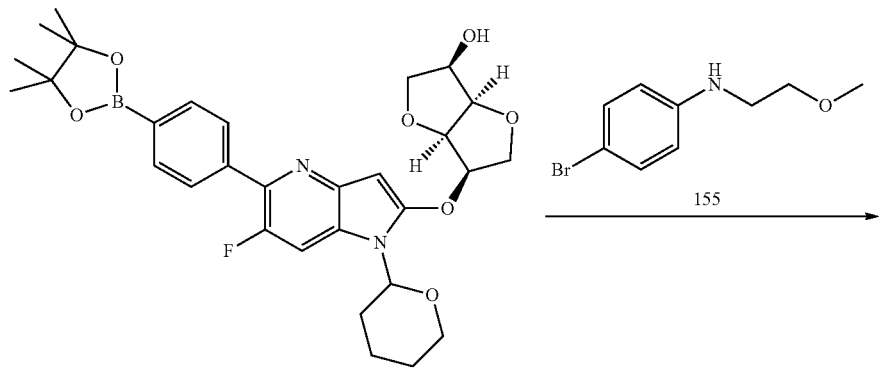

-continued

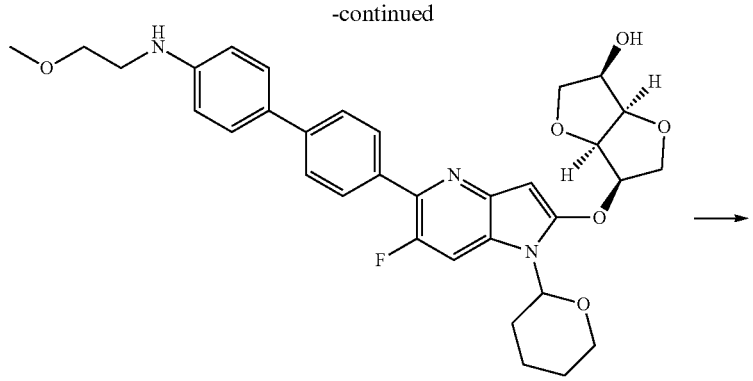

160

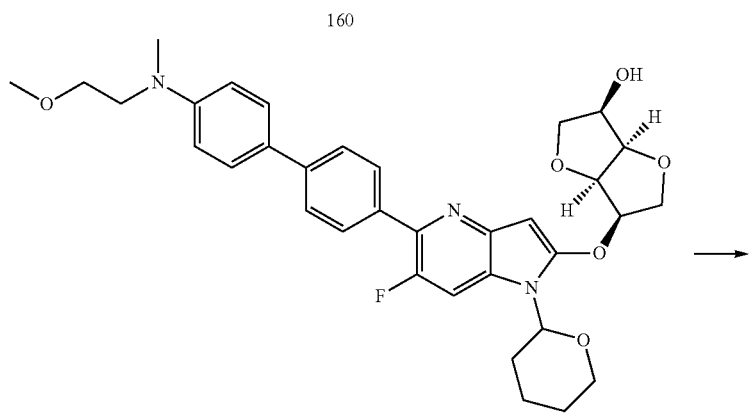

161

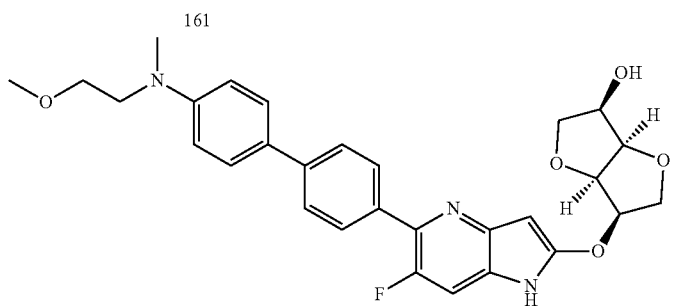

I-2-12

Compound 160 was synthesized from Compound 55 and CompoundlS, in a similar way that Compound 132 was synthesized from Compound 55 and Compound 131.

Compound 160 Method B

LC/MS retention time=1.85 min.

MS (ESI) m/z=590.35 (M+H)+.

Compound 161 was synthesized from Compound 160, in a similar way that Compound 106 was synthesized from Compound 105.

Compound 161 Method B

LC/MS retention time=2.03 min.

MS (ESI) m/z=604.40 (M+H)+.

Compound (I-2-12) was synthesized from Compound 161, in a similar way that Compound (I-1-01) was synthesized from Compound 7.

Compound (I-2-12) Method B

LC/MS retention time=1.40 min.

MS (ESI) m/z=520.35 (M+H)+.

EXAMPLE 56

[Chemical formula 97]

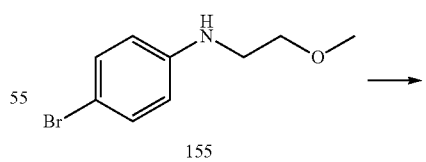

155

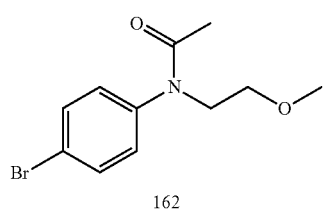

162

Compound 155 (54 mg, 0.235 mmol) was dissolved in dichloromethane (0.5 ml) under nitrogen atmosphere and the mixture was stirred at 0° C. Acetyl chloride (0.025 ml, 0.352 mmol) was added thereto and the mixture was stirred at 0° C. Water was added thereto, and the mixture was extracted with ethyl acetate. The obtained organic layer was washed with a saturated aqueous solution of sodium chloride, then was dried over magnesium sulfate and filtered. The obtained residue was concentrated under reduced pressure to obtain crude Compound 162 (61 mg, 96%).
Compound 162; Method B
LC/MS retention time=1.65 min.
MS (ESI) m/z=270.00 (M+H)+.

EXAMPLE 57

[Chemical formula 98]

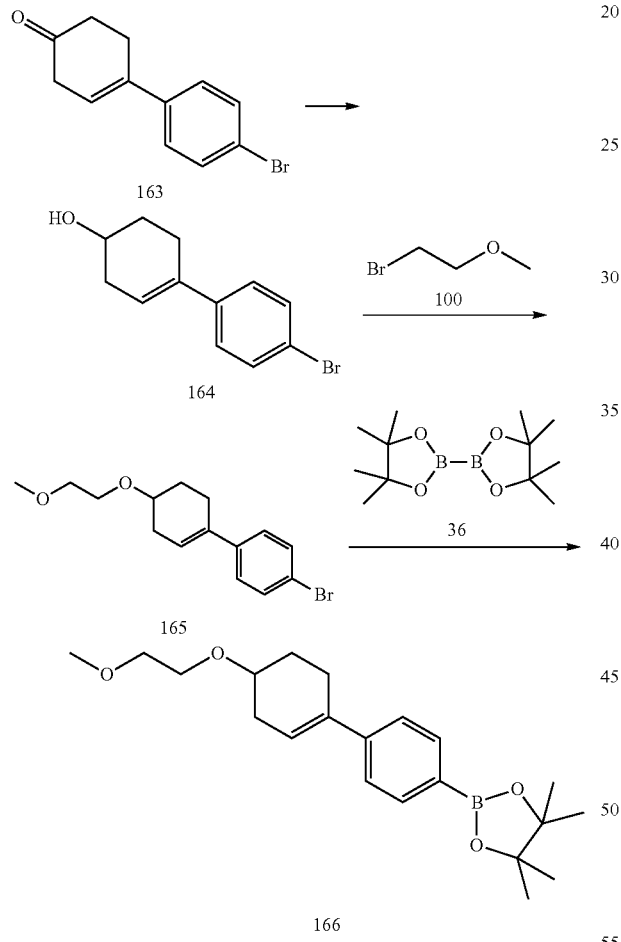

Compound 163 (1.3 g, 5.18 mmol) was dissolved in methanol (30 ml) under nitrogen atmosphere and sodium borohydride (392 mg, 10.35 mmol) was added thereto, and the mixture was stirred at room temperature. A saturated aqueous solution of ammonium chloride was added thereto, and the mixture was extracted with ethyl acetate. The obtained organic layer was washed with a saturated aqueous solution of sodium chloride, then was dried over magnesium sulfate, filtered, and concentrated under reduced pressure. The obtained residue was filtered by adding hexane to obtain Compound 164 (668 mg, 51%).

Compound 164; Method A
LC/MS retention time=2.02 min.
MS (ESI) m/z=252.9 (M+H)+.
Compound 165 was synthesized from Compound 164 and Compound 100, in a similar way that Compound 101 was synthesized from Compound 99 and Compound 100.
Compound 165; Method B
LC/MS retention time=2.53 min.
MS (ESI) m/z=311.60 (M+H)+.
Compound 166 was synthesized from Compound 165 and Compound 36, in a similar way that Compound 102 was synthesized from Compound 101 and Compound 36.
Compound 166; Method B
LC/MS retention time=2.70 min.
MS (ESI) m/z=359.3 (M+H)+.

EXAMPLE 58

[Chemical formula 99]

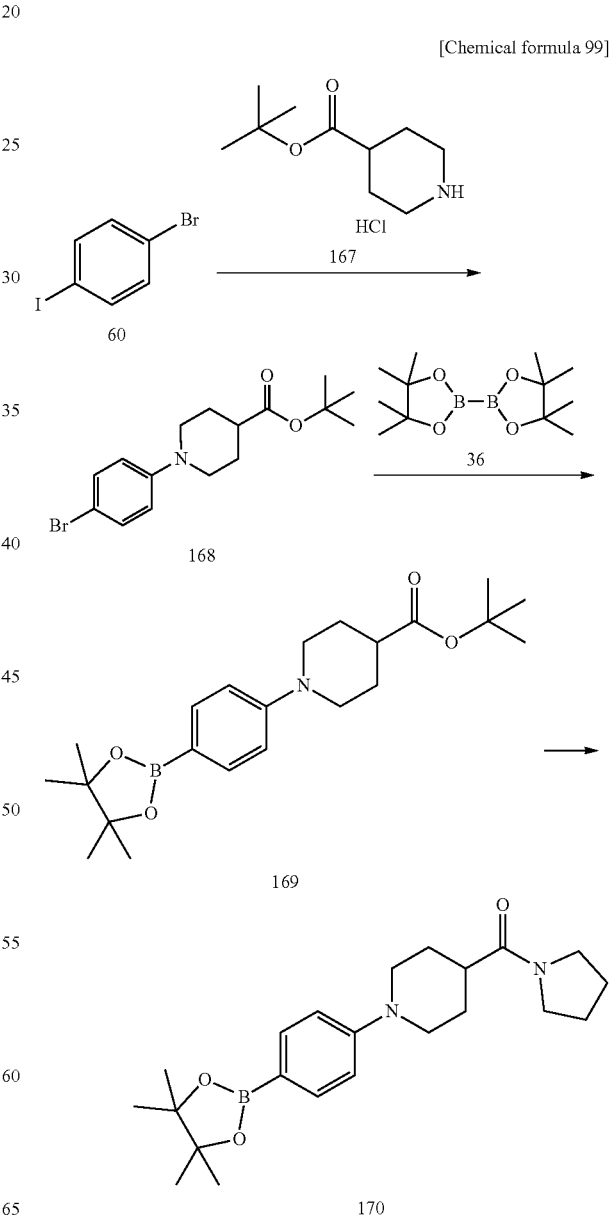

Compound 60 (2 g, 7.07 mmol), Compound 167 (3.14 g, 14.1 mmol), 2-(dimethylamino) ethanol (2.34 mL, 23.3 mmol), Copper (I) iodide (135 mg, 0.707 mmol) and tripotassium phosphate (4.50 g, 21.2 mmol) was dissolved in DMF (18 ml), and the mixture was stirred at 100° C. under nitrogen atmosphere. Water was added thereto, and the mixture was extracted with ethyl acetate. The obtained organic layer was washed with water and a saturated aqueous solution of sodium chloride, then was dried over magnesium sulfate, filtered, and concentrated under reduced pressure. The obtained residue was purified by silica gel column chromatography to obtain Compound 168 (340 mg, 14%).

Compound 168; Method B
LC/MS retention time=2.80 min.
MS (ESI) m/z=340.15 (M+H)+.

Compound 169 was synthesized from Compound 168 and Compound 36, in a similar way that Compound 102 was synthesized from Compound 101 and Compound 36.

Compound 169; Method B
LC/MS retention time=2.91 min.
MS (ESI) m/z=388.05 (M+H)+.

Compound 169 (200 mg, 0.516 mmol) was dissolved in dichloromethane (2 ml). TFA (3 ml) was added thereto and the mixture was stirred at room temperature for 30 minutes. The reaction mixture was concentrated and DMF (2 ml), diisopropylethylamine (0.565 mL, 3.23 mmol), and pyrrolidine (0.134 mL, 1.617 mmol) was added to the obtained residue, and the mixture was stirred at 0° C. HATU (492 mg, 1.29 mmol) was added thereto, and the mixture was stirred at room temperature for 5 hours. A saturated aqueous solution of ammonium chloride was added thereto, and the mixture was extracted with ethyl acetate. The obtained organic layer was washed with water and a saturated aqueous solution of sodium chloride, then was dried over magnesium sulfate, filtered, and concentrated under reduced pressure. The obtained residue was purified by silica gel column chromatography to obtain Compound 170 (17 mg, 9%).

Compound 170; Method A
LC/MS retention time=1.88 min.
MS (ESI) m/z=385.2 (M+H)+.

EXAMPLE 59

[Chemical formula 100]

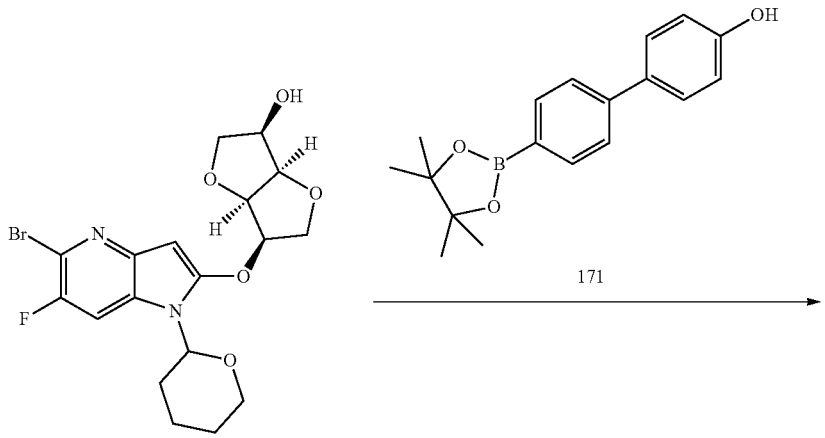

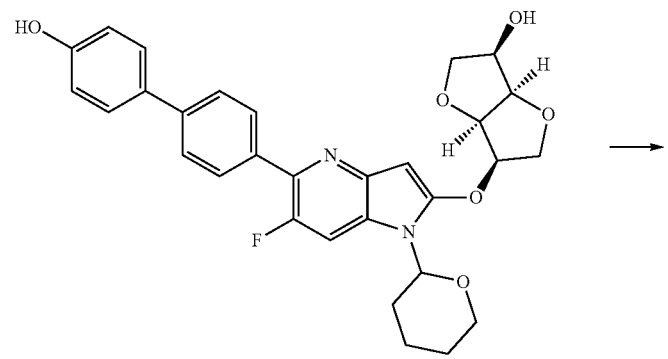

-continued

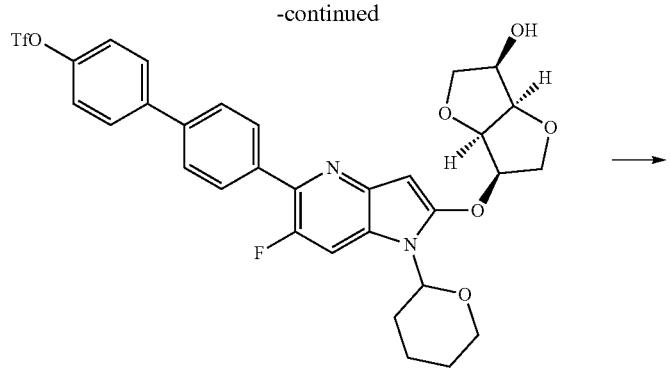

173

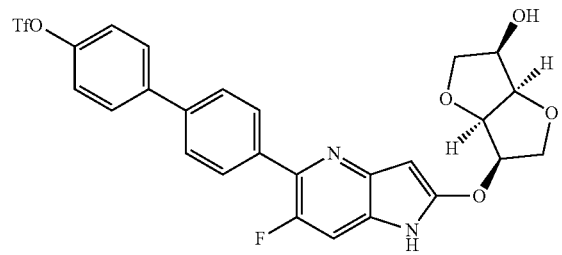

174

Compound 172 was synthesized from Compound 26 and Compound 171, in a similar way that Compound 7 was synthesized from Compound 5 and Compound 6.

Compound 172; Method A
LC/MS retention time=1.79 min.
MS (ESI) m/z=533.2 (M+H)+.

Compound 172 (32 mg, 0.060 mmol) was dissolved in dichloromethane (1 ml) and the mixture was stirred at 0° C. Pyridine (9.70 uL, 0.120 mmol) and trifluoromethanesulfonic anhydride (0.015 mL, 0.090 mmol) was added thereto, and the mixture was stirred at room temperature. After completion of the reaction, water was added thereto, and the mixture was extracted with ethyl acetate. The obtained organic layer was washed with water and a saturated aqueous solution of sodium chloride. The obtained organic layer was dried over magnesium sulfate, filtered, and concentrated under reduced pressure. The obtained residue was purified by silica gel column chromatography to obtain Compound 173 (13 mg, 32%).

Compound 173; Method A
LC/MS retention time=2.65 min.
MS (ESI) m/z=665.1 (M+H)+.

Compound 174 was synthesized from Compound 173, in a similar way that Compound (I-1-01) was synthesized from Compound 7.

Compound 174; Method A
LC/MS retention time=2.19 min.
MS (ESI) m/z=581.1 (M+H)+.

EXAMPLE 60

[Chemical formula 101]

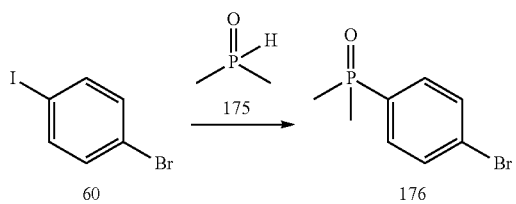

Compound 176 was synthesized from Compound 60 and Compound 175, in a similar way that Compound 52 was synthesized from Compound 50 and Compound 51.

Compound 176; Method B
LC/MS retention time=1.11 min.
MS (ESI) m/z=233.20 (M+H)+.

EXAMPLE 61

[Chemical formula 102]

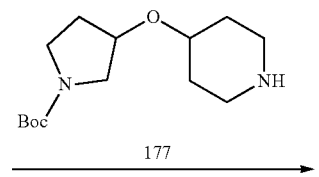

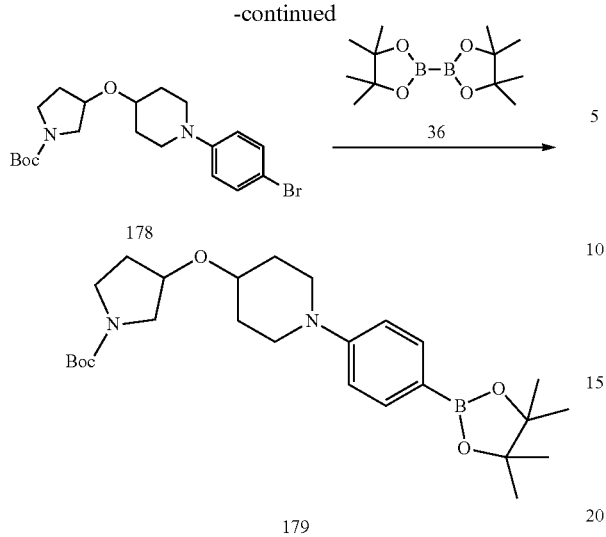

Compound 178 was synthesized from Compound 60 and Compound 177, in a similar way that Compound 52 was synthesized from Compound 50 and Compound 51.

Compound 178; Method B
  LC/MS retention time=2.59 min.
  MS (ESI) m/z=425.15 (M+H)+.

Compound 179 was synthesized from Compound 178 and Compound 36, in a similar way that Compound 102 was synthesized from Compound 101 and Compound 36.

Compound 179; Method B
  LC/MS retention time=2.69 min.
  MS (ESI) m/z=473.35 (M+H)+.

EXAMPLE 62

[Chemical formula 103]

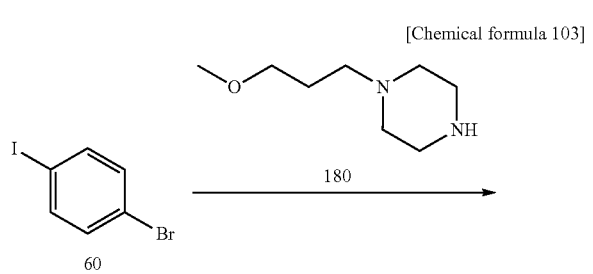

[Chemical formula 104]

Compound 181 was synthesized from Compound 60 and Compound 180, in a similar way that Compound 52 was synthesized from Compound 50 and Compound 51.

Compound 181; Method A
  LC/MS retention time=1.30 min.
  MS (ESI) m/z=313.1 (M+H)+.

Compound 182 was synthesized from Compound 36 and Compound 181, in a similar way that Compound 102 was synthesized from Compound 101 and Compound 36.

Compound 182; Method A
  LC/MS retention time=1.57 min.
  MS (ESI) m/z=361.5 (M+H)+.

EXAMPLE 63

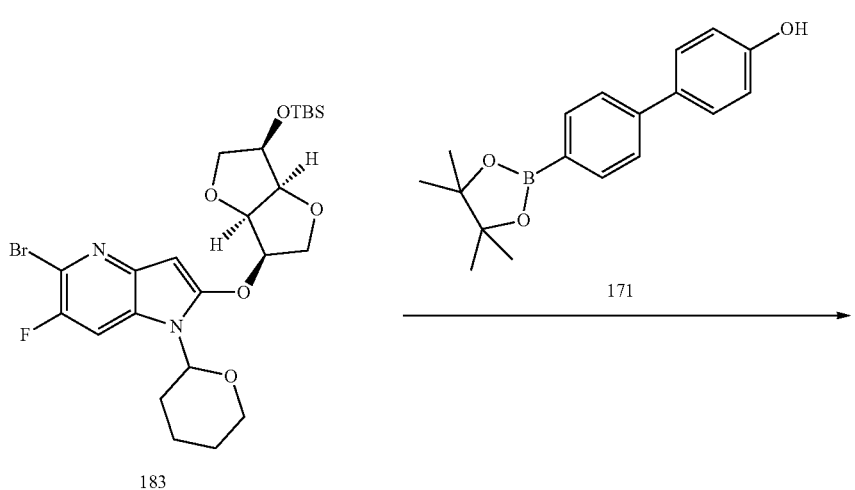

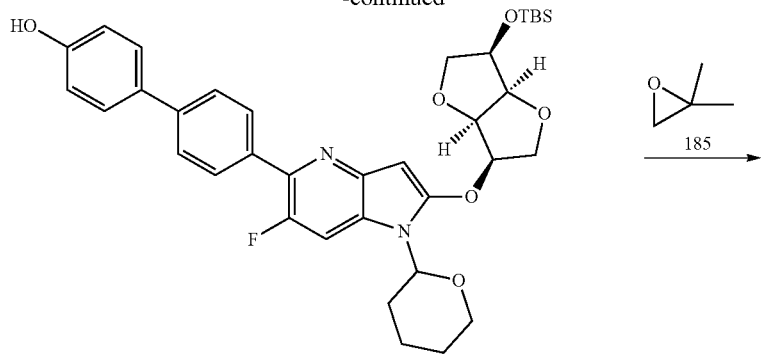

184

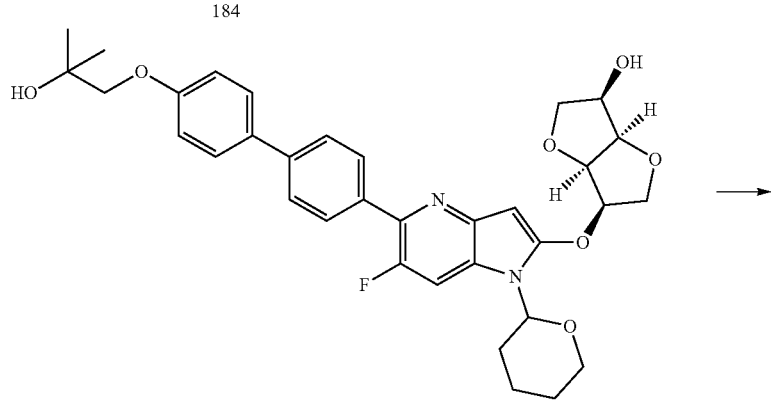

186

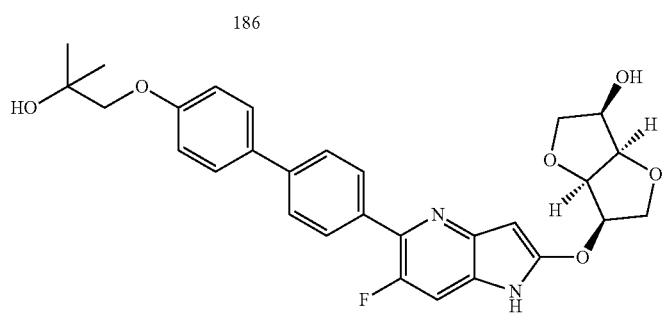

I-2-13

Compound 184 was synthesized from Compound 183 and Compound 171, in a similar way that Compound 7 was synthesized from Compound 5 and Compound 6.

Compound 184; Method A

LC/MS retention time=3.02 min.

MS (ESI) m/z=647.6 (M+H)+.

Compound 184 (52 mg, 0.080 mmol) was dissolved in DMF (0.5 ml). Cesium carbonate (79 mg, 0.241 mmol) and Compound 185 (0.217 mL, 2.412 mmol) were added thereto, and the mixture was stirred at 100° C. The obtained mixture was purified by silica gel column chromatography to obtain Compound 186 (46 mg, 95%).

Compound 186; Method B

LC/MS retention time=1.92 min.

MS (ESI) m/z=605.25 (M+H)+.

Compound (I-2-13) was synthesized from Compound 186, in a similar way that Compound (I-1-01) was synthesized from Compound 7.

Compound (I-2-13); Method B

LC/MS retention time=1.34 min.

MS (ESI) m/z=521.15 (M+H)+.

EXAMPLE 64

[Chemical formula 105]

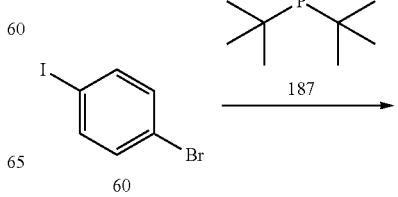

-continued

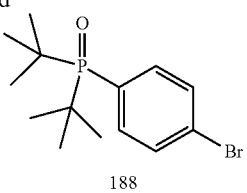
188

Compound 188 was synthesized from Compound 60 and Compound 187, in a similar way that Compound 52 was synthesized from Compound 50 and Compound 51.
Compound 188; Method A
LC/MS retention time=1.88 min.
MS (ESI) m/z=317.4 (M+H)+.

EXAMPLE 65

[Chemical formula 106]

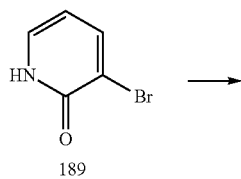
189

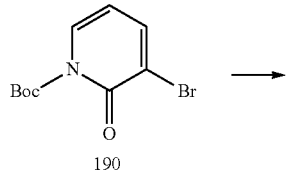
190

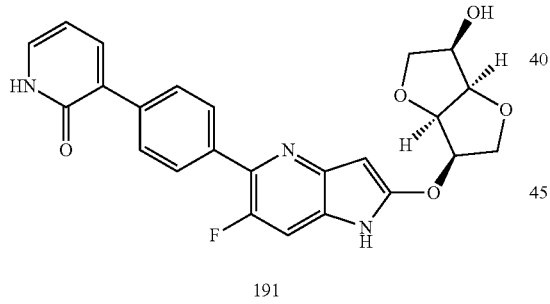
191

Compound 189 (100 mg, 0.575 mmol) was dissolved in THF (1 ml) and the mixture was stirred at 0° C. N-(4-Pyridyl) dimethylamine (7.0 mg, 0.057 mmol) and di-tert-butyl dicarbonate (0.200 mL, 0.862 mmol) were added thereto and the mixture was stirred at room temperature. After completion of the reaction, water was added thereto, and the mixture was extracted with ethyl acetate. The obtained organic layer was washed with water and a saturated aqueous solution of sodium chloride, then was dried over magnesium sulfate, filtered, and concentrated under reduced pressure. The obtained residue was purified by silica gel column chromatography to obtain Compound 190 (72 mg, 46%).
Compound 190; Method B
LC/MS retention time=1.99 min.
MS (ESI) m/z=274.05 (M+H)+.

Compound 191 was synthesized from Compound 190, in a similar way that Compound (I-2-10) was synthesized from Compound 143.
Compound 191; Method A
LC/MS retention time=0.89 min.
MS (ESI) m/z=450.30 (M+H)+.

EXAMPLE 66

[Chemical formula 107]

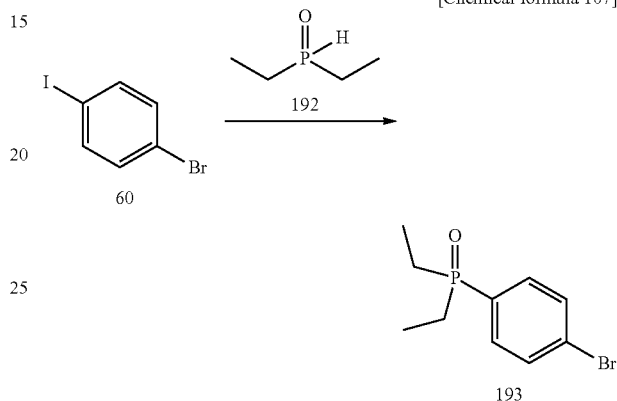

Compound 193 was synthesized from Compound 60 and Compound 192, in a similar way that Compound 52 was synthesized from Compound 50 and Compound 51.
Compound 193; Method B
LC/MS retention time=1.40 min.
MS (ESI) m/z=260.90 (M+H)+.

EXAMPLE 67

[Chemical formula 108]

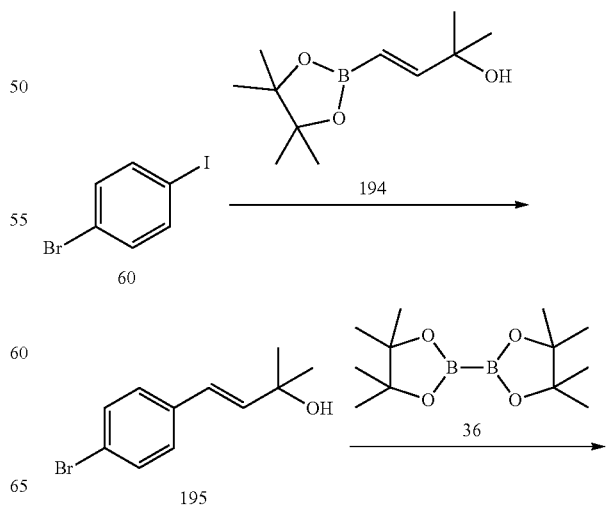

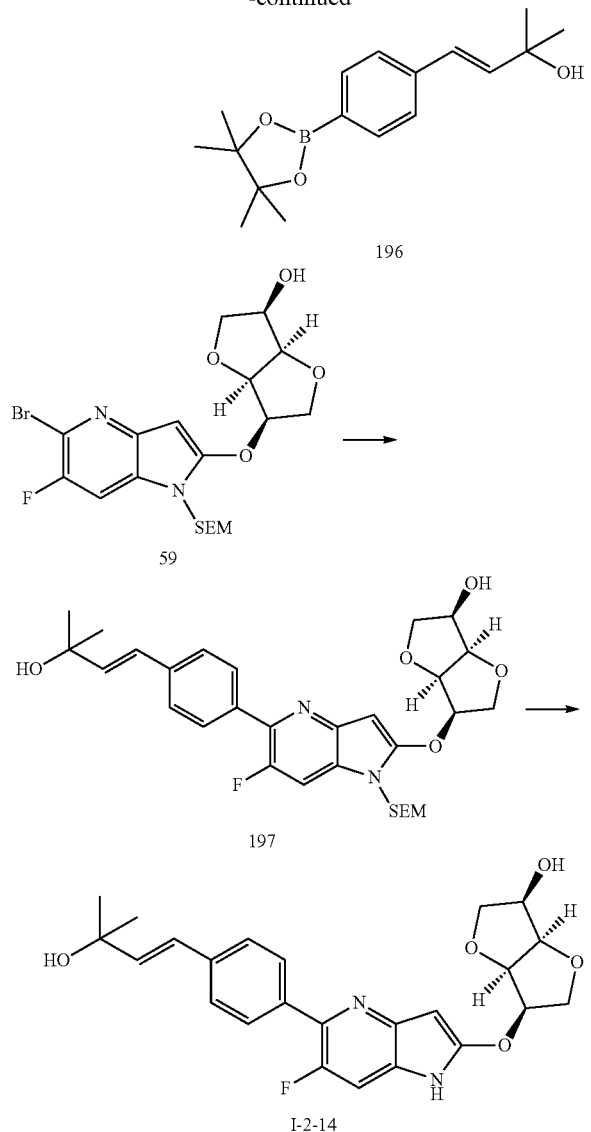

Compound 60 (200 mg, 0.707 mmol) was dissolved in 1,4-dioxane (2 ml). Compound 194 (65 mg, 0.778 mmol), PdCl$_2$(dtbpf) (92 mg, 0.141 mmol) and a 2 mol/L aqueous solution of potassium carbonate were added thereto and the mixture was stirred at 60° C. under nitrogen atmosphere. After completion of the reaction, the obtained mixture was purified by silica gel column chromatography to obtain Compound 195 (45 mg, 26%). Compound 196 was synthesized from Compound 195 and Compound 36, in a similar way that Compound 102 was synthesized from Compound 101 and Compound 36.

Compound 196; Method B
LC/MS retention time=2.24 min.
MS (ESI) m/z=288.90 (M+H)+.

Compound 197 was synthesized from Compound 59 and Compound 196, in a similar way that Compound 117 was synthesized from Compound 12 and Compound 81.

Compound 197; Method A
LC/MS retention time=2.22 min.
MS (ESI) m/z=571.4 (M+H)+.

Compound (I-2-14) was synthesized from Compound 197, in a similar way that Compound (I-1-28) was synthesized from Compound 109.

Compound (I-2-14); Method B
LC/MS retention time=1.06 min.
MS (ESI) m/z=441.05 (M+H)+.

EXAMPLE 68

[Chemical formula 109]

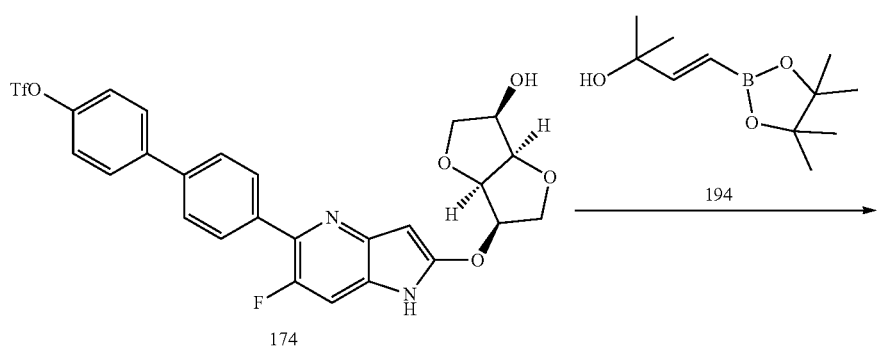

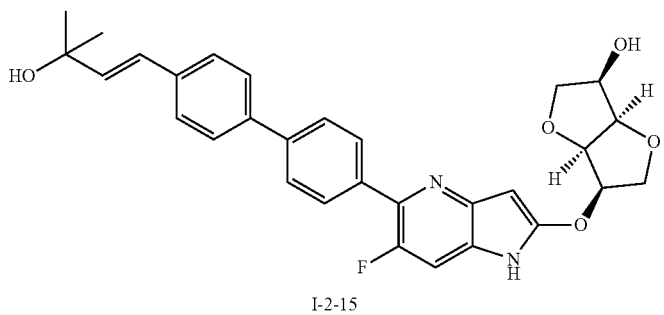

I-2-15

Compound 174 (17 mg, 0.029 mmol) was dissolved in DMF (0.4 ml). Compound 194 (12 mg, 0.059 mmol), a 2 mol/L aqueous solution of potassium carbonate (0.029 ml, 0.059 mmol) and PdCl$_2$(dtbpf) (7.6 mg, 0.012 mmol) were added thereto and the mixture was stirred at 60° C. under nitrogen atmosphere. After completion of the reaction, the obtained mixture was purified by silica gel column chromatography to obtain Compound (I-2-15) (8.8 mg, 58%).

Compound (I-2-15); Method B
LC/MS retention time=1.46 min.
MS (ESI) m/z=517.40 (M+H)+.

EXAMPLE 69

[Chemical formula 110]

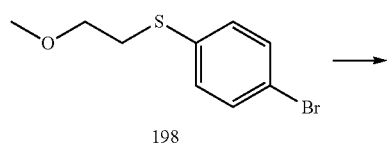

198

-continued

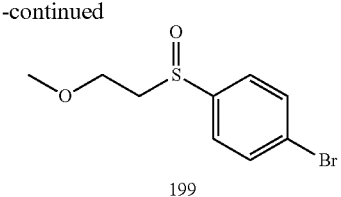

199

Compound 198 (200 mg, 0.809 mmol) was dissolved in dichloromethane (2 ml) and the mixture was stirred at 0° C. 3-Chloroperbenzoic acid (180 mg, 0.728 mmol) was added thereto, and the mixture was stirred at room temperature. After completion of the reaction, a saturated aqueous solution of sodium thiosulfate was added thereto, and the mixture was extracted with chloroform. The obtained organic layer was washed with a saturated aqueous solution of sodium chloride, then was dried over magnesium sulfate, filtered, and concentrated under reduced pressure. The obtained residue was purified by silica gel column chromatography to obtain Compound 199 (178 mg, 84%).

Compound 199; Method B
LC/MS retention time=1.38 min.
MS (ESI) m/z=262.90 (M+H)+.

EXAMPLE 70

[Chemical formula 111]

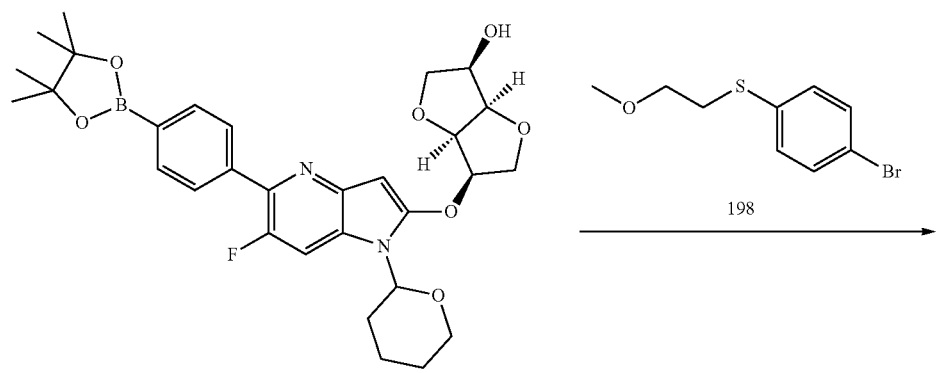

55

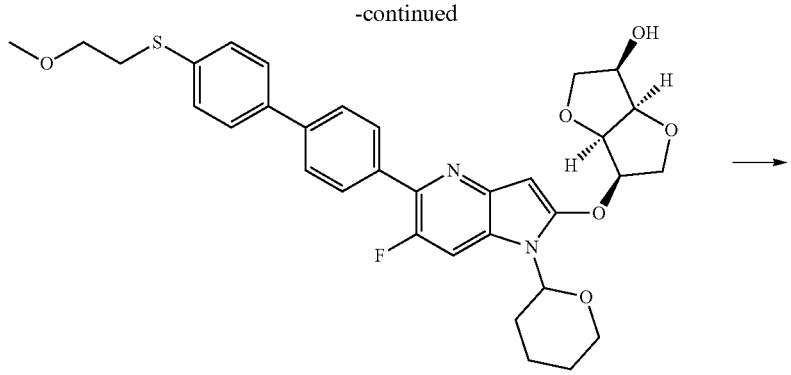

200

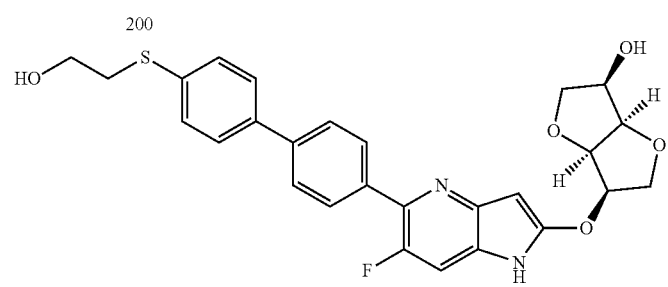

I-2-16

Compound (I-2-16) was synthesized from Compound 55 and Compound 198, in a similar way that Compound (I-2-6) was synthesized from Compound 137 and Compound 135.

LC/MS retention time 1.29 min.
MS (ESI) m/z=n509.35 (M+H)+.

EXAMPLE 71

[Chemical formula 112]

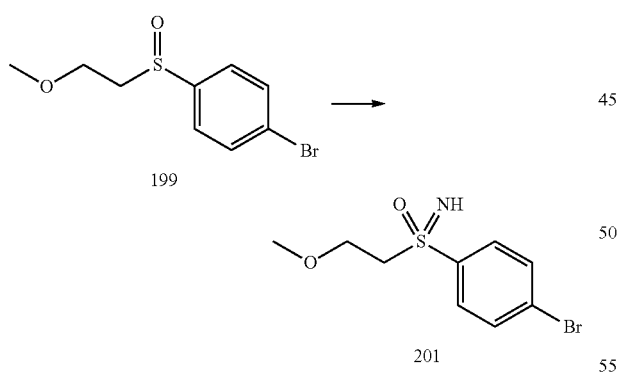

Compound 199 (98 mg, 0.372 mmol) was dissolved in methanol (1 ml). Iodosobenzene diacetate (360 mg, 1.117 mmol) and ammonium carbamate (116 mg, 1.49 mmol) were added thereto and the mixture was stirred at room temperature. After completion of the reaction, the obtained residue was purified by silica gel column chromatography to obtain Compound 201 (78 mg, 75%).

Compound 201; Method B

LC/MS retention time=1.21 min.
MS (ESI) m/z=277.95 (M+H)+.

EXAMPLE 72

[Chemical formula 113]

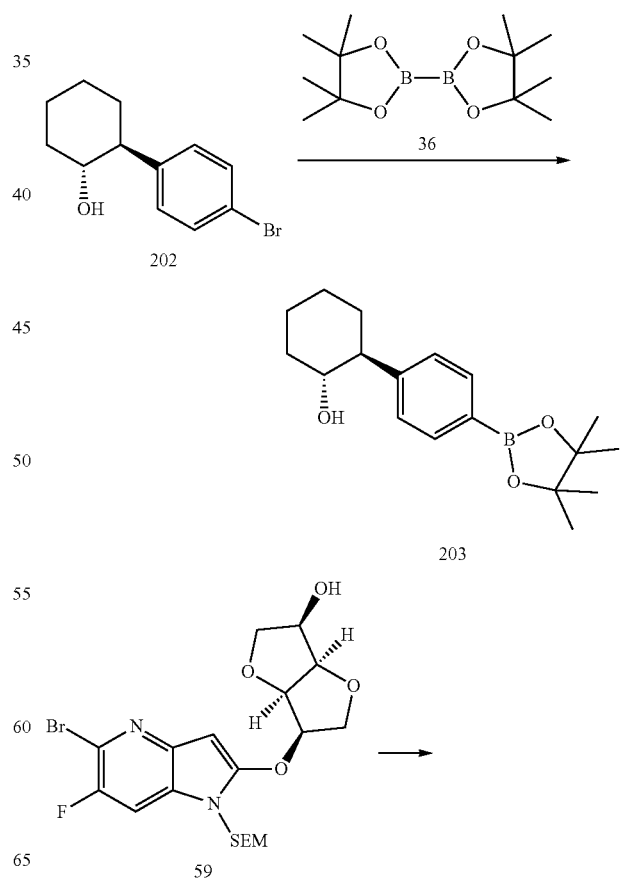

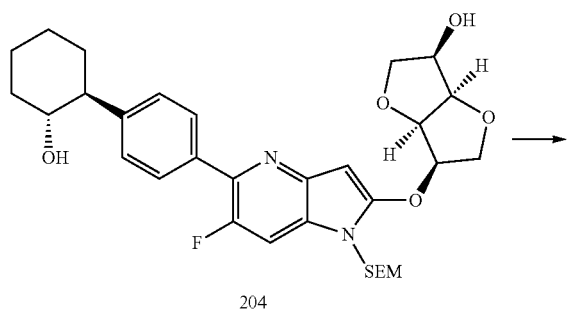

204

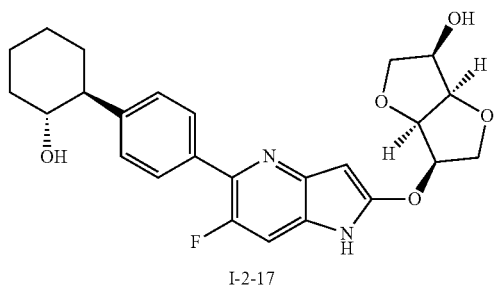

I-2-17

Compound 203 was synthesized from Compound 202 and Compound 36, in a similar way that Compound 102 was synthesized from Compound 101 and Compound 36.

Compound 203; Method B

LC/MS retention time=2.40 min.

MS (ESI) m/z=303.55 (M+H)+.

Compound (I-2-17) was synthesized from Compound 59 and Compound 203, in a similar way that Compound (I-1-17) was synthesized from Compound 59 and Compound 58.

Compound (I-2-17); Method B

LC/MS retention time=1.20 min.

MS (ESI) m/z=455.10 (M+H)+.

EXAMPLE 73

[Chemical formula 114]

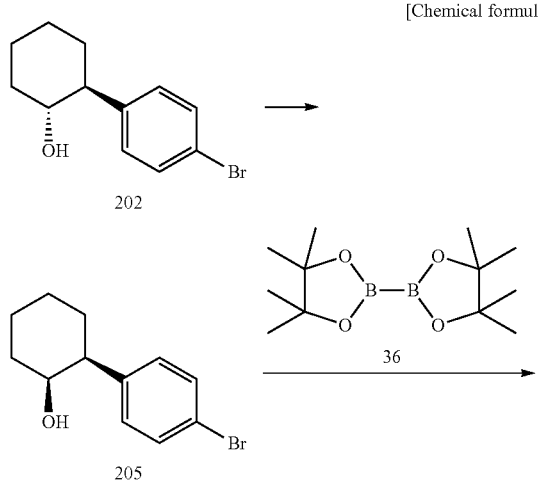

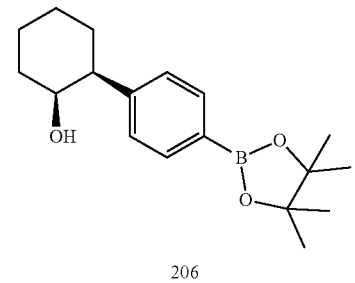

206

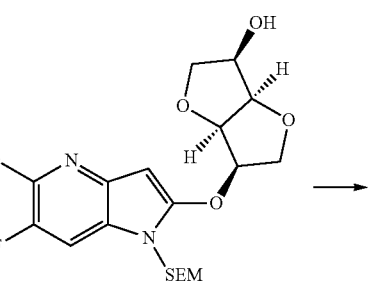

59

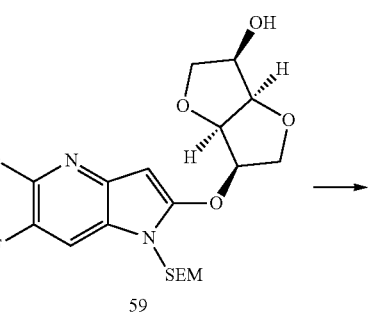

207

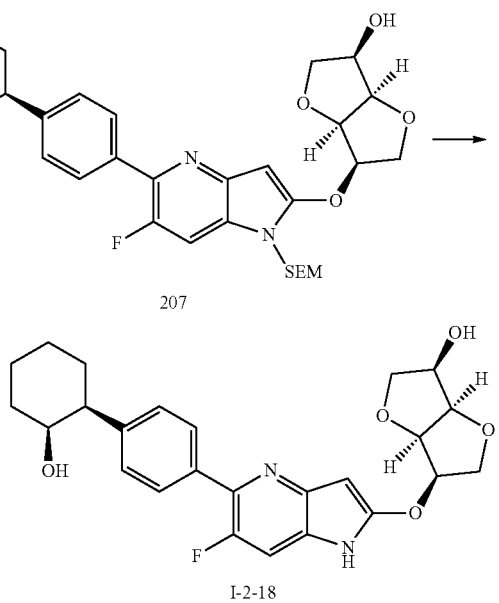

I-2-18

Compound 202 (118 mg, 0.462 mmol) was dissolved in ethyl acetate (4 ml), then 2-iodoxybenzoic acid (647 mg, 2.31 mmol) was added thereto. The reaction mixture was stirred at 85° C. After completion of the reaction, the reaction mixture was filtered with celite and the resulting mixture was concentrated under reduced pressure. The obtained residue was dissolved in THF (1 ml) and the mixture was stirred at 0° C. To the reaction mixture was added potassium hexamethyldisilazide dissolved in THF (0.699 mL, 0.699 mmol) and the mixture was stirred at room temperature. After completion of the reaction, a saturated aqueous solution of ammonium chloride was added thereto, and the mixture was extracted with ethyl acetate. The obtained organic layer was washed with a saturated aqueous solution of sodium chloride and was dried over magnesium sulfate, filtered, and concentrated under reduced pressure. The obtained residue was purified by silica gel column chromatography to obtain Compound 205 (44 mg, 37%).

Compound 205;

1H-NMR (CDCl$_3$) δ: 1.20-1.42 (3H, m), 1.61-1.70 (3H, m), 1.87-2.04 (3H, m), 2.68-2.71 (1H, m), 4.00 (1H, brs), 7.15 (2H, d, J=8.4 Hz), 7.45 (2H, d, J=8.4 Hz).

Compound 206 was synthesized from Compound 205 and Compound 36, in a similar way that Compound 102 was synthesized from Compound 101 and Compound 36.

Compound 206;

1H-NMR (CDCl$_3$) δ: 1.24-1.27 (2H, m), 1.34 (12H, s), 1.36-1.40 (1H, m), 1.64-1.71 (3H, m), 1.88-2.11 (3H, m), 2.75-2.78 (1H, m), 4.02 (1H, brs), 7.28 (2H, d, J=8.0 Hz), 7.78 (2H, d, J=8.0 Hz).

Compound (I-2-18) was synthesized from Compound 59 and Compound 206, in a similar way that Compound (I-1-28) was synthesized from Compound 28 and Compound 108.

Compound (I-2-18); Method B

LC/MS retention time=1.24 min.

MS (ESI) m/z=455.10 (M+H)+.

EXAMPLE 74

[Chemical formula 115]

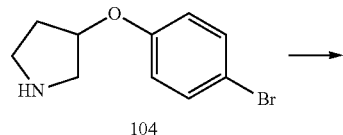

Compound 104 (92 mg, 0.38 mmol) was dissolved in THF (1 ml), then pyridine (0.046 mL, 0.57 mmol) and methyl chloroformate (0.044 mL, 0.57 mmol) were added thereto and the mixture was stirred at room temperature. After completion of the reaction, a saturated aqueous solution of ammonium chloride was added thereto, and the mixture was extracted with ethyl acetate. The obtained organic layer was washed with a saturated aqueous solution of sodium chloride, then was dried over magnesium sulfate, filtered, and concentrated under reduced pressure. The obtained residue was purified by silica gel column chromatography to obtain Compound 208 (58 mg, 51%).

Compound 208; Method A

LC/MS retention time=2.04 min.

MS (ESI) m/z=299.9 (M+H)+.

EXAMPLE 75

[Chemical formula 116]

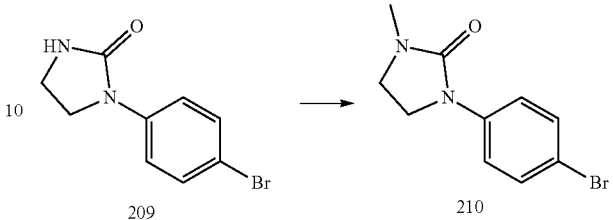

Compound 209 (75 mg, 0.311 mmol) was dissolved in THF (1 ml), and the reaction mixture was stirred at 0° C. A 60 wt % sodium hydride (15 mg, 0.37 mmol) was added thereto and the mixture was stirred at 0° C. for 30 minutes. After that, iodomethane (0.025 mL, 0.040 mmol) was added thereto and the mixture was stirred at room temperature. After completion of the reaction, water was added thereto, and the mixture was extracted with ethyl acetate. The obtained organic layer was washed with a saturated aqueous solution of sodium chloride, then was dried over magnesium sulfate, filtered, and concentrated under reduced pressure to obtain Compound 210 (82 mg).

Compound 210; Method A

LC/MS retention time=1.70 min.

MS (ESI) m/z=255.3 (M+H)+.

EXAMPLE 76

[Chemical formula 117]

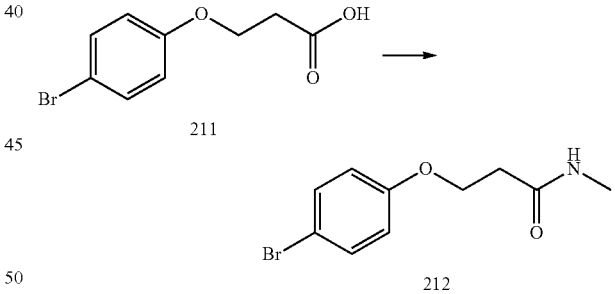

Compound 211 (200 mg, 0.816 mmol) was dissolved in DMF (2 ml), then methylamine hydrochloride (110 mg, 1.63 mmol), N-methylmorpholine (0.269 mL, 2.25 mmol) and HATU (465 mg, 1.22 mmol) were added thereto. The reaction mixture was stirred at room temperature. After completion of the reaction, water was added thereto, and the mixture was extracted with ethyl acetate. The obtained organic layer was washed with a saturated aqueous solution of sodium chloride, then was dried over magnesium sulfate, filtered, and concentrated under reduced pressure to obtain Compound 212 (238 mg).

Compound 212; Method A

LC/MS retention time=1.49 min.

MS (ESI) m/z=258.3 (M+H)+.

EXAMPLE 77

[Chemical formula 118]

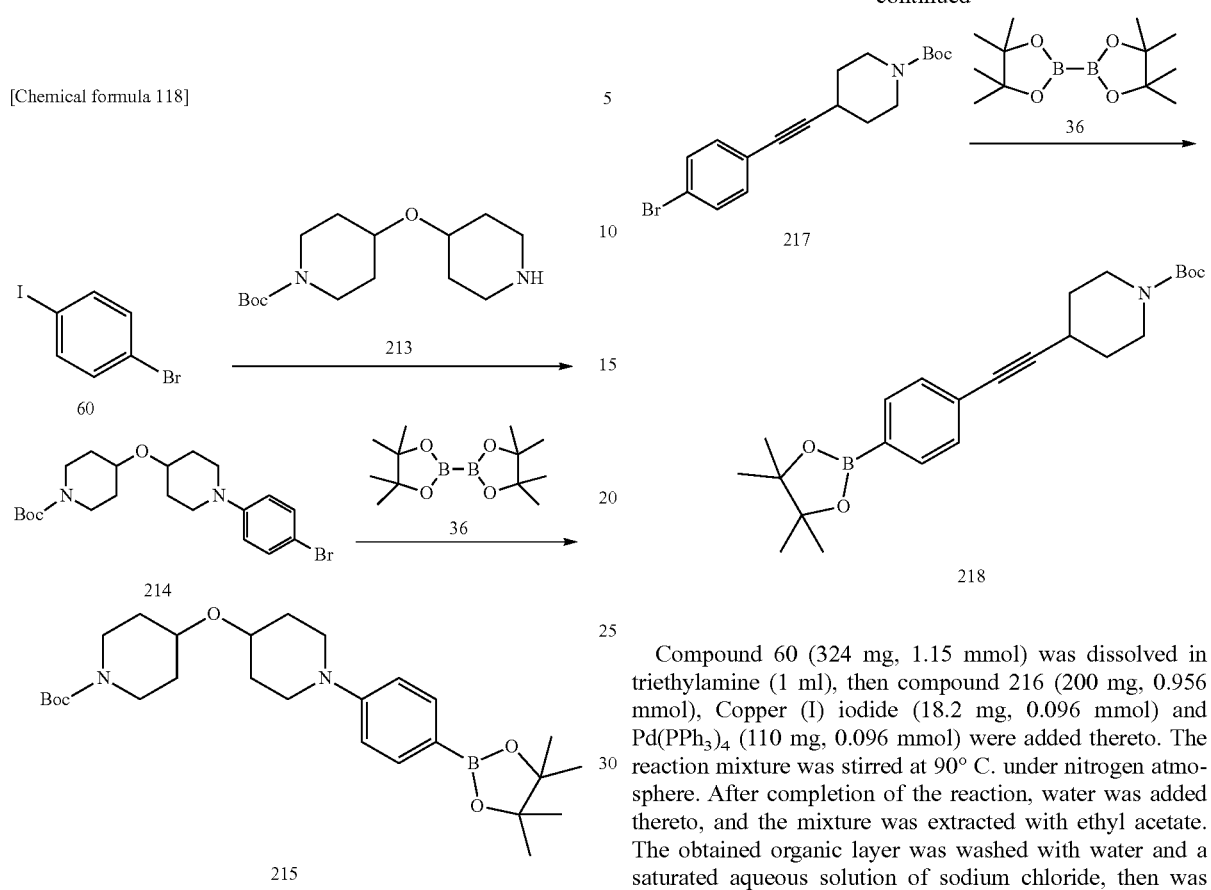

Compound 214 was synthesized from Compound 60 and Compound 213, in a similar way that Compound 52 was synthesized from Compound 50 and Compound 51.

Compound 214; Method C

LC/MS retention time=2.81 min.

MS (ESI) m/z=439.45 (M+H)+.

Compound 215 was synthesized from Compound 214 and Compound 36, in a similar way that Compound 102 was synthesized from Compound 101 and Compound 36.

Compound 215; Method C

LC/MS retention time=2.78 min.

MS (ESI) m/z=487.35 (M+H)+.

Compound 60 (324 mg, 1.15 mmol) was dissolved in triethylamine (1 ml), then compound 216 (200 mg, 0.956 mmol), Copper (I) iodide (18.2 mg, 0.096 mmol) and Pd(PPh$_3$)$_4$ (110 mg, 0.096 mmol) were added thereto. The reaction mixture was stirred at 90° C. under nitrogen atmosphere. After completion of the reaction, water was added thereto, and the mixture was extracted with ethyl acetate. The obtained organic layer was washed with water and a saturated aqueous solution of sodium chloride, then was dried over magnesium sulfate, filtered, and concentrated under reduced pressure. The obtained residue was purified by silica gel column chromatography to obtain Compound 217 (251 mg, 72%).

Compound 217; Method A

LC/MS retention time=3.00 min.

MS (ESI) m/z=364.0 (M+H)+.

Compound 218 was synthesized from Compound 217 and Compound 36, in a similar way that Compound 102 was synthesized from Compound 101 and Compound 36.

Compound 218; Method A

LC/MS retention time=3.15 min.

MS (ESI) m/z=412.3 (M+H)+.

EXAMPLE 78

[Chemical formula 119]

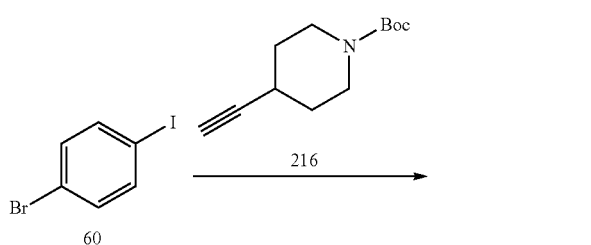

EXAMPLE 79

[Chemical formula 120]

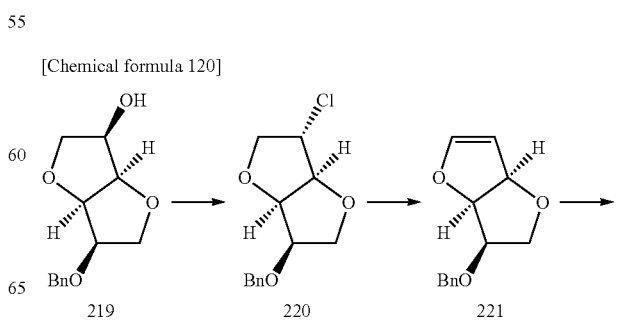

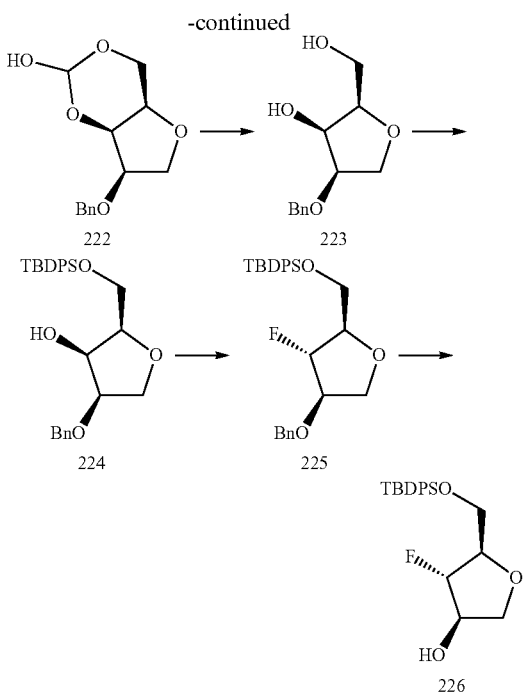

Compound 219 was synthesized according to the method described in the following treatise.

Heterocycles, 2003, 793-804

To Compound 219 (6.16 g, 5.20 mmol) dissolved in acetonitrile (62 ml) was added hexachloroethane (8.52 g, 36.0 mmol), triethylamine (6.66 ml, 48.0 mmol) and triphenylphosphine (1.67 g, 6.35 mmol). The mixture was stirred at 80° C. for 2 hours. The reaction solution was concentrated under reduced pressure. To the obtained residue was added ethyl acetate and water for liquid separating. The organic layer was concentrated under reduced pressure. To the obtained residue was added ethyl acetate (20 ml) and hexane (20 ml) for filtration. The mother liquor was concentrated under reduced pressure. The obtained residue was purified by silica gel column chromatography to obtain Compound 220 (5.85 g, 95.6%).

Compound 220;

1H-NMR (CDCl3) δ: 3.64 (1H, t, J=8.3 Hz), 3.91 (1H, t, J=8.3 Hz), 4.07-4.15 (1H, m), 4.15 (1H, d, J=11.0 Hz), 4.21 (1H, d, J=10.0 Hz), 4.32 (1H, s), 4.57 (1H, d, J=11.5 Hz), 4.61 (1H, s), 4.78 (1H, d, J=11.5 Hz), 4.80 (1H, s), 7.26-7.40 (6H, m).

To Compound 220 (772 mg, 3.03 mmol) dissolved in DMSO (15 ml) was added potassium tert-butoxide (340 mg, 3.03 mmol) and the mixture was stirred at room temperature for 30 minutes. Water was added thereto and the mixture was extracted with diethylether. The organic layer was concentrated under reduced pressure. The obtained residue was purified by silica gel column chromatography to obtain Compound 221 (649.3 mg, 98.1%).

Compound 221;

1H-NMR (CDCl3) δ: 3.31 (1H, dd, J=9.8, 8.5 Hz), 3.88 (1H, dd, J=8.5, 6.5 Hz), 4.09 (1H, dt, J=11.0, 5.1 Hz), 4.62 (1H, d, J=11.9 Hz), 4.76 (1H, d, J=11.9 Hz), 4.80 (1H, d, J=5.8 Hz), 5.05 (1H, t, J=2.6 Hz), 5.35 (1H, dd, J=6.3, 2.6 Hz), 6.70 (1H, d, J=2.5 Hz), 7.28-7.42 (5H, m).

To Compound 221 (772 mg, 3.03 mmol) dissolved in mixed solution of dichloromethane (121 ml) and methanol (24 ml) was added sodium hydrogen carbonate (1.17 g, 13.9 mmol). The mixture was cooled to −78° C. and ventilated with ozone gas. After completion of the reaction, the mixture was ventilated with oxygen gas and sodium borohydride (1.58 g, 41.6 mmol) was added thereto. The mixture was stirred under ice-cooling. A 2 mol/L aqueous solution of hydrochloric acid was added thereto, and the mixture was extracted with chloroform. The organic layer was concentrated under reduced pressure. The obtained residue was purified by silica gel column chromatography to obtain Compound 222 (3.43 g, 97.9%).

Compound 222;

1H-NMR (CDCl3) δ: 3.58-3.65 (1H, m), 3.83-4.21 (7H, m), 4.55-4.62 (2H, m), 4.74 (1H, d, J=12.0 Hz), 7.27-7.42 (5H, m).

To Compound 222 (3.43 g, 13.4 mmol) dissolved in dichloromethane (40 ml) and the mixture was cooled to −78° C. DIBAL-H in hexane (29.6 ml, 30.5 mmol) was added dropwise thereto, and the mixture was stirred at −78° C. After completion of the reaction, water was added thereto and the mixture was diluted with hexane and ethyl acetate. The precipitated solid was separated by filtration. The mother liquor was concentrated under reduced pressure. The obtained was purified by silica gel column chromatography to obtain Compound 223 (2.50 g, 80.4%).

Compound 223;

1H-NMR (CDCl3) δ: 2.48 (1H, t, J=6.2 Hz), 3.06 (1H, d, J=6.0 Hz), 3.82 (1H dd, J=9.7, 5.5 Hz), 3.87 (2H, dd, J=6.2, 4.3 Hz), 3.92 (1H, dd, J=9.7, 4.6 Hz), 3.95 (1H, q, J=4.5 Hz), 4.13 (1H, q, J=5.1 Hz), 4.39 (1H, q, J=5.6 Hz), 4.64 (2H, t, J=12.4 Hz), 7.30-7.41 (5H, m)

Compound 223 (2.50 g, 11.2 mmol) dissolved in dichloromethane (25 ml) was cooled with ice. Triethylamine (1.85 mL, 13.4 mmol), DMAP (0.136 g, 1.115 mmol) and tert-butyldiphenylchlorosilane (3.01 mL, 11.7 mmol) were added thereto and the mixture was stirred at room temperature. After completion of the reaction, the organic layer was concentrated under reduced pressure. Ethyl acetate and water was added thereto for liquid separation. The organic layer was concentrated under reduced pressure. The obtained residue was purified by silica gel column chromatography to obtain Compound 224 (649.3 mg, 98.1%).

Compound 224

1H-NMR (CDCl3) δ: 1.05 (9H, s), 3.81-3.96 (4H, m), 4.02 (1H, dd, J=10.3, 5.5 Hz), 4.15 (1H, dd, J=11.5, 6.7 Hz), 4.30 (1H, q, J=4.4 Hz), 4.57 (1H, d, J=11.7 Hz), 4.65 (1H, d, J=11.7 Hz), 7.31-7.43 (11H, m), 7.69 (4H, td, J=7.6, 1.4 Hz).

Compound 224 (88.2 mg, 0.191 mmol) dissolved in dichloromethane (12 ml) was cooled with ice. DAST (0.151 ml, 1.14 mmol) was added thereto and the mixture was stirred at room temperature. After completion of the reaction, sodium hydrogen carbonate and water were added thereto for neutralization and the resulting mixture was extracted with ethyl acetate. The organic layer was concentrated under reduced pressure. The obtained residue was purified by silica gel column chromatography to obtain Compound 225 (48.3 mg, 54.5%).

Compound 225;

1H-NMR (CDCl3) δ: 1.06 (9H, s), 3.75 (1H, dd, J=10.4, 7.5 Hz), 3.81 (1H, ddd, J=10.4, 5.5, 1.8 Hz), 3.94-4.02 (2H, m), 4.07-4.24 (2H, m), 4.51 (1H, d, J=11 0.8 Hz), 4.57 (1H, d, J=11.8 Hz), 5.17 (1H, dt, J=52.4, 1.7 Hz), 7.26-7.44 (11H, m), 7.64-7.68 (4H, m).

Compound 225 (59.2 mg, 0.127 mmol) dissolved in dichloromethane (2 ml) was cooled to −78° C. A 1.0 mol/l solution of boron tribromide dichloromethane (0.510 ml, 0.510 mmol) was added thereto and the mixture was stirred at −78° C. After completion of the reaction, sodium hydrogen carbonate and water were added thereto for neutralization and the resulting mixture was extracted with ethyl acetate. The organic layer was concentrated under reduced pressure. The obtained residue was purified by silica gel column chromatography to obtain Compound 226 (32.1 mg, 67.3%).

Compound 226;

1H-NMR (CDCl3) δ: 1.06 (10H, s), 3.75 (1H, dd, J=11.3, 1.8 Hz), 3.86 (1H, dd, J=11.3, 2.8 Hz), 3.93-4.02 (2H, m), 4.04-4.15 (2H, m), 4.28 (1H, td, J=11.0, 2.5 Hz), 5.06 (1H, d, J=52.1 Hz), 7.39-7.49 (6H, m), 7.65-7.72 (4H, m).

EXAMPLE 80

[Chemical formula 121]

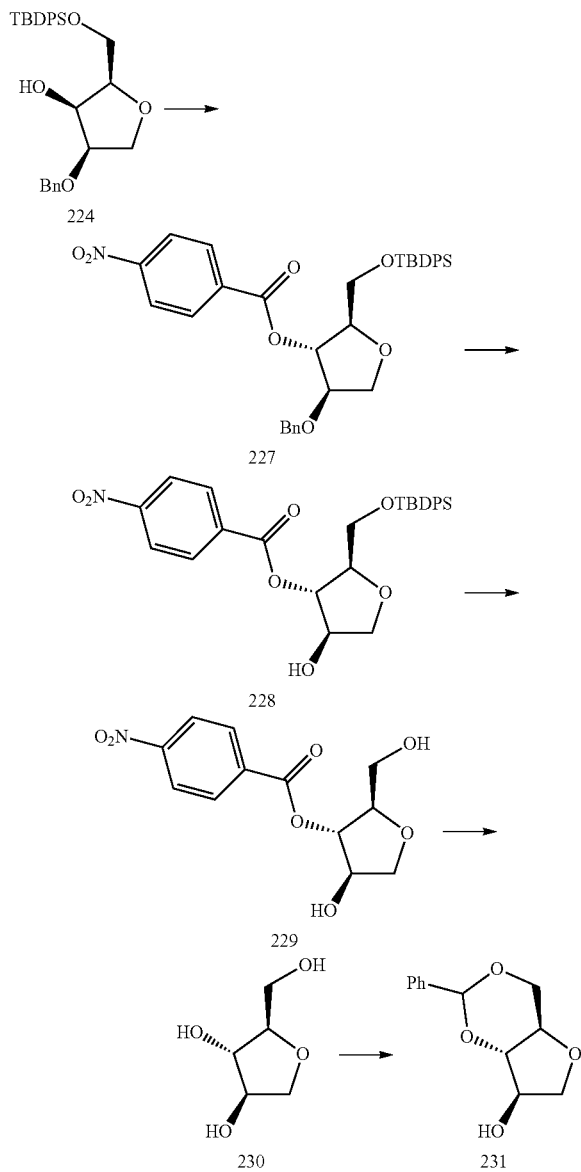

Compound 224 (919 mg, 1.99 mmol), 4-nitrobenzoic acid (0.498 g, 2.98 mmol) and triphenylphosphine (0.782 g, 2.98 mmol) dissolved in THF (10 ml) was cooled with ice. A 1.9 mol/l solution of DIAD-in toluene (1.57 mL, 2.98 mmol) was added dropwise thereto and the mixture was stirred at room temperature for 3 hours. The organic layer was concentrated under reduced pressure. The obtained residue was purified by silica gel column chromatography to obtain Compound 227 (1.15 g, 94.8%).

Compound 227;

H-NMR (CDCl3) δ: 1.04 (9H, s), 3.87 (1H, dd, J=10.5, 7.1 Hz), 3.93 (1H, dd, J=10.4, 5.6 Hz), 4.03 (2H, d, J=3.5 Hz), 4.14-4.20 (2H, m), 4.59 (1H, d, J=1 2.0 Hz), 4.71 (1H, d, J=12.0 Hz), 5.64 (1H, s), 7.29-7.41 (11H, m), 7.67 (4H, d, J=6.7 Hz), 8.20 (2H, d, J=8.8 Hz), 8.31 (2H, d, J=8.8 Hz).

Compound 227 (1.15 g, 1.89 mmol) dissolved in dichloromethane (11 ml) was cooled to −78° C. A 1.0 mol/l solution of boron tribromide dichloromethane (2.83 mL, 2.83 mmol) was added thereto and the mixture was stirred at −78° C. After completion of the reaction, sodium hydrogen carbonate (161 mg, 1.91 mmol) and water were added thereto for neutralization and the resulting mixture was extracted with ethyl acetate. The organic layer was concentrated under reduced pressure. The obtained residue was purified by silica gel column chromatography to obtain Compound 228 (773 mg, 78.6%).

Compound 228;

1H-NMR (CDCl3) δ: 1.09 (9H, s), 3.88-3.98 (2H, m), 4.00-4.19 (4H, m), 4.37 (1H, d, J=10.0 Hz), 5.39 (1H, s), 7.40-7.46 (6H, m), 7.73 (4H, t, J=6.7 Hz), 8.18 (2H, d, J=8.5 Hz), 8.30 (2H, d, J=8.5 Hz).

Compound 228 (721 mg, 1.38 mmol) dissolved in THF (7 ml) was added to TBAF-in 1 mol/L THF (1.66 mL, 1.66 mmol) and the mixture was stirred at room temperature. After the reaction, the reaction mixture was concentrated. The obtained residue was added water and ethyl acetate for extraction. The organic layer was concentrated under reduced pressure. The obtained residue was purified by silica gel column chromatography to obtain Compound 229 (106 mg, 27.0%).

Compound 229; Method C

LC/MS retention time=1.18 min.

MS (ESI) m/z=284.10 (M+H)+.

To Compound 229 (100 mg, 0.354 mmol) dissolved in mixed solutions of THF (2 ml) and methanol (1 ml) was added a 2.0 mol/L aqueous solution of sodium hydroxide (0.354 mL, 0.708 mmol), and the mixture was stirred at room temperature. After completion of the reaction, a 2 mol/L aqueous solution of hydrochloric acid was added thereto. The reaction mixture was concentrated and the obtained residue was diluted with ethyl acetate and THF. The precipitated solid was separated by filtration. The obtained filtrate was concentrated to obtain Compound 230 as a crude product.

To Compound 230 (45.3 mg, 0.338 mmol) dehydrated by toluene azeotrope dissolved in acetonitrile (2 mL) was added to benzaldehyde dimethyl acetal (0.076 mL, 0.507 mmol) and p-toluenesulfonic acid monohydrate (24.4 mg, 0.128 mmol). The reaction mixture was refluxed for 30 minutes after stirring at room temperature for 1 hour. Benzaldehyde dimethyl acetal (0.076 mL, 0.507 mmol) was added thereto, and refluxed for 30 minutes. Benzaldehyde dimethyl acetal (0.076 mL, 0.507 mmol) was further added thereto, and refluxed for 1 hour. After completion of the reaction, an aqueous solution of sodium hydrogen carbonate was added thereto for neutralization and the resulting mixture was extracted with ethyl acetate. The organic layer was concentrated under reduced pressure. The obtained residue was purified by silica gel column chromatography to obtain Compound 231 (29.0 mg, 38.6%).

Compound 231; Method C
LC/MS retention time=1.37 min.
MS (ESI) m/z=223.15 (M+H)+.

EXAMPLE 81

[Chemical formula 122]

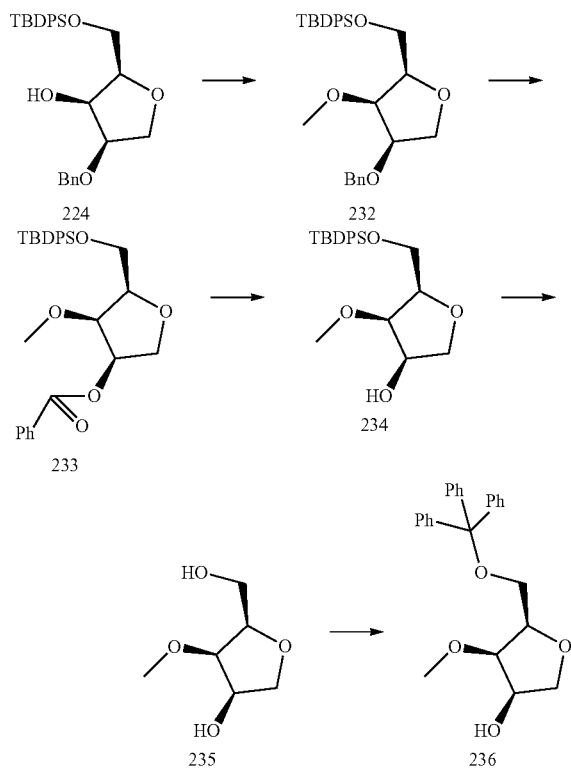

Compound 224 (158 mg, 0.342 mmol) dissolved in DMF (1.58 ml) was cooled with ice. Iodomethane (0.214 mL, 3.42 mmol) and sodium hydride (60 wt %, 20.5 mg, 0.512 mmol) were added thereto and stirred at room temperature for 1 hour. Water was added thereto and extracted with ethyl acetate. The organic layer was concentrated under reduced pressure. The obtained residue was purified by silica gel column chromatography to obtain Compound 232 (154 mg, 94.8%).

Compound 232; Method C
LC/MS retention time=3.03 min.
MS (ESI) m/z=477.15 (M+H)+.

To Compound 232 (146 mg, 0.307 mmol) dissolved in mixed solutions of carbon tetrachloride (3 ml), acetonitrile (3 ml) and water (4.5 ml) was added sodium periodate (276 mg, 1.29 mmol) and ruthenium (IV) oxide hydrate (1.8 mg, 0.012 mmol). The mixture was stirred at room temperature. Water was added thereto and the mixture was extracted with ethyl acetate. The organic layer was filtrated and concentrated under reduced pressure to obtain mixed product of Compound 233 (109 mg, 72.6%) and unreacted Compound 232 (31.2 mg, 21.2%). The mixture ratio of the compounds was decided by 1H NMR.

Compound 233; Method C
LC/MS retention time=3.02 min.
MS (ESI) m/z=513.13 (M+H)+.

To mixed solution of Compound 233 (107 mg, 0.219 mmol) and Compound 232 (30.5 mg, 0.064 mmol) dissolved in THF (2 ml) and methanol (1 ml) were added a 2 mol/L aqueous solution of sodium hydroxide (0.354 mL, 0.708 mmol) The mixture was stirred at room temperature. After completion of the reaction, water was added thereto and the mixture was extracted with ethyl acetate. The organic layer was concentrated under reduced pressure. The obtained residue was purified by silica gel column chromatography to obtain Compound 234 (62.4 mg, 73.7%).

Compound 234;
1H-NMR (CDCl3) δ: 1.07 (9H, s), 3.53 (3H, s), 3.68-3.77 (2H, m), 3.83-3.95 (2H, m), 3.98-4.09 (2H, m), 4.20 (1H, d, J=10.5 Hz), 4.26-4.34 (1H, m), 7.35-7.47 (6H, m), 7.74 (4H, d, J=6.5 Hz).

To Compound 234 (61.7 mg, 0.160 mmol) dissolved in THF (1 mL) was added TBAF (a 1.0 mol/L solution of THF, 0.239 mL, 0.239 mmol) and stirred at room temperature. After completion of the reaction, the reaction solution was concentrated. The obtained residue was purified by silica gel column chromatography to obtain Compound 235 (23.0 mg, 97.3%).

Compound 235;
1H-NMR (CDCl3) δ: 2.37 (1H, br s), 3.50 (3H, s), 3.53 (1H, br s), 3.70-3.82 (3H, m), 3.95 (1H, d, J=10.3 Hz), 4.01-4.13 (2H, m), 4.28 (1H, d, J=0.8 Hz).

To Compound 235 (22.0 mg, 0.148 mmol) and triphenylchloromethane (45.5 g, 0.163 mmol) dissolved in dichloromethane (2 mL) was added triethylamine (0.031 ml, 0.223 mmol) and DMAP (1.8 mg, 0.015 mmol), and stirred at room temperature. After completion of the reaction, the reaction solution was concentrated. The obtained residue was purified by silica gel column chromatography to obtain Compound 236 (16.4 g, 79.0%).

Compound 236;
1H-NMR (CDCl3) δ: 1H-NMR (CDCl$_3$) δ: 3.29 (1H, s), 3.30 (2H, d, J=8.0 Hz), 3 0.35 (3H, s), 3.80 (1H, dd, J=9.7, 3.8 Hz), 3.86 (1H, d, J=5.1 Hz), 3.89 (1H, d, J=5.6 Hz), 4.11-4.15 (1H, m), 4.28-4.34 (1H, m), 7.23 (3H, t, J=7.3 Hz), 7.30 (6H, t, J=7.5 Hz), 7.47 (6H, d, J=7.4 Hz).

EXAMPLE 82

[Chemical formula 123]

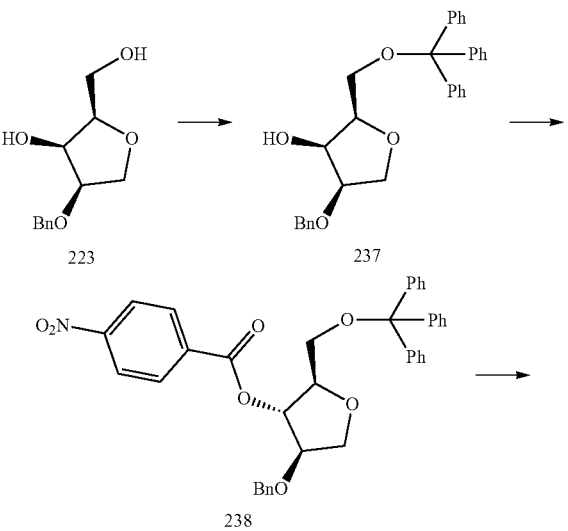

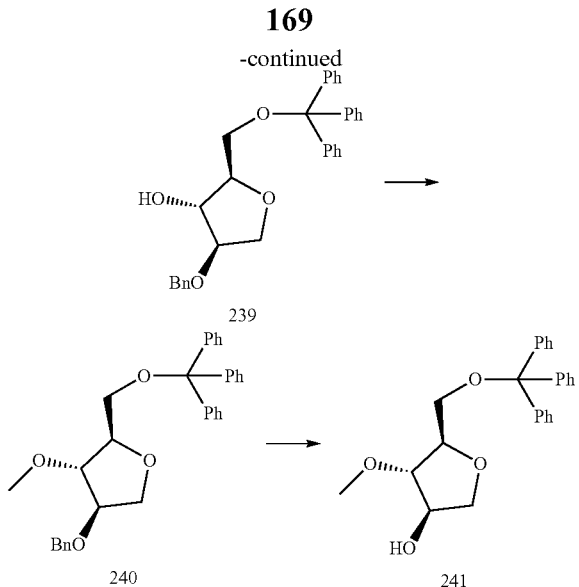

To Compound 223 (10.0 g, 44.6 mmol) and triphenyl-chloromethane (14.3 g, 51.3 mmol) dissolved in dichloromethane (100 ml) was added trimethylamine (8.65 ml, 62.4 mmol) and DMAP (0.545 g, 4.46 mmol) and the mixture was stirred at room temperature. After completion of the reaction, the reaction solution was concentrated under reduced pressure. To the obtained residue was added ethyl acetate and water for liquid separating. The organic layer was concentrated under reduced pressure. The obtained residue was purified by silica gel column chromatography and crystallized with ethyl acetate and hexane to obtain Compound 237 (16.4 g, 79.0%).

Compound 237;

1H-NMR (CDCl3) δ: 2.66 (1H, d, J=4.8 Hz), 3.36 (1H, dd, J=9.8, 6.3 Hz), 3.4 3 (1H, dd, J=9.8, 5.0 Hz), 3.85 (1H, dd, J=9.2, 6.3 Hz), 3.91 (1H, dd, J=9.2, 6.7 Hz), 3.99 (1H, dd, J=10.3, 4.9 Hz), 4.15 (1H, dd, J=11.6, 6.2 Hz), 4.26 (1H, q, J=4.6 Hz), 4.56 (1H, d, J=11.7 Hz), 4.63 (1H, d, J=11.7 Hz), 7.21 (3H, t, J=7.2 Hz), 7.24-7.38 (10H, m), 7.47 (6H, d, J=7.4 Hz).

Compound 237 (6.00 g, 12.9 mmol), 4-nitrobenzoic acid (3.22 g, 19.3 mmol) and triphenylphosphine (5.06 g, 19.3 mmol) dissolved in THF (60 ml) was cooled with ice. A 1.9 mol/l solution of DIAD-in toluene (10.2 mL, 19.3 mmol) was added dropwise thereto and the mixture was stirred at room temperature. The reaction mixture was concentrated under reduced pressure. The obtained residue was purified by silica gel column chromatography to obtain Compound 238 (7.89 g, 99.6%).

Compound 238; Method C

LC/MS retention time=3.11 min.

MS (ESI) m/z=638.45 (M+H)+.

To Compound 238 (1.25 g, 2.03 mmol) dissolved in mixed solution of THF (12 ml) and methanol (6 ml) was added a 2.0 mol/L aqueous solution of sodium hydroxide (2.03 mL, 4.06 mmol). The mixture was stirred at room temperature. After completion of the reaction, water was added thereto and the resulting mixture was extracted with ethyl acetate. The organic layer was concentrated under reduced pressure. The obtained residue was crystallized with isopropyl ether and hexane to obtain Compound 239 (912 mg, 96.2%).

Compound 239;

1H-NMR (CDCl3) δ: $^1$H-NMR (CDCl$_3$) δ: 3.18-3.25 (1H, m), 3.39-3.46 (1H, m), 3.8 2-3.95 (2H, m), 4.00-4.06 (2H, m), 4.21 (1H, s), 4.50 (1H, d, J=11.5 Hz), 4.56 (1H, d, J=11.5 Hz), 7.18-7.33 (17H, m), 7.44 (6H, d, J=7.0 Hz).

To Compound 239 (500 mg, 1.07 mmol) dissolved in DMF (2 ml) was added methyl iodide (0.134 mL, 2.14 mmol), sodium hydride (60 wt %, 64.3 mg, 1.61 mmol). The mixture was stirred at room temperature. Water was added thereto and the resulting mixture was extracted with ethyl acetate. The organic layer was concentrated under reduced pressure to obtain Compound 240. Compound 240 was used for next step without purification.

To Compound 240 (512 mg, 1.07 mmol) and sodium bromate (485 mg, 3.22 mmol) dissolved in mixed solution of ethyl acetate (5.2 ml) and water (3.1 ml) was added dropwise 1 mL sodium dithionite (75%, 497 mg, 2.14 mmol). The mixture was stirred at room temperature. After the reaction, a saturated aqueous solution of sodium thiosulfate was added thereto and the obtained residue was extracted with ethyl acetate. The organic layer was concentrated under reduced pressure. The obtained residue was purified by silica gel column chromatography to obtain Compound 241 (105 mg, 25.1%).

Compound 241;

1H-NMR (CDCl3) δ: 3.20 (1H, d, J=10.3 Hz), 3.31 (3H, s), 3.34 (1H, d, J=10.3 Hz), 3.57-3.65 (2H, m), 3.83-3.90 (2H, m), 3.98 (1H, d, J=9.8 Hz), 4.12-4.16 (1H, m), 7.29 (9H, dt, J=30.8, 5.9 Hz), 7.21-7.28 (5H, m), 7.32 (6H, t, J=7.3 Hz), 7.44 (6H, d, J=7.5 Hz).

EXAMPLE 83

[Chemical formula 124]

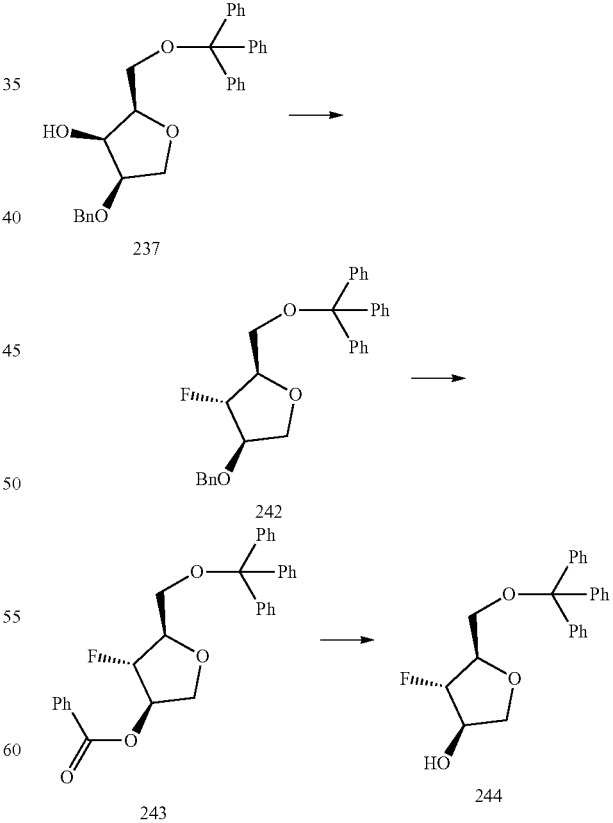

Compound 242 was synthesized from Compound 237, in a similar way that Compound 225 was synthesized from Compound 224.

Compound 242; Method C
 LC/MS retention time=2.84 min.
 MS (ESI) m/z=491.05 (M+H)+.

To mixed solution of Compound 242 (282.0 mg, 0.602 mmol) dissolved carbon tetrachloride (5.6 ml), acetonitrile (5.1 ml) and distilled water (7.2 ml) was added sodium periodate (282.0 mg, 0.602 mmol) and ruthenium (IV) oxide hydrate (14.6 mg, 0.097 mmol). The mixture was stirred at room temperature. After completion of the reaction, the reaction solution was concentrated under reduced pressure. To the obtained residue was added ethyl acetate and water for liquid separating. The obtained organic layer was filtrated and concentrated under reduced pressure. The residue containing Compound 243 was diluted with THF (2 ml) and methanol (1ml), and a 2 mol/L aqueous solution of sodium hydroxide was added. The mixture was stirred at room temperature. After completion of the reaction, the reaction solution was concentrated under reduced pressure. To the obtained residue was added water and ethyl acetate for liquid separating. The organic layer was concentrated under reduced pressure. The obtained residue was purified by silica gel column chromatography to obtain Compound 244 (129.6 mg, 46.0%).

Compound 244;
 1H-NMR (CDCl3) δ: 3.25 (1H, dd, J=10.4, 2.1 Hz), 3.53 (1H, d, J=10.8 Hz), 3.61-3.66 (1H, m), 3.93-3.99 (1H, m), 4.04-4.15 (2H, m), 4.22-4.30 (1H, m), 4.84 (1H, d, J=52.2 Hz), 7.23-7.29 (8H, m), 7.33 (6H, t, J=7.4 Hz), 7.42 (6H, d, J=7.9 Hz).

EXAMPLE 84

[Chemical formula 125]

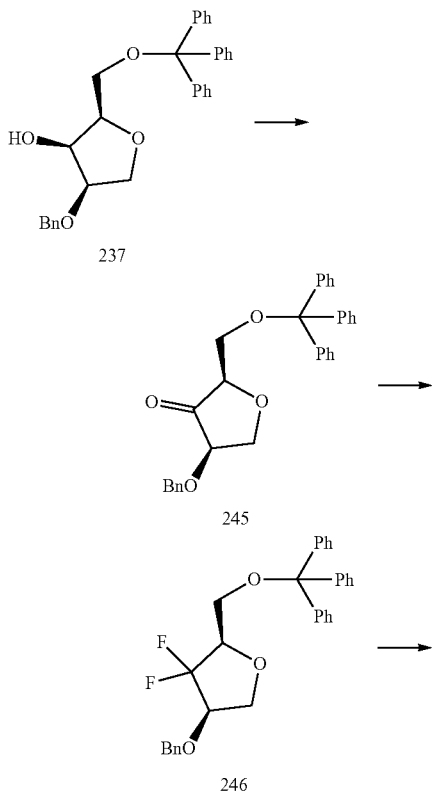

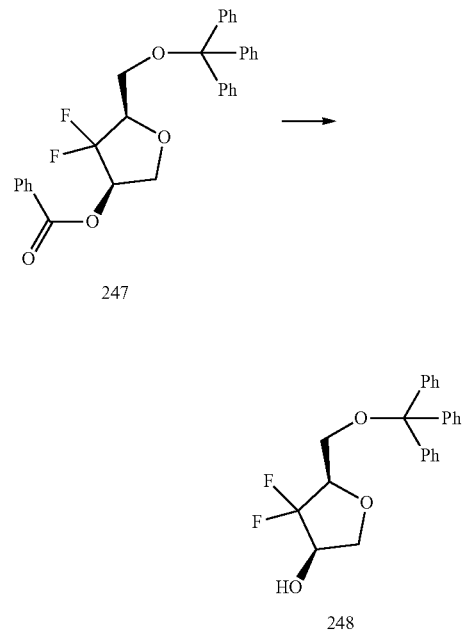

To Dess-Martin Periodinane (2.73 g, 6.43 mmol) dissolved dichloromethane (80 ml) was added Compound 237 (2.00 g, 4.29 mmol) The mixture was stirred at room temperature. After completion of the reaction, the reaction solution was concentrated under reduced pressure and diluted with hexane and ethyl acetate (1:1). The precipitated solid was separated by filtration. The obtained residue by concentrating the filtrate under reduced pressure was purified by silica gel column chromatography to obtain Compound 245 (1.80 g, 90.2%).

Compound 245; Method C
 LC/MS retention time=2.77 min.
 MS (ESI) m/z=487.30 (M+H)+.

To Compound 245 (638 mg, 1.37 mmol) dissolved in 1,2-dichloroethane (6.4 mL) was added DAST (0.725 ml, 5.49 mmol). The reaction mixture was refluxed at 80° C. for 4 hours. The reaction solution cooled to room temperature was added to sodium hydrogen carbonate (2.31 g, 27.5 mmol) and ice water. To the obtained residue was added ethyl acetate and water for liquid separating. The obtained organic layer was concentrated under reduced pressure. The obtained residue was purified by silica gel column chromatography to obtain Compound 246 (450 mg, 67.4%).

Compound 246; Method C
 LC/MS retention time=2.86 min.
 MS (ESI) m/z=509.00 (M+H)+

To mixed solution of Compound 246 (449 mg, 0.922 mmol) dissolved in carbon tetrachloride (9 ml) and acetonitrile (9 ml), and water (13.5 ml) was added sodium periodate (986 mg, 4.61 mmol) and ruthenium (IV) oxide hydrate (7.0 mg, 0.046 mmol). The mixture was stirred at room temperature for 1 hour. Water was added thereto and the resulting mixture was extracted with ethyl acetate. The organic layer was filtrated and the filtrate was concentrated under reduced pressure to obtain Compound 247 as a crude product.

To mixed solutions of Compound 247 (461 mg, 0.922 mmol) dissolved in THF (2 ml) and methanol (1 ml) was added a 2.0 mol/L aqueous solution of sodium hydroxide (0.692 mL, 1.38 mmol) The mixture was stirred at room temperature. After completion of the reaction, water was added thereto and the resulting mixture was extracted with ethyl acetate. The organic layer was concentrated under reduced pressure. The obtained residue was purified by silica gel column chromatography to obtain Compound 248 (37.7 mg, 10.3%).

Compound 248;

1H-NMR (CDCl3) δ: 3.25 (1H, d, J=10.5 Hz), 3.52 (1H, d, J=10.5 Hz), 3.61 (1H, d, J=9.5 Hz), 4.00-4.21 (4H, m), 7.22-7.28 (3H, m), 7.32 (6H, t, J=7.2 Hz), 7.45 (6H, d, J=7.4 Hz).

EXAMPLE 85

[Chemical formula 126]

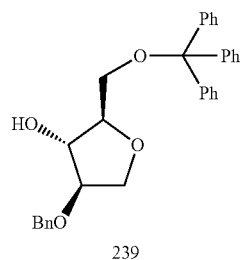

239

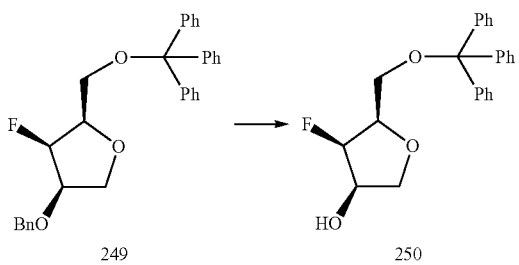

249                250

To Compound 239 (504 mg, 1.08 mmol) dissolved in 1,2-dichloroethane (5 mL) was added DAST (0.570 mL, 4.32 mmol). The reaction mixture was refluxed at 80° C. for 3.5 hours. To the reaction solution was added ice, and the mixture was neutralized with an aqueous solution of sodium hydrogen carbonate. To the obtained residue was added ethyl acetate for liquid separating. The obtained organic layer was concentrated under reduced pressure. The obtained residue was purified by silica gel column chromatography to obtain Compound 249 (393 mg, 77.8%).

Compound 249; Method C

LC/MS retention time=2.86 min.

MS (ESI) m/z=509.00 (M+H)+

To Compound 249 (780 mg, 1.90 mmol) and sodium bromate (429 mg, 2.84 mmol) suspended in ethyl acetate 17.8 mL) was added dropwise an aqueous solution of sodium dithionite (75%, 440 mg, 1.90 mmol). The mixture was stirred at room temperature. After completion of the reaction, sodium thiosulfate pentahydrate (470 mg, 1.90 mmol) was added thereto and neutralized with a 2.0 mol/L aqueous solution of sodium carbonate. The resulting mixture was extracted with ethyl acetate. The organic layer was concentrated under reduced pressure. The obtained residue was purified by silica gel column chromatography to obtain Compound 250 (242 mg, 33.6%).

Compound 250;

1H-NMR (CDCl3) δ: 3.39 (1H, t, J=3.1 Hz), 3.44 (1H, dd, J=10.2, 3.5 Hz), 3. 57 (1H, dd, J=10.2, 5.6 Hz), 4.03-4.09 (1H, m), 4.15-4.20 (1H, m), 4.22-4.27 (1H, m), 4.42 (1H, d, J=9.8 Hz), 5.05 (1H, dd, J=51.8, 3.2 Hz), 7.22-7.36 (9H, m), 7.41-7.46 (6H, m).

EXAMPLE 86

[Chemical formula 127]

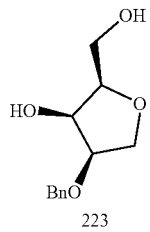
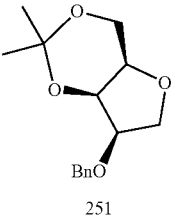
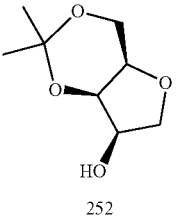
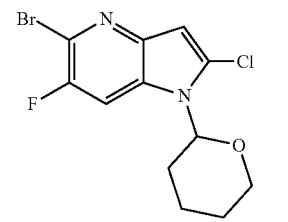

223          251          252

-continued
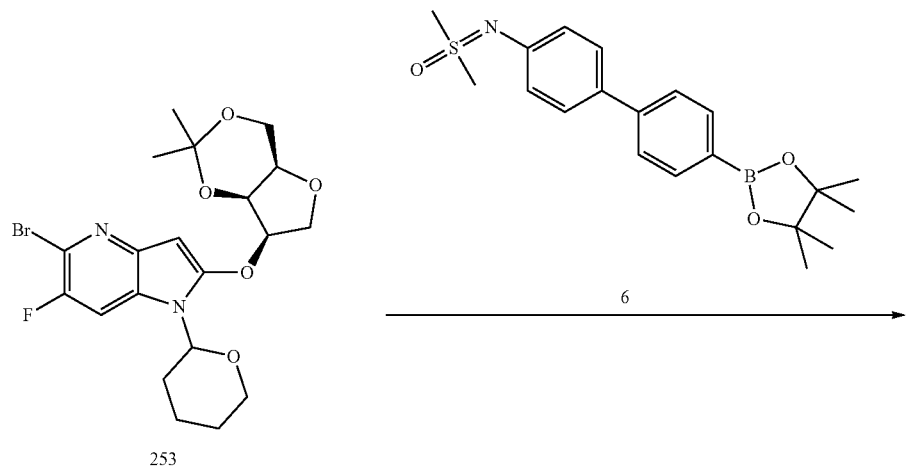
253
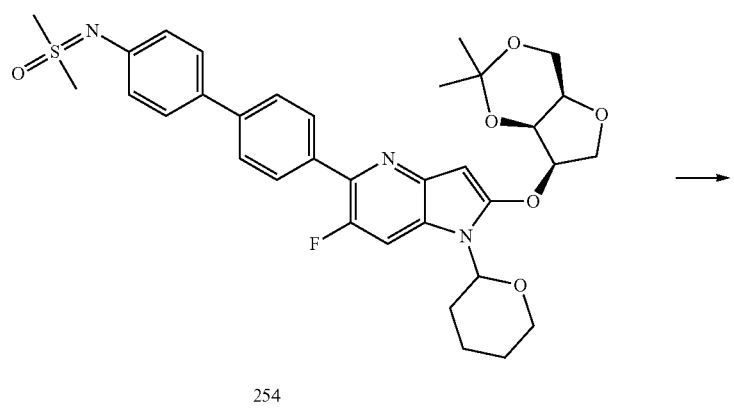
254
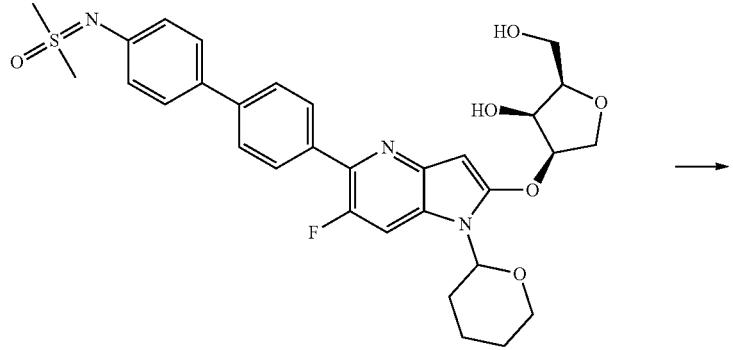
255
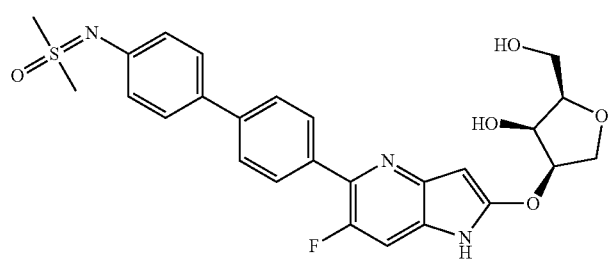
I-2-19

Compound 223 (500 mg, 2.230 mmol) was dissolved in dichloromethane (5 ml), then 2,2-dimethoxypropane (0.546 mL, 4.46 mmol) and p-toluenesulfonic acid monohydrate (85 mg, 0.446 mmol) were added thereto, and the mixture was stirred at room temperature. Triethylamine (0.309 mL, 2.230 mmol) was added thereto, and the mixture was concentrated under reduced pressure, and the residue was purified by silica gel column chromatography to obtain Compound 251 (490.7 mg, 83.3%).

Compound 251;

1H-NMR (CDCl3) δ: 1.43 (3H, s), 1.48 (3H, s), 3.77 (1H, q, J=2.9 Hz), 3.86 (1H, dd, J=12.9, 2.6 Hz), 3.93-4.01 (3H, m), 4.12 (1H, ddd, J=9.4, 7.5, 3.9 Hz), 4.26 (1H, dd, J=3.6, 3.1 Hz), 4.60 (1H, d, J=12.2 Hz), 4.65 (1H, d, J=12.2 Hz), 7.29-7.39 (5H, m).

Compound 251 (490.7 mg, 1.856 mmol) was dissolved in THF (10 ml), then Pd/C (5%, 250 mg) was added thereto, and the mixture was stirred at room temperature under hydrogen atmosphere. The reaction mixture was filtered and the resulting filtrate was concentrated under reduced pressure. The obtained residue was purified by silica gel column chromatography to obtain Compound 252 (168.8 mg, 52.2%). Compound 253 was synthesized from Compound 252, in a similar way that Compound 12 was synthesized from Compound 9.

Compound 253; Method C

LC/MS retention time=2.32 min.

MS (ESI) m/z=471.20 (M+H)+.

To Compound 253 (107.9 mg, 0.229 mmol), Compound 6 (102 mg, 0.275 mmol) and Pd(PPh3)4 (26.5 mg, 0.023 mmol) were added 1,4-dioxane (1.079 ml). A 2 mol/L aqueous solution of potassium carbonate was added thereto, and the mixture was stirred at 130° C. under microwave irradiation. The mixture was diluted with ethyl acetate and hexane and reaction mixture was filtered. The filtrate was concentrated under reduced pressure and the obtained residue was purified by silica gel column chromatography. To the obtained Compound 254 was added methanol (4 mL) and p-toluenesulfonic acid monohydrate (47.9 mg, 0.252 mmol) and the mixture was stirred at room temperature. A 2 mol/L aqueous solution of sodium carbonate was added thereto and the mixture was concentrated under reduced pressure. The obtained residue was purified by silica gel column chromatography to obtain Compound 255 (16.7 mg, 12.2%).

Compound 255; Method C

LC/MS retention time=1.62 min.

MS (ESI) m/z=596.25 (M+H)+.

To Compound 255 (16.7 mg, 0.028 mmol) was added TFA (1.00 mL) and the mixture was stirred at 60° C. The reaction solution was concentrated under reduced pressure and diluted with ethyl acetate and water for liquid separating. The obtained organic layer was washed with water and concentrated under reduced pressure. The obtained residue was purified by silica gel column chromatography to obtain Compound (I-2-19) (3.8 mg, 26.5%).

Compound (I-2-19); Method C

LC/MS retention time=1.20 min.

MS (ESI) m/z=512.20 (M+H)+

The compounds shown below were synthesized in a similar way. The measurement results of NMR or LC/MS of the respective compounds are shown.

TABLE 1

| No. | Structure | retention time | Mass (M + H) | method |
|---|---|---|---|---|
| I-1-01 | 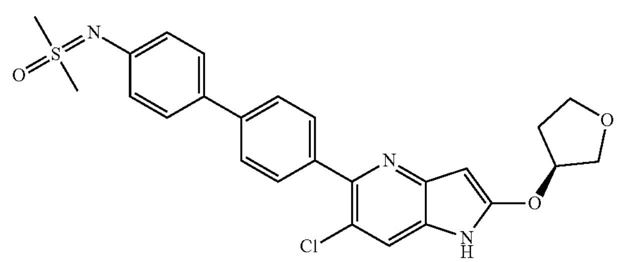 [SMILES: CS(C)(=O)=Nc1ccc(-c2ccc(-c3nc4cc(O[C@H]5CCOC5)[nH]c4cc3Cl)cc2)cc1] | 1.28 | 482.2 | B |
| I-1-02 | 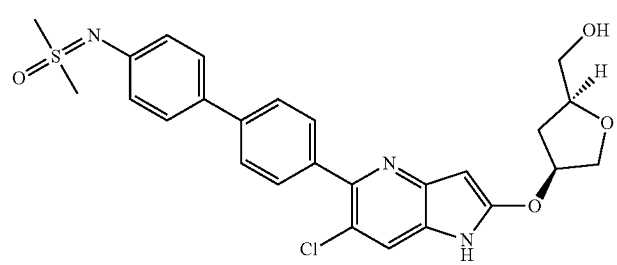 [SMILES: CS(C)(=O)=Nc1ccc(-c2ccc(-c3nc4cc(O[C@@H]5CO[C@H](CO)C5)[nH]c4cc3Cl)cc2)cc1] | 1.17 | 512.3 | B |

TABLE 1-continued

| No. | Structure | retention time | Mass (M + H) | method |
|---|---|---|---|---|
| I-1-03 | 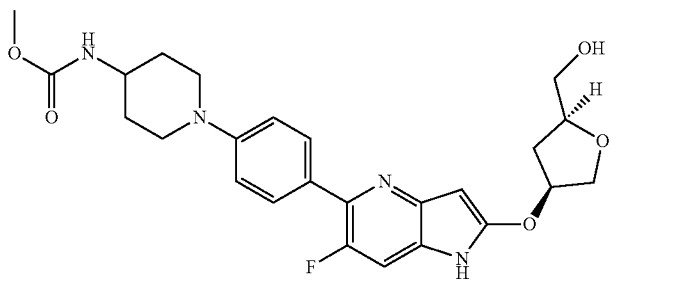 [SMILES: COC(=O)NC1CCN(c2ccc(-c3nc4cc(O[C@@H]5CO[C@H](CO)C5)[nH]c4cc3F)cc2)CC1] | 1.08 | 485.35 | B |
| I-1-04 | 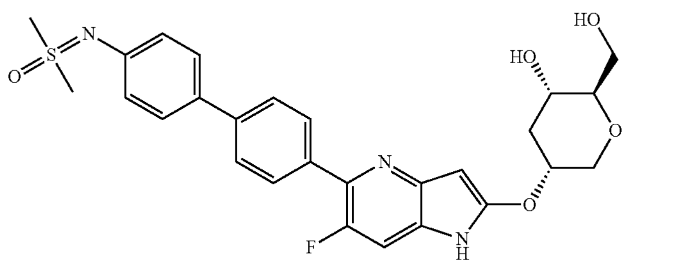 [SMILES: CS(C)(=O)=Nc1ccc(-c2ccc(-c3nc4cc(O[C@H]5CO[C@H](CO)[C@@H](O)C5)[nH]c4cc3F)cc2)cc1] | 1.09 | 526.35 | B |
| I-1-05 | 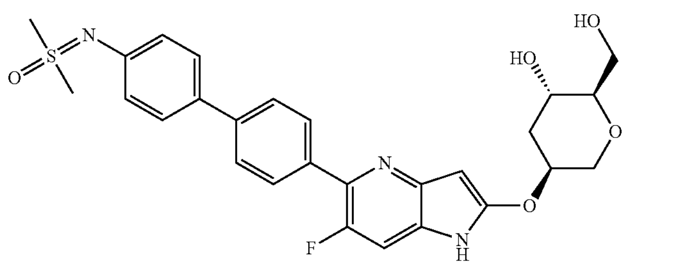 [SMILES: CS(C)(=O)=Nc1ccc(-c2ccc(-c3nc4cc(O[C@@H]5CO[C@H](CO)[C@@H](O)C5)[nH]c4cc3F)cc2)cc1] | 0.96 | 526.5 | B |
| I-1-06 | 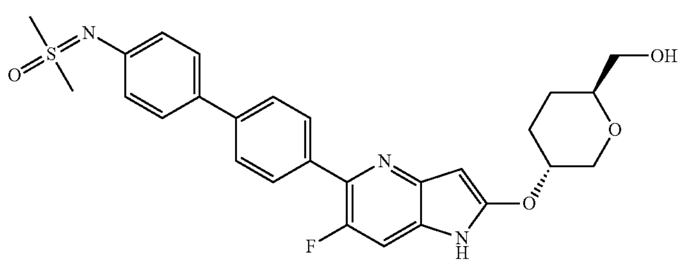 [SMILES: CS(C)(=O)=Nc1ccc(-c2ccc(-c3nc4cc(O[C@@H]5CC[C@@H](CO)OC5)[nH]c4cc3F)cc2)cc1] | 1.26 | 510.2 | A |

TABLE 2

| | | | | |
|---|---|---|---|---|
| I-1-07 | | 1.17 | 538.35 | B |

TABLE 2-continued

| | | | | |
|---|---|---|---|---|
| I-1-08 | (structure) | 1.13 | 505.3 | B |
| I-1-09 | (structure) | 1.35 | 530.35 | B |
| I-1-10 | (structure) | 1.21 | 527.4 | B |
| I-1-11 | (structure) | 1.4 | 581.35 | B |
| I-1-12 | (structure) | 0.97 | 511.4 | B |

TABLE 3
| | | | | |
|---|---|---|---|---|
| I-1-13 | 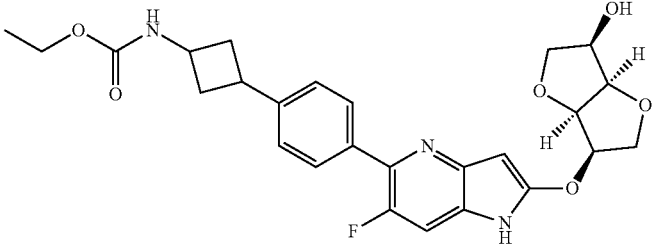 [SMILES: CCOC(=O)NC1CC(c2ccc(-c3nc4cc(O[C@@H]5CO[C@H]6[C@@H]5OC[C@H]6O)[nH]c4cc3F)cc2)C1] | 1.23 | 497.2 | B |
| I-1-14 | 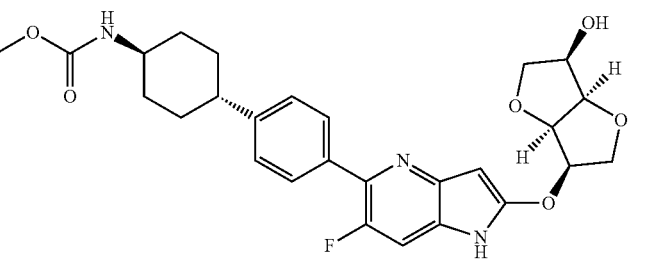 | 1.35 | 526.35 | B |
| I-1-15 | 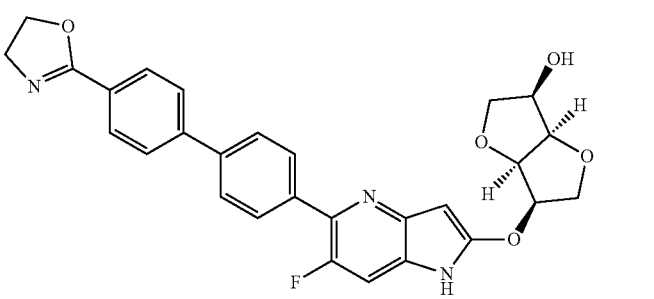 [SMILES: O[C@@H]1CO[C@H]2[C@@H]1OC[C@H]2Oc1cc2nc(-c3ccc(-c4ccc(C5=NCCO5)cc4)cc3)c(F)cc2[nH]1] | 1.1 | 502.3 | B |
| I-1-16 | 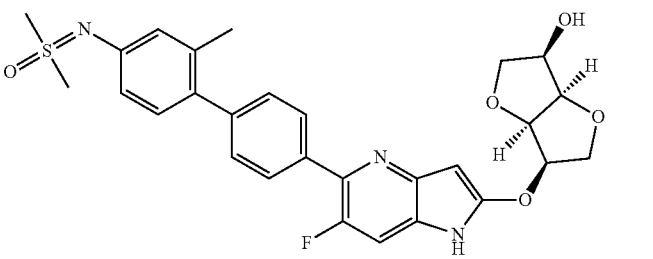 [SMILES: Cc1cc(N=S(C)(C)=O)ccc1-c1ccc(-c2nc3cc(O[C@@H]4CO[C@H]5[C@@H]4OC[C@H]5O)[nH]c3cc2F)cc1] | 1.24 | 538.2 | A |
| I-1-17 | 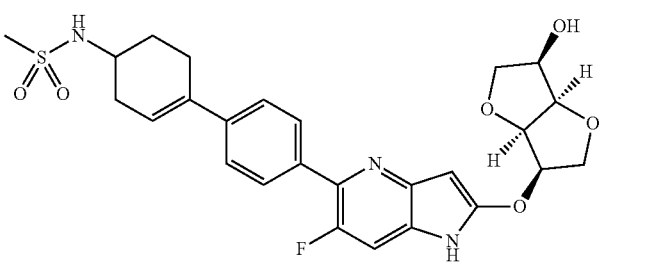 [SMILES: CS(=O)(=O)NC1CC=C(c2ccc(-c3nc4cc(O[C@@H]5CO[C@H]6[C@@H]5OC[C@H]6O)[nH]c4cc3F)cc2)CC1] | 1.26 | 530.3 | A |
| I-1-18 | 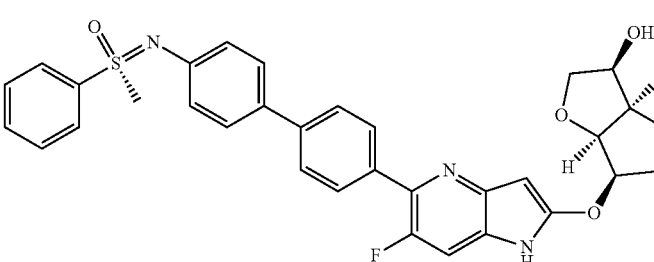 | 1.57 | 586.3 | A |

TABLE 4

| I-1-19 | | 1.58 | 586.3 | A |
| I-1-20 | | 1.25 | 580.3 | A |
| I-1-21 | | 1.58 | 498.1 | A |
| I-1-22 | | 1.38 | 510.3 | A |
| I-1-23 | | 1.36 | 510.3 | A |
| I-1-24 | | 1.36 | 480.2 | A |

TABLE 5
| | | | | |
|---|---|---|---|---|
| I-1-25 | 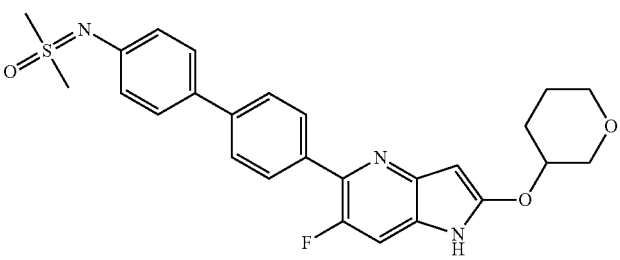 [SMILES: CS(C)(=O)=Nc1ccc(-c2ccc(-c3nc4cc(OC5CCCOC5)[nH]c4cc3F)cc2)cc1] | 1.37 | 480.2 | A |
| I-1-26 | 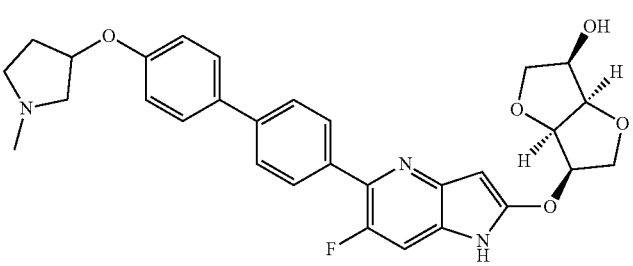 [SMILES: CN1CCC(Oc2ccc(-c3ccc(-c4nc5cc(O[C@@H]6CO[C@H]7[C@@H]6OC[C@H]7O)[nH]c5cc4F)cc3)cc2)C1] | 1.21 | 532.2 | A |
| I-1-27 | 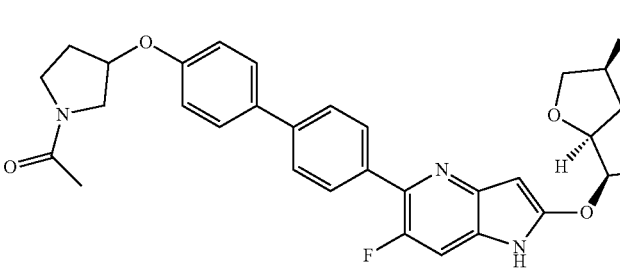 | 1.37 | 560.6 | A |
| I-1-28 | 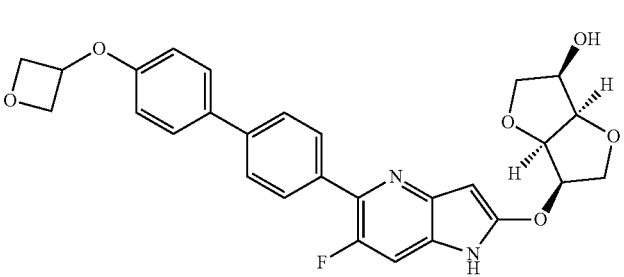 [SMILES: O[C@@H]1CO[C@H]2[C@@H]1OC[C@H]2Oc1cc2nc(-c3ccc(-c4ccc(OC5COC5)cc4)cc3)c(F)cc2[nH]1] | 1.49 | 505.1 | A |
| I-1-29 | 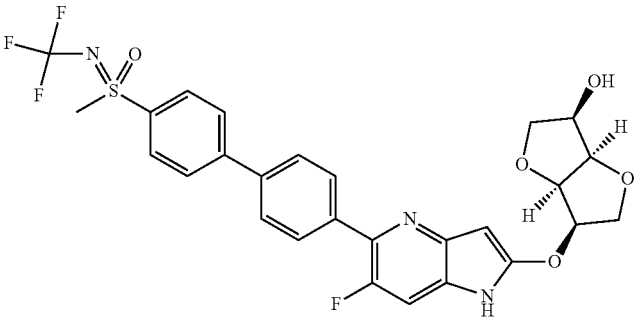 [SMILES: CS(=O)(=NC(F)(F)F)c1ccc(-c2ccc(-c3nc4cc(O[C@@H]5CO[C@H]6[C@@H]5OC[C@H]6O)[nH]c4cc3F)cc2)cc1] | 1.67 | 578.1 | A |

TABLE 5-continued
| I-1-30 | 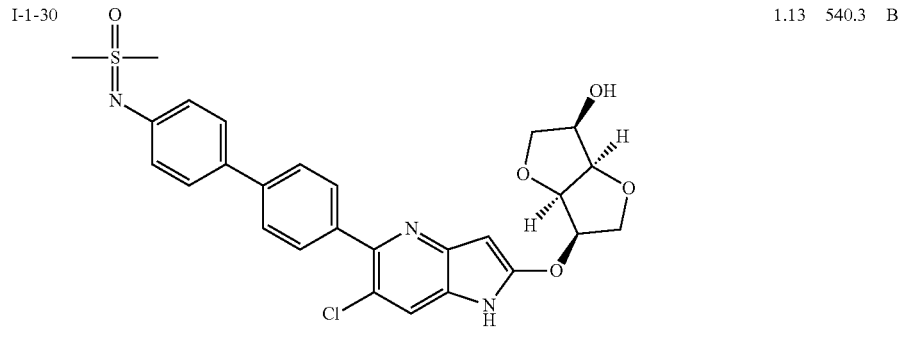 | 1.13 | 540.3 | B |
TABLE 6
| I-1-31 | 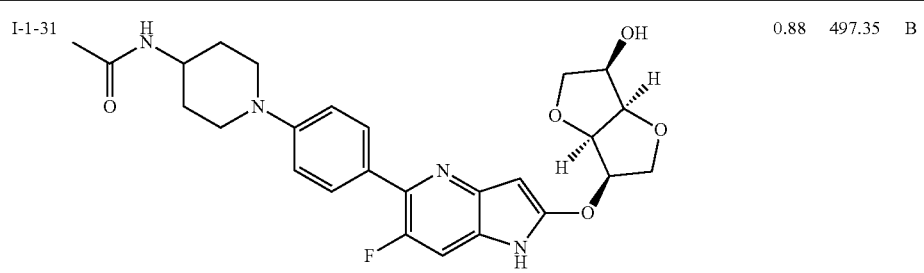 | 0.88 | 497.35 | B |
| I-1-32 | 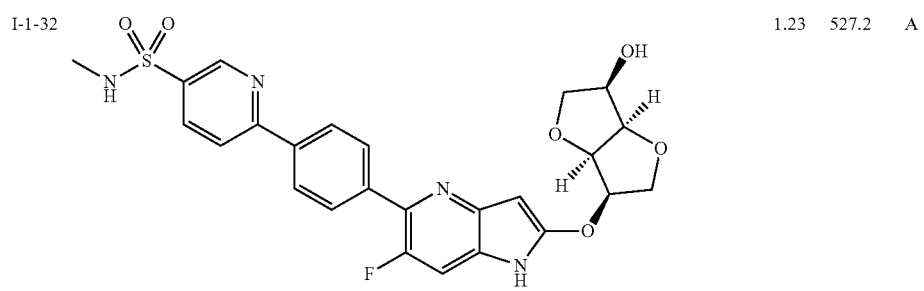 | 1.23 | 527.2 | A |
| I-1-33 | 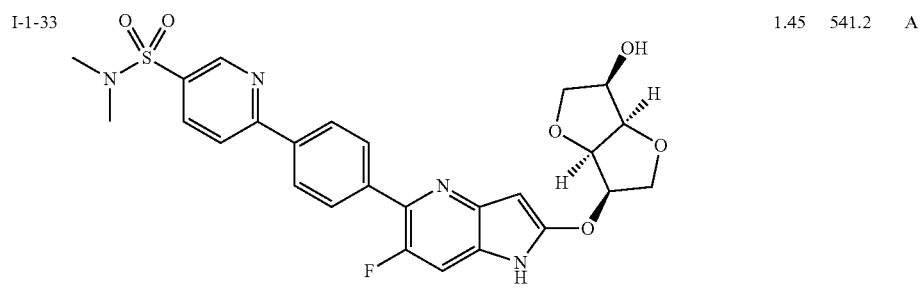 | 1.45 | 541.2 | A |
| I-1-34 | 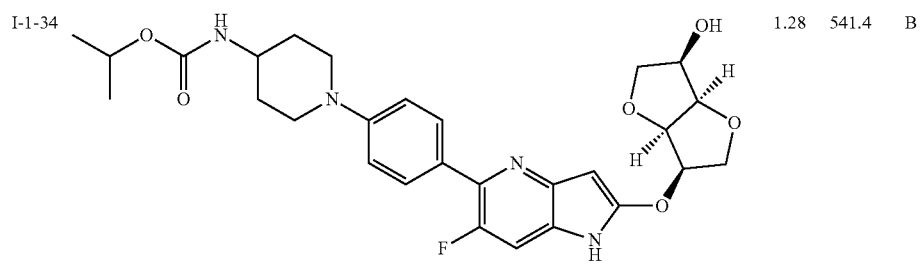 | 1.28 | 541.4 | B |

TABLE 6-continued

| ID | Structure | a | b | c |
|---|---|---|---|---|
| I-1-35 | 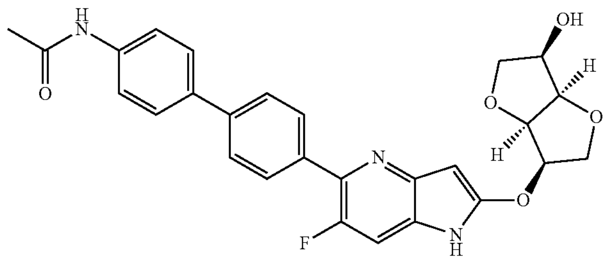 [SMILES: CC(=O)Nc1ccc(-c2ccc(-c3nc4cc(O[C@@H]5CO[C@H]6[C@@H]5OC[C@H]6O)[nH]c4cc3F)cc2)cc1] | 1.23 | 490.2 | A |
| I-1-36 | 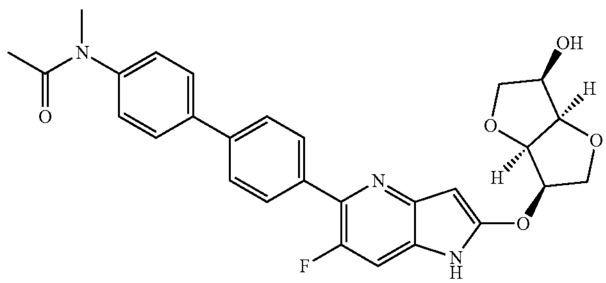 [SMILES: CC(=O)N(C)c1ccc(-c2ccc(-c3nc4cc(O[C@@H]5CO[C@H]6[C@@H]5OC[C@H]6O)[nH]c4cc3F)cc2)cc1] | 1.29 | 504.3 | A |

TABLE 7

| ID | Structure | a | b | c |
|---|---|---|---|---|
| I-1-37 | 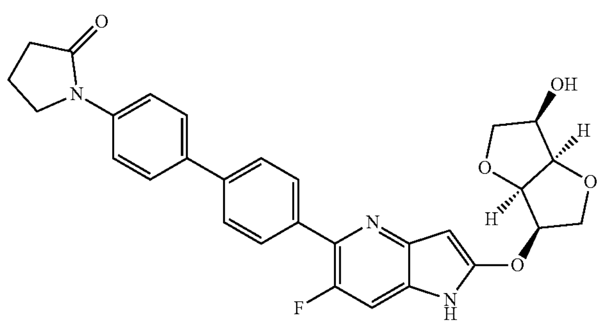 [SMILES: O=C1CCCN1c1ccc(-c2ccc(-c3nc4cc(O[C@@H]5CO[C@H]6[C@@H]5OC[C@H]6O)[nH]c4cc3F)cc2)cc1] | 1.41 | 516.3 | A |
| I-1-38 | 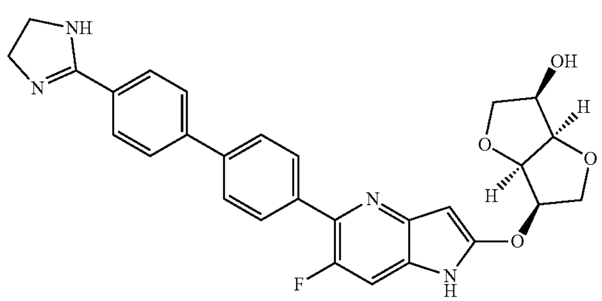 | 0.81 | 501.35 | B |
| I-1-39 | 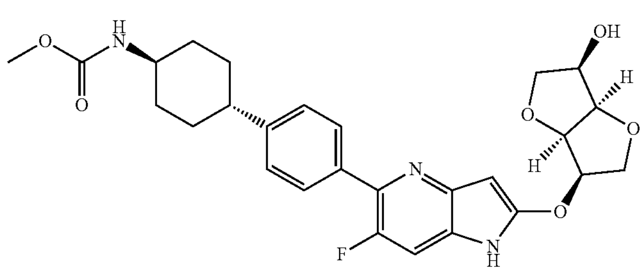 [SMILES: COC(=O)N[C@H]1CC[C@H](c2ccc(-c3nc4cc(O[C@@H]5CO[C@H]6[C@@H]5OC[C@H]6O)[nH]c4cc3F)cc2)CC1] | 1.24 | 512.35 | B |

TABLE 7-continued

| | | | | |
|---|---|---|---|---|
| I-1-40 | [structure] | 1.04 | 482.3 | B |
| I-1-41 | [structure] | 1.06 | 496.35 | B |
| I-1-42 | [structure] | 1.26 | 566.2 | A |

TABLE 8

| | | | | |
|---|---|---|---|---|
| I-1-43 | [structure] | 1.39 | 496.2 | A |
| I-1-44 | [structure] | 1.39 | 550.35 | B |

TABLE 8-continued
| | | | | |
|---|---|---|---|---|
| I-1-45 | 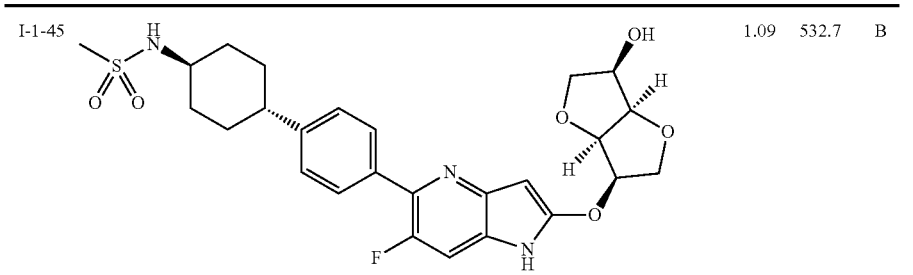 | 1.09 | 532.7 | B |
| I-1-46 | 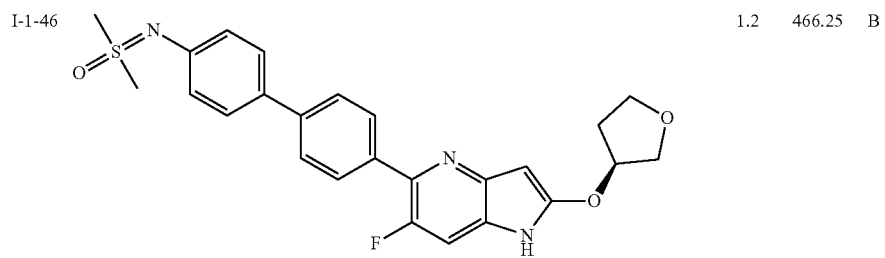 | 1.2 | 466.25 | B |
| I-1-47 | 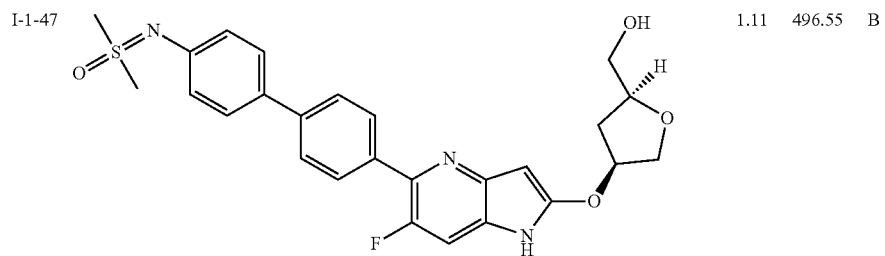 | 1.11 | 496.55 | B |
| I-1-48 | 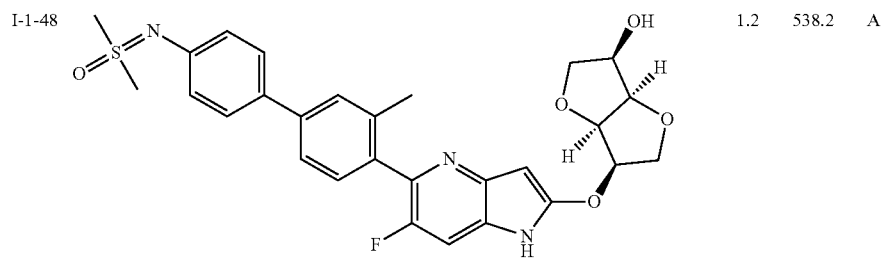 | 1.2 | 538.2 | A |
TABLE 9
| | | | | |
|---|---|---|---|---|
| I-1-49 | 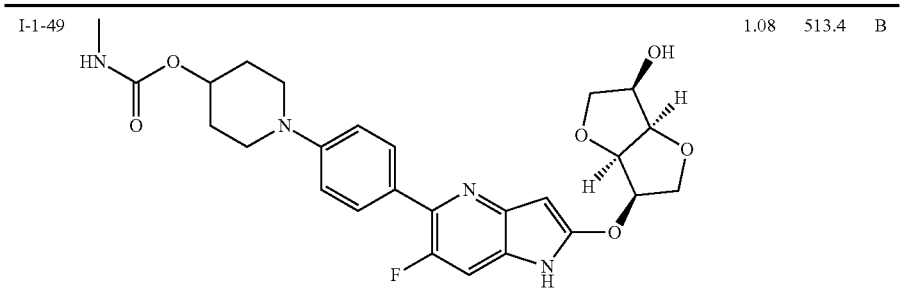 | 1.08 | 513.4 | B |

TABLE 9-continued
| | | | | |
|---|---|---|---|---|
| I-1-50 | 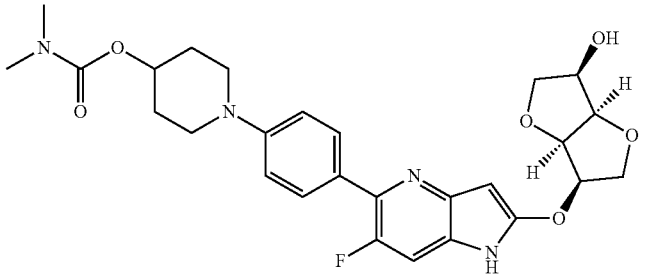 [SMILES: CN(C)C(=O)OC1CCN(c2ccc(-c3nc4cc(O[C@@H]5CO[C@H]6[C@@H]5OC[C@H]6O)[nH]c4cc3F)cc2)CC1] | 1.27 | 527.45 | B |
| I-1-51 | 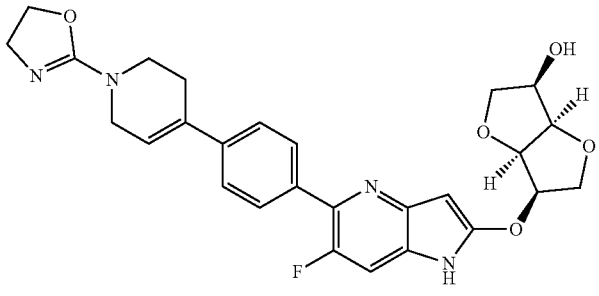 [SMILES: O[C@@H]1CO[C@H]2[C@@H]1OC[C@H]2Oc1cc2nc(-c3ccc(C4=CCN(C5=NCCO5)CC4)cc3)c(F)cc2[nH]1] | 0.94 | 507.2 | A |
| I-1-52 | 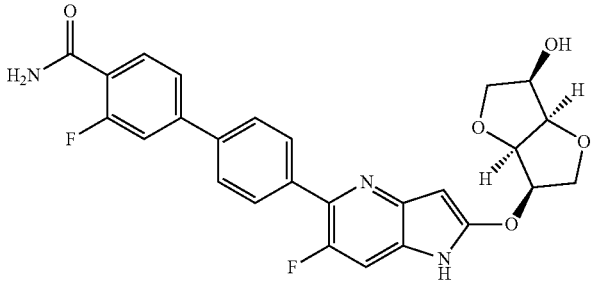 [SMILES: NC(=O)c1ccc(-c2ccc(-c3nc4cc(O[C@@H]5CO[C@H]6[C@@H]5OC[C@H]6O)[nH]c4cc3F)cc2)cc1F] | 1.13 | 494.1 | A |
| I-1-53 | 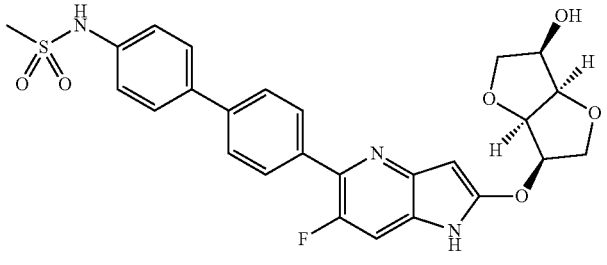 [SMILES: CS(=O)(=O)Nc1ccc(-c2ccc(-c3nc4cc(O[C@@H]5CO[C@H]6[C@@H]5OC[C@H]6O)[nH]c4cc3F)cc2)cc1] | 1.28 | 526.1 | A |
| I-1-54 | 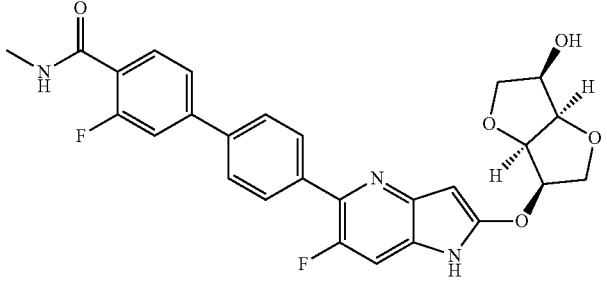 [SMILES: CNC(=O)c1ccc(-c2ccc(-c3nc4cc(O[C@@H]5CO[C@H]6[C@@H]5OC[C@H]6O)[nH]c4cc3F)cc2)cc1F] | 1.23 | 508.1 | A |

TABLE 10
| | | | | |
|---|---|---|---|---|
| I-1-55 | 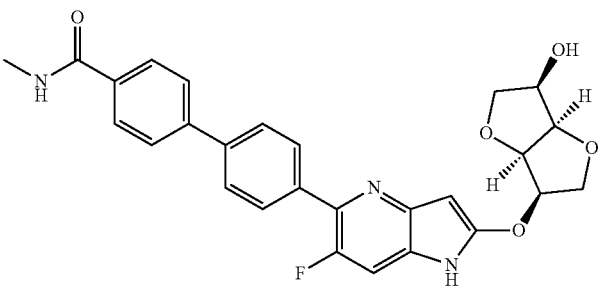 [SMILES: CNC(=O)c1ccc(-c2ccc(-c3nc4cc(O[C@@H]5CO[C@H]6[C@@H]5OC[C@H]6O)[nH]c4cc3F)cc2)cc1] | 1.14 | 490.1 | A |
| I-1-56 | 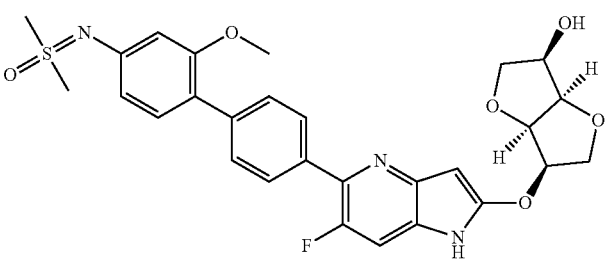 [SMILES: COc1cc(N=S(C)(C)=O)ccc1-c1ccc(-c2nc3cc(O[C@@H]4CO[C@H]5[C@@H]4OC[C@H]5O)[nH]c3cc2F)cc1] | 1.18 | 554.1 | A |
| I-1-57 | 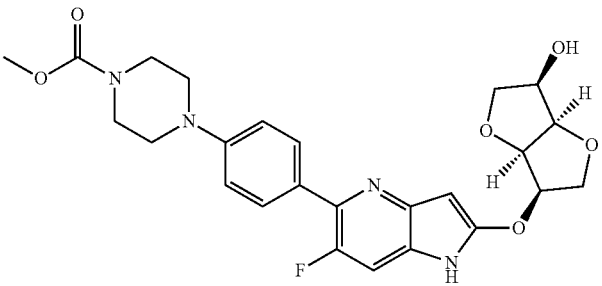 [SMILES: COC(=O)N1CCN(c2ccc(-c3nc4cc(O[C@@H]5CO[C@H]6[C@@H]5OC[C@H]6O)[nH]c4cc3F)cc2)CC1] | 1.27 | 499.2 | A |
| I-1-58 | 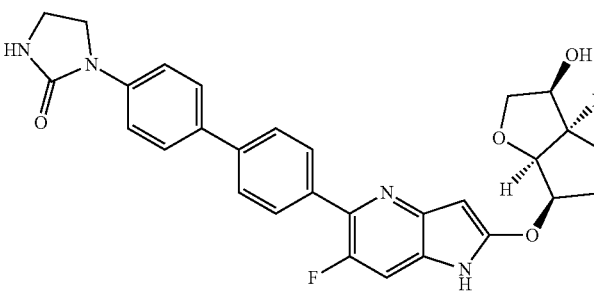 | 1.31 | 517.1 | A |
| I-1-59 | 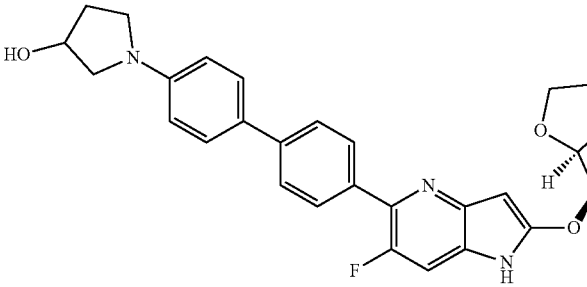 | 1.45 | 518.1 | A |

TABLE 10-continued
| I-1-60 | 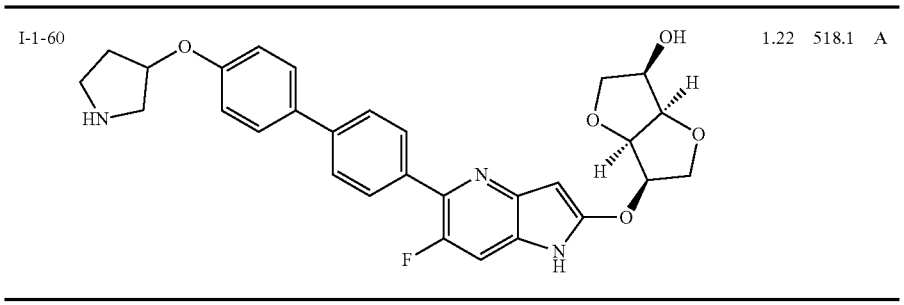 | 1.22 | 518.1 | A |
TABLE 11
| I-1-61 | 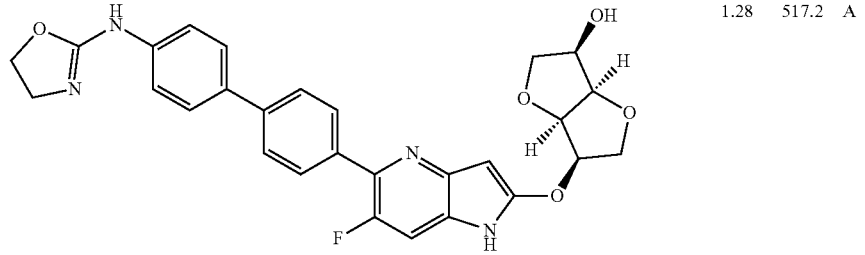 | 1.28 | 517.2 | A |
| I-1-62 | 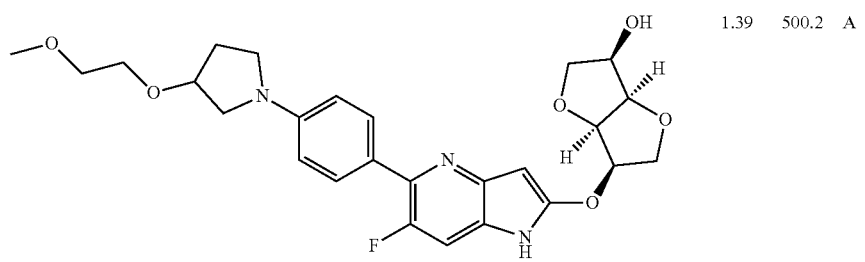 | 1.39 | 500.2 | A |
| I-1-63 | 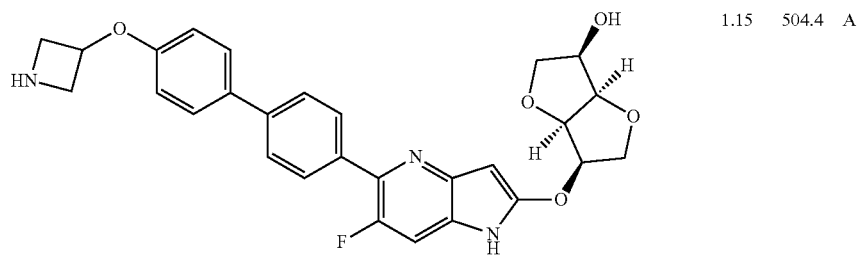 | 1.15 | 504.4 | A |
| I-1-64 | 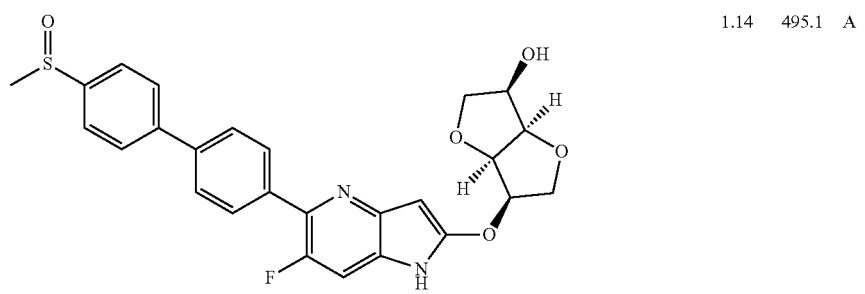 | 1.14 | 495.1 | A |

TABLE 11-continued

| | | | | |
|---|---|---|---|---|
| I-1-65 | [structure] | 1.28 | 449.1 | A |
| I-1-66 | [structure] | 1.6 | 507.1 | A |

TABLE 12

| | | | | |
|---|---|---|---|---|
| I-1-67 | [structure] | 0.78 | 442.1 | A |
| I-1-68 | [structure] | 1.09 | 520.1 | A |
| I-1-69 | [structure] | 0.9 | 506.1 | A |
| I-1-70 | [structure] | 1.24 | 532.1 | A |

TABLE 12-continued

| No. | Structure | retention time | Mass (M + H) | method |
|---|---|---|---|---|
| I-1-71 | 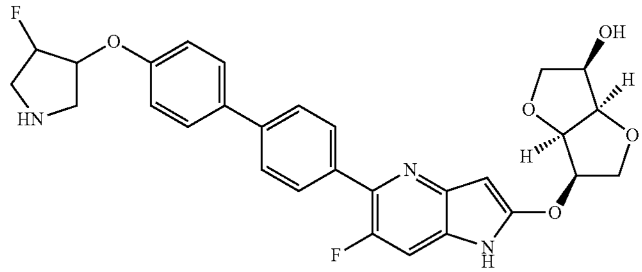 [SMILES: O[C@@H]1CO[C@H]2[C@@H]1OC[C@H]2Oc1cc2nc(-c3ccc(-c4ccc(OC5CNCC5F)cc4)cc3)c(F)cc2[nH]1] | 1.11 | 536.1 | A |
| I-1-72 | 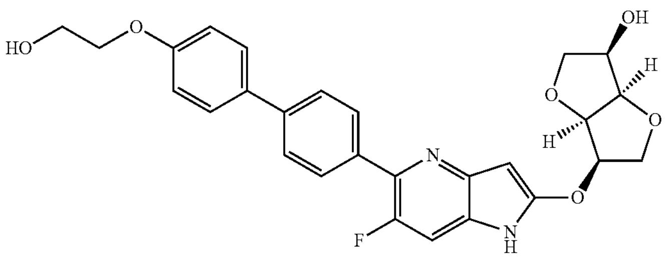 [SMILES: OCCOc1ccc(-c2ccc(-c3nc4cc(O[C@@H]5CO[C@H]6[C@@H]5OC[C@H]6O)[nH]c4cc3F)cc2)cc1] | 1.4 | 493.5 | A |

TABLE 13

| No. | Structure | retention time | Mass (M + H) | method |
|---|---|---|---|---|
| I-2-01 | 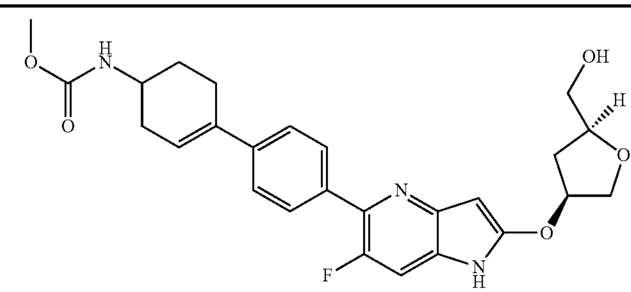 | 1.22 | 482.9 | B |
| I-2-02 | 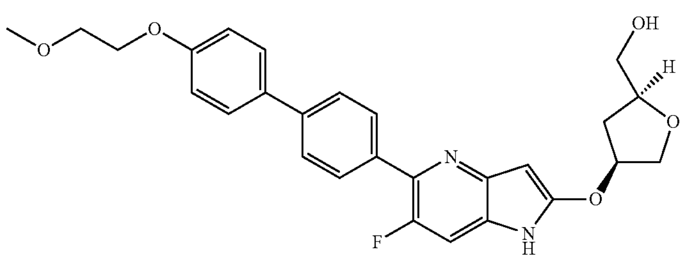 [SMILES: COCCOc1ccc(-c2ccc(-c3nc4cc(O[C@@H]5CO[C@H](CO)C5)[nH]c4cc3F)cc2)cc1] | 1.39 | 479.9 | B |
| I-2-03 | 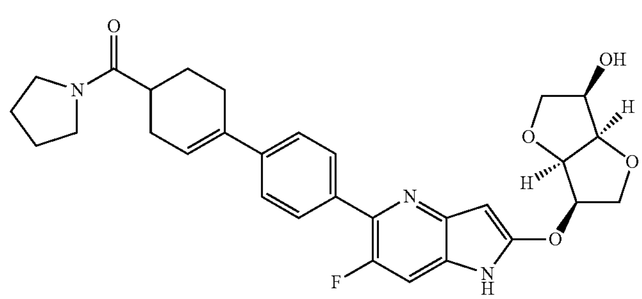 [SMILES: O=C(C1CC=C(c2ccc(-c3nc4cc(O[C@@H]5CO[C@H]6[C@@H]5OC[C@H]6O)[nH]c4cc3F)cc2)CC1)N1CCCC1] | 1.24 | 534.4 | B |

TABLE 13-continued

| No. | Structure | retention time | Mass (M + H) | method |
|---|---|---|---|---|
| I-2-04 | 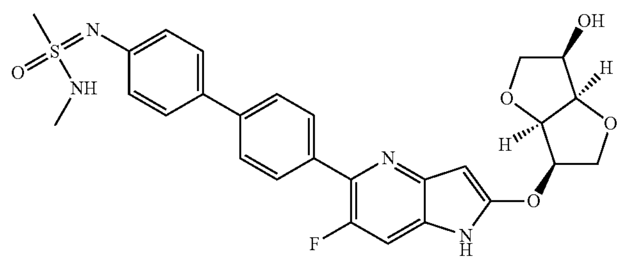 [SMILES: CNS(C)(=O)=Nc1ccc(-c2ccc(-c3nc4cc(O[C@@H]5CO[C@H]6[C@@H]5OC[C@H]6O)[nH]c4cc3F)cc2)cc1] | 0.99 | 539.3 | B |
| I-2-05 | 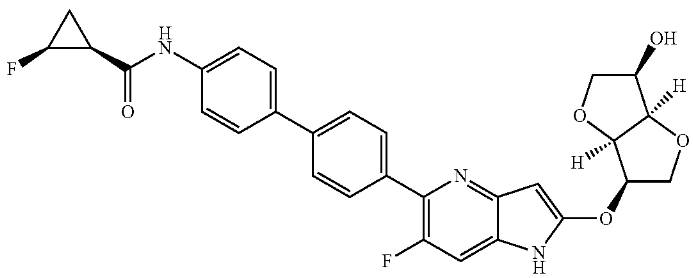 [SMILES: O=C(Nc1ccc(-c2ccc(-c3nc4cc(O[C@@H]5CO[C@H]6[C@@H]5OC[C@H]6O)[nH]c4cc3F)cc2)cc1)[C@@H]1C[C@@H]1F] | 1.21 | 534.3 | B |
| I-2-06 | 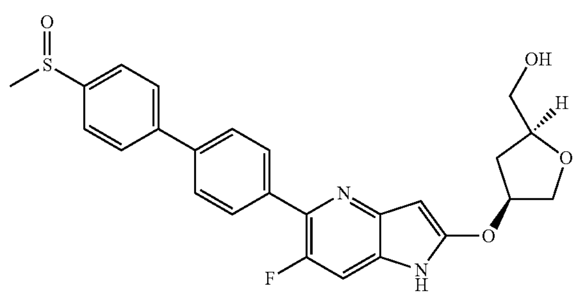 [SMILES: CS(=O)c1ccc(-c2ccc(-c3nc4cc(O[C@@H]5CO[C@H](CO)C5)[nH]c4cc3F)cc2)cc1] | 1.08 | 467.1 | B |
| I-2-07 | 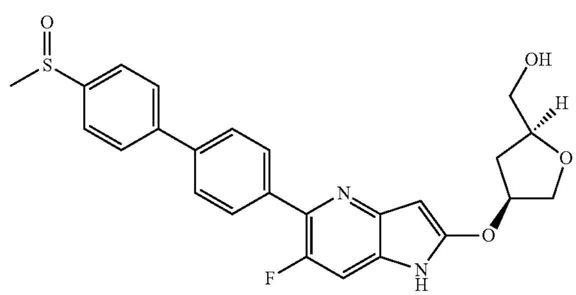 [SMILES: CS(=O)c1ccc(-c2ccc(-c3nc4cc(O[C@@H]5CO[C@H](CO)C5)[nH]c4cc3F)cc2)cc1] | 1.08 | 467.0 | B |

TABLE 14

| I-2-08 | | 1.05 | 495.1 | B |
|---|---|---|---|---|

TABLE 14-continued

| | | | | |
|---|---|---|---|---|
| I-2-09 | | 1.05 | 495.1 | B |
| I-2-10 | | 1.19 | 520.2 | B |
| I-2-11 | | 1.15 | 539.3 | B |
| I-2-12 | | 1.4 | 520.4 | B |
| I-2-13 | | 1.34 | 521.2 | B |

TABLE 14-continued
| I-2-14 | 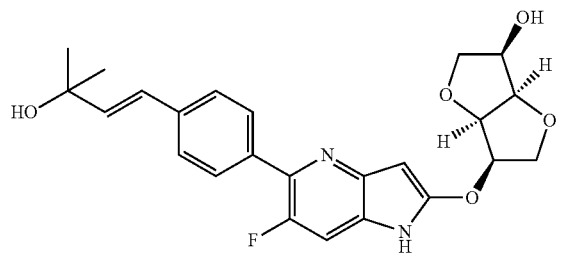 [SMILES: CC(C)(O)/C=C/c1ccc(-c2nc3cc(O[C@@H]4CO[C@H]5[C@@H]4OC[C@H]5O)[nH]c3cc2F)cc1] | 1.06 | 441.1 | B |
TABLE 15
| I-2-15 | 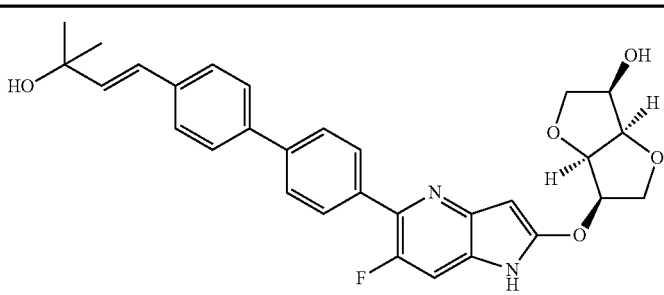 | 1.46 | 517.4 | B |
| I-2-16 | 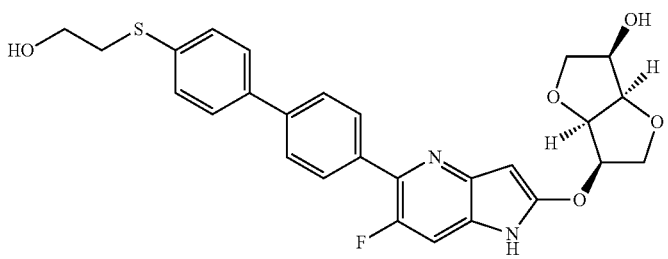 | 1.29 | 509.4 | B |
| I-2-17 | 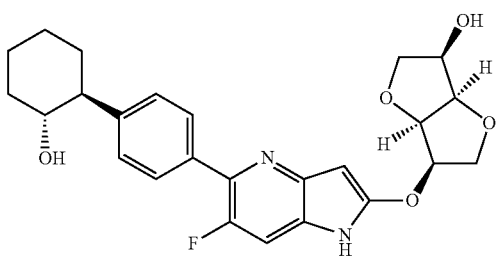 [SMILES: O[C@@H]1CO[C@H]2[C@@H]1OC[C@H]2Oc1cc2nc(-c3ccc([C@@H]4CCCC[C@H]4O)cc3)c(F)cc2[nH]1] | 1.20 | 455.1 | B |
| I-2-18 | 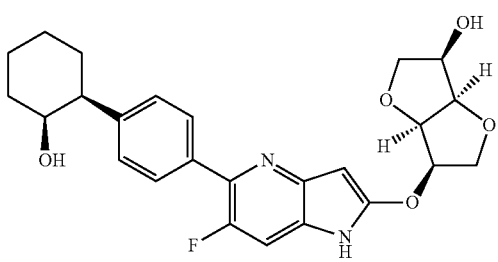 [SMILES: O[C@@H]1CO[C@H]2[C@@H]1OC[C@H]2Oc1cc2nc(-c3ccc([C@@H]4CCCC[C@@H]4O)cc3)c(F)cc2[nH]1] | 1.24 | 455.1 | B |

TABLE 15-continued

| I-2-19 | [structure] | 1.20 | 512.2 | C |

| I-2-20 | [structure] | 1.58 | 518.1 | B |

| I-2-21 | [structure] | 1.38 | 476.6 | A |

TABLE 16

| I-2-22 | [structure] | 0.92 | 532.2 | A |

| I-2-23 | [structure] | 1.20 | 512.1 | C |

TABLE 16-continued
| I-2-24 | 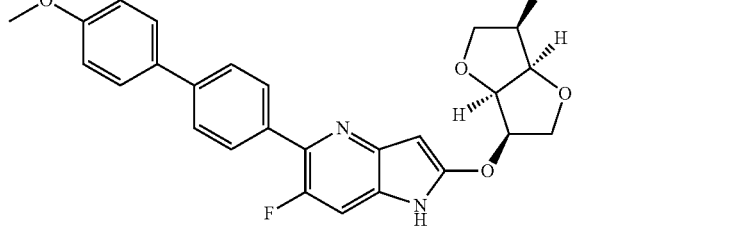 | 1.68 | 463.1 | A |
| I-2-25 | 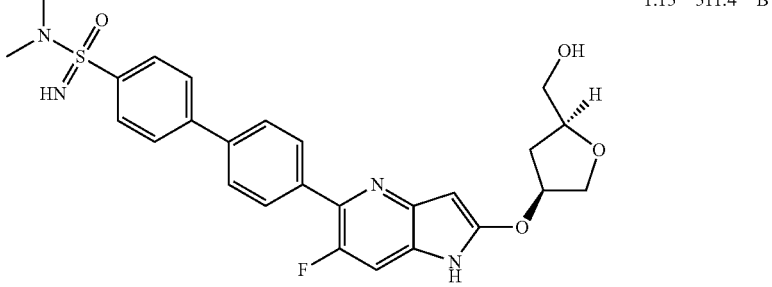 | 1.15 | 511.4 | B |
| I-2-26 | 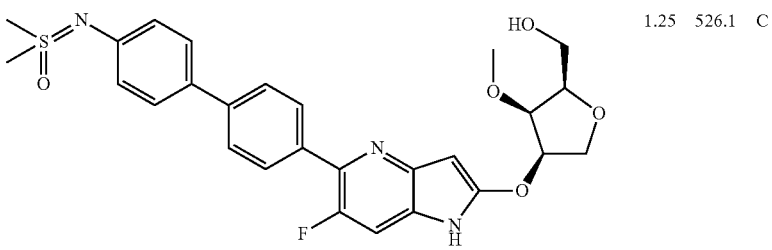 | 1.25 | 526.1 | C |
| I-2-27 | 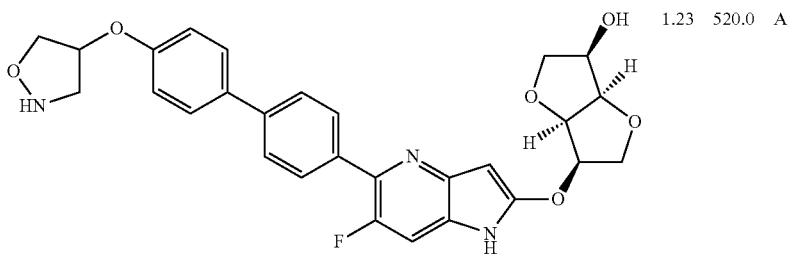 | 1.23 | 520.0 | A |
| I-2-28 | 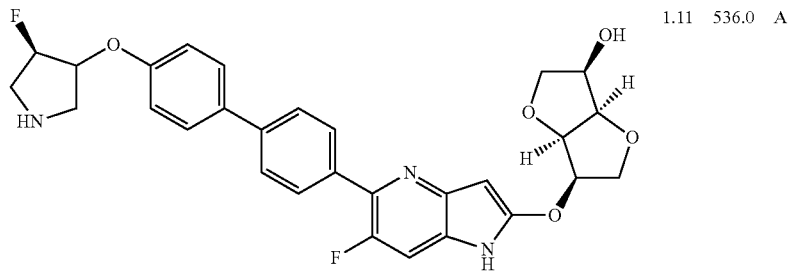 | 1.11 | 536.0 | A |

TABLE 17

| ID | | | |
|---|---|---|---|
| I-2-29 | 1.61 | 505.3 | B |
| I-2-30 | 1.38 | 491.1 | B |
| I-2-31 | 1.28 | 506.3 | B |
| I-2-32 | 1.21 | 546.3 | B |
| I-2-33 | 1.50 | 533.6 | B |
| I-2-34 | 1.28 | 514.2 | B |

TABLE 17-continued
| | | | | |
|---|---|---|---|---|
| I-2-35 | 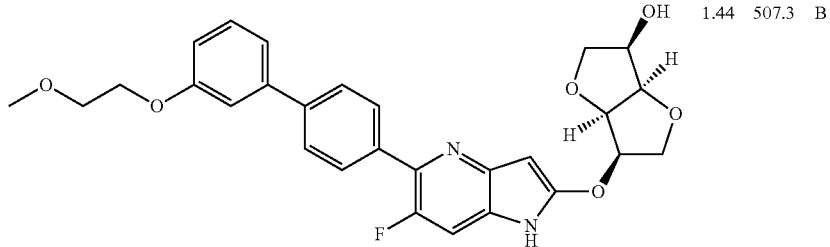 | 1.44 | 507.3 | B |
TABLE 18
| | | | | |
|---|---|---|---|---|
| I-2-36 | 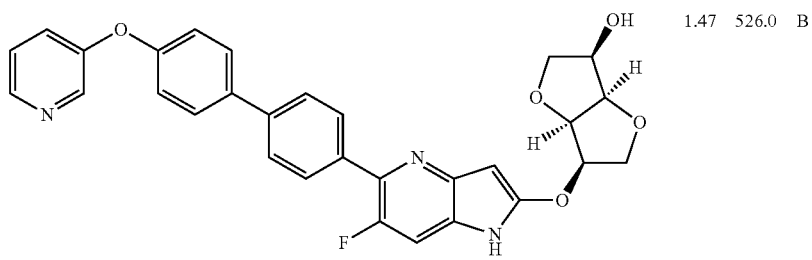 | 1.47 | 526.0 | B |
| I-2-37 | 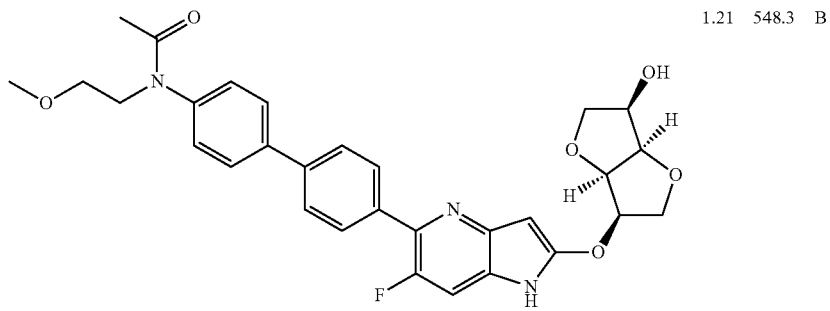 | 1.21 | 548.3 | B |
| I-2-38 | 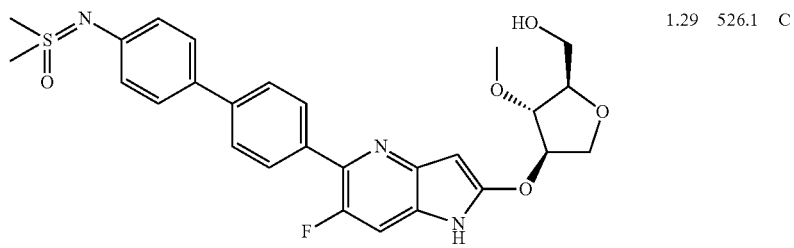 | 1.29 | 526.1 | C |
| I-2-39 | 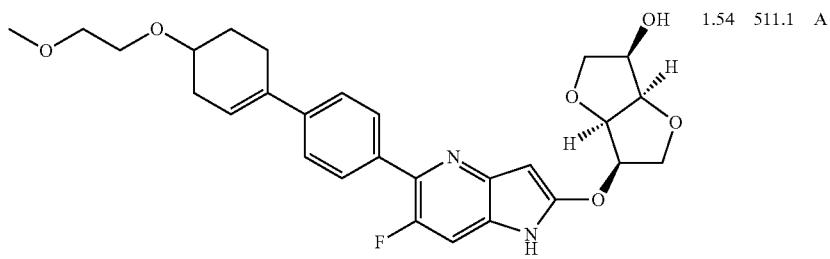 | 1.54 | 511.1 | A |

TABLE 18-continued
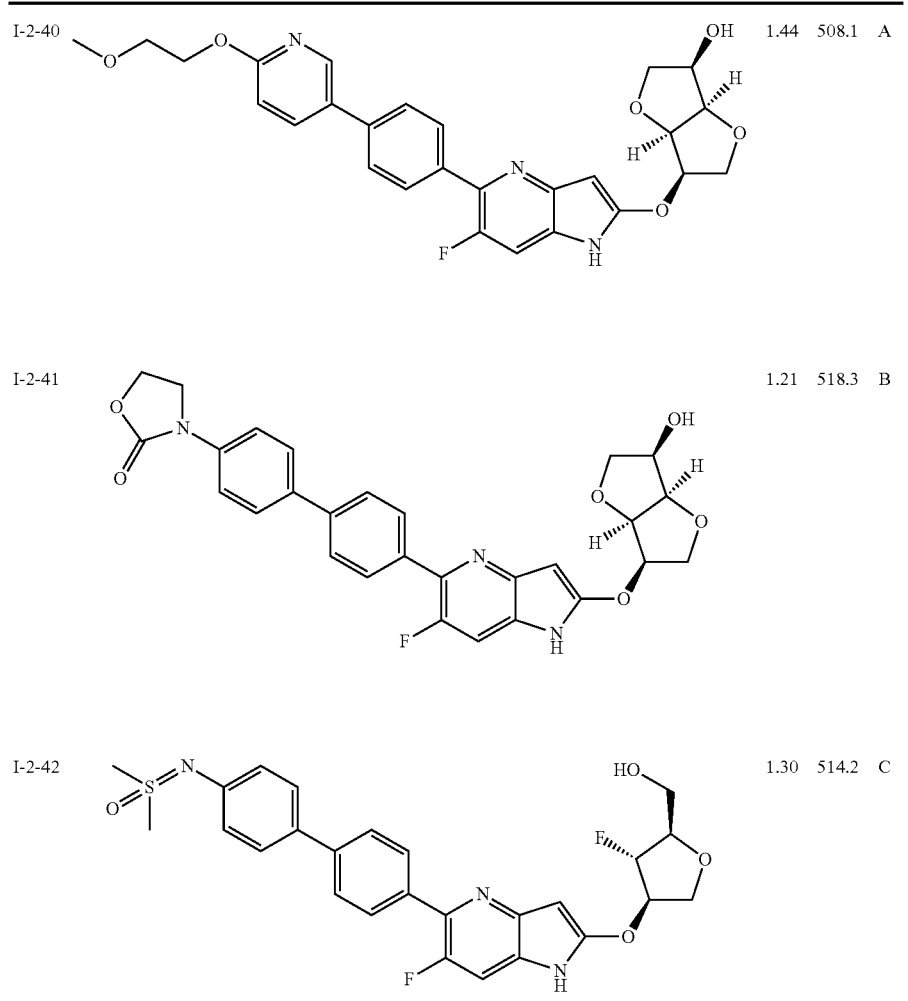
TABLE 19
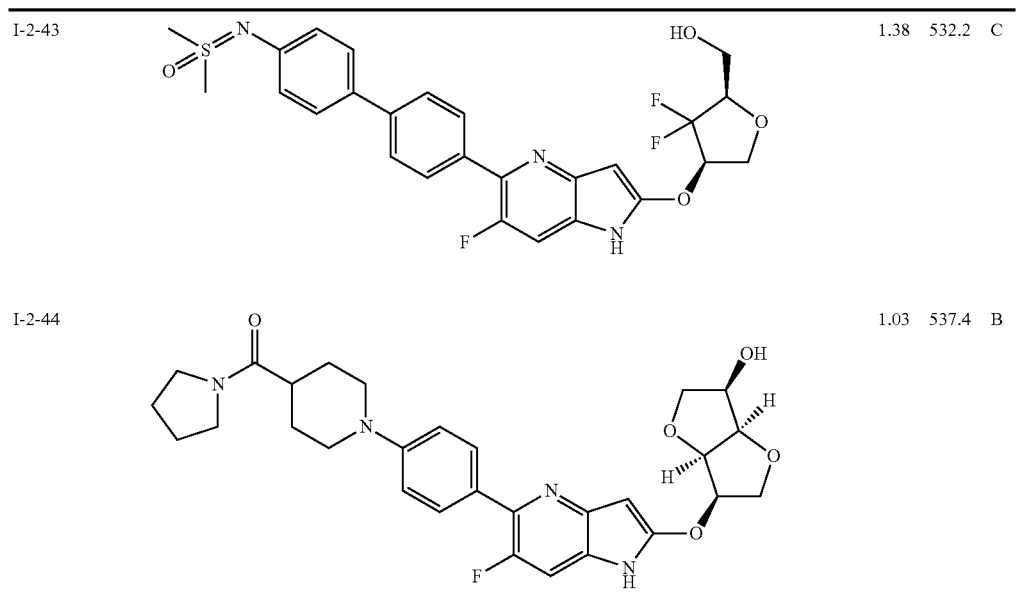

TABLE 19-continued
| | | | | |
|---|---|---|---|---|
| I-2-45 | 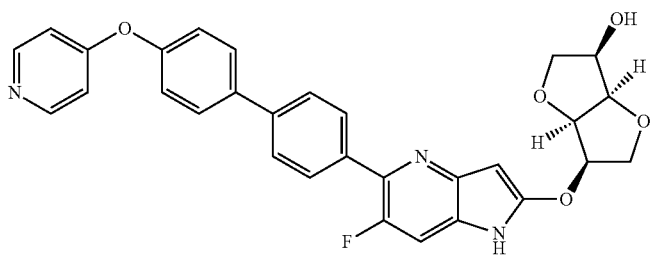 [SMILES: O[C@@H]1CO[C@H]2[C@@H]1OC[C@H]2Oc1cc2nc(-c3ccc(-c4ccc(Oc5ccncc5)cc4)cc3)c(F)cc2[nH]1] | 1.25 | 526.2 | A |
| I-2-46 | 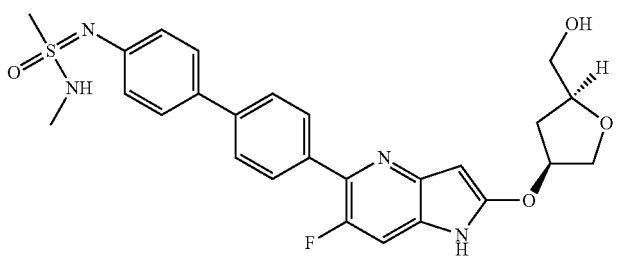 [SMILES: CNS(C)(=O)=Nc1ccc(-c2ccc(-c3nc4cc(O[C@@H]5CO[C@H](CO)C5)[nH]c4cc3F)cc2)cc1] | 1.09 | 511.3 | B |
| I-2-47 | 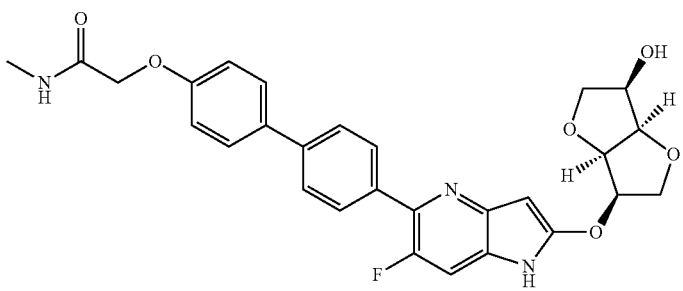 [SMILES: CNC(=O)COc1ccc(-c2ccc(-c3nc4cc(O[C@@H]5CO[C@H]6[C@@H]5OC[C@H]6O)[nH]c4cc3F)cc2)cc1] | 1.28 | 520.2 | A |
| I-2-48 | 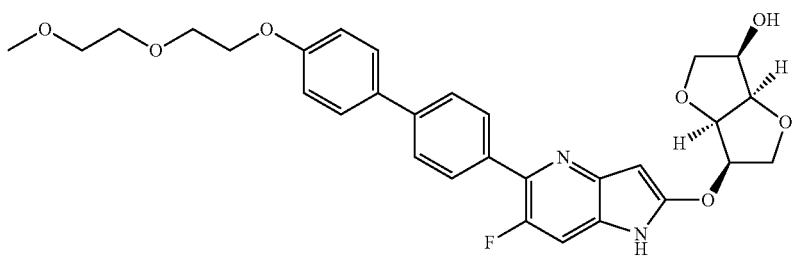 [SMILES: COCCOCCOc1ccc(-c2ccc(-c3nc4cc(O[C@@H]5CO[C@H]6[C@@H]5OC[C@H]6O)[nH]c4cc3F)cc2)cc1] | 1.46 | 551.4 | B |
| I-2-49 | 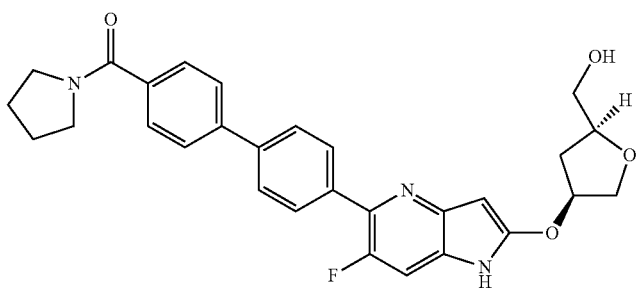 [SMILES: O=C(c1ccc(-c2ccc(-c3nc4cc(O[C@@H]5CO[C@H](CO)C5)[nH]c4cc3F)cc2)cc1)N1CCCC1] | 1.32 | 502.4 | B |

TABLE 20
| | | | | |
|---|---|---|---|---|
| I-2-50 | 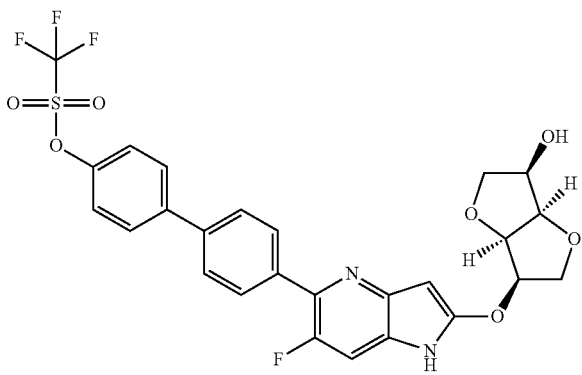 [SMILES: O=S(=O)(Oc1ccc(-c2ccc(-c3nc4cc(O[C@@H]5CO[C@H]6[C@@H]5OC[C@H]6O)[nH]c4cc3F)cc2)cc1)C(F)(F)F] | 2.19 | 581.1 | A |
| I-2-51 | 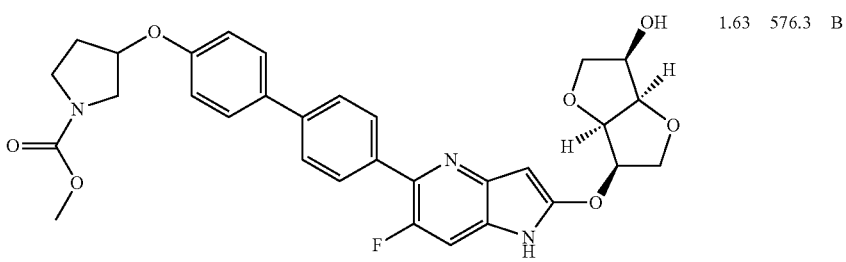 | 1.63 | 576.3 | B |
| I-2-52 | 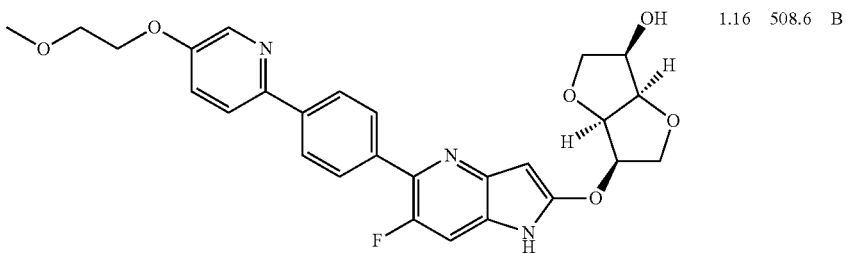 | 1.16 | 508.6 | B |
| I-2-53 | 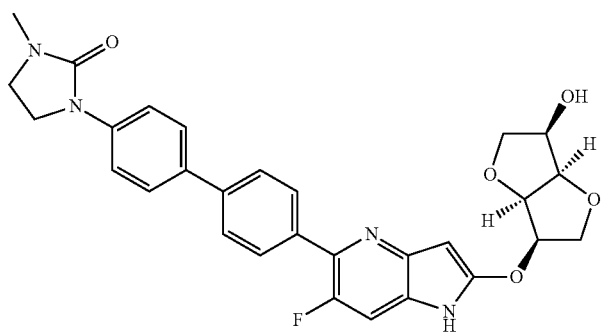 [SMILES: CN1CCN(c2ccc(-c3ccc(-c4nc5cc(O[C@@H]6CO[C@H]7[C@@H]6OC[C@H]7O)[nH]c5cc4F)cc3)cc2)C1=O] | 1.27 | 531.4 | B |
| I-2-54 | 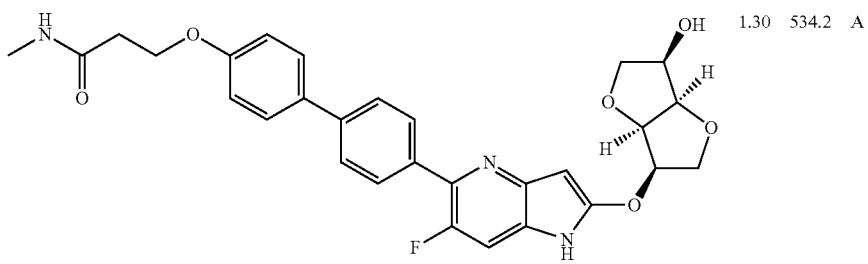 | 1.30 | 534.2 | A |

TABLE 20-continued
| I-2-55 | 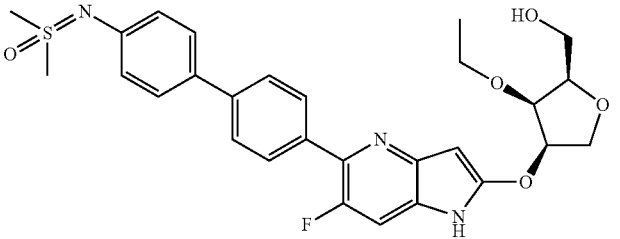 [SMILES: CCO[C@H]1[C@@H](CO)OC[C@H]1Oc1cc2nc(-c3ccc(-c4ccc(N=S(C)(C)=O)cc4)cc3)c(F)cc2[nH]1] | 1.35 | 540.2 | C |
| I-2-56 | 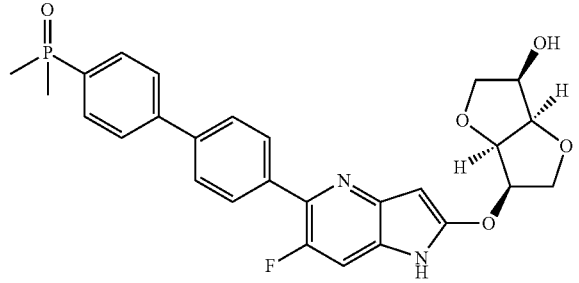 [SMILES: CP(C)(=O)c1ccc(-c2ccc(-c3nc4cc(O[C@@H]5CO[C@H]6[C@@H]5OC[C@H]6O)[nH]c4cc3F)cc2)cc1] | 1.08 | 509.1 | A |
TABLE 21
| I-2-57 | 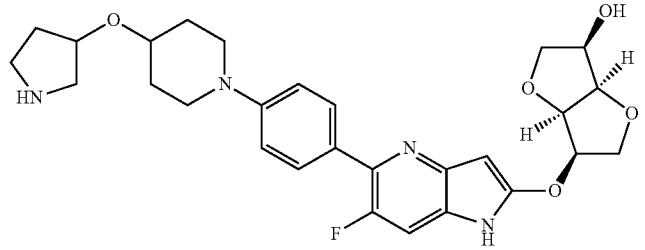 [SMILES: O[C@@H]1CO[C@H]2[C@@H]1OC[C@H]2Oc1cc2nc(-c3ccc(N4CCC(OC5CCNC5)CC4)cc3)c(F)cc2[nH]1] | 0.72 | 525.4 | B |
| I-2-58 | 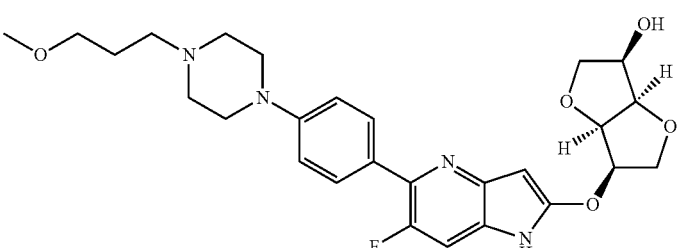 | 0.99 | 513.4 | A |
| I-2-59 | 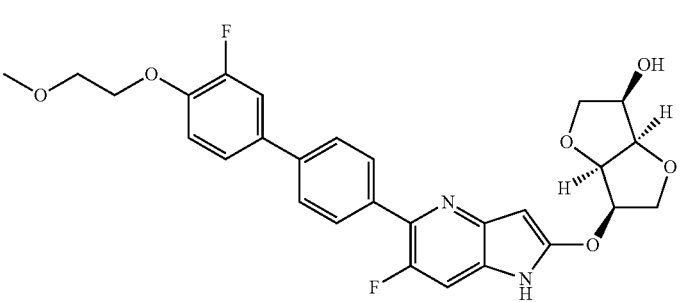 [SMILES: COCCOc1ccc(-c2ccc(-c3nc4cc(O[C@@H]5CO[C@H]6[C@@H]5OC[C@H]6O)[nH]c4cc3F)cc2)cc1F] | 1.72 | 525.1 | A |

TABLE 21-continued

| ID | Structure | c1 | c2 | c3 |
|---|---|---|---|---|
| I-2-60 | 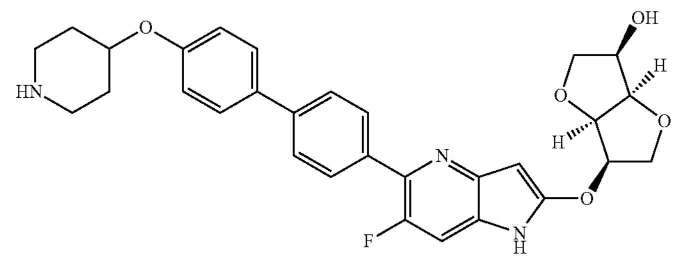 [SMILES: O[C@@H]1CO[C@H]2[C@@H]1OC[C@H]2Oc1cc2nc(-c3ccc(-c4ccc(OC5CCNCC5)cc4)cc3)c(F)cc2[nH]1] | 0.97 | 532.4 | B |
| I-2-61 | 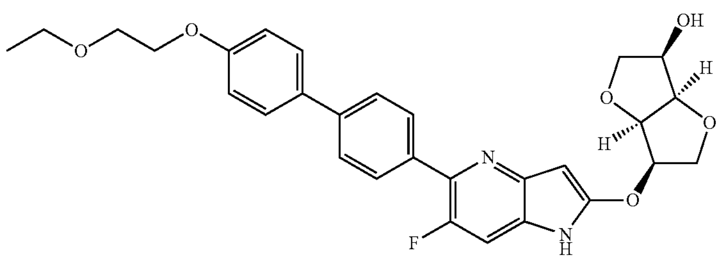 [SMILES: CCOCCOc1ccc(-c2ccc(-c3nc4cc(O[C@@H]5CO[C@H]6[C@@H]5OC[C@H]6O)[nH]c4cc3F)cc2)cc1] | 1.85 | 521.2 | A |
| I-2-62 | 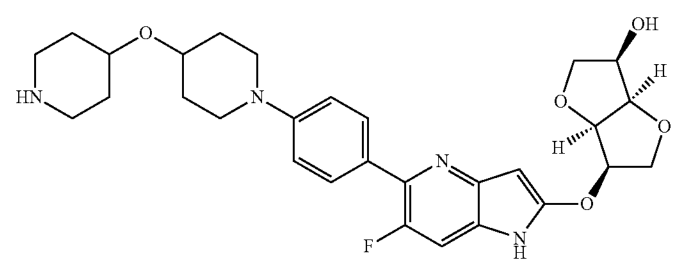 [SMILES: O[C@@H]1CO[C@H]2[C@@H]1OC[C@H]2Oc1cc2nc(-c3ccc(N4CCC(OC5CCNCC5)CC4)cc3)c(F)cc2[nH]1] | 0.70 | 539.2 | B |
| I-2-63 | 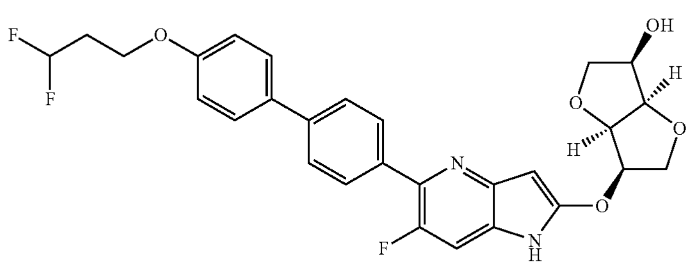 [SMILES: O[C@@H]1CO[C@H]2[C@@H]1OC[C@H]2Oc1cc2nc(-c3ccc(-c4ccc(OCCC(F)F)cc4)cc3)c(F)cc2[nH]1] | 1.97 | 527.1 | A |

TABLE 22

| ID | Structure | c1 | c2 | c3 |
|---|---|---|---|---|
| I-2-64 | 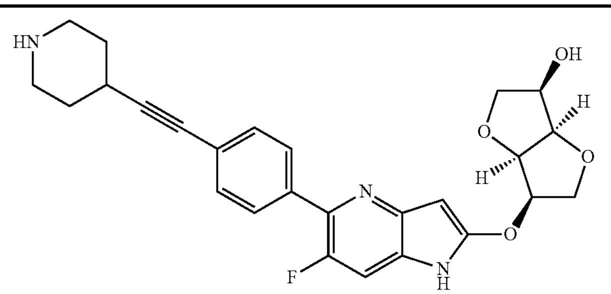 | 0.77 | 464.1 | B |

TABLE 22-continued

| | | | | |
|---|---|---|---|---|
| I-2-65 | | 0.99 | 481.1 | B |
| I-2-66 | | 0.95 | 427.3 | B |
| I-2-67 | | 1.48 | 593.3 | B |
| I-2-68 | | 0.89 | 450.3 | B |
| I-2-69 | | 1.39 | 519.2 | B |
| I-2-70 | | 0.96 | 464.1 | B |

TABLE 23

| | | | | |
|---|---|---|---|---|
| I-2-71 | | 1.5 | 565.1 | B |
| I-2-72 | | 1.15 | 537.2 | B |
| I-2-73 | | 0.87 | 499.6 | B |
| I-2-74 | | 1.21 | 492.2 | B |
| I-2-75 | | 1.36 | 514.1 | C |
| I-2-76 | | 1.54 | 543.5 | B |

TABLE 23-continued
| | | | | |
|---|---|---|---|---|
| I-2-77 | 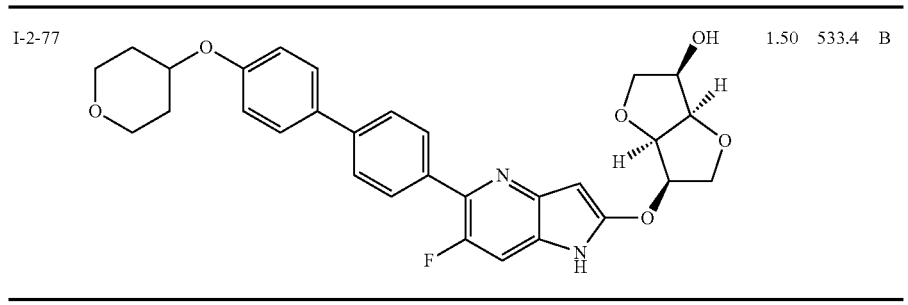 | 1.50 | 533.4 | B |
TABLE 24
| | | | | |
|---|---|---|---|---|
| I-2-78 | 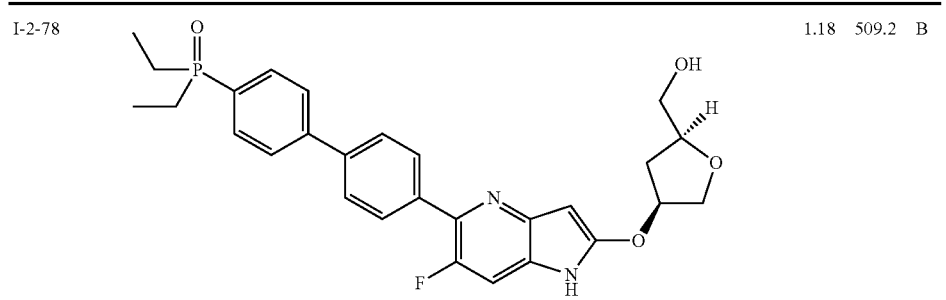 | 1.18 | 509.2 | B |
| I-2-79 | 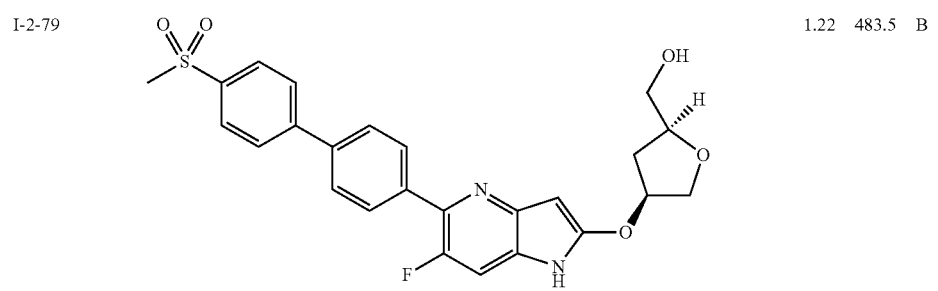 | 1.22 | 483.5 | B |
| I-2-80 | 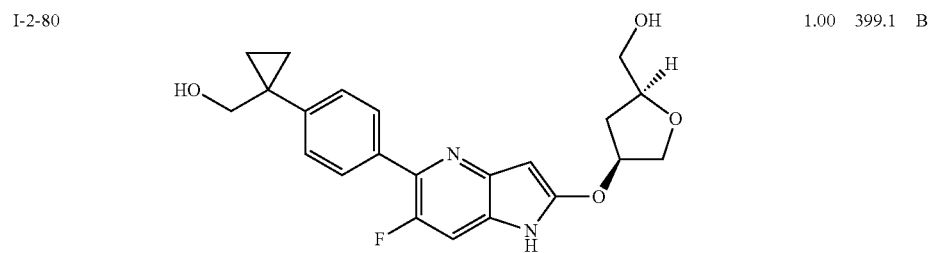 | 1.00 | 399.1 | B |
| I-2-81 | 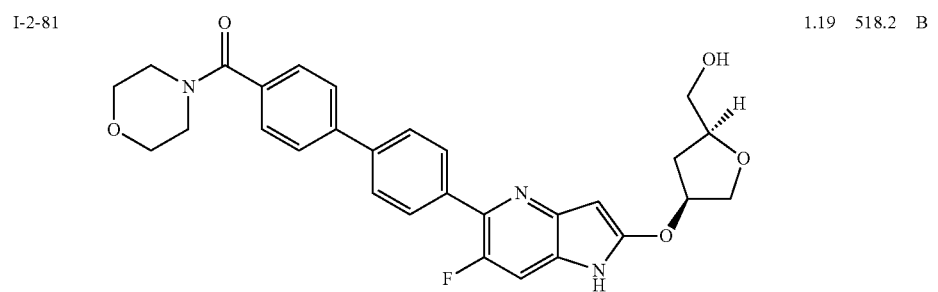 | 1.19 | 518.2 | B |

TABLE 24-continued

| ID | Structure | RT | MS | Class |
|---|---|---|---|---|
| I-2-82 | 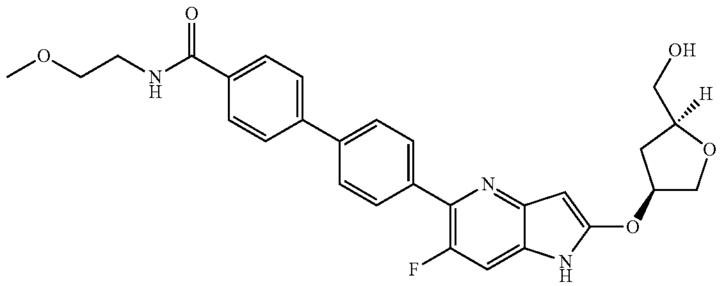 [SMILES: COCCNC(=O)c1ccc(-c2ccc(-c3nc4cc(O[C@@H]5CO[C@H](CO)C5)[nH]c4cc3F)cc2)cc1] | 1.17 | 506.2 | B |
| I-2-83 | 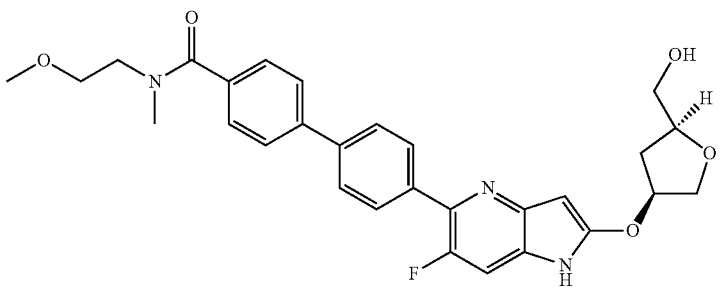 [SMILES: COCCN(C)C(=O)c1ccc(-c2ccc(-c3nc4cc(O[C@@H]5CO[C@H](CO)C5)[nH]c4cc3F)cc2)cc1] | 1.26 | 520.2 | B |
| I-2-84 | 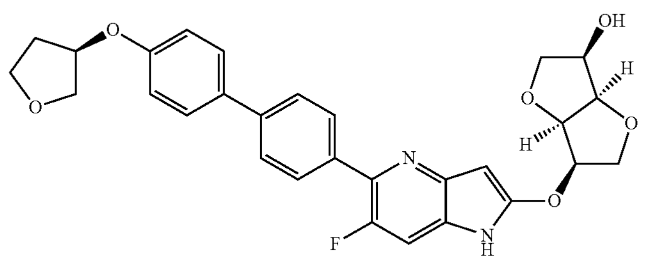 [SMILES: O[C@@H]1CO[C@H]2[C@@H]1OC[C@H]2Oc1cc2nc(-c3ccc(-c4ccc(O[C@@H]5CCOC5)cc4)cc3)c(F)cc2[nH]1] | 1.43 | 519.2 | B |

TABLE 25

| ID | Structure | RT | MS | Class |
|---|---|---|---|---|
| I-2-85 | 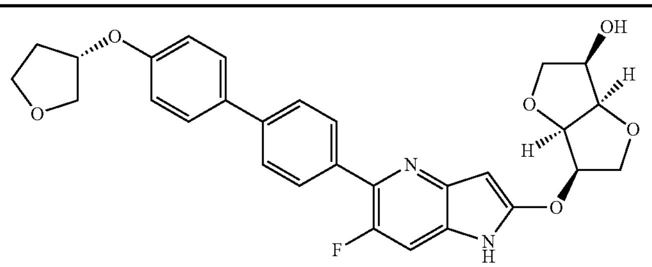 | 1.43 | 519.2 | B |
| I-2-86 | 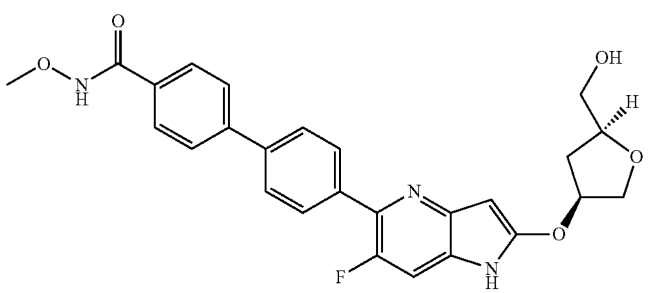 [SMILES: CONC(=O)c1ccc(-c2ccc(-c3nc4cc(O[C@@H]5CO[C@H](CO)C5)[nH]c4cc3F)cc2)cc1] | 1.08 | 478.2 | B |

TABLE 25-continued

| ID | Structure | RT | MS | Method |
|---|---|---|---|---|
| I-2-87 | 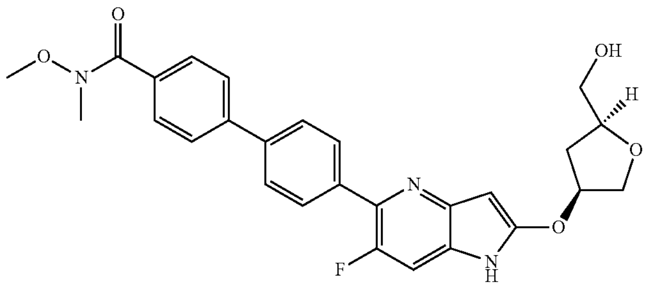 [SMILES: CON(C)C(=O)c1ccc(-c2ccc(-c3nc4cc(O[C@@H]5CO[C@H](CO)C5)[nH]c4cc3F)cc2)cc1] | 1.28 | 492.2 | B |
| I-2-88 | 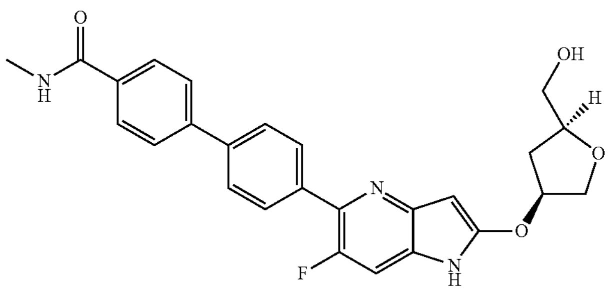 [SMILES: CNC(=O)c1ccc(-c2ccc(-c3nc4cc(O[C@@H]5CO[C@H](CO)C5)[nH]c4cc3F)cc2)cc1] | 1.07 | 462.1 | B |
| I-2-89 | 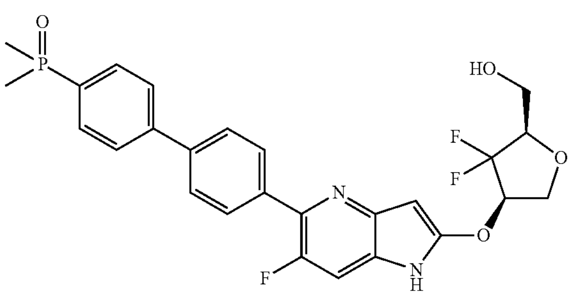 [SMILES: CP(C)(=O)c1ccc(-c2ccc(-c3nc4cc(O[C@@H]5CO[C@H](CO)C5(F)F)[nH]c4cc3F)cc2)cc1] | 1.38 | 517.1 | C |
| I-2-90 | 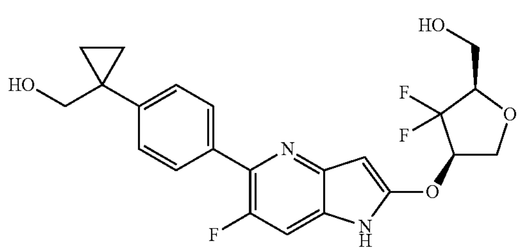 [SMILES: OC[C@H]1OC[C@@H](Oc2cc3nc(-c4ccc(C5(CO)CC5)cc4)c(F)cc3[nH]2)C1(F)F] | 1.35 | 435.1 | C |
| I-2-91 | 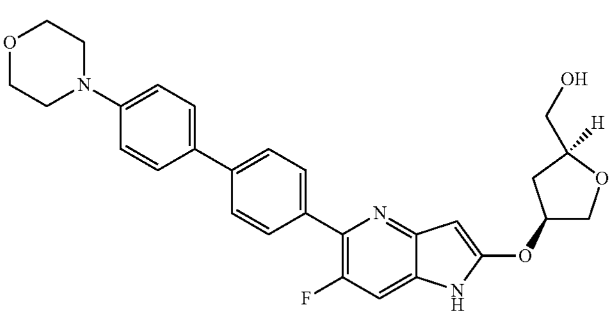 [SMILES: OC[C@@H]1C[C@H](Oc2cc3nc(-c4ccc(-c5ccc(N6CCOCC6)cc5)cc4)c(F)cc3[nH]2)CO1] | 1.35 | 490.2 | B |

TABLE 26

| ID | Structure | Col1 | Col2 | Col3 |
|---|---|---|---|---|
| I-2-92 | 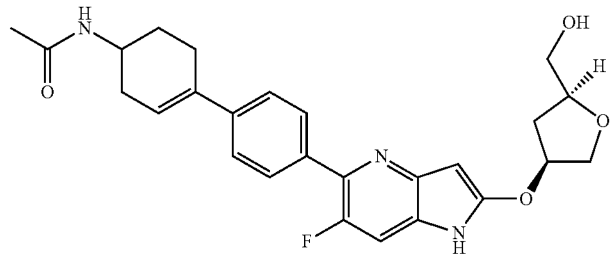 [SMILES: CC(=O)NC1CC=C(c2ccc(-c3nc4cc(O[C@@H]5CO[C@H](CO)C5)[nH]c4cc3F)cc2)CC1] | 1.05 | 466.2 | B |
| I-2-93 | 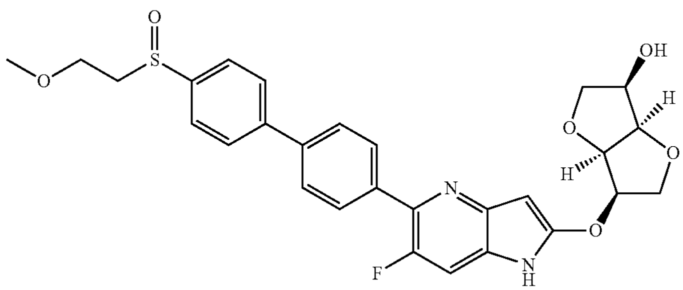 [SMILES: COCCS(=O)c1ccc(-c2ccc(-c3nc4cc(O[C@@H]5CO[C@H]6[C@@H]5OC[C@H]6O)[nH]c4cc3F)cc2)cc1] | 1.12 | 539.2 | B |
| I-2-94 | 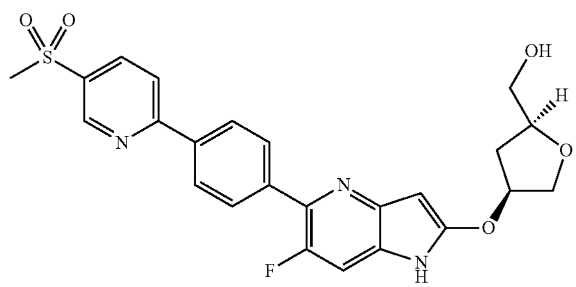 [SMILES: CS(=O)(=O)c1ccc(-c2ccc(-c3nc4cc(O[C@@H]5CO[C@H](CO)C5)[nH]c4cc3F)cc2)nc1] | 1.12 | 484.4 | B |
| I-2-95 | 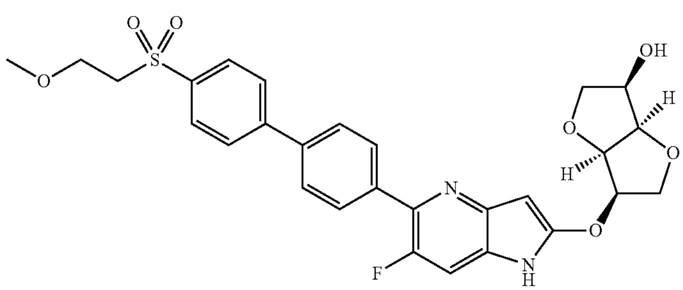 [SMILES: COCCS(=O)(=O)c1ccc(-c2ccc(-c3nc4cc(O[C@@H]5CO[C@H]6[C@@H]5OC[C@H]6O)[nH]c4cc3F)cc2)cc1] | 1.27 | 555.4 | B |
| I-2-96 | 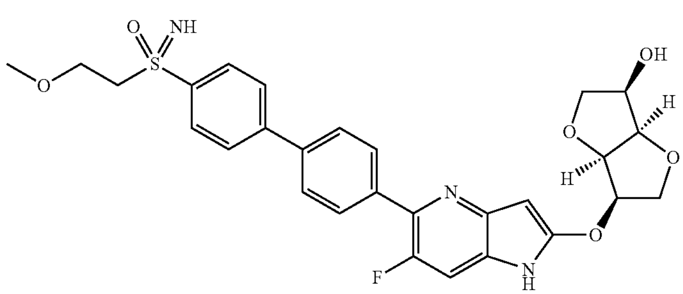 [SMILES: COCCS(=N)(=O)c1ccc(-c2ccc(-c3nc4cc(O[C@@H]5CO[C@H]6[C@@H]5OC[C@H]6O)[nH]c4cc3F)cc2)cc1] | 1.05 | 554.4 | B |

TABLE 26-continued

| | | | |
|---|---|---|---|
| I-2-97 | 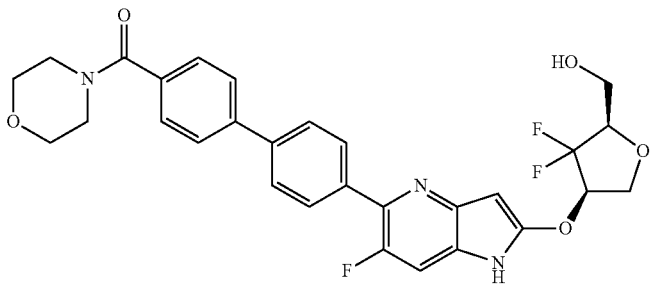 [SMILES: O=C(c1ccc(-c2ccc(-c3nc4cc(O[C@@H]5CO[C@H](CO)C5(F)F)[nH]c4cc3F)cc2)cc1)N1CCOCC1] | 1.54 554.2 | C |

Evaluation Method of an Activator for AMP-Activated Protein Kinase (AMPK)

TEST EXAMPLE 1

To a buffer solution consisting of a 50 mM HEPES-NaOH buffer solution (pH 7.0), 100 mM NaCl, 10 mM magnesium chloride, 0.1% bovine serum albumin, 0.2 mM sodium orthovanadate(V), 1 mM ethylene glycol-bis(2-aminoethyl ether)-N,N,N',N'-tetraacetic acid (EGTA), 5 mM disodium β-glycerophosphate and 2 mM dithiothreitol, a human AMPK α1β1γ1 enzyme (manufactured by Carna Biosciences, Inc.) was added in an amount to give a conversion rate of approximately 10% by reaction for 2 hours, and a compound dissolved in DMSO was added thereto so as to have a 1% DMSO concentration. The resulting liquid was left to stand for 10 minutes.

To the liquid, a substrate solution consisting of a 50 mM HEPES-NaOH buffer solution (pH 7.0), 100 mM NaCl, 10 mM magnesium chloride, 0.1% bovine serum albumin, 0.2 mM sodium orthovanadate(V), 1 mM ethylene glycol-bis (2-aminoethyl ether)-N,N,N',N'-tetraacetic acid (EGTA), 5 mM disodium β-glycerophosphate, 2 mM dithiothreitol, 0.4 mM ATP and 3 μM FL-Peptide 7 (manufactured by Caliper Life Sciences, Inc.) was added in equal amount (10 μl in total). The resulting liquid was allowed to react at 25° C. for 2 hours, then 10 μl of 20 mM EDTA was added thereto to stop the reaction.

To detect phosphorylated fluorescent substrates, the reaction mixture was applied to a measuring device, LabChip EZ Reader II manufactured by Caliper Life Science, Inc., for detecting fluorescence by using differences in mobility due to differences in charge. The setting conditions for the device were pressure, −1.5 PSI; upstream voltage, −2250 V; downstream voltage, −400 V; post sample buffer sip time, 40 seconds; final delay, 120 seconds; and peak order, Product First.

A conversion rate was calculated from the peak heights of the obtained substrate and product. The conversion rate when not containing a compound was used as a control, and a concentration dependent curve was made by plotting the rate of increase in activity to the control at each concentration of a compound. The compound concentration showing 150% relative to the control (100%) was used as the EC 150 value, and the maximum rate of increase in activity within the measurement range was used as Emax.

Preparation Method of Human AMPK α2β2γ1

The full length cDNAs of human AMPK β2 (NM_005399.3) and human AMPK α2 (NM_006252.3) were inserted into the MCS1 and MCS2 of the pETDuet-1 vector to prepare a human AMPK β2 and human AMPK α2 (6×His tag at the 5' terminus) expressing plasmid. The plasmid was cotransfected with an expression plasmid, in which the full length cDNA of human AMPK γ1 (NM_002733.3) had been inserted into pET28b(+), into BL21 CodonPlus (DE3)-RIL to obtain an expression strain. The expression strain was cultured in TB medium, followed by induction with 0.5 mM IPTG, and cultured at 25° C. for 3 hours and then harvested. After ultrasonication, supernatant was collected and applied to Histrap FF column (GE) and RESOUECE Q column (GE) to prepare 12.5 mg of purified sample containing three types of subunit from 1.8 L of broth.

Preparation Method of Human CaMKK2 Used to Impart Activity to AMPK

An expression vector, in which the full length cDNA of human CAMKK β (NM_172226.1) had been inserted into pGEX-6P-3, was transfected into BL21 Star (DE3). The expression strain was cultured in TB medium, followed by induction with 0.5 mM IPTG, and cultured at 25° C. for 3 hours and then harvested. After ultrasonication, supernatant was collected and applied to GSTrap FF column (GE) to prepare 14 mg of GST-fused CAMKK β from 720 ml of broth.

Evaluation Method of an Activator for AMP-Activated Protein Kinase (AMPK)

TEST EXAMPLE 2

Human AMPK α2β2γ1 prepared in *Escherichia coli* was not phosphorylated and did not exhibit activity. Thus, phosphorylation treatment was carried out as pretreatment.

Human AMPK α2β2γ1 in an amount to give a conversion rate of approximately 10% by reaction for 2 hours, and CaMKK2 in an amount capable of sufficiently imparting activity to AMPK for one hour were mixed in a buffer solution consisting of a 50 mM HEPES-NaOH buffer solution (pH 7.0), 100 mM NaCl, 5 mM magnesium chloride, 0.1% bovine serum albumin, 0.2 mM sodium orthovanadate (V), 1 mM ethylene glycol-bis(2-aminoethyl ether)-N,N,N', N'-tetraacetic acid (EGTA), 5 mM disodium β-glycerophosphate, 1 mM dithiothreitol and 0.2 mM ATP, and the resulting liquid was left to stand at 25° C. for 1 to 1.5 hours to sufficiently phosphorylate AMPK.

After that, to the enzyme liquid, which had been subjected to phosphorylation treatment, a compound dissolved in DMSO was added so as to have a 1% DMSO concentration. The resulting liquid was left to stand for 10 minutes.

To the liquid, a substrate solution consisting of a 50 mM HEPES-NaOH buffer solution (pH 7.0), 100 mM NaCl, 10 mM magnesium chloride, 0.1% bovine serum albumin, 0.2 mM sodium orthovanadate(V), 1 mM ethylene glycol-bis (2-aminoethyl ether)-N,N,N',N'-tetraacetic acid (EGTA), 5 mM disodium β-glycerophosphate, 2 mM dithiothreitol, 0.4 mM ATP and 3 µM FL-Peptide 7 (manufactured by Caliper Life Sciences, Inc.) was added in equal amount (10 µl in total). The resulting liquid was allowed to react at 25° C. for 2 hours, then 10 µl of 20 mM EDTA was added thereto to stop the reaction.

To detect phosphorylated fluorescent substrates, the reaction mixture was applied to a measuring device, LabChip EZ Reader II manufactured by Caliper Life Science, Inc., for detecting fluorescence by using differences in mobility due to differences in charge. The setting conditions for the device were pressure, −1.5 PSI; upstream voltage, −2250 V; downstream voltage, −400 V; post sample buffer sip time, 40 seconds; final delay, 120 seconds; and peak order, Product First.

A conversion rate was calculated from the peak heights of the obtained substrate and product. The conversion rate when not containing a compound was used as a control, and a concentration dependent curve was made by plotting the rate of increase in activity to the control at each concentration of a compound. The compound concentration showing 150% relative to the control (100%) was used as the EC 150 value, and the maximum rate of increase in activity within the measurement range was used as Emax.

The results of Test Example 2 are shown below.
Compound (I-1-01): EC150=24 nM, Emax=282%
Compound (I-1-02): EC150=2.2 nM, Emax=510%
Compound (I-1-03): EC150=9.8 nM, Emax=556%
Compound (I-1-04): EC150=6.2 nM, Emax=332%
Compound (I-1-06): EC150=19 nM, Emax=263%
Compound (I-1-07): EC150=15 nM, Emax=189%
Compound (I-1-08): EC150=4.7 nM, Emax=444%
Compound (I-1-09): EC150=4.8 nM, Emax=475%
Compound (I-1-10): EC150=13 nM, Emax=490%
Compound (I-1-12): EC150=31 nM, Emax=497%
Compound (I-1-12): EC150=8.3 nM, Emax=523%
Compound (I-1-14): EC150=24 nM, Emax=513%
Compound (I-1-15): EC150=0.58 nM, Emax=525%
Compound (I-1-17): EC150=3.4 nM, Emax=483%
Compound (I-1-18): EC150=19 nM, Emax=415%
Compound (I-1-19): EC150=5.8 nM, Emax=477%
Compound (I-1-20): EC150=8.3 nM, Emax=457%
Compound (I-1-22): EC150=3.8 nM, Emax=422%
Compound (I-1-23): EC150=2.9 nM, Emax=436%
Compound (I-1-26): EC150=1.5 nM, Emax=353%
Compound (I-1-27): EC150=5.8 nM, Emax=332%
Compound (I-1-28): EC150=15 nM, Emax=596%
Compound (I-1-30): EC150=1.7 nM, Emax=500%
Compound (I-1-31): EC150=9.5 nM, Emax=539%
Compound (I-1-32): EC150=8 nM, Emax 456%
Compound (I-1-33): EC150=6.5 nM, Emax=464%
Compound (I-1-34): EC150=8.6 nM, Emax=518%
Compound (I-1-35): EC150=5.9 nM, Emax=432%
Compound (I-1-36): EC150=1.7 nM, Emax=437%
Compound (I-1-37): EC150=6.5 nM, Emax=405%
Compound (I-1-38): EC150=0.99 nM, Emax=470%
Compound (I-1-39): EC150=13 nM, Emax=552%
Compound (I-1-40): EC150=29 nM, Emax=541%
Compound (I-1-41): EC150=7.8 nM, Emax=562%
Compound (I-1-42): EC150=5.3 nM, Emax=472%
Compound (I-1-43): EC150=7 nM, Emax=514%
Compound (I-1-45): EC150=19 nM, Emax=482%
Compound (I-1-46): EC150=6.6 nM, Emax=276%
Compound (I-1-47): EC150=0.96 nM, Emax=542%
Compound (I-1-48): EC150=2.9 nM, Emax=576%
Compound (I-1-49): EC150=19 nM, Emax=551%
Compound (I-1-50): EC150=23 nM, Emax=539%
Compound (I-1-51): EC150=12 nM, Emax=486%
Compound (I-1-52): EC150=2.2 nM, Emax=469%
Compound (I-1-53): EC150=1.6 nM, Emax=533%
Compound (I-1-54): EC150=3.3 nM, Emax=416%
Compound (I-1-55): EC150=0.34 nM, Emax=431%
Compound (I-1-57): EC150=32 nM, Emax=550%
Compound (I-1-58): EC150=1.3 nM, Emax=494%
Compound (I-1-59): EC150=2.9 nM, Emax=470%
Compound (I-1-60): EC150<0.051 nM, Emax=486%
Compound (I-1-61): EC150=2.3 nM, Emax=383%
Compound (I-1-62): EC150=21 nM, Emax=392%
Compound (I-1-63): EC150=3.2 nM, Emax=361%
Compound (I-1-64): EC150=1.6 nM, Emax=375%
Compound (I-1-66): EC150=8.5 nM, Emax=333%
Compound (I-1-68): EC150=2.5 nM, Emax=360%
Compound (I-1-69): EC150=1.6 nM, Emax=359%
Compound (I-1-71):EC150=4.33 nM, Emax=340%
Compound (I-1-72):EC150=3 nM, Emax=353%
Compound (I-2-01):EC150=14 nM, Emax=376%
Compound (I-2-02):EC150=2.9 nM, Emax=537%
Compound (I-2-04):EC150=0.67 nM, Emax=638%
Compound (I-2-05):EC150=6.8 nM, Emax=632%
Compound (I-2-06):EC150=0.46 nM, Emax=621%
Compound (I-2-07):EC150=0.68 nM, Emax=638%
Compound (I-2-08):EC150=1.6 nM, Emax=598%
Compound (I-2-09):EC150=1.9 nM, Emax=598%
Compound (I-2-10):EC150=2.9 nM, Emax=636%
Compound (I-2-11):EC150=2.1 nM, Emax=408%
Compound (I-2-12):EC150=6.9 nM, Emax=367%
Compound (I-2-13):EC150=3 nM, Emax=652%
Compound (I-2-14):EC150=9.9 nM, Emax=507%
Compound (I-2-15):EC150=11 nM, Emax=505%
Compound (I-2-16):EC150=1.8 nM, Emax=623%
Compound (I-2-17):EC150=15 nM, Emax=600%
Compound (I-2-18):EC150=12 nM, Emax=618%
Compound (I-2-19):EC150=67 nM, Emax=192%
Compound (I-2-20):EC150=2.3 nM, Emax=375%
Compound (I-2-21):EC150=13 nM, Emax=249%
Compound (I-2-22):EC150=5.9 nM, Emax=348%
Compound (I-2-23):EC150=28 nM, Emax=224%
Compound (I-2-24):EC150=11 nM, Emax=364%
Compound (I-2-25):EC150=1.9 nM, Emax=426%
Compound (I-2-26):EC150=8.6 nM, Emax=298%
Compound (I-2-27):EC150=3.7 nM, Emax=375%
Compound (I-2-28):EC150=4.4 nM, Emax=398%
Compound (I-2-29):EC150=48 nM, Emax=367%
Compound (I-2-30):EC150=4.3 nM, Emax=605%
Compound (I-2-31):EC150=6.8 nM, Emax=478%
Compound (I-2-32):EC150=1.3 nM, Emax=379%
Compound (I-2-33):EC150=20 nM, Emax=362%
Compound (I-2-34):EC150=20 nM, Emax=425%
Compound (I-2-36):EC150=43 nM, Emax=385%
Compound (I-2-37):EC150=4.5 nM, Emax=415%
Compound (I-2-38):EC150=9.2 nM, Emax=597%
Compound (I-2-40):EC150=16 nM, Emax=384%
Compound (I-2-41):EC150=0.8 nM, Emax=634%
Compound (I-2-42):EC150=2.6 nM, Emax=647%
Compound (I-2-43):EC150=6.2 nM, Emax=514%
Compound (I-2-44):EC150=35 nM, Emax=661%
Compound (I-2-45):EC150=5 nM, Emax=613%
Compound (I-2-46):EC150=2.8 nM, Emax=699%
Compound (I-2-47):EC150=2.2 nM, Emax=635%
Compound (I-2-48):EC150=1.1 nM, Emax=635%
Compound (I-2-49):EC150=0.88 nM, Emax=684%
Compound (I-2-51):EC150=9.7 nM, Emax=590%
Compound (I-2-52):EC150=7.2 nM, Emax=532%
Compound (I-2-53):EC150=4.2 nM, Emax=638%
Compound (I-2-54):EC150=1.7 nM, Emax=633%

Compound (I-2-55):EC150=19 nM, Emax=507%
Compound (I-2-56):EC150=1.6 nM, Emax=618%
Compound (I-2-57):EC150=26 nM, Emax=601%
Compound (I-2-58):EC150=56 nM, Emax=514%
Compound (I-2-59):EC150=40 nM, Emax=458%
Compound (I-2-60):EC150=2 nM, Emax=564%
Compound (I-2-61):EC150=5.1 nM, Emax=562%
Compound (I-2-62):EC150=47 nM, Emax=514%
Compound (I-2-63):EC150=21 nM, Emax=520%
Compound (I-2-64):EC150=16 nM, Emax=536%
Compound (I-2-65):EC150=0.6 nM, Emax=673%
Compound (I-2-66):EC150=1.1 nM, Emax=580%
Compound (I-2-67):EC150=22 nM, Emax=555%
Compound (I-2-69):EC150=13 nM, Emax=557%
Compound (I-2-72):EC150=2.7 nM, Emax=591%
Compound (I-2-73):EC150=4.2 nM, Emax=681%
Compound (I-2-74):EC150=1.2 nM, Emax=656%
Compound (I-2-76):EC150=20 nM, Emax=490%
Compound (I-2-78):EC150=1.5 nM, Emax=573%
Compound (I-2-79):EC150=0.69 nM, Emax=591%
Compound (I-2-80):EC150=2 nM, Emax=558%
Compound (I-2-81):EC150=0.78 nM, Emax=591%
Compound (I-2-82):EC150=0.5 nM, Emax=591%
Compound (I-2-83):EC150=0.73 nM, Emax=581%
Compound (I-2-84):EC150=4.3 nM, Emax=514%
Compound (I-2-85):EC150=1.5 nM, Emax=500%
Compound (I-2-86):EC150=0.53 nM, Emax=592%
Compound (I-2-88):EC150=0.62 nM, Emax=683%
Compound (I-2-89):EC150=0.94 nM, Emax=556%
Compound (I-2-90):EC150=1.9 nM, Emax=406%
Compound (I-2-92):EC150=0.87 nM, Emax=702%
Compound (I-2-93):EC150=1.1 nM, Emax=652%
Compound (I-2-94):EC150=0.99 nM, Emax=652%
Compound (I-2-95):EC150=2.6 nM, Emax=634%
Compound (I-2-96):EC150=2.9 nM, Emax=631%
Compound (I-2-97):EC150=4.6 nM, Emax=527%

The compounds of the present invention have an excellent activating effect on an AMPK α1 trimer and/or an AMPK α2 trimer.

Evaluation Method of an Activator for AMP-activated Protein Kinase (AMPK)

TEST EXAMPLE 3

Cell-based assay for AMPK activation potency of compounds was performed with L6-GLUT4myc myoblasts (J. Biol. Chem. 278:17953-62, 2003) in a 96-well or 384-well plate by detecting the phosphorylation of endogenous acetyl-CoA carboxylase (ACC) using cell-based ELISA method. The cells were seeded in a 96-well plate at a density of $2 \times 10^4$ cells per well or in a 384-well plate at a density of $3.5 \times 10^3$ cells per well in minimum essential media (α-MEM) supplemented with 10% fetal bovine serum, 100 U/mL penicillin, 100 µg/mL streptomycin, 2 µg/mL blasticidin S hydrochloride and 0.5 mg/mL G418 disulfate, and maintained in a humidified atmosphere of 95% air and 5% $CO_2$ at 37° C. for 24 hours. Following the overnight culture with an assay buffer consisting of 0.1% bovine serum albumin (BSA), 100 U/mL penicillin and 100 µg/mL streptomycin, cells were treated with varying concentrations of compounds or vehicle (dimethyl sulfoxide at a final concentration of 0.33%) in the presence of 0.1% BSA or 4% BSA for 3 hours at room temperature. After fixing cells with ice-cold 4% formaldehyde in Tris-buffered saline (TBS) for 30 min, the fixed cells were rinsed with TBS containing 0.1% or 0.01% Triton X-100 (TBS-T) and quenched with 0.6% hydrogen peroxide in TBS-T, and blocked with a blocking reagent (Blocking One P manufactured by Nacalai Tesque). Then, anti-phospho-ACC (Ser79) antibody as the primary antibody (manufactured by Cell Signaling Technology) diluted with TBS-T containing 5% Blocking One P was added to each well and the plate was incubated overnight at 4° C. After rinsing each well with TBS-T, horseradish peroxidase (HRP)-conjugated anti-rabbit IgG as the secondary antibody diluted with TBS-T containing 5% Blocking One P was added to each well and the plate was incubated for 1 hour in 96-well plate or for 5 hours in 384-well plate at room temperature. Each well of the plate was rinsed with TBS-T and added a chemiluminescent reagent (ImmunoStar® LD manufactured by Wako Pure Chemical Industries) for detection of HRP conjugates. Ten minutes later, the luminescence intensity was measured using luminometer (ViewLux or ARVO manufactured by PerkinElmer). The luminescence in the presence of compound was calculated as the rate of change relative to vehicle control, which is in the absence of compound. The compound concentration causing 150% relative to the control (100%) was defined as EC 150, and the maximum response (%) within varying concentrations of each compound was defined as Emax.

The results of Test Example 3 are shown below.
Compound (I-1-02): EC150=11.3 nM, Emax=968%
Compound (I-1-27): EC150=168 nM, Emax=473%
Compound (I-1-47): EC150=3.9 nM, Emax=547%
Compound (I-1-60): EC150=19 nM, Emax=495%
Compound (I-1-64): EC150=21 nM, Emax=509%
Compound (I-1-66): EC150=103 nM, Emax=635%
Compound (I-1-70): EC150=156 nM, Emax=512%
Compound (I-2-13): EC150=160 nM, Emax=650%
Compound (I-2-18): EC150=164 nM, Emax=612%
Compound (I-2-31): EC150=134 nM, Emax=656%
Compound (I-2-32): EC150=86 nM, Emax=531%
Compound (I-2-84): EC150=79n M, Emax=684%

The compounds of the present invention have an excellent activating effect on an AMPK under the condition of cell addition.

CYP3A4 Fluorescent MBI Test

The CYP3A4 fluorescent MBI test is a test of evaluating Mechanism based inhibition (MBI) ability from enhancement by a metabolism reaction for CYP3A4 inhibition of the compound of the present invention. CYP3A4 inhibition was evaluated as an index 1-hydroxylation reaction of midazolam (MDZ) using pooled human hepatic microsomes.

The reaction conditions were as follows: substrate, 10 µmol/L MDZ; pre-reaction time, 0 or 30 minutes; reaction time, 2 minutes; reaction temperature, 37° C.; pooled human hepatic microsomes, at pre-reaction 0.5 mg/mL, at reaction 0.05 mg/mL (at 10-fold dilution); concentration of the compound of the present invention at pre-reaction, 1, 5, 10, 20 µmol/L (four points).

Pooled human hepatic microsomes in a K-Pi buffer (pH 7.4) and a solution of the compound of the present invention as a pre-reaction mixture were added to a 96-well plate at the composition of the pre-reaction, a part of it was transferred to another a 96-well plate at the composition of the pre-reaction, a part of it was transferred to another 96-well plate so that it was 1/10 diluted with a substrate and a K-Pi buffer, NADPH as a coenzyme was added to initiate a reaction as an index (without pre-reaction) and, after a predetermined time of a reaction, a methanol/acetonitrile=1/1 (V/V) solution was added to stop the reaction. In addition, NADPH was added to a remaining pre-reaction mixture to initiate a pre-reaction (with pre-reaction) and, after a predetermined time of a pre-reaction, a part was transferred to another plate so that it was 1/10 diluted with a substrate and a K-Pi buffer to initiate a reaction as an index. After a predetermined time of a reaction, a methanol/acetonitrile=1/1 (V/V) solution was added to stop the reaction. The plate on which each index reaction had been performed was centrifuged at 3000 rpm for 15 minutes, and then midazolam 1-hydroxylation in the centrifuge supernatant was quantified by LC/MS/MS.

Addition of only DMSO being a solvent dissolving the compound of the present invention to a reaction system was adopted as a control (100%), remaining activity (%) was calculated at each concentration of the compound of the present invention added, and IC was calculated by reverse presumption by a logistic model using a concentration and an inhibition rate. "IC value at start of pre-reaction/IC value at 30 minutes after start of pre-reaction" was defined as Shifted IC value. When Shifted IC was 1.5 or more, this was defined as (+), and when Shifted IC was 1.0 or less, this was defined as (−).

CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenadine hydroxylation (CYP3A4) as typical substrate metabolism reactions of human main five CYP enzyme forms (CYP1A2, 2C9, 2C19, 2D6, 3A4), an inhibitory degree of each metabolite production amount by a test compound was assessed.

The reaction conditions were as follows: substrate, 0.5 μmol/L ethoxyresorufin (CYP1A2), 100 μmol/L tolbutamide (CYP2C9), 50 μmol/L S-mephenytoin (CYP2C19), 5 μmol/L dextromethorphan (CYP2D6), 1 μmol/L terfenadine (CYP3A4); reaction time, 15 minutes; reaction temperature, 37° C.; enzyme, pooled human hepatic microsome 0.2 mg protein/mL; test drug concentration, 1, 5, 10, 20 μmol/L (four points).

Each five kinds of substrates, human hepatic microsome, or a test drug in 50 mM Hepes buffer as a reaction solution was added to a 96-well plate at the composition as described above, NADPH, as a coenzyme was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the centrifuge supernatant was quantified by a fluorescent multilabel counter, and tolbutamide hydroxide (CYP2C9 metabolite), mephenytoin 4' hydroxide (CYP2C$_{19}$ metabolite), dextromethorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%), remaining activity (%) was calculated at each concentration of a test drug added as the solution, and $IC_{50}$ was calculated by reverse presumption by a logistic model using a concentration and an inhibition rate.

FAT Test

Each 20 μL of freeze-stored *Salmonella typhimurium* (strains TA98 and TA100) is inoculated in 10 mL of liquid nutrient medium (2.5% Oxoid nutrient broth No. 2), and the cultures are preincubated at 37° C. under shaking for 10 hours. 9 mL of TA98 culture is centrifuged (2000×g, 10 minutes) to remove medium, and the bacteria is suspended in 9 mL of Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4 \cdot 7H_2O$: 0.1 g/L), and the suspension is added to 110 mL of Exposure medium (Micro F buffer containing Biotin: 8 μg/mL, histidine: 0.2 μg/mL, glucose: 8 mg/mL). 3.16 mL of TA100 culture is added to 120 mL of Exposure medium to prepare the test bacterial solution. 588 μL of the test bacterial solution (a mixed solution of 498 μL of the test bacterial solution and 90 μL of the S9 mix in the case with metabolic activation conditions) is mixed with each 12 μL of the following solution: DMSO solution of the test substance (eight dose levels from maximum dose 50 mg/mL at 2-fold ratio); DMSO as negative control; 50 μg/mL of 4-nitroquinoline-1-oxide DMSO solution as positive control for strain TA98 without metabolic activation conditions; 0.25 μg/mL of 2-(2-furyl)-3-(5-nitro-2-furyl)acrylamide DMSO solution as positive control for strain TA100 without metabolic activation conditions; 40 μg/mL of 2-aminoanthracene DMSO solution as positive control for strain TA98 with metabolic activation conditions; or 20 μg/mL of 2-aminoanthracene DMSO solution as positive control for strain TA100 with metabolic activation conditions, and the mixture is incubated at 37° C. under shaking for 90 minutes. 460 μL of the culture exposed to the test substance is mixed with 2300 μL of Indicator medium (Micro F buffer containing biotin: 8 μg/mL, histidine: 0.2 μg/mL, glucose: 8 mg/mL, Bromo Cresol Purple: 37.5 μg/mL), each 50 μL is dispensed into 48 wells per dose in the microplates, and is subjected to stationary cultivation at 37° C. for 3 days. A well containing the bacteria, which has obtained the ability of proliferation by mutation in the gene coding amino acid (histidine) synthetase, turns the color from purple to yellow due to pH change. Thus, the number of the yellow wells among the 48 total wells per dose is counted to evaluate the mutagenicity by comparing with the negative control group.

Solubility Test

The solubility of a compound was determined under a condition in which 1% DMSO was added. A 10 mM compound solution was prepared using DMSO, and then 6 μL of the compound solution was added to 594 μL of artificial intestinal juice in pH 6.8 (to 250 mL of a 0.2 mol/L potassium dihydrogen phosphate reagent solution were added 118 mL of a 0.2 mol/L NaOH reagent solution and water to provide a final volume of 1000 mL). After standing at 25° C. for 16 hours, the mixed solution was filtrated with suction. The filtrate was diluted twice with methanol/water (1/1), and then a concentration in the filtration was measured with HPLC or LC/MS/MS by the absolute calibration method.

Metabolic Stability Test

Using commercially available pooled human hepatic microsomes, an object compound was reacted for a constant time, a remaining rate was calculated by comparing a reacted sample and an unreacted sample, thereby, a degree of metabolism in hepatic was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human hepatic microsomes. After the reaction, 50 μL of the reaction mixture was added to 100 μL of a methanol/acetonitrile=1/1 (v/v) solution, and the mixture was mixed and centrifuged at 3000 rpm for 15 minutes. The test compound in the centrifuge supernatant was quantified by LC/MS/MS, and a remaining amount of the test compound after the reaction was calculated, letting a compound amount at 0 minute reaction time to be 100%. Hydrolysis reaction was performed in the absence of NADPH and glucuronidation reaction was performed in the presence of 5 mM UDP-glucuronic acid in place of NADPH, followed by similar operations.

hERG Test

For the purpose of assessing risk of an electrocardiogram QT interval prolongation, effects on delayed rectifier K$^+$ current ($I_{Kr}$), which plays an important role in the ventricular repolarization process, is studied using HEK293 cells expressing human ether-a-go-go related gene (hERG) channel.

After a cell is retained at a membrane potential of −80 mV by whole cell patch clamp method using an automated patch clamp system (PatchXpress 7000A, Axon Instruments Inc.), $I_{Kr}$ induced by depolarization pulse stimulation at +40 mV for 2 seconds and, further, repolarization pulse stimulation at −50 mV for 2 seconds is recorded. After the generated current is stabilized, extracellular solution (NaCl: 135 mmol/L, KCl: 5.4 mmol/L, NaH$_2$PO$_4$: 0.3 mmol/L, CaCl$_2$.2H$_2$O: 1.8 mmol/L, MgCl$_2$.6H$_2$O: 1 mmol/L, glucose: 10 mmol/L, HEPES (4-(2-hydroxyethyl)-1-piperazine ethanesulfonic acid): 10 mmol/L, pH=7.4) in which the test compound has been dissolved at an objective concentration is applied to the cell under the room temperature condition for 10 minutes. From the recording $I_{Kr}$, an absolute value of the tail peak current is measured based on the current value at the resting membrane potential using an analysis software (DataXpress ver. 1, Molecular Devices Corporation). Further, the % inhibition relative to the tail peak current before application of the test substance is calculated, and compared with the vehicle-applied group (0.1% dimethyl sulfoxide solution) to assess influence of the test substance on $I_{Kr}$.

Powder Solubility Test

Appropriate amounts of the test substances are put into appropriate containers. To the respective containers are added 200 µL of JP-1 fluid (sodium chloride 2.0 g, hydrochloric acid 7.0 mL and water to reach 1000 mL), 200 µL of JP-2 fluid (phosphate buffer (pH 6.8) 500 mL and water 500 mL), and 200 µL of 20 mmol/L TCA (sodium taurocholate)/JP-2 fluid (TCA 1.08 g and water to reach 100 mL). In the case that the test liquid is dissolved after the addition of the test fluid, the bulk powder is added as appropriate. The containers are sealed, and shaken for 1 hour at 37° C. The mixtures are filtered, and 100 µL of methanol is added to each of the filtrate (100 µL) so that the filtrates are two-fold diluted. The dilution ratio is changed if necessary. After confirmation of no bubbles and precipitates, the containers are sealed and shaken. Quantification is performed by HPLC with an absolute calibration method.

BA Test

Materials and Methods for Studies on Oral Absorption
(1) Animals: mice or rats
(2) Animal husbandry: Mice and rats had free access to solid food and sterilized bottled tap water.
(3) Setting of dose and group compositions: orally or intravenously administered at a predetermined dose Group compositions were as shown below. (Dose depends on the compound)
Oral: 1 to 30 mg/kg (n=2 to 3)
Intravenous: 0.5 to 10 mg/kg (n=2 to 3)
(4) Preparation of administration formulation: for oral administration, in a solution or a suspension state; for intravenous administration, in a solubilized state
(5) Dosing procedure: In oral administration study, the test substance was forcibly administered to the stomach by using a gavage tube. In intravenous administration study, the test substance was administered via tail vein using a syringe with a needle.
(6) Evaluation items: Blood was collected at each time point, and plasma concentration of the drug was determined by LC/MS/MS.
(7) Data analysis: Regarding the transition of the plasma concentration, area under the plasma concentration-time curve (AUC) was calculated by means of WinNonlin® program, respectively. Bioavailability (BA) was calculated from AUCs of the oral administration group and intravenous administration group.

The results of BA test (rats) are shown below.
Compound (I-1-27): 19.6%
Compound (I-1-64): 17.8%
Compound (I-1-66): 38.8%
Compound (I-1-70): 25.5%
Compound (I-2-13): 59.0%
Compound (I-2-18): 18.6%
Compound (I-2-31): 40.5%
Compound (I-2-32): 28.6%
Compound (I-2-84): 52.1%

The compounds of the present invention have an excellent BA.

Formulation Examples are shown below.

FORMULATION EXAMPLE 1

Tablets

The compound of the present invention, lactose and calcium stearate are mixed. The mixture is crushed, granulated and dried to give a suitable size of granules. Next, calcium stearate is added to the granules, and the mixture is compressed and molded to give tablets.

FORMULATION EXAMPLE 2

Capsules

The compound of the present invention, lactose and calcium stearate are mixed uniformly to obtain powder medicines in the form of powder or fine granules. The powder medicines are filled into capsule containers to give capsules.

FORMULATION EXAMPLE 3

Granules

The compound of the present invention, lactose and calcium stearate are mixed uniformly, and the mixture is compressed and molded. Then, it is crushed, granulated and sieved to give a suitable size of granules.

FORMULATION EXAMPLE 4

Orally Disintegrating Tablets

The compound of the present invention and crystalline cellulose are mixed and granulated, then tableted to give orally disintegrating tablets.

FORMULATION EXAMPLE 5

Dry Syrups

The compound of the present invention and lactose are mixed, crushed, granulated and sieved to give a suitable size of dry syrups.

FORMULATION EXAMPLE 6

Injections

The compound of the present invention and phosphate buffer are mixed to give injections.

FORMULATION EXAMPLE 7

Infusions

The compound of the present invention and phosphate buffer are mixed to give injections.

FORMULATION EXAMPLE 8

Inhalations

The compound of the present invention and lactose are mixed and crushed finely to give inhalations.

FORMULATION EXAMPLE 9

Ointments

The compound of the present invention and petrolatum are mixed to give ointments.

FORMULATION EXAMPLE 10

Patches

The compound of the present invention and base such as adhesive plaster or the like are mixed to give patches.

INDUSTRIAL APPLICABILITY

As is apparent from the above test examples, the compounds of the present invention show an AMPK activating effect. Therefore, the compounds of the present invention are very useful as a therapeutic agent for type II diabetes, hyperglycemia, metabolic syndrome, obesity, hypercholesterolemia and hypertension.

The invention claimed is:
1. A compound represented by formula (I):

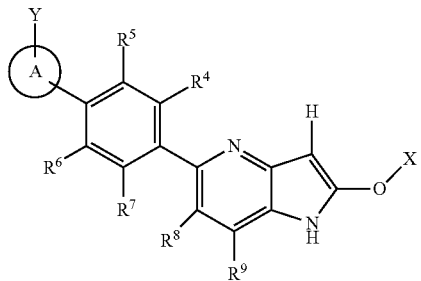

(I)

or its pharmaceutically acceptable salt,
wherein
X is substituted or unsubstituted monocyclic heterocyclyl, or

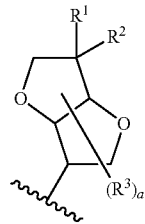

wherein $R^1$ and $R^2$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

$R^3$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

a is an integer from 0 to 7;

with the proviso that the compounds wherein one of $R^1$ and $R^2$ is hydrogen, the other is hydroxy, and a is 0 are excluded;

ring A is substituted aryl, substituted heteroaryl, substituted cycloalkyl, substituted cycloalkenyl, or substituted heterocyclyl, the ring A may further have (a) substituent(s) other than Y;

Y is halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted alkyloxycarbonyl, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted alkylsulfinyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted alkylaminosulfonyl, substituted or unsubstituted acyl, substituted or unsubstituted carbamoyl, substituted or unsubstituted carbamoyloxy, substituted or unsubstituted sulfamoyl, substituted or unsubstituted amino, $R^SR^{S'}(O=)S=N-$, $R^SR^{S'}(O=)S=N-R^{2f}-$, $R^SR^{S'}$ (O=)S=N—C(=O)—, $(R^N)N$=S(=O)$(R^S)$—, $(R^N)$N=S(=O)$(R^S)$—$R^{2f}$—, $R^S R^{S'}(R^{N'}$—N=)S=N—, $((R^N)N$=$)_2$ S$(R^S)$—, $(R^N R^{N'})$N—C(=O)—O—, $R^O$O—C(=O)—N$(R^N)$—, $R^O$O—C(=O)—O—, $R^S(R^N R^{N'}$N)(O=)S=N—, $R^S(R^N R^{N'}$N)(O=)S=N—$R^{2f}$—, $(R^{N''})$N=S(=O)(N$R^N R^{N'})$—, $(R^{N''})$N=S(=O)(N$R^N R^{N'})$—$R^{2f}$—, $R^{P1} R^{P2}$ (O=)P—

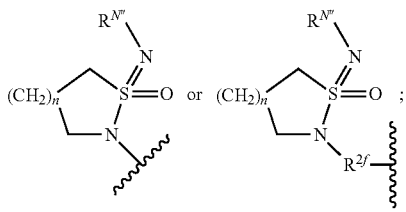

wherein n is an integer 1 or 2;

$R^S$ and $R^{S'}$ are each independently substituted or unsubstituted alkyl, substituted or unsubstituted cycloalkyl, substituted or unsubstituted heterocyclyl, substituted or unsubstituted aryl, substituted or unsubstituted heteroaryl, or substituted or unsubstituted amino;

$R^S$ and $R^{S'}$ bound to the same sulfur atom may form a substituted or unsubstituted ring together with the sulfur atom;

$R^{2f}$ is substituted or unsubstituted alkylene;

$R^N$ is each independently hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl, or substituted or unsubstituted carbamoyl;

$R^N$ together with the adjacent nitrogen atom may form a substituted or unsubstituted ring when Y is $((R^N)N$=$)_2$ S$(R^S)$—;

$R^{N'}$ is hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl or substituted or unsubstituted carbamoyl;

$R^N$ and $R^{N'}$ bound to the same nitrogen atom may form a substituted or unsubstituted ring together with the nitrogen atom;

$R^{N''}$ is hydrogen, cyano, substituted or unsubstituted alkyl, substituted or unsubstituted alkenyl, substituted or unsubstituted alkynyl, substituted or unsubstituted alkylcarbonyl, substituted or unsubstituted alkyloxycarbonyl, substituted or unsubstituted alkylcarbamoyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heterocyclyl, substituted or unsubstituted acyl, substituted or unsubstituted aryloxycarbonyl, substituted or unsubstituted arylsulfonyl, substituted or unsubstituted alkylsulfonyl, or substituted or unsubstituted carbamoyl;

$R^O$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^{P1}$ and $R^{P2}$ is each independently substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^4$, $R^5$, $R^6$ and $R^7$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

$R^8$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

$R^9$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

with the proviso that compounds shown below are excluded:

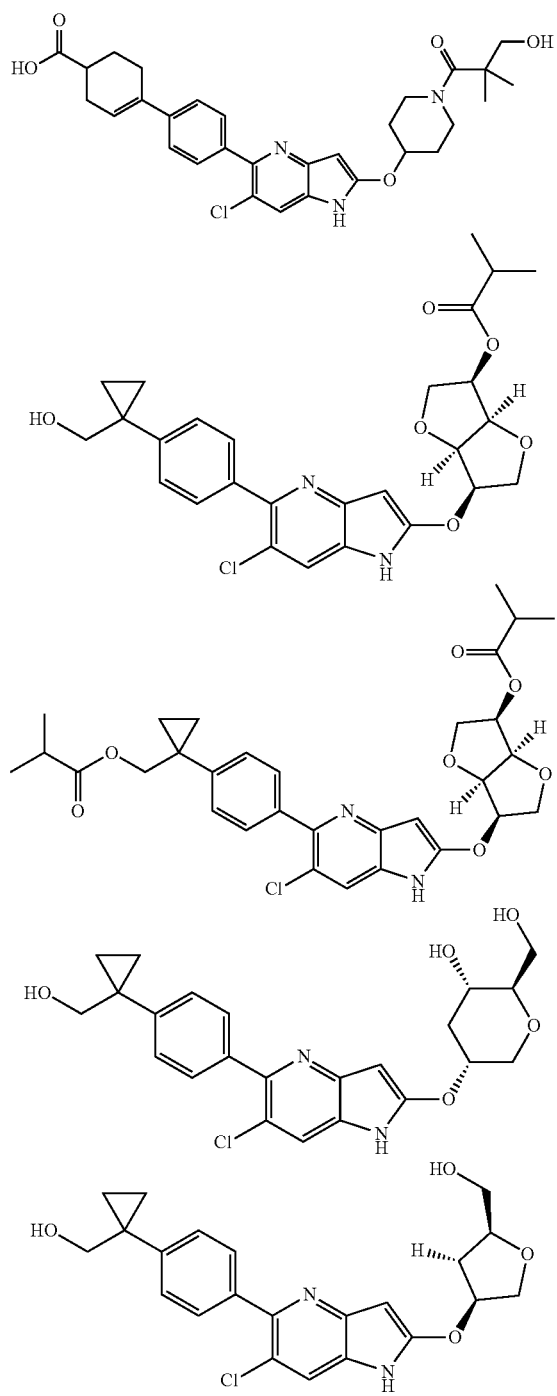

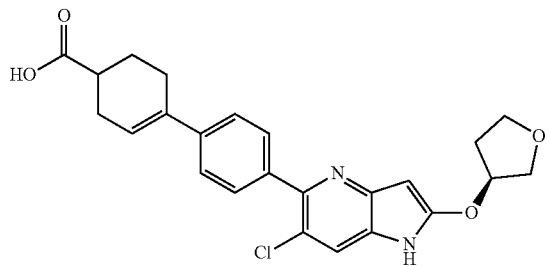

-continued

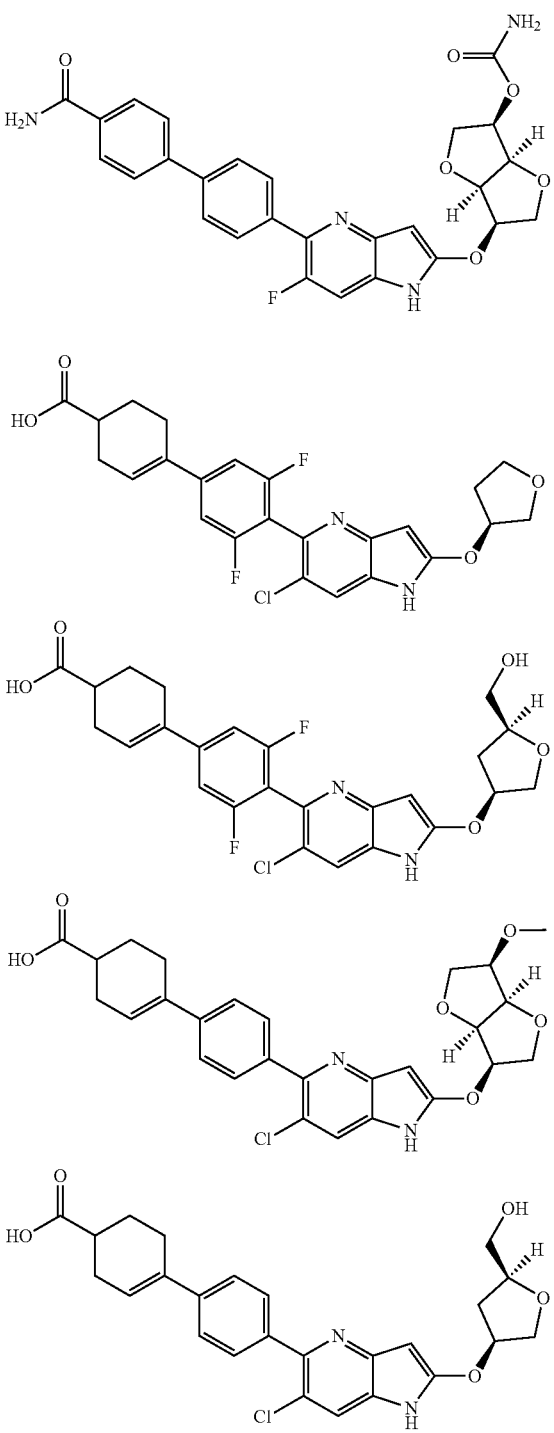

-continued

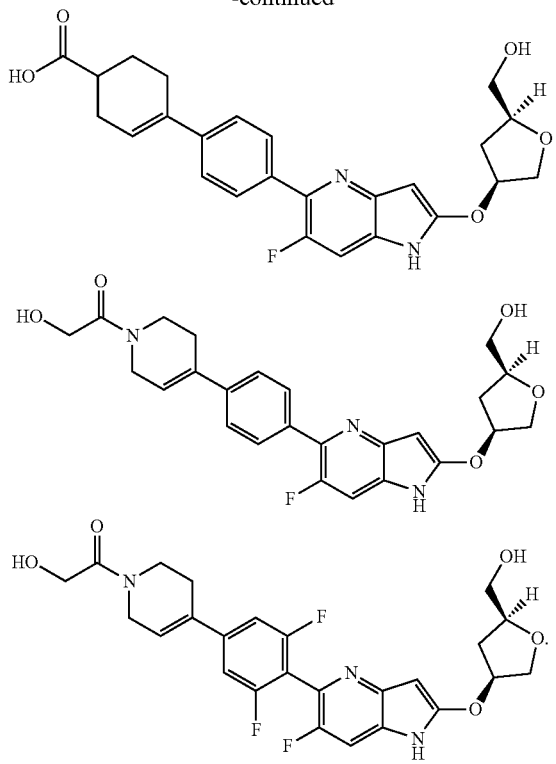

2. The compound according to claim 1 or its pharmaceutically acceptable salt, wherein X is substituted or unsubstituted monocyclic heterocyclyl.

3. The compound according to claim 2 or its pharmaceutically acceptable salt, wherein X is

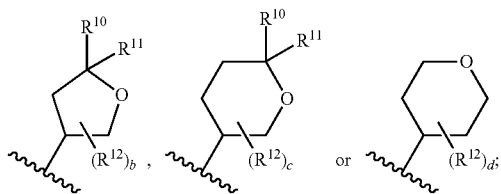

wherein $R^{10}$ and $R^{11}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

$R^{12}$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

b is an integer from 0 to 5;
c is an integer from 0 to 7;
d is an integer from 0 to 9.

4. The compound according to claim 3 or its pharmaceutically acceptable salt, wherein $R^{10}$ and $R^{11}$ are each independently hydrogen, halogen, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, or substituted or unsubstituted carbamoyl.

5. The compound according to claim 3 or its pharmaceutically acceptable salt, wherein one of $R^{10}$ and $R^{11}$ is hydrogen, halogen, or carboxy;
the other of $R^{10}$ and $R^{11}$ is substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, or substituted or unsubstituted carbamoyl.

6. The compound according to claim 3 or its pharmaceutically acceptable salt, wherein $R^{12}$ is each independently halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;
b is an integer from 0 to 3;
c is an integer from 0 to 3;
d is an integer from 0 to 4.

7. The compound according to claim 3 or its pharmaceutically acceptable salt, wherein one of $R^{10}$ and $R^{11}$ is hydrogen;
the other of $R^{10}$ and $R^{11}$ is halogen, hydroxy, cyano, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;
b is an integer from 0 to 3;
c is an integer from 0 to 3;
d is an integer from 0 to 4.

8. A compound represented by formula (I):

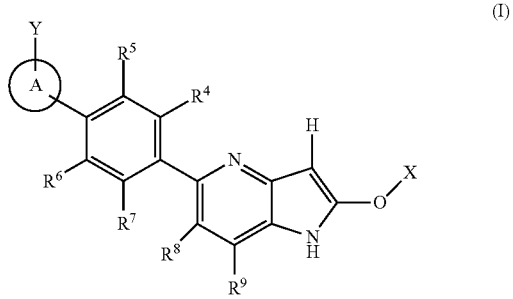

or its pharmaceutically acceptable salt, wherein
X is

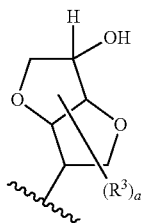

wherein R³ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

a is an integer from 0 to 7;

ring A is substituted aryl, substituted heteroaryl, substituted cycloalkyl, substituted cycloalkenyl, or substituted heterocyclyl, the ring A may further have (a) substituent(s) other than Y;

Y is $R^{Y1}$—O— or $(R^{Y2}R^{Y3})N$—;

$R^{Y1}$ is substituted or unsubstituted alkyl, substituted or unsubstituted alkenyl, substituted or unsubstituted alkynyl, substituted or unsubstituted acyl, substituted or unsubstituted aryl, substituted or unsubstituted heteroaryl, substituted or unsubstituted cycloalkyl, substituted or unsubstituted cycloalkenyl, substituted or unsubstituted heterocyclyl, $(R^N R^{N'})N$—C(=O)—, or $R^O$—O—C(=O)—;

$R^{Y2}$ is hydrogen, substituted or unsubstituted alkyl, substituted or unsubstituted alkenyl, substituted or unsubstituted alkynyl, substituted or unsubstituted acyl, substituted or unsubstituted aryl, substituted or unsubstituted heteroaryl, substituted or unsubstituted cycloalkyl, substituted or unsubstituted cycloalkenyl, substituted or unsubstituted heterocyclyl, $(R^N R^{N'})N$—C(=O)—, or $R^O$—O—C(=O)—;

$R^{Y3}$ is is substituted or unsubstituted alkyl, substituted or unsubstituted alkenyl, substituted or unsubstituted alkynyl, substituted or unsubstituted acyl, substituted or unsubstituted aryl, substituted or unsubstituted heteroaryl, substituted or unsubstituted cycloalkyl, substituted or unsubstituted cycloalkenyl, substituted or unsubstituted heterocyclyl $(R^N R^{N'})N$—C(=O)—, or $R^O$—O—C(=O)—;

$R^N$ is each independently hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl, or substituted or unsubstituted carbamoyl;

$R^{N'}$ is hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl or substituted or unsubstituted carbamoyl;

$R^N$ and $R^{N'}$ attached to the same N-atom may form a substituted or unsubstituted ring together with the N-atom;

$R^O$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl;

$R^4$, $R^5$, $R^6$ and $R^7$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

$R^8$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

$R^9$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

with the proviso that compounds shown below are excluded:

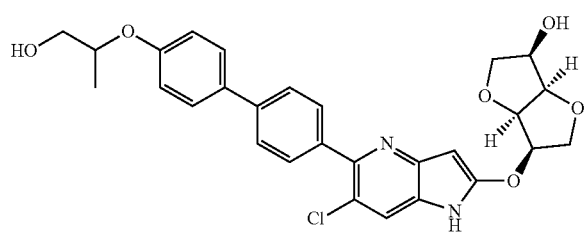

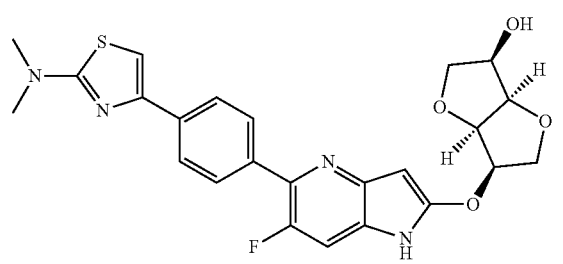

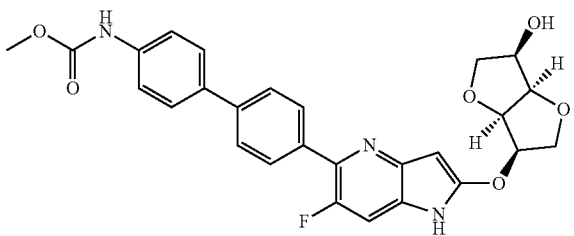

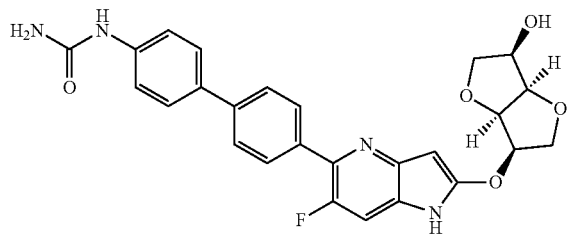

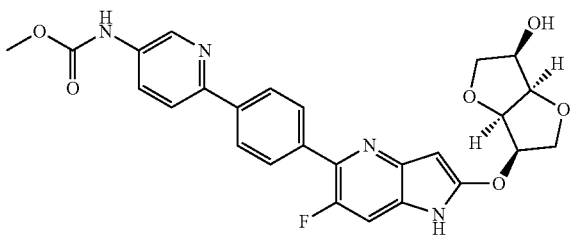

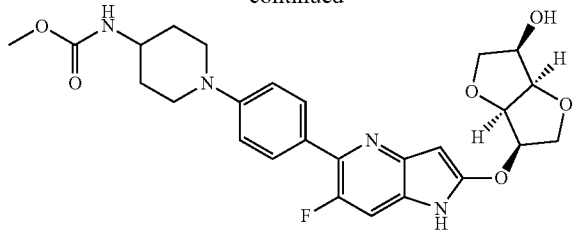

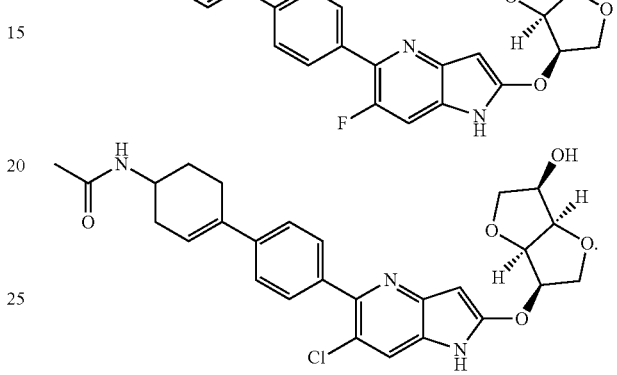

9. The compound according to claim 1 or its pharmaceutically acceptable salt, wherein ring A is substituted aryl, substituted heteroaryl, substituted cycloalkenyl, or substituted heterocyclyl.

10. The compound according to claim 1 or its pharmaceutically acceptable salt, wherein ring A is substituted aryl.

11. The compound according to claim 1 or its pharmaceutically acceptable salt, wherein Y is substituted or unsubstituted alkyloxy, substituted or unsubstituted alkyloxycarbonyl, substituted or unsubstituted alkylsulfinyl, substituted or unsubstituted acyl, substituted or unsubstituted carbamoyloxy, substituted or unsubstituted amino, $R^S R^{S'}(O=)S=N-$, $(R^N)N=S(=O)(R^S)-$, $R^O$ $O-C(=O)-N(R^N)-$, $R^{Y1}-O-$ or $(R^{Y2}R^{Y3})N-$.

12. The compound according to claim 1 or its pharmaceutically acceptable salt, wherein $R^4$, $R^5$, $R^6$ and $R^7$ are each independently hydrogen, halogen, hydroxy, cyano, substituted or unsubstituted alkyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

13. The compound according to claim 1 or its pharmaceutically acceptable salt, wherein $R^8$ is hydrogen, halogen, cyano, carboxy, substituted or unsubstituted alkyl, substituted or unsubstituted alkylsulfonyl, or substituted or unsubstituted carbamoyl.

14. The compound according to claim 13 or its pharmaceutically acceptable salt, wherein $R^8$ is hydrogen, fluoro, chloro, cyano, or substituted or unsubstituted alkyl, wherein the substituent of the substituted alkyl is halogen.

15. The compound according to claim 1 or its pharmaceutically acceptable salt, wherein $R^9$ is hydrogen.

16. The compound according to claim 1 or its pharmaceutically acceptable salt, wherein the compound is selected from 265
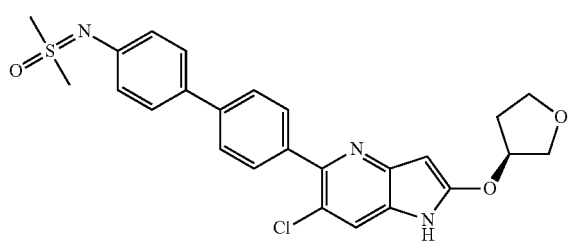
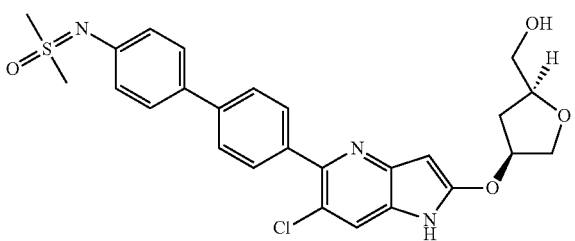
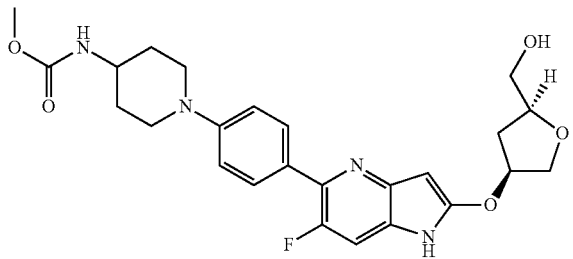
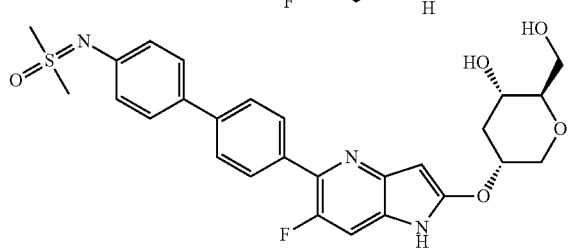
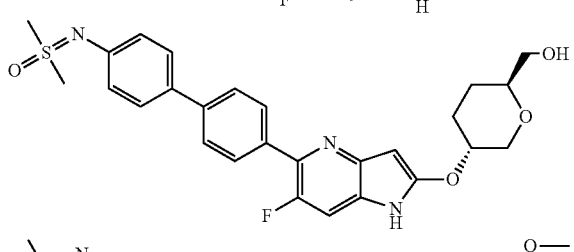
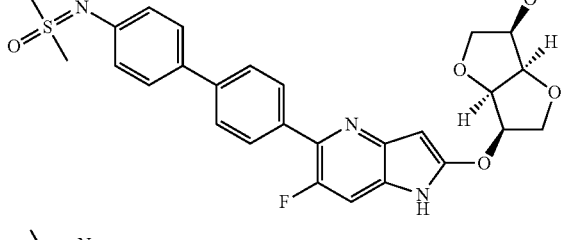
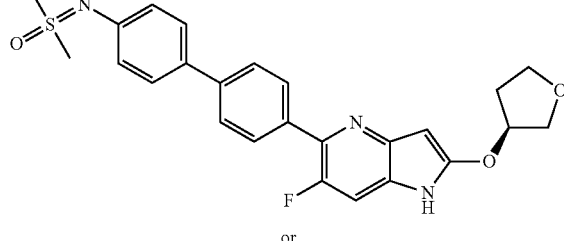
or
266
-continued
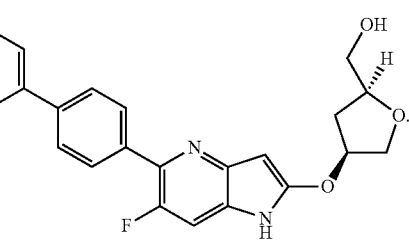
17. The compound according to claim 8 or its pharmaceutically acceptable salt, wherein the compound is selected from
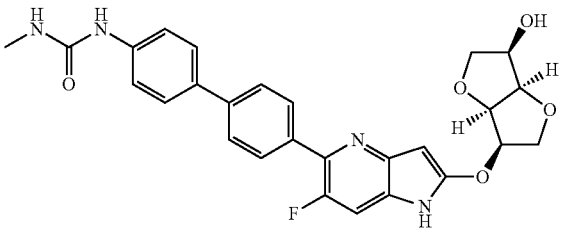
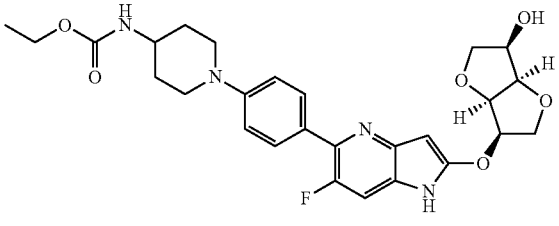
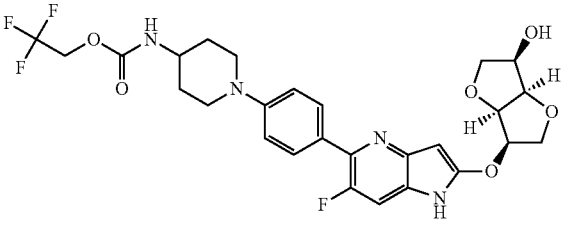
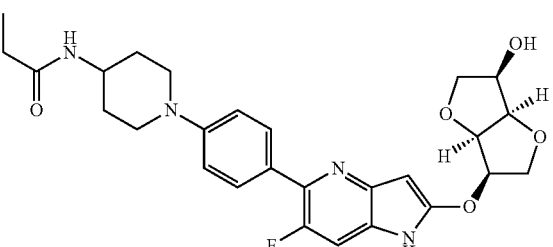
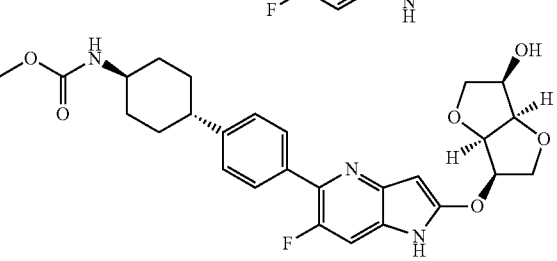

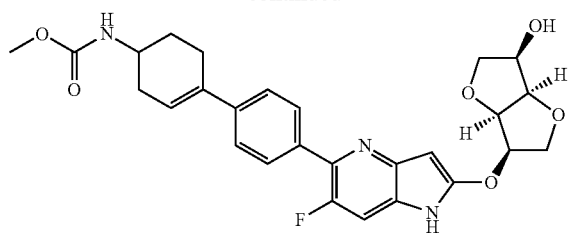
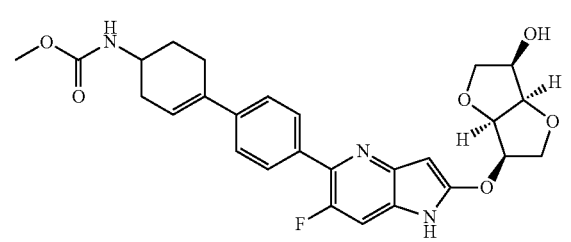
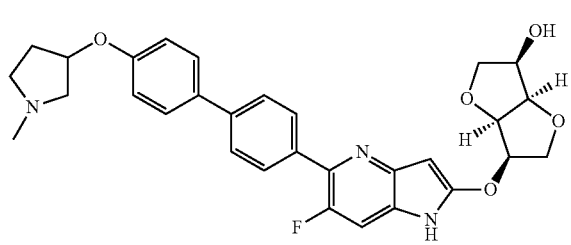
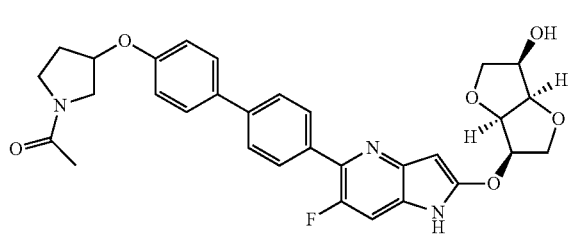
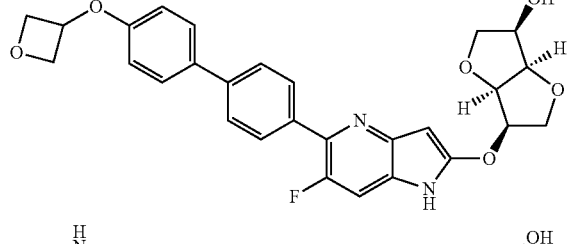
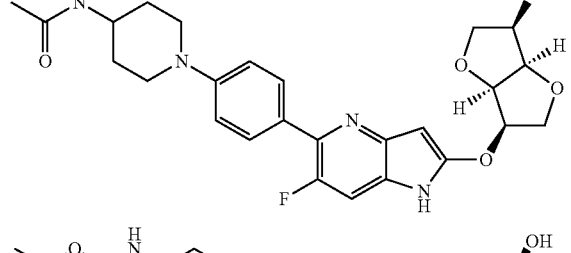
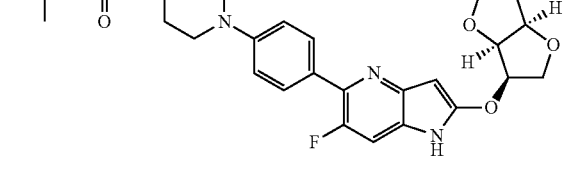
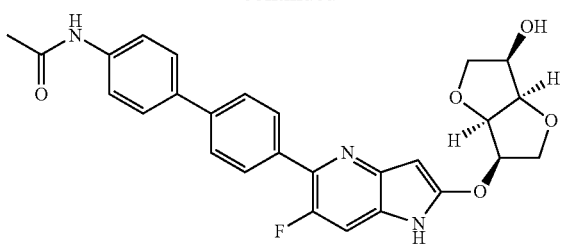
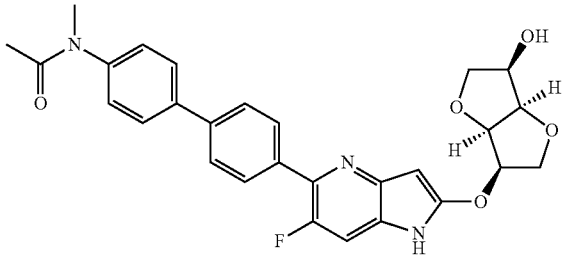
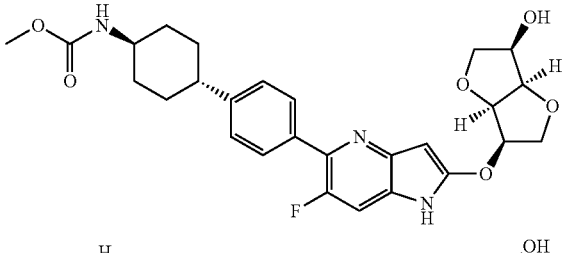
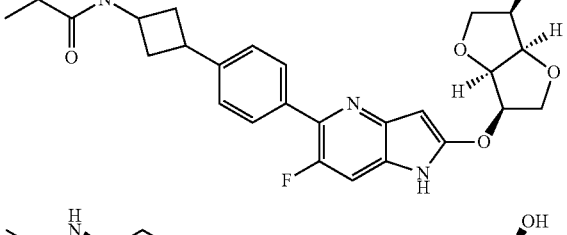
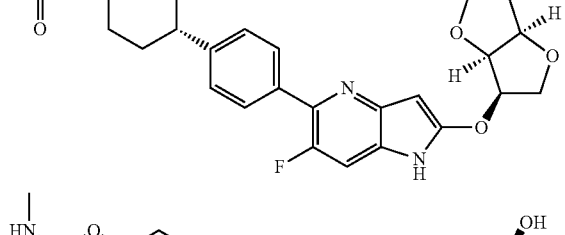
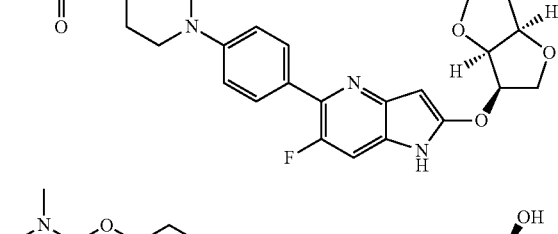
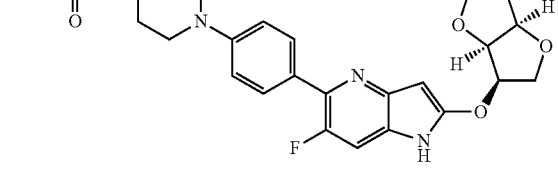

269
-continued
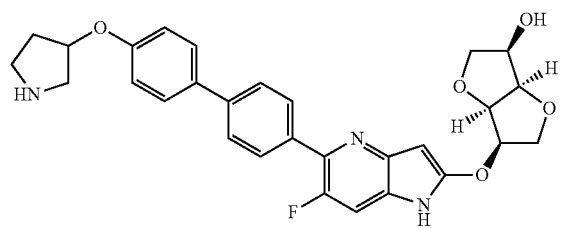
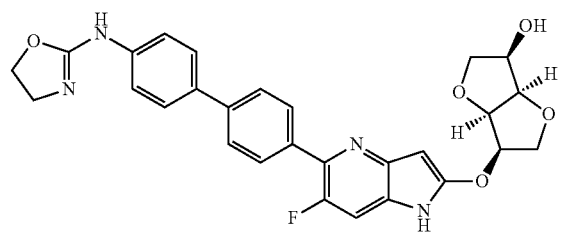
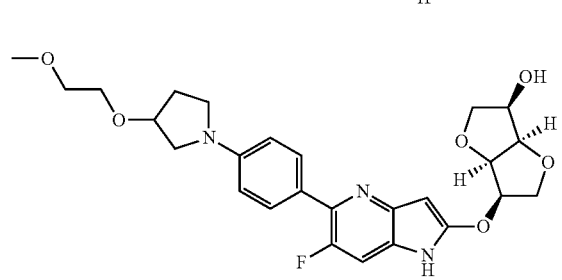
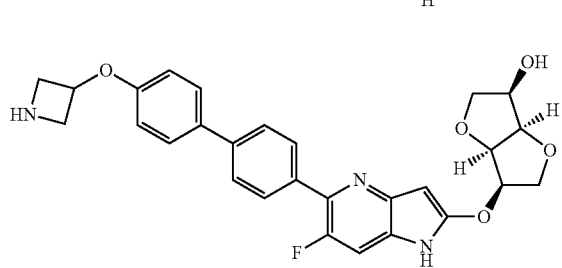
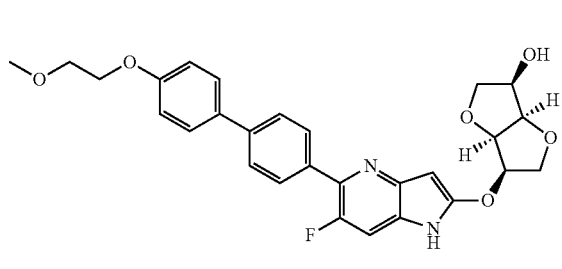
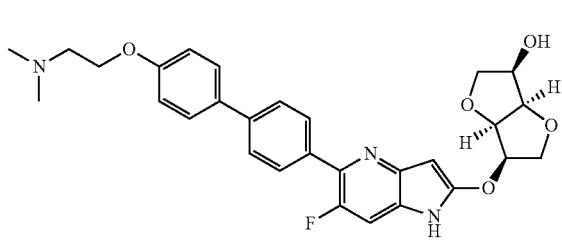
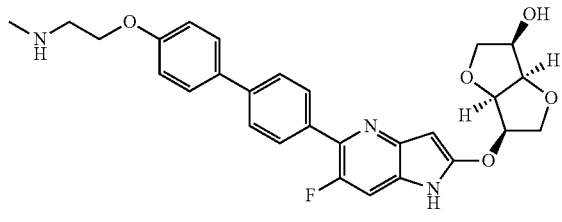
270
-continued
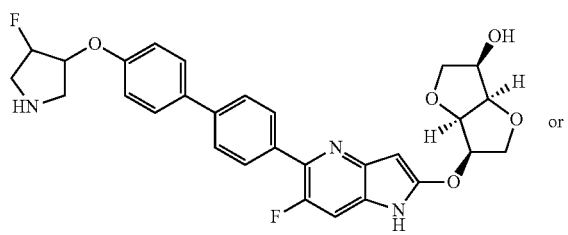
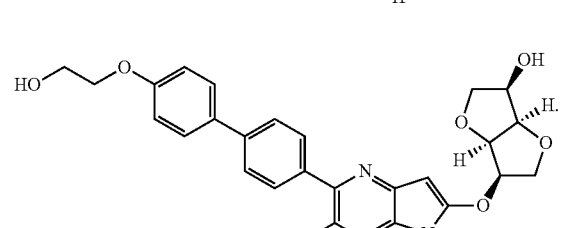
18. The compound according to claim 1 or its pharmaceutically acceptable salt, wherein the compound is selected from
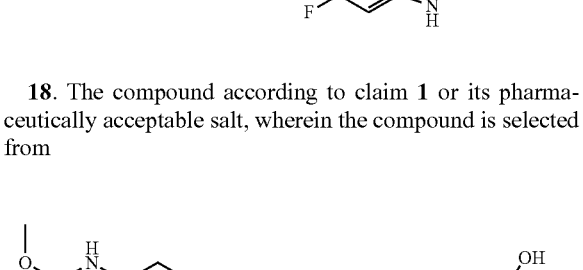
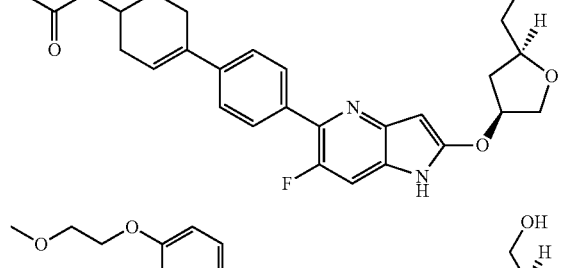
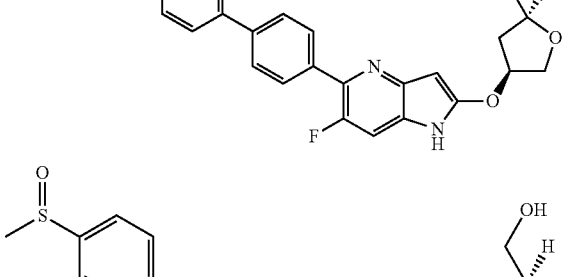
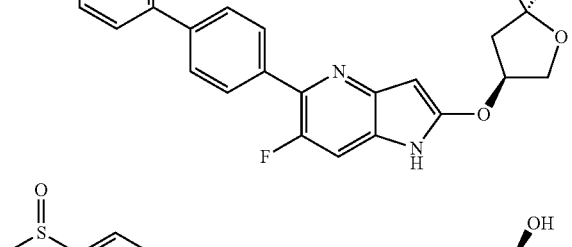
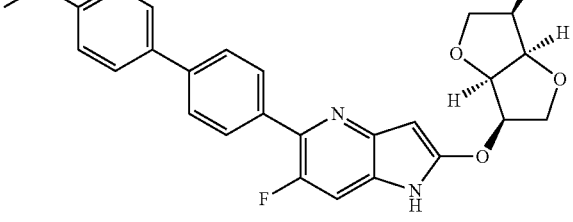
or 271
-continued
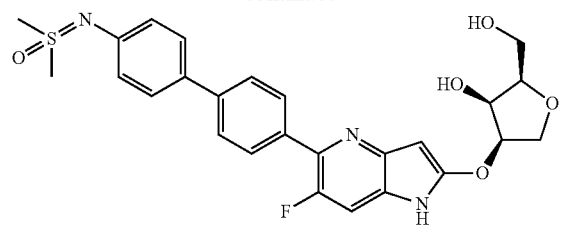
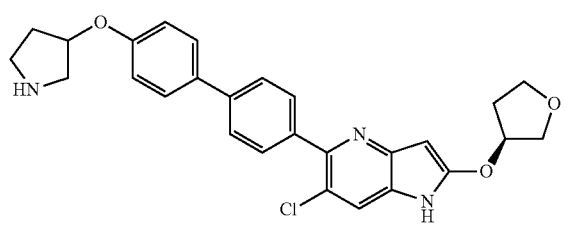
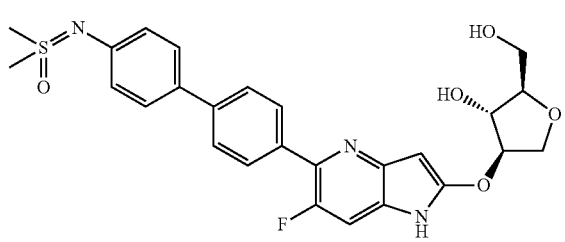
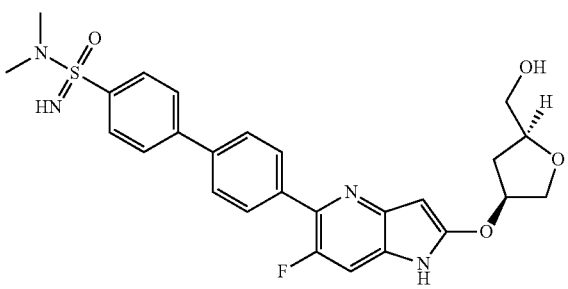
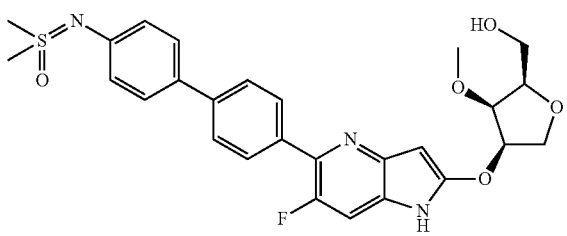
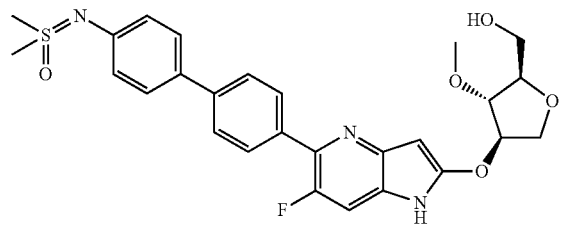
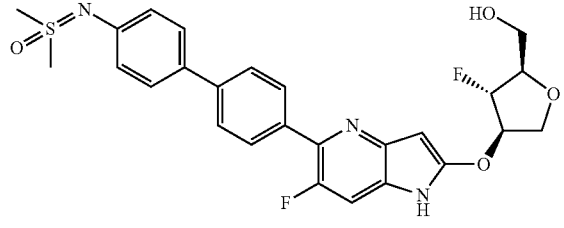
272
-continued
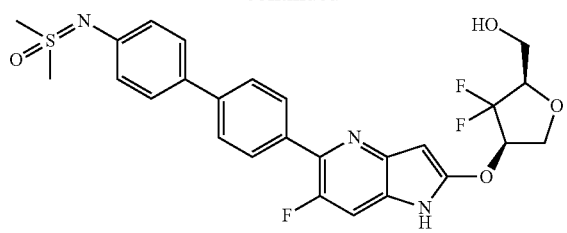
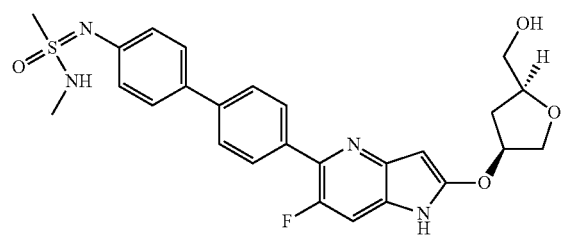
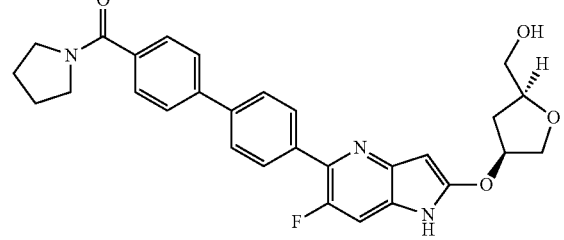
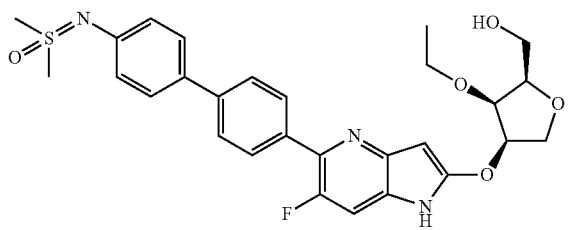
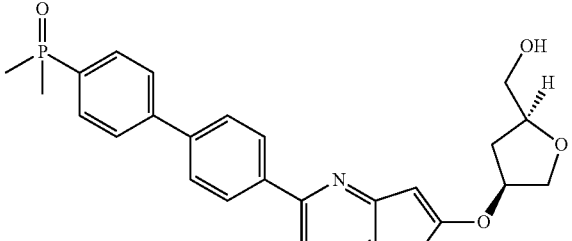
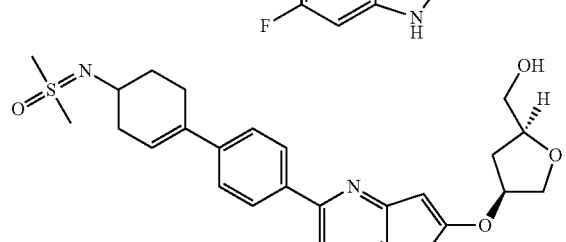
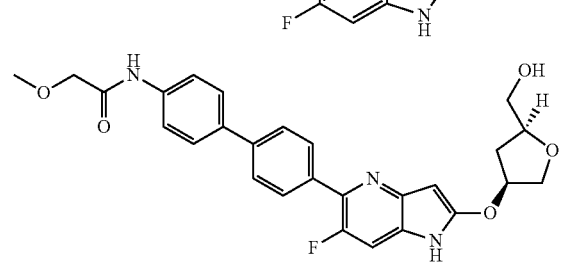

273
-continued
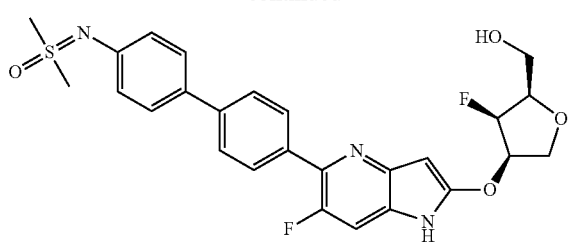
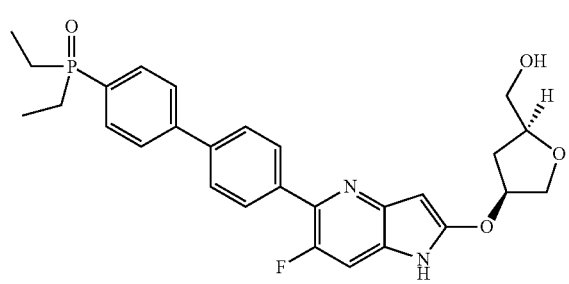
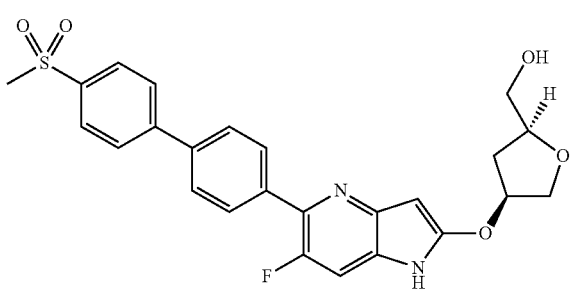
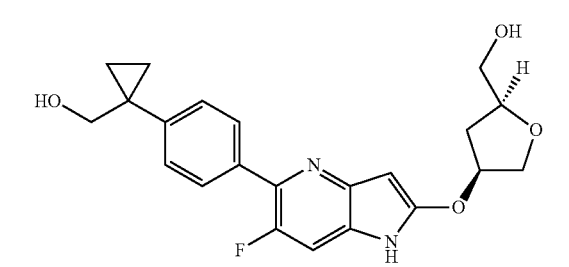
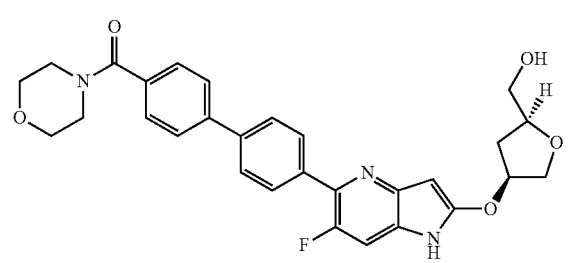
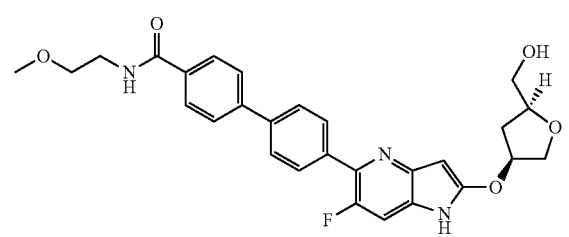
274
-continued
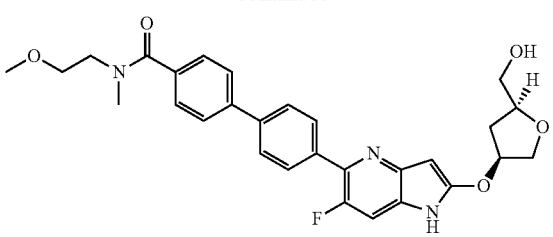
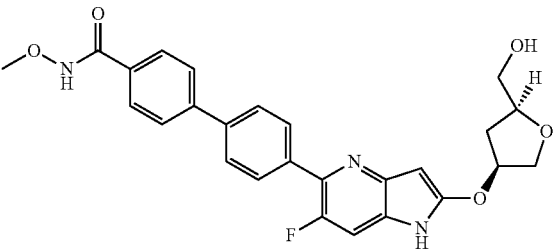
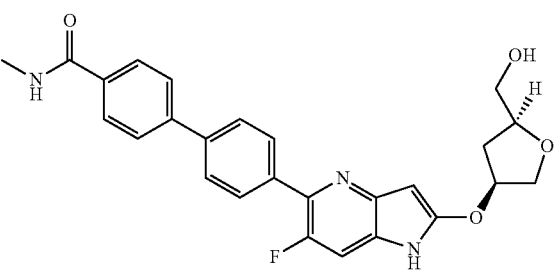
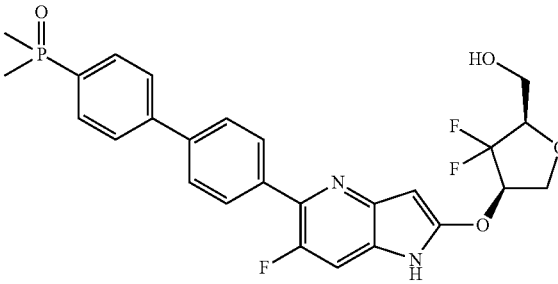
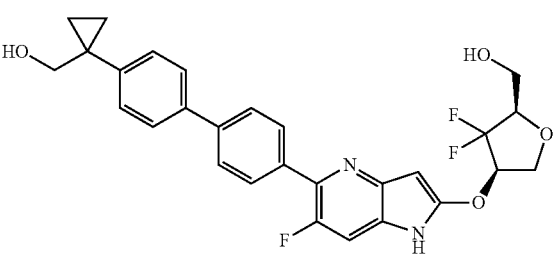
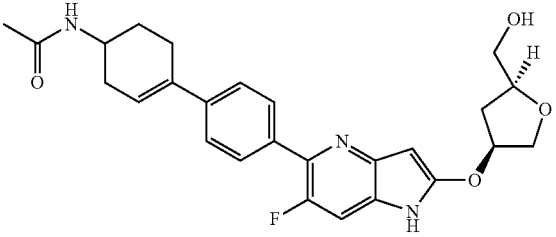

275
-continued
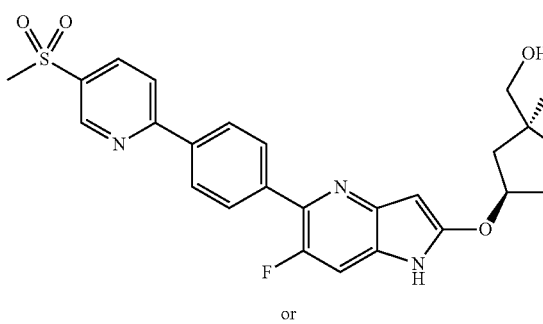
or
276
-continued
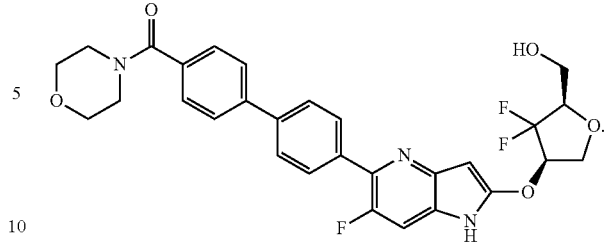
19. The compound according to claim 8 or its pharmaceutically acceptable salt, wherein the compound is selected from
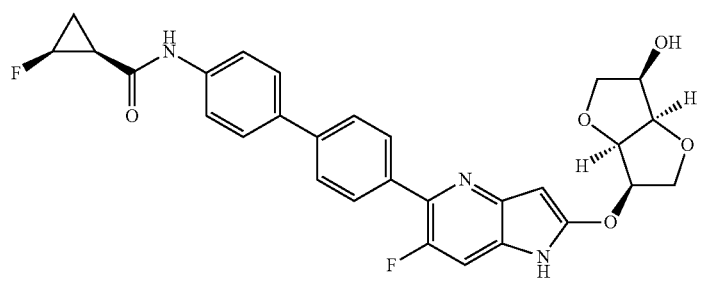
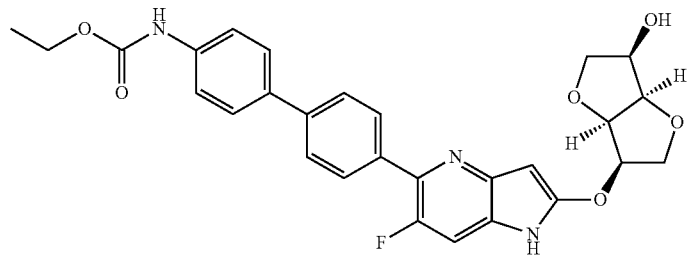
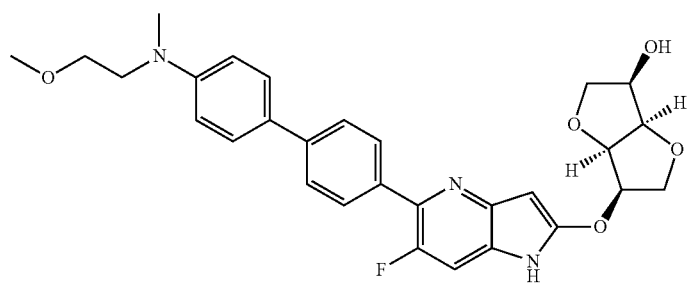
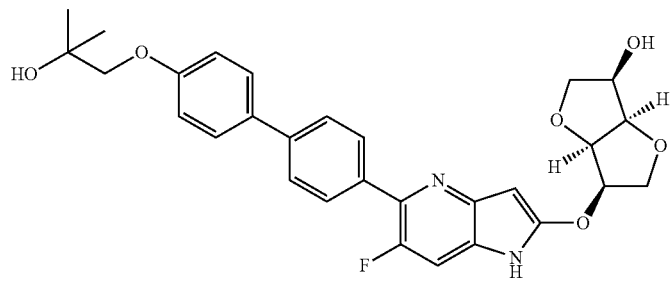

-continued
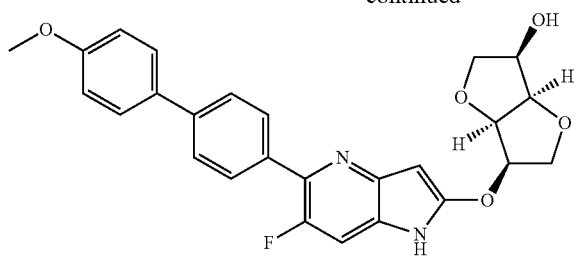
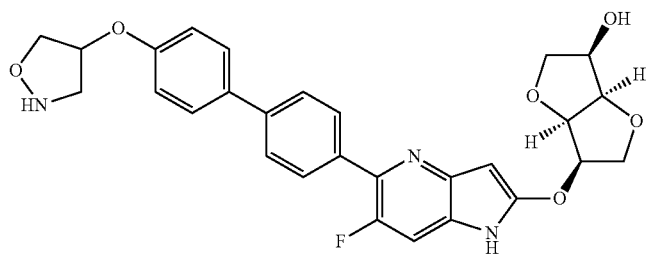
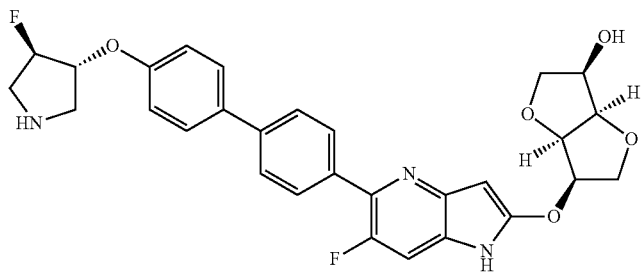
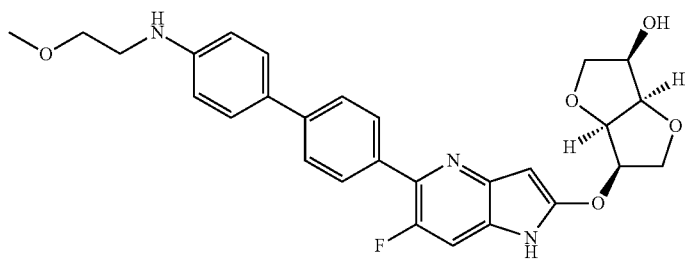
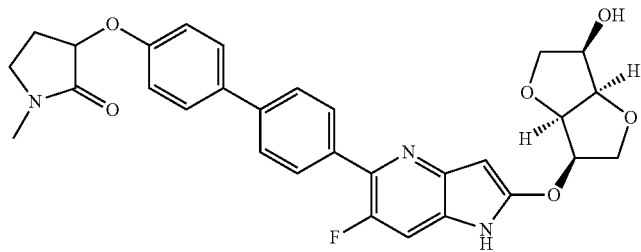
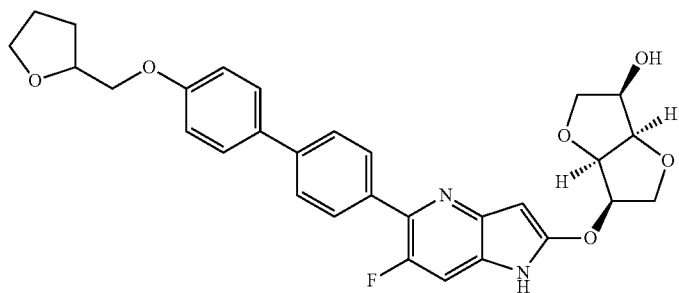

-continued
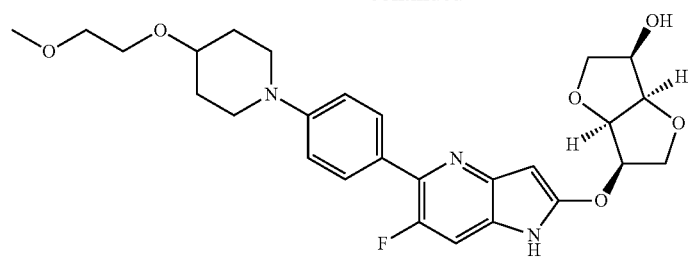
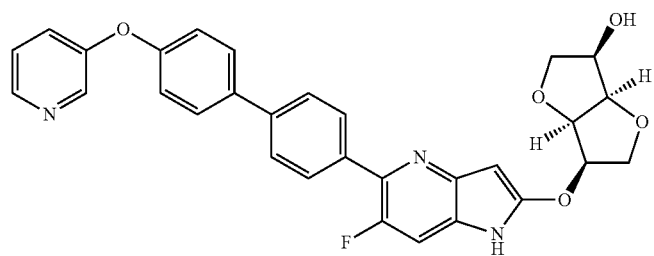
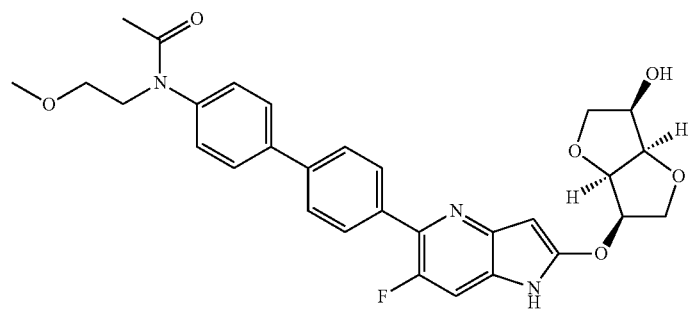
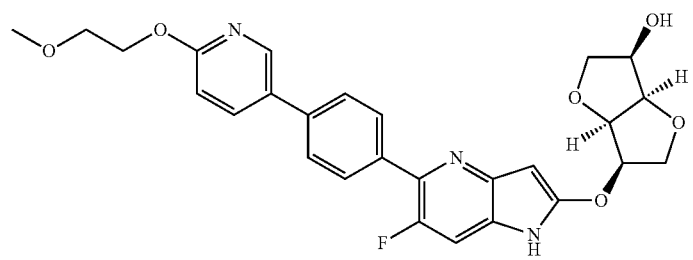
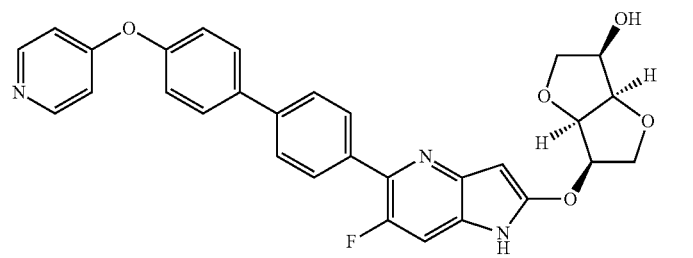
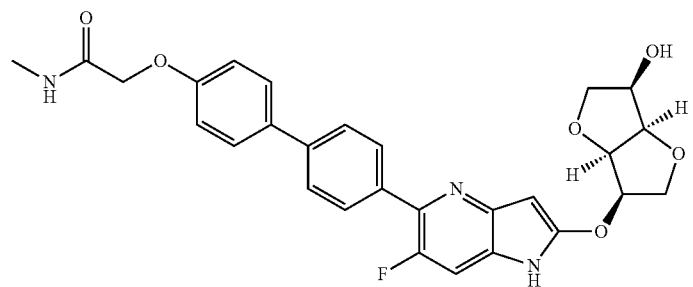

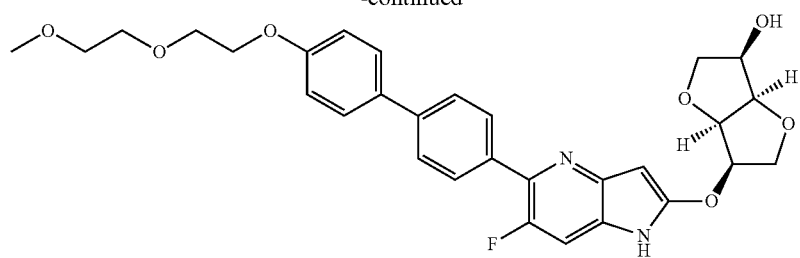
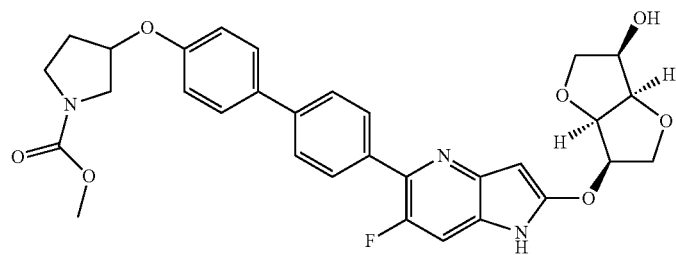
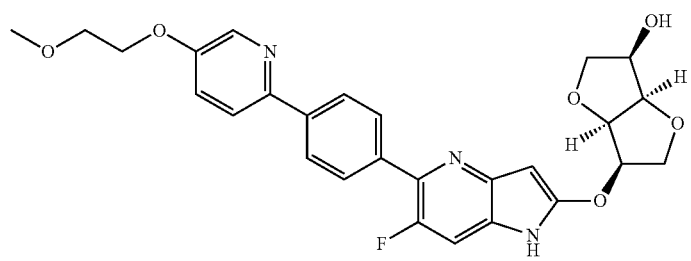
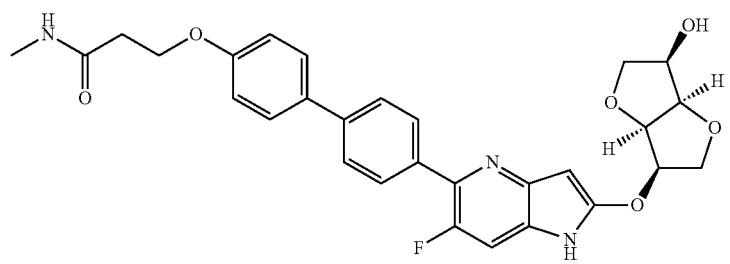
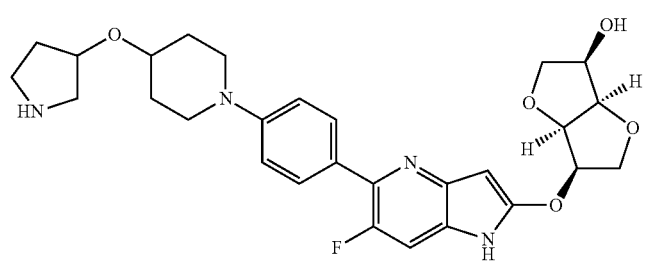
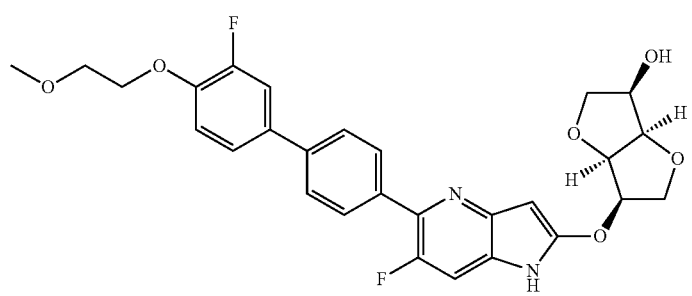

-continued
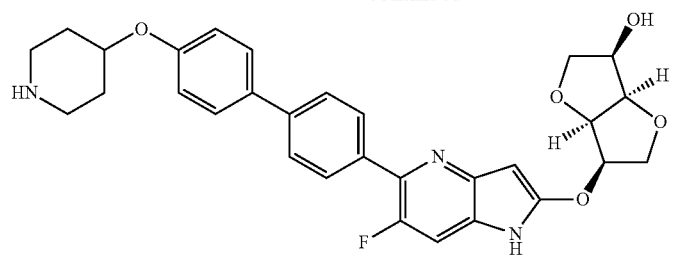
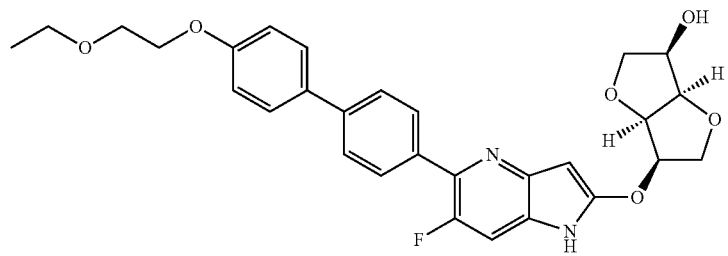
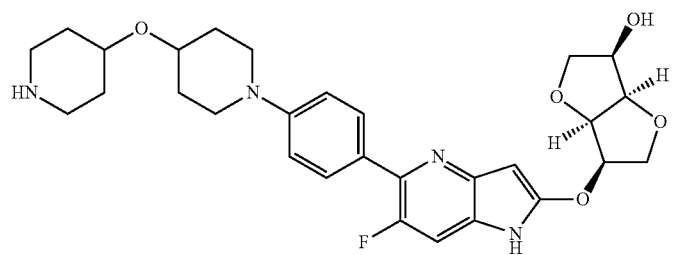
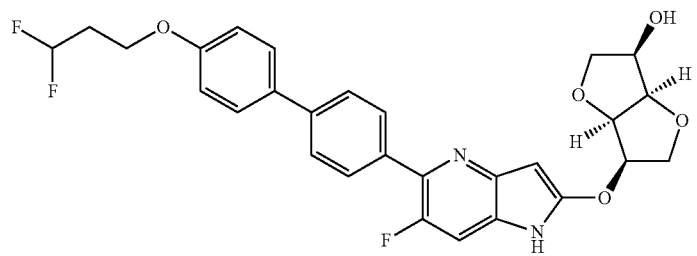
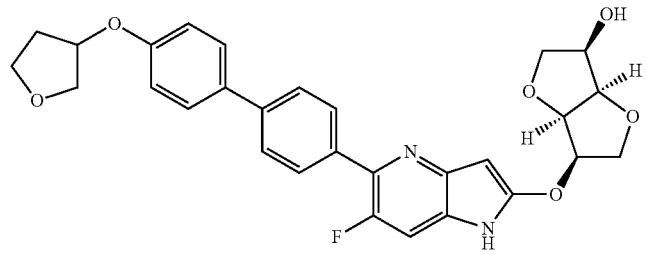
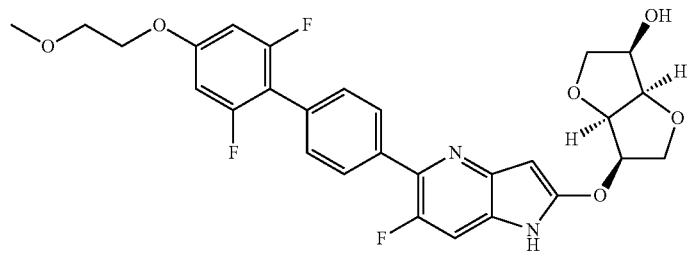

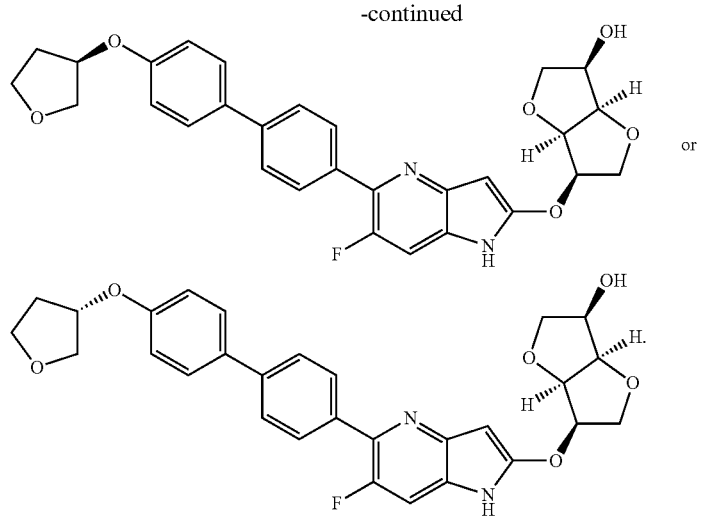
20. A compound or its pharmaceutically acceptable salt, wherein the compound is selected from
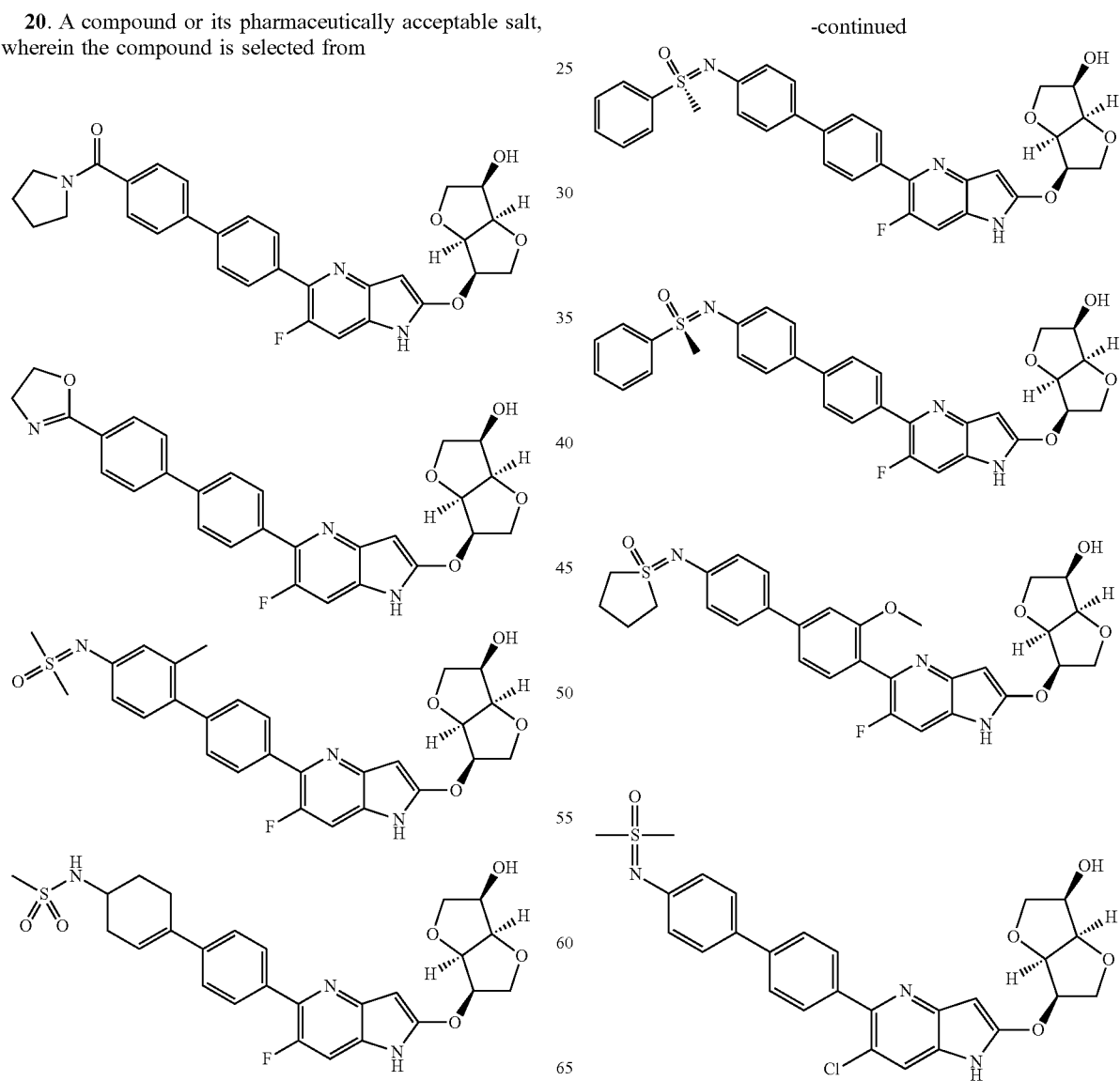

287
-continued
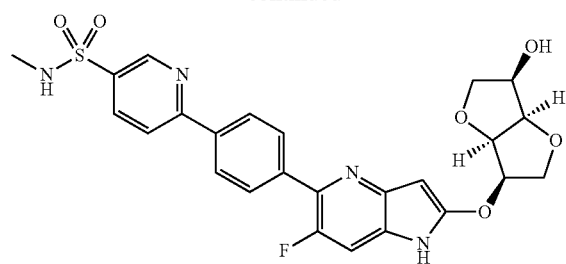
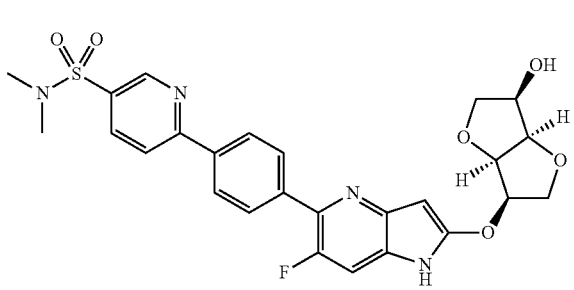
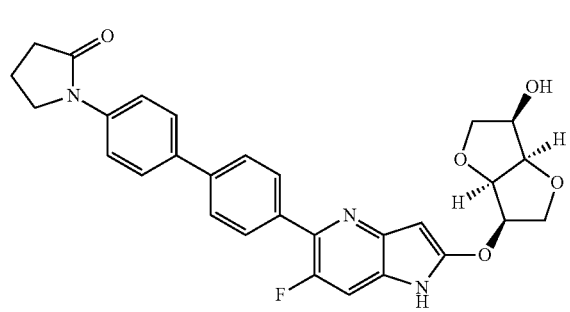
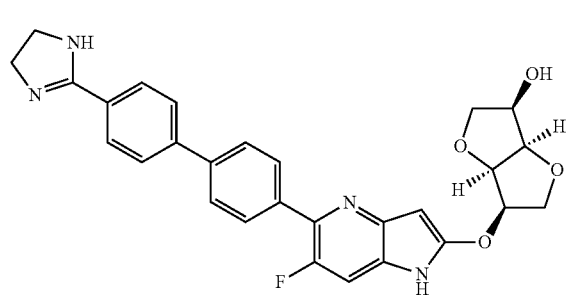
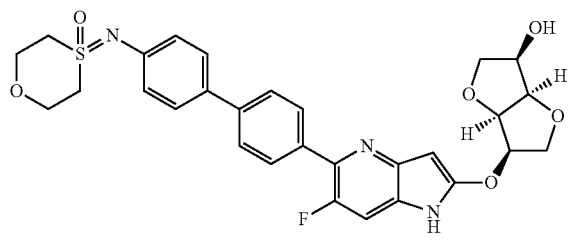
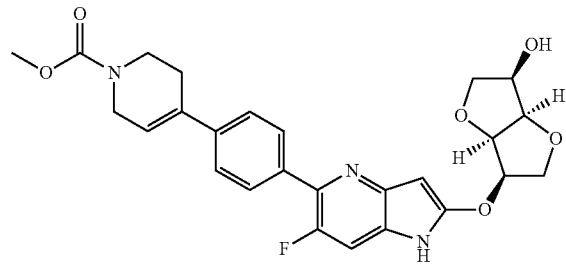
288
-continued
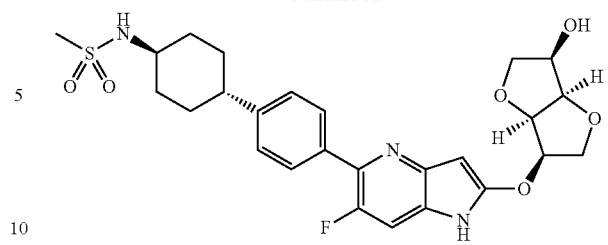
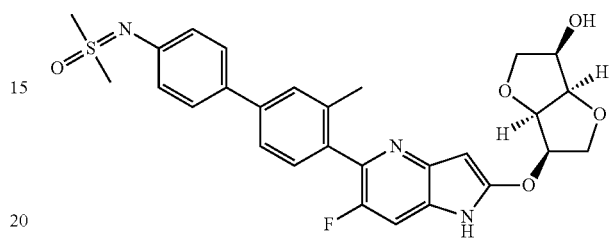
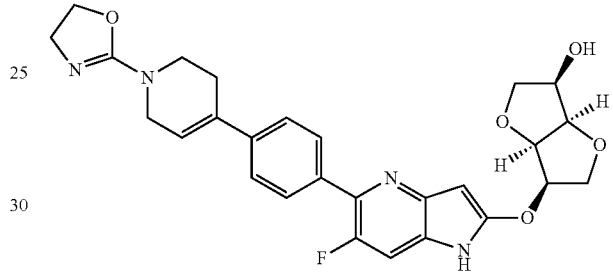
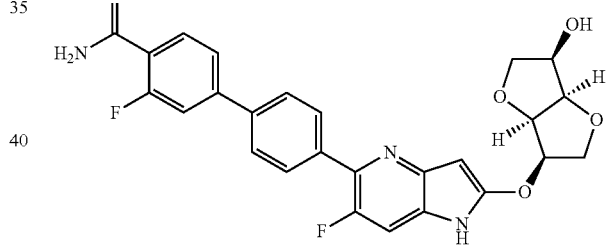
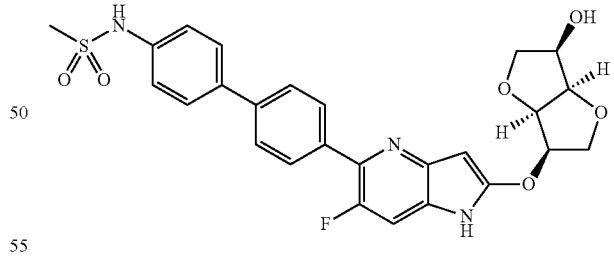
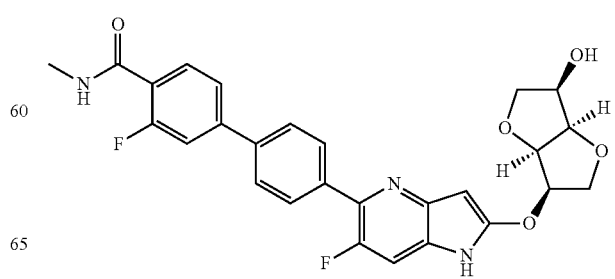

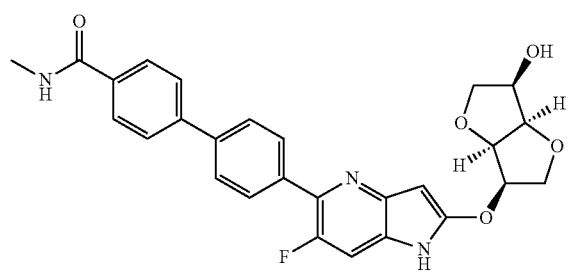
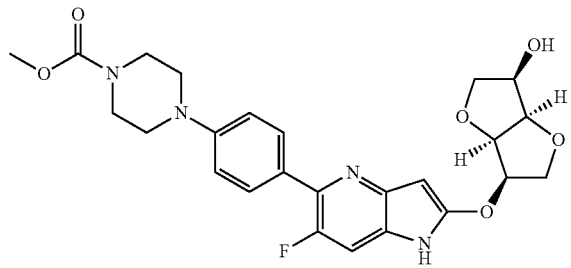
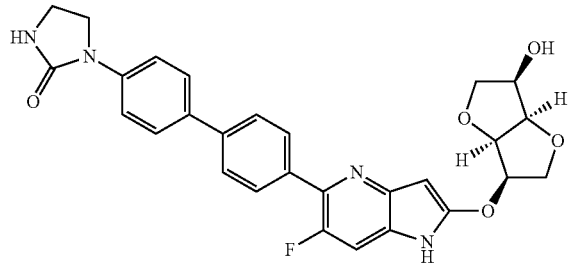
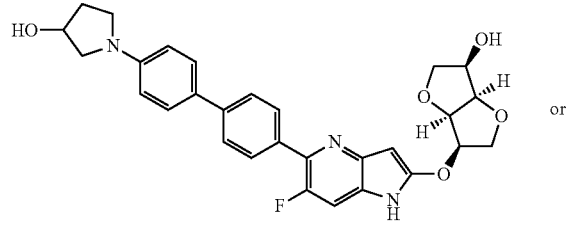
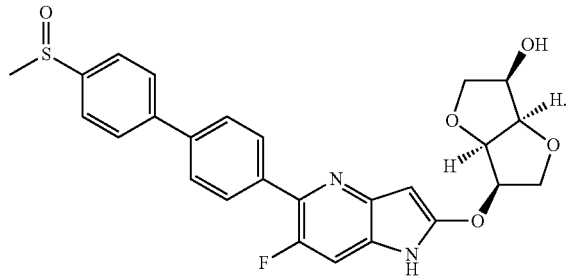
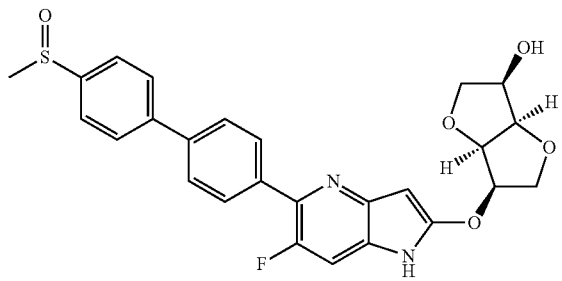
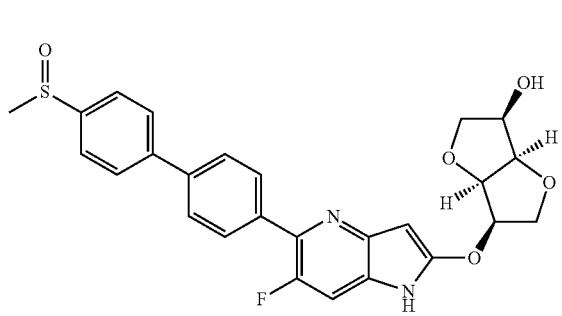
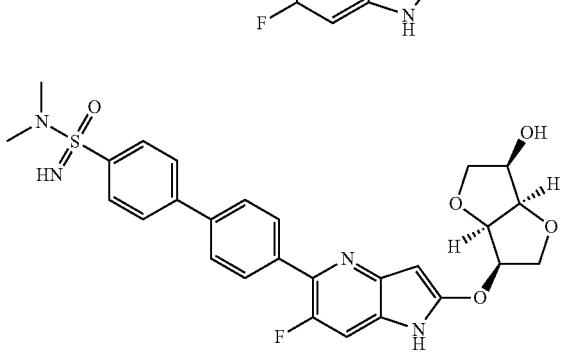
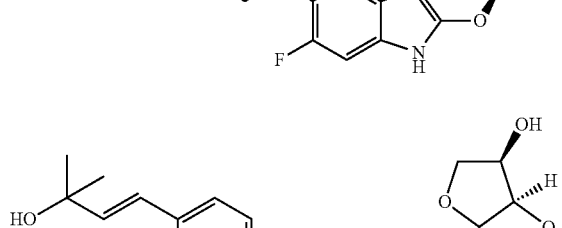
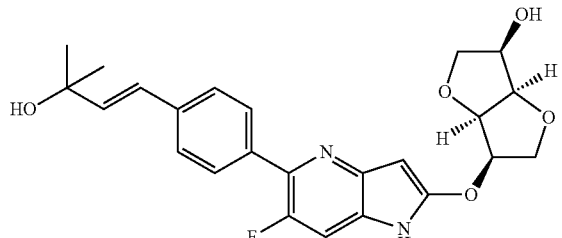
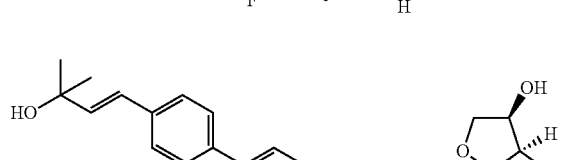
21. A compound or its pharmaceutically acceptable salt, wherein the compound is selected from
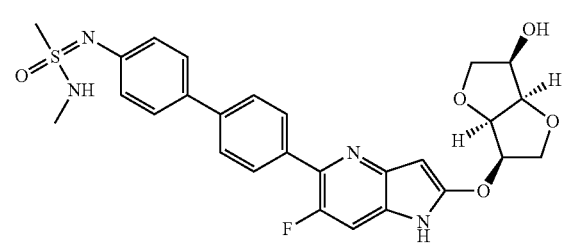
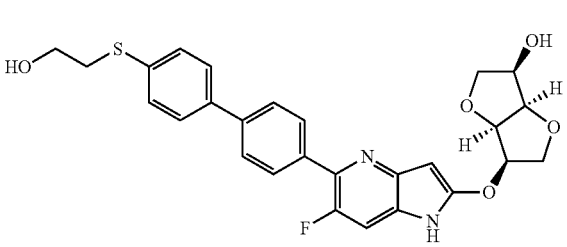

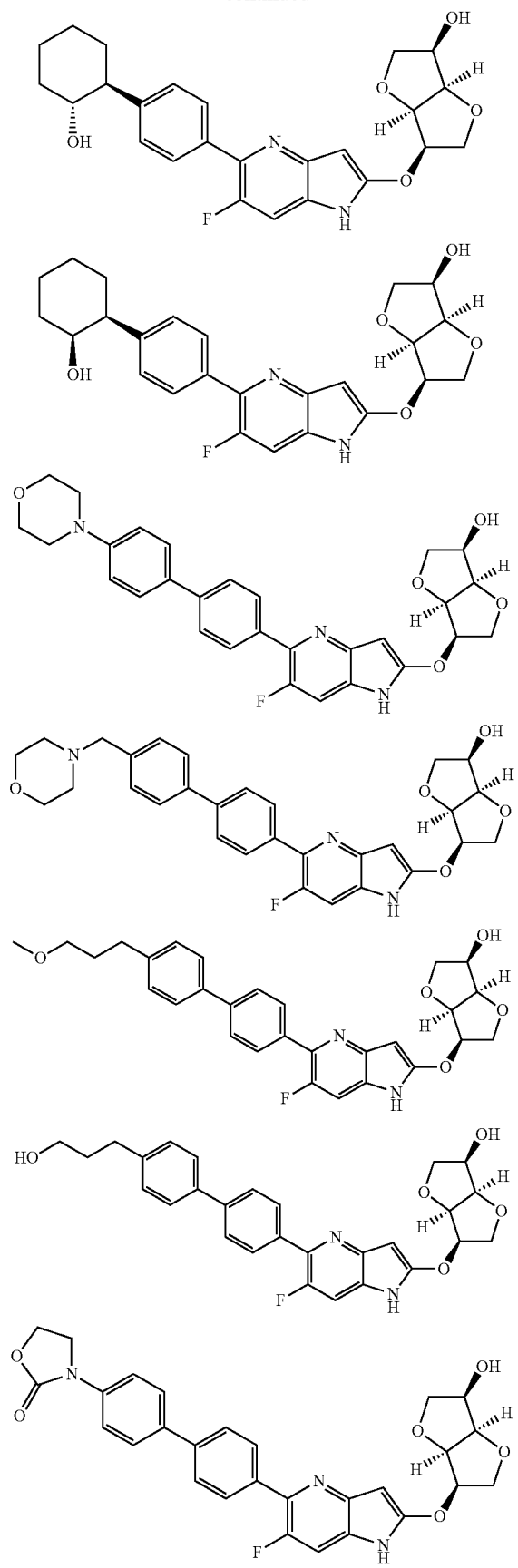
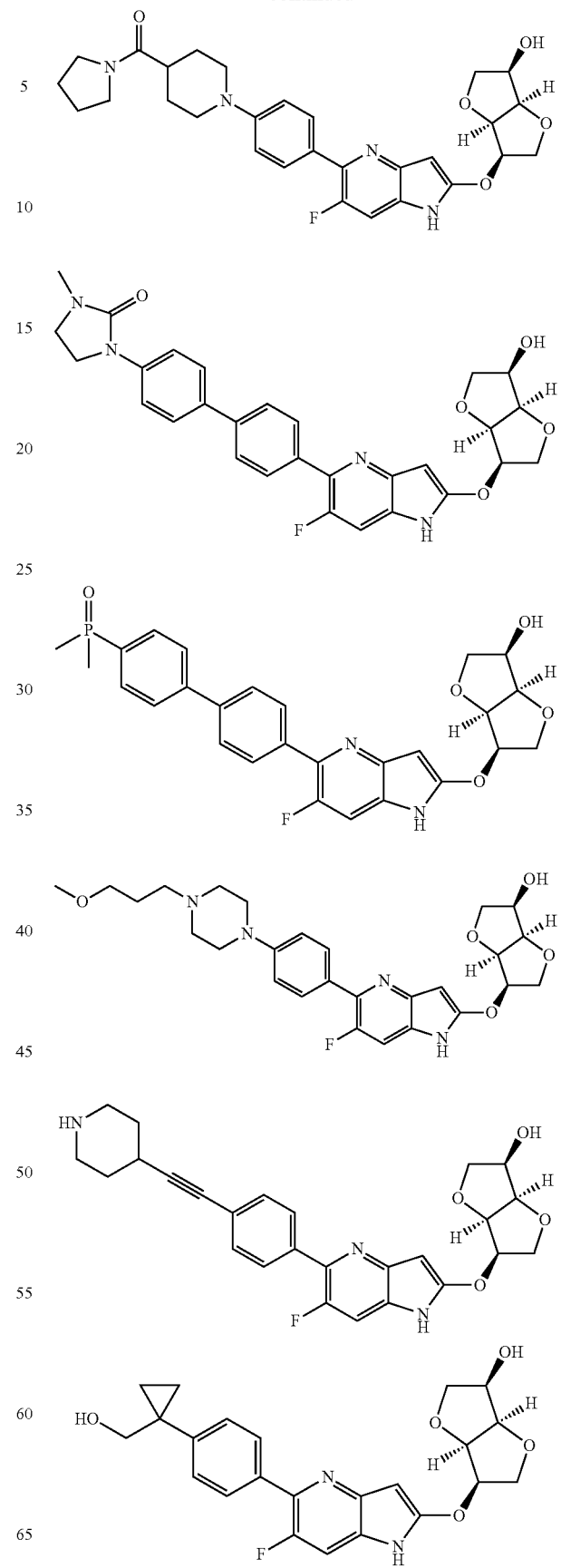

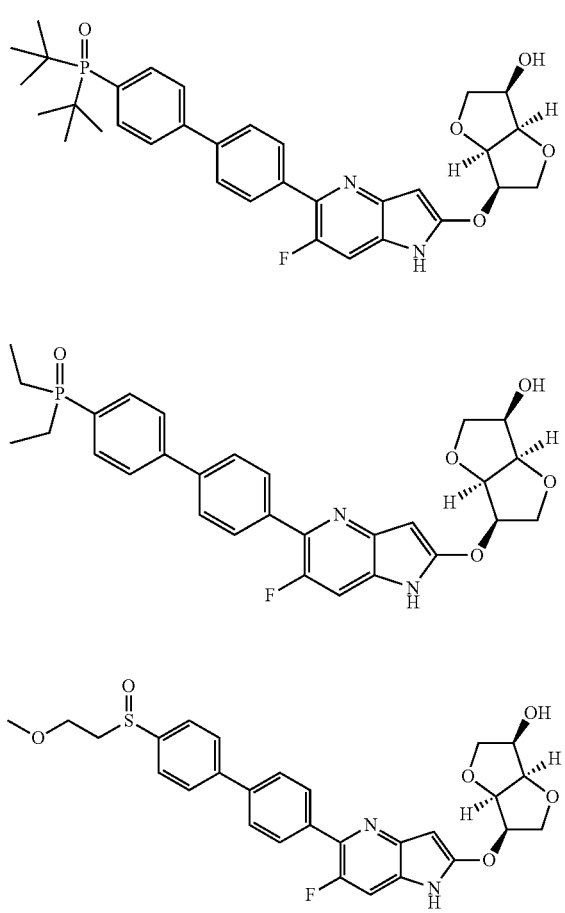

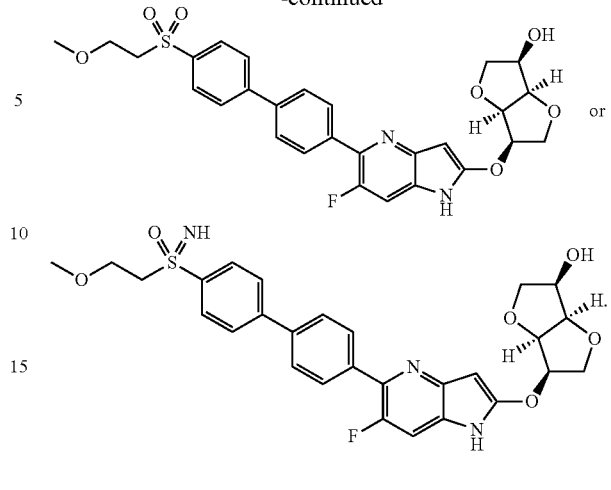

22. A pharmaceutical composition comprising the compound according to claim 1 or its pharmaceutically acceptable salt and a pharmaceutical additive.

23. The pharmaceutical composition according to claim 22, which has an activating effect on adenosine monophosphate-activated protein kinase.

24. The pharmaceutical composition according to claim 22 for the treatment of diabetes.

25. A method for treating diabetes, comprising administering an effective amount of the compound according to claim 1, or its pharmaceutically acceptable salt to subject in need thereof.

26. The compound according to claim 1, or its pharmaceutically acceptable salt, for the treatment of diabetes.

* * * * *